(12) United States Patent
Forsell

(10) Patent No.: US 12,350,138 B2
(45) Date of Patent: Jul. 8, 2025

(54) IMPLANTABLE URETHRA RESTRICTION DEVICE

(71) Applicant: Peter Forsell, Sachseln (CH)

(72) Inventor: Peter Forsell, Sachseln (CH)

( * ) Notice: Subject to any disclaimer, the term of this patent is extended or adjusted under 35 U.S.C. 154(b) by 280 days.

(21) Appl. No.: 17/460,366

(22) Filed: Aug. 30, 2021

(65) Prior Publication Data

US 2023/0067834 A1    Mar. 2, 2023

(51) Int. Cl.
*A61F 2/00* (2006.01)

(52) U.S. Cl.
CPC ...... *A61F 2/004* (2013.01); *A61F 2250/0003* (2013.01); *A61F 2250/0013* (2013.01)

(58) Field of Classification Search
CPC .............. A61F 2/004; A61F 2250/0003; A61F 2250/0013
See application file for complete search history.

(56) References Cited

U.S. PATENT DOCUMENTS

| | | | | |
|---|---|---|---|---|
| 4,969,474 A | * | 11/1990 | Schwarz | A61F 2/004 128/885 |
| 6,135,945 A | * | 10/2000 | Sultan | A61B 5/0031 607/40 |
| 2006/0211913 A1 | * | 9/2006 | Dlugos | A61F 5/0003 600/37 |
| 2011/0015473 A1 | * | 1/2011 | Forsell | A61F 2/0036 600/30 |
| 2014/0364686 A1 | * | 12/2014 | McClurg | A61F 2/004 600/31 |

* cited by examiner

*Primary Examiner* — Samuel G Gilbert

(57) ABSTRACT

An implantable constriction device (10) for constricting a urethra (U) of a patient. The implantable constriction device (10) has at least one operable hydraulic constriction element (101a) configured to be inflated to constrict the urethra (U) for restricting the flow of urine therethrough, and a controller for controlling the inflation of the at least one operable hydraulic constriction element (101a).

18 Claims, 47 Drawing Sheets

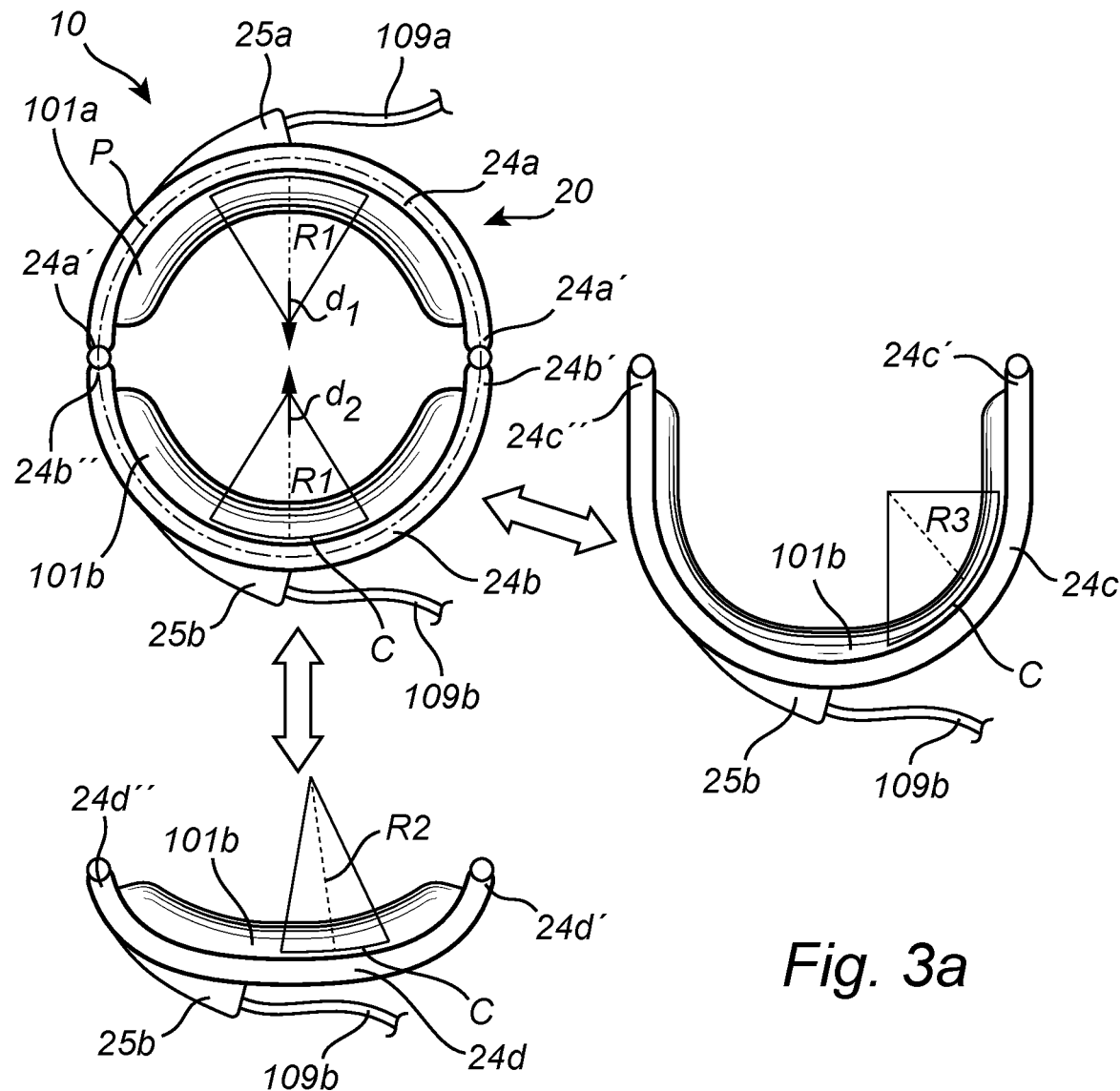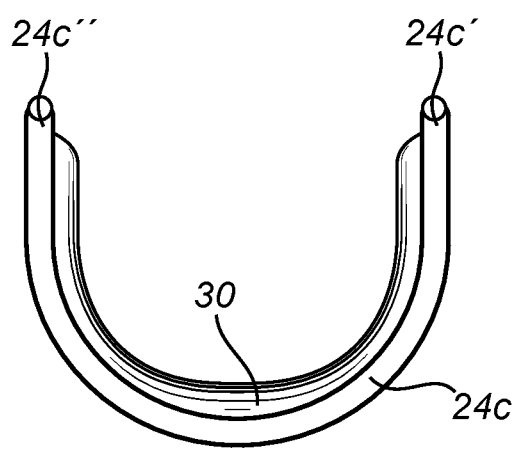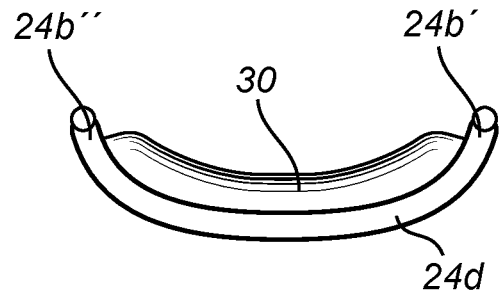
Fig. 3a
Fig. 3b
Fig. 3c

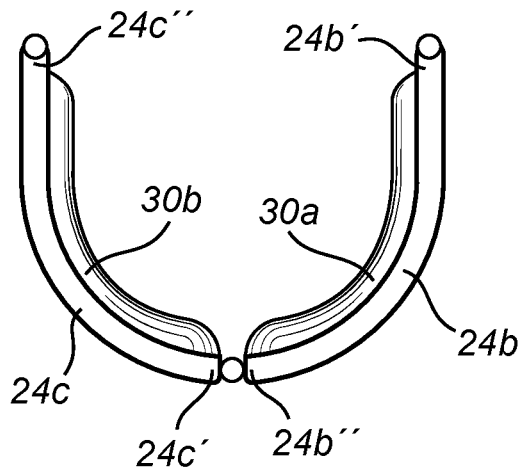
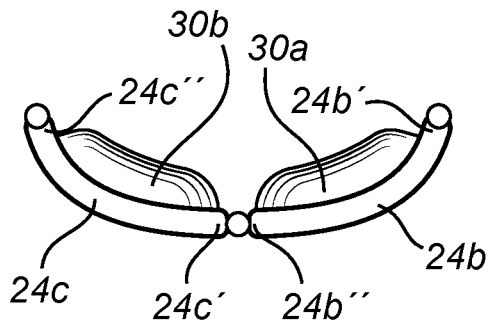
Fig. 3d  Fig. 3e
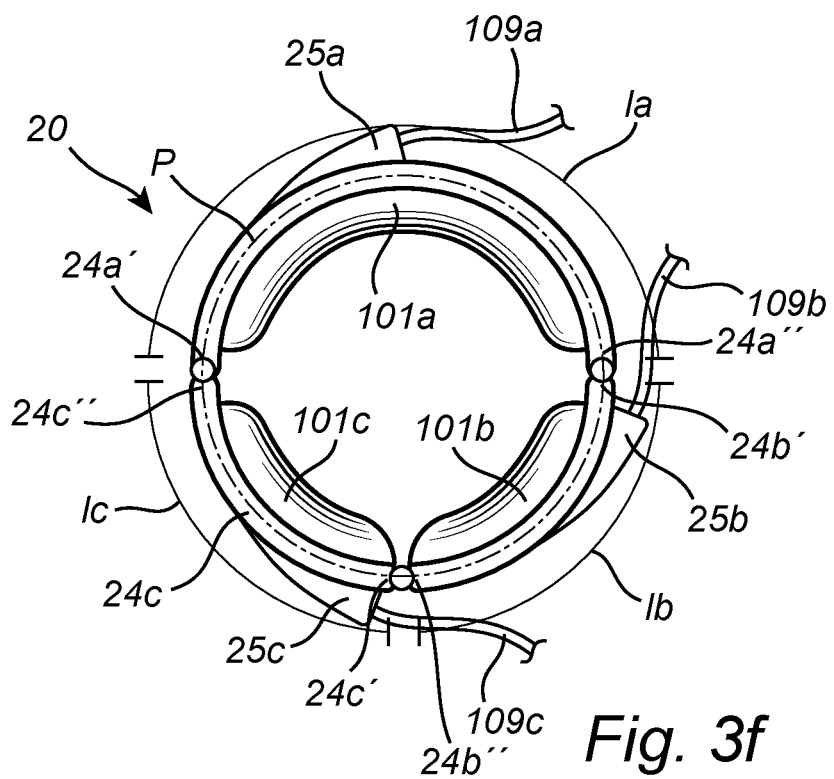
Fig. 3f

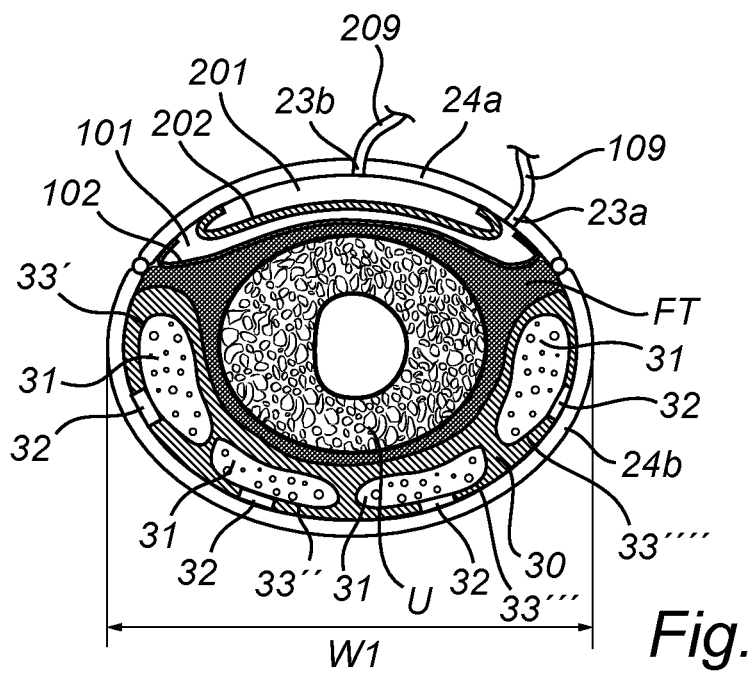
Fig. 11f
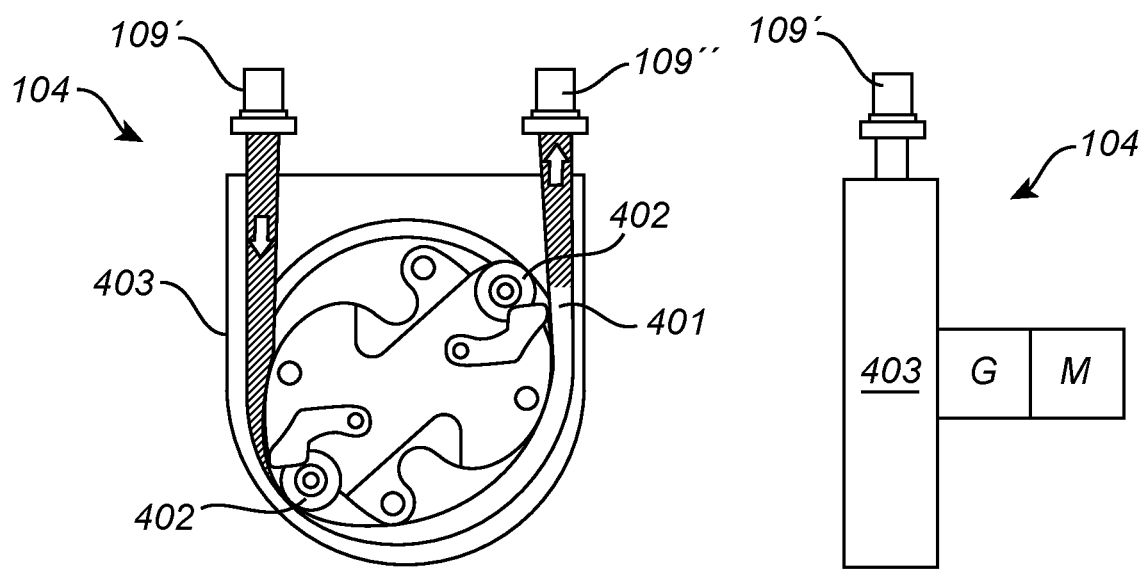
Fig. 12a
Fig. 12b

IMPLANTABLE URETHRA RESTRICTION DEVICE

TECHNICAL FIELD

The present invention relates to medical implants. More specifically the invention relates to medical implants for restricting the flow of urine in the urethra.

BACKGROUND

Restricting the urethra of a patient may be damaging to the urethra, it would therefore be advantageous to have a restriction device adapted to restrict the urethra in a less damaging way than the devices of the prior art.

SUMMARY

A support element for an implantable constriction device for constricting a urethra of a patient is provided. The support element is configured to form at least a portion of a surrounding structure configured to surround and support at least one operable hydraulic constriction element configured to constrict the urethra for restricting the flow of urine therethrough. The support element comprises at least one fluid conduit at least partially integrated in the support element. Integrating the fluid conduit in the support element enables the fluid entry to an operable hydraulic constriction element to be protected and encapsulated by the support element which reduces the space occupied by the operable hydraulic constriction element and reduces the amount of protruding portions thus reducing the risk of damaging the urethra.

In one embodiment, the at least one fluid conduit is completely integrated in the support element.

In one embodiment, the support element comprises a connection portion for connecting the support element to another support element for at least partially forming the surrounding structure. The support element may comprise a portion of a hinge for hingedly connecting the support element to another support element for at least partially forming the surrounding structure. In one embodiment, the support element comprises the portion of a hinge at a first end of the support element and the support element comprises another connection portion at a second end for connecting to another portion of the support element or another support element, for at least partially forming the surrounding structure.

In one embodiment, the support element comprises an inner surface configured to be directed towards the urethra, when implanted. The inner surface may comprise a fixation surface for fixating at least one operable hydraulic constriction element, and the fixation surface may comprise at least one outlet from the at least partially integrated fluid conduit, such that a fluid can flow through the at least partially integrated fluid conduit into the operable hydraulic constriction element for constricting the urethra. In one embodiment, the inner surface comprises a fixation surface for fixating at least two operable hydraulic constriction elements.

In one embodiment, the support element comprises a second fluid conduit at least partially integrated in the support element. The first at least partially integrated fluid conduit is configured to conduct fluid to the first operable hydraulic constriction element and the second at least partially integrated fluid conduit is configured to conduct fluid to the second operable hydraulic constriction element.

In one embodiment, the support element comprises at least one operable hydraulic constriction element configured to constrict the urethra for restricting the flow of urine therethrough, and the at least one operable hydraulic constriction element is in fluid connection with the at least one fluid conduit at least partially integrated in the support element.

In one embodiment, the support element comprises a second operable hydraulic constriction element, and at least one second operable hydraulic constriction element is in fluid connection with the second fluid conduit at least partially integrated in the support element.

In one embodiment, the first operable hydraulic constriction element has a larger volume than the second operable hydraulic constriction element. The first operable hydraulic constriction element may have a volume which is at least 1.5 times larger than the volume of the second operable hydraulic constriction element, or may have a volume which is more than 2 times larger than the volume of the second operable hydraulic constriction element.

In one embodiment, the support element comprises an outer surface configured to be directed away from the urethra, when implanted. The outer surface may comprise at least one inlet to the at least one fluid conduit, and the at least one inlet may be configured to be in fluid connection with a hydraulic pump for pumping fluid to the operable hydraulic constriction element for constricting the urethra.

In one embodiment, the support element has a length in the axial direction of the urethra, when implanted, and at least one operable hydraulic constriction element has a length in the axial direction of the urethra U, when implanted. The length of the at least one operable hydraulic constriction element is longer than the length of the support element.

In one embodiment, the support element further comprises an electrode arrangement configured to be arranged between the support element and the urethra and to engage and electrically stimulate muscle tissue of the urethra to exercise the muscle tissue to improve the conditions for long term implantation of the implantable constriction device.

The support element, or second, third or fourth support element in any of the embodiments herein may have at least one curvature adapted for the curvature of the urethra.

The support element, or second, third or fourth support element in any of the embodiments herein may have a curvature having a radius in the range 3 mm-50 mm, or in the range 5 mm-30 mm.

The support element, or second, third or fourth support element in any of the embodiments herein may have a first curvature having a first radius, and a second curvature having a second radius, wherein the first radius is smaller than the second radius.

The support element, or second, third or fourth support element in any of the embodiments herein may be substantially rigid and have a modulus of elasticity (E) in the range 0.2 GPa-1000 GPa or in the range 1 GPa-400 GPa, and a major portion of the support element could be made from a material having a modulus of elasticity (E) in the range 0.2 GPa-1000 GPa or in the range 1 GPa-400 GPa.

A surrounding structure for an implantable constriction device for constricting a urethra of a patient is further provided. The surrounding structure is configured to surround the urethra when implanted and comprises at least one support element according to any of the embodiments herein comprising at least one fluid conduit at least partially integrated in the support element.

In one embodiment, the surrounding structure comprises a second support element, and the first and second support elements are configured to be connected and together form at least a portion of the surrounding structure. The first and second support elements may be configured for forming the surrounding structure and thereby surround the urethra.

In one embodiment, the first and second support elements are hingedly connected to each other for forming the surrounding structure, such that a periphery of the surrounding structure is possible to open, such that the surrounding structure can be placed around the urethra.

In one embodiment, the second support element comprises at least one operable hydraulic constriction element configured to constrict the urethra for restricting the flow of urine therethrough. The at least one operable hydraulic constriction element may be in fluid connection with at least one fluid conduit at least partially integrated in the second support element.

In one embodiment, the second support element comprises at least a second operable hydraulic constriction element, and the at least one second operable hydraulic constriction element is in fluid connection with a second fluid conduit at least partially integrated in the second support element.

In one embodiment, the second support element comprises at least one cushioning element configured to contact the urethra. The cushioning element may be more resilient and/or more elastic than the support element.

The surrounding structure may further comprise an electrode arrangement configured to be arranged between the surrounding structure and the urethra and to engage and electrically stimulate muscle tissue of the urethra to exercise the muscle tissue to improve the conditions for long term implantation of the implantable constriction device.

A surrounding structure for an implantable constriction device for constricting a urethra of a patient is further provided. The surrounding structure may have a periphery surrounding the urethra when implanted. The surrounding structure comprises at least two support elements connected to each other for forming at least a portion of the periphery of the surrounding structure. At least one of the support elements are configured to support at least one first operable hydraulic constriction element configured to constrict the urethra for restricting the flow of urine therethrough. Having a surrounding structure supporting operable hydraulic constriction element(s) ensures that the operable hydraulic constriction element(s) have good support and counter force for exerting a pressure on the urethra. The surrounding structure may also serve as a mount for the operable hydraulic constriction element(s) and serve as a fluid conduit for conducting hydraulic fluid to the operable hydraulic constriction element(s).

In one embodiment, the first and second support elements are configured for forming the surrounding structure and thereby surround the urethra. The support elements may be hingedly connected to each other for at least partially forming the surrounding structure, such that a periphery of the surrounding structure is possible to open, such that the surrounding structure can be placed around the urethra.

In one embodiment, the first support element comprises the first operable hydraulic constriction element configured to constrict the urethra for restricting the flow of urine therethrough, and in one embodiment, the first support element comprises at least one second operable hydraulic constriction element configured to constrict the urethra for restricting the flow of urine therethrough.

The first operable hydraulic constriction element may have a larger volume than the second operable hydraulic constriction element.

In one embodiment, the second support element comprises a third operable hydraulic constriction element configured to constrict the urethra for restricting the flow of urine therethrough and in one embodiment, the second support element comprises a fourth operable hydraulic constriction element configured to constrict the urethra for restricting the flow of urine therethrough.

The third operable hydraulic constriction element may have a larger volume than the fourth operable hydraulic constriction element.

In one embodiment, the second support element may comprise at least one cushioning element configured to contact the urethra and the cushioning element may be more resilient than at least one of the support elements.

In one embodiment, the surrounding structure has a length in the direction of the axial direction of the urethra, when implanted, and the at least one first operable hydraulic constriction element has a length in the direction of the axial direction of the urethra, when implanted, and the length of the at least one first operable hydraulic constriction element is longer than the length of the surrounding structure.

In one embodiment, the surrounding structure further comprises an electrode arrangement configured to be arranged between the surrounding structure and the urethra and to engage and electrically stimulate muscle tissue of the urethra to exercise the muscle tissue to improve the conditions for long term implantation of the implantable constriction device.

The surrounding structure in any of the embodiments herein may have at least one curvature C adapted for the curvature of the urethra.

The surrounding structure in any of the embodiments herein may have a curvature having a radius in the range 3 mm-50 mm, or in the range 5 mm-30 mm.

The surrounding structure in any of the embodiments herein may have a first curvature having a first radius, and a second curvature having a second radius, wherein the first radius is smaller than the second radius.

The surrounding structure in any of the embodiments herein may be substantially rigid and have a modulus of elasticity (E) in the range 0.2 GPa-1000 GPa or in the range 1 GPa-400 GPa, and a major portion of the support element could be made from a material having a modulus of elasticity (E) in the range 0.2 GPa-1000 GPa or in the range 1 GPa-400 GPa.

An implantable constriction device comprising the surrounding structure in any of the embodiments herein is further provided. The implantable constriction device further comprises at least one hydraulic pump and a control unit. The control unit is configured to control the flow of fluid from the hydraulic pump, such that the first operable hydraulic constriction element is inflated, and the second operable hydraulic constriction element is deflated, for constricting the urethra and restricting the flow of urine therethrough.

In one embodiment, the control unit is further configured to control the flow of fluid from the hydraulic pump, such that the third operable hydraulic constriction element is inflated, and the fourth operable hydraulic constriction element is deflated, for constricting the urethra and restricting the flow of urine therethrough.

In one embodiment, the control unit is further configured to control the flow of fluid from the hydraulic pump, such that: the first operable hydraulic constriction element is deflated, and the second operable hydraulic constriction element is inflated, for releasing the constriction of the urethra for restoring the flow of urine therethrough.

In one embodiment, the control unit is further configured to control the flow of fluid from the hydraulic pump, such that: the third operable hydraulic constriction element is deflated, and the fourth operable hydraulic constriction element is inflated, for releasing the constriction of the urethra for restoring the flow of urine therethrough.

In one embodiment, the implantable constriction device further comprises an electrode arrangement configured to be arranged between the implantable constriction device and the urethra and configured to engage and electrically stimulate muscle tissue of the urethra to exercise the muscle tissue to improve the conditions for long term implantation of the implantable constriction device.

In one embodiment, the implantable constriction device comprises a first, second and third urethra contacting elements. The first urethra contacting element comprises a first operable hydraulic constriction element configured to be inflated to constrict the urethra for restricting the flow of urine therethrough, the second urethra contacting element comprises a second operable hydraulic constriction element configured to be inflated to assist in releasing the constriction of the urethra for restoring the flow of urine therethrough, and the third urethra contacting element comprises at least one cushioning element configured to contact the urethra.

In one embodiment, the implantable constriction device comprises a surrounding structure having a periphery surrounding the urethra when implanted, and at least one of the first, second and third urethra contacting elements may be connected to the surrounding structure.

In one embodiment, the surrounding structure could be the surrounding structure in any of the embodiments herein and could be comprised of at least a first and a second support element.

In one embodiment, the first urethra contacting element is connected to the first supporting element and the second urethra contacting element is connected to the second support element.

In one embodiment, the third urethra contacting element is connected to the second support element.

In one embodiment, the first urethra contacting element is connected to the first support element, the second urethra contacting element is connected to the second support element and the third urethra contacting element is connected to a third support element.

In one embodiment, at least one of the first, second and third support elements have a curvature adapted for the curvature of the urethra and the curvature may have a radius in the range 3 mm-50 mm or in the range 5 mm-30 mm.

For forming the surrounding structure, at least two of the support elements may be hingedly connected to each other.

The implantable constriction device may further comprise at least one hydraulic pump and a controller configured to control the flow of fluid from the hydraulic pump, such that the first operable hydraulic constriction element is inflated, and the second operable hydraulic constriction element is deflated, for constricting the urethra and restricting the flow of urine therethrough.

In one embodiment, the controller is further configured to control the flow of fluid from the hydraulic pump, such that the first operable hydraulic constriction element is deflated, and the second operable hydraulic constriction element is inflated, for releasing the constriction of the urethra for restoring the flow of urine therethrough.

In one embodiment, the first and second operable hydraulic constriction elements are connected to a shared hydraulic system, such that the hydraulic fluid is pumped from the first operable hydraulic constriction element to the second operable hydraulic constriction element for releasing the constriction of the urethra for restoring the flow of urine therethrough, and pumped from the second operable hydraulic constriction element to the first operable hydraulic constriction element for constricting the urethra and restricting the flow of urine therethrough.

In one embodiment, the surrounding structure has a length in the axial direction of the urethra, when implanted, and at least one of the first, second and third urethra contacting element has a length in the axial direction of the urethra, when implanted, and the length of at least one of the first, second and third urethra contacting element is longer than the length of the surrounding structure.

The implantable constriction device 10 according to any one of the preceding claims, wherein the implantable constriction device 10 further comprises an electrode arrangement configured to be arranged between the implantable constriction device 10 and the urethra U and to engage and electrically stimulate muscle tissue of the urethra U to exercise the muscle tissue to improve the conditions for long term implantation of the implantable constriction device 10.

A kit for a surrounding structure for an implantable constriction device for constricting a urethra of a patient is further provided. The surrounding structure is configured to have a periphery surrounding the urethra when implanted. The kit comprises at least a first, second and third support element, and the second support element is configured to be connected to the first support element for forming at least a portion of the surrounding structure. The third support element is configured to be connected to the first support element for forming at least a portion of the surrounding structure, and at least one of the second and third support element is connected to the first support element for forming at least a portion of the surrounding structure when the surrounding structure is implanted. By providing a kit of support elements, the surrounding structure can be easily adapted for different urethras and more complex parts of the implantable constriction device could remain the same whereas more simple part are replaced for adapting the implantable constriction device to a specific patient.

In one embodiment, the first support element is configured to support at least one first operable hydraulic constriction element configured to constrict the urethra for restricting the flow of urine therethrough.

In one embodiment, at least one of the first, second and third support elements have a curvature adapted for the curvature of the urethra and the curvature may have a radius in the range 3 mm-50 mm or in the range 5 mm-30 mm.

In one embodiment, the second support element comprises a second curvature adapted for the curvature of a first urethra, the third support element comprises a third curvature adapted for the curvature of a second urethra, and the second curvature is different than the third curvature. As such urethras having different curvatures can be supported be assembly of the kit in different ways.

In one embodiment, the second curvature has a second radius, the third curvature has a third radius, and the second radius is larger than the third radius. The second radius could be more than 1.2 times as large as the third radius.

In one embodiment, the second support element has a second length configured to extend along a portion of the periphery of the surrounding structure, the third support element has a third length extending along a portion of the periphery of the surrounding structure, and the third length is longer than the second length.

The surrounding structure could have a modulus of elasticity (E), radially, in the range 0.2 GPa-1000 GPa or in the range 1 GPa-400 GPa and a major portion of at least one of the first, second and third support structures of the kit could be made from a material having a modulus of elasticity E in the range 0.2 GPa-1000 GPa or in the range 1 GPa-400 GPa In one embodiment, the first and second support elements could be configured to form the surrounding structure and thereby surround the urethra, or the first and third support elements could be configured to form the surrounding structure and thereby surround the urethra.

The second and third support elements may be configured to be hingedly connected to the first support element at least partially forming the surrounding structure, such that a periphery of the surrounding structure is possible to open, such that the surrounding structure can be placed around the urethra.

The first support element may comprise the first operable hydraulic constriction element configured to constrict the urethra for restricting the flow of urine therethrough. In one embodiment, the first support element comprises at least one second operable hydraulic constriction element configured to constrict the urethra for restricting the flow of urine therethrough.

In one embodiment, the first operable hydraulic constriction element has a larger volume than the second operable hydraulic constriction element.

In one embodiment, at least one of the second and third support elements comprises a third operable hydraulic constriction element configured to constrict the urethra for restricting the flow of urine therethrough.

In one embodiment, at least one of the second and third support elements comprises at least one cushioning element configured to contact the urethra, and the cushioning element may be more resilient and/or elastic than at least one of the support elements.

In one embodiment, the surrounding structure has a length in the axial direction of the urethra, when implanted, and the at least one first operable hydraulic constriction element has a length in the axial direction of the urethra, when implanted, and the length of the at least one first operable hydraulic constriction element is longer than the length of the surrounding structure.

In one embodiment, at least one of the first, second and third support elements comprises an electrode arrangement configured to be arranged between at least one of the first, second and third support elements and the urethra and to engage and electrically stimulate muscle tissue of the urethra to exercise the muscle tissue to improve the conditions for long term implantation of the implantable constriction device.

In one embodiment, the implantable constriction device comprises a first operable hydraulic constriction element configured to be inflated to constrict the urethra for restricting the flow of urine therethrough, a second operable hydraulic constriction element configured to be inflated to constrict the urethra for restricting the flow of urine therethrough, and an interconnecting fluid conduit fluidly connecting the first operable hydraulic constriction element to the second operable hydraulic constriction element. The first operable hydraulic constriction element is configured to be placed at a first portion of the urethra for constricting the first portion of the urethra for restricting the flow of urine therethrough, the second operable hydraulic constriction element is configured to be placed at a second portion of the urethra, downstream the first portion, for constricting the second portion of the urethra for restricting the flow of urine therethrough, and the interconnecting fluid conduit is configured to conduct fluid from the first operable hydraulic constriction element to the second operable hydraulic constriction element when the pressure increases in the first operable hydraulic constriction element, such that second operable hydraulic constriction element constricts the second portion of the urethra further.

In one embodiment, a lumen of the first operable hydraulic constriction element has a larger volume than a lumen of the second operable hydraulic constriction element.

In one embodiment, the lumen of the first operable hydraulic constriction element has a volume which is more than 1.5 times larger than the volume of the lumen of the second operable hydraulic constriction element.

The first interconnecting fluid conduit may in any of the embodiments herein comprise a first electrically operable valve, such that a flow of fluid between the first operable hydraulic constriction element and the second operable hydraulic constriction element can be controlled. The electrically operable valve could be a solenoid valve.

The first interconnecting fluid conduit may in any of the embodiments herein comprise a check valve, such that fluid can flow in a direction from the first operable hydraulic constriction element to the second operable hydraulic constriction element, but not in a direction from the second operable hydraulic constriction element to the first operable hydraulic constriction element.

In one embodiment, the implantable constriction device further comprises a second interconnecting fluid conduit fluidly connecting the first operable hydraulic constriction element to the second operable hydraulic constriction element. A cross-section of a tubular lumen of the second interconnecting fluid conduit has an area which is less than 0.5 times a cross section area of a tubular lumen of the first interconnecting fluid conduit.

The implantable constriction device according to any one of the preceding claims further comprises a hydraulic pump, a reservoir for holding hydraulic fluid, and a first reservoir conduit fluidly connecting the reservoir to the first operable hydraulic constriction element. The hydraulic pump may be configured to pump fluid from the reservoir to the first operable hydraulic constriction element through the first reservoir conduit for constricting the first portion of the urethra for restricting the flow of urine therethrough.

The first reservoir conduit may in any of the embodiments herein comprise a second electrically operable valve, such that a flow of fluid between the reservoir and the first operable hydraulic constriction element can be controlled.

In one embodiment, the implantable constriction device further comprises a second reservoir conduit fluidly connecting the reservoir to the second operable hydraulic constriction element.

The second reservoir conduit may in any one of the embodiments herein comprise a check valve such that fluid can flow in a direction from the reservoir to the second operable hydraulic constriction element but not in a direction from the second operable hydraulic constriction element to the reservoir.

The implantable constriction device may further comprise an injection port in fluid connection with the reservoir, for injecting fluid into the reservoir when the reservoir is implanted.

In one embodiment, the injection port is configured to be placed subcutaneously, and the implantable constriction device may further comprise an injection port conduit fluidly connecting the injection port to the reservoir.

The implantable constriction device may further comprise at least one of a first pressure sensor configured to sense the pressure in the first operable hydraulic constriction element, and a second pressure sensor configured to sense the pressure in the second operable hydraulic constriction element.

In one embodiment, the implantable constriction device further comprises a controller configured to receive a pressure sensor signal from at least one of the first and second pressure sensor, and control at least one of: the first electrically operable valve and the second operable valve and the hydraulic pump, on the basis of the received pressure sensor signal.

In one embodiment, the controller comprises a pressure threshold value, and the controller is configured to open the first electrically operable valve if the received pressure sensor signal from the second pressure sensor exceeds the pressure threshold value.

In one embodiment, the implantable constriction device further comprises a supporting operable hydraulic constriction element configured to be placed along at least a portion of the first portion of the urethra and along at least a portion of the second portion of the urethra, and further configured to assist in the constriction of the first and second portions of the urethra.

The supporting operable hydraulic constriction element may in any one of the embodiments herein be connected to the first and second operable hydraulic constriction elements. The supporting operable hydraulic constriction element may be less resilient than at least one of the first and second operable hydraulic constriction element, for making the combined operable hydraulic constriction element (made up the operable hydraulic constriction element and the supporting operable hydraulic constriction element) more rigid and less prone to deformation.

In one embodiment, each of the first, second and supporting operable hydraulic constriction elements comprises a lumen surrounded by a resilient wall. The resilient wall of the supporting operable hydraulic constriction element may be thicker than the wall of at least one of the first and second operable hydraulic constriction element.

In one embodiment, the implantable constriction device further comprises a second hydraulic pump, a second reservoir for holding hydraulic fluid, and a supporting reservoir conduit fluidly connecting the second reservoir to the supporting operable hydraulic constriction element. The second hydraulic pump is configured to pump fluid from the second reservoir to the supporting operable hydraulic constriction element through the supporting reservoir conduit, for assisting in the constriction of the urethra.

The implantable constriction device may further comprise a third pressure sensor configured to sense the pressure in the supporting operable hydraulic constriction element.

The implantable constriction device may further comprise a second injection port in fluid connection with the second reservoir, for injecting fluid into the second reservoir when the second reservoir is implanted. The second injection port may be configured to be placed subcutaneously, and the implantable constriction device may further comprise a second injection port conduit fluidly connecting the second injection port to the second reservoir.

In one embodiment, the supporting operable hydraulic constriction element has a length in the axial direction of the urethra, when implanted, and the first and second operable hydraulic constriction element has a combined length in the axial direction of the urethra. The combined length is longer than the length of the supporting operable hydraulic constriction element.

The surrounding structure may in any of the embodiments herein comprise an inner surface configured to face the urethra, when implanted, and the supporting operable hydraulic constriction device may be fixated to the inner surface of the surrounding structure, such that the supporting operable hydraulic constriction device can use the surrounding structure as support for constricting the urethra.

The implantable constriction device may further comprise at least one cushioning element configured to contact the urethra, and the cushioning element may be fixated to the inner surface of the surrounding structure and be more resilient than the surrounding structure.

The surrounding structure may in any of the embodiment herein be comprised of at least a first and a second supporting element configured to be connected to each other for forming at least a portion of the periphery of the surrounding structure.

The supporting operable hydraulic constriction device may be fixated to the first supporting element, and the at least one cushioning element may be fixated to the second supporting element.

An implantable constriction device for constricting a urethra of a patient is further provided. The urethra is a tubular, luminary organ having a substantially circular cross section and being elongated in an axial direction. The implantable constriction device may comprise a first operable hydraulic constriction element configured to be inflated and thereby expand in a first direction towards the urethra to constrict a first portion of the urethra for restricting the flow of urine therethrough. The implantable constriction device may further comprise a supporting operable hydraulic constriction element configured to be inflated and thereby expand in the first direction towards the urethra to support the first operable hydraulic constriction element in constricting the first portion of the urethra for restricting the flow of urine therethrough. The combination of the first operable hydraulic constriction element and the supporting operable hydraulic constriction element may make the combined operable hydraulic constriction element more rigid which means that the compression of the urethra will be more accurate and the risk of leakage when the implantable constriction device is closed will be reduced.

The supporting operable hydraulic constriction element may in one embodiment be connected to the first operable hydraulic constriction element.

In one embodiment of the implantable constriction device, the supporting operable hydraulic constriction element may be less resilient than the first operable hydraulic constriction element.

In one embodiment, the first operable hydraulic constriction element may comprise a lumen surrounded by a resilient wall and the supporting operable hydraulic constriction element may comprise a lumen surrounded by a resilient wall. A portion of the resilient wall of the supporting operable hydraulic constriction element may be thicker than a portion of the resilient wall of the first operable hydraulic constriction element.

In one embodiment, a portion of the resilient wall of the supporting operable hydraulic constriction element may be more than 1.5 times thicker than a portion of the resilient wall of the first operable hydraulic constriction element, and in one embodiment, a portion of the resilient wall of the supporting operable hydraulic constriction element is more than 2 times as thick as a portion of the resilient wall of the first operable hydraulic constriction element.

In one embodiment, the first operable hydraulic constriction element comprises a lumen surrounded by a resilient wall and the supporting operable hydraulic constriction element comprises a lumen surrounded by a resilient wall, and a portion of the resilient wall of the first operable hydraulic constriction element comprises a first material, and a portion of the resilient wall of the supporting operable hydraulic constriction element may comprise a second material. The second material may have a modulus of elasticity which is higher than a modulus of elasticity of the first material.

In one embodiment, the modulus of elasticity of the second material is more than 1.5 times as high as the modulus of elasticity of the first material and in another embodiment, the modulus of elasticity of the second material is more than 2 times as high as the modulus of elasticity of the first material.

In one embodiment, the implantable constriction device further comprises a first hydraulic pump, a second hydraulic pump, a first reservoir for holding hydraulic fluid, a second reservoir for holding hydraulic fluid, a first reservoir conduit, fluidly connecting the first reservoir to the first operable hydraulic constriction element, and a supporting reservoir conduit, fluidly connecting the second reservoir to the supporting operable hydraulic constriction element. The first hydraulic pump may be configured to pump fluid from the first reservoir to the first operable hydraulic constriction element through the first reservoir conduit for constricting the urethra, and the second hydraulic pump may be configured to pump fluid from the second reservoir to the supporting operable hydraulic constriction element through the supporting reservoir conduit, for assisting in the constriction of the urethra.

The implantable constriction device may further comprise a first pressure sensor configured to sense the pressure in the first operable hydraulic constriction element. The implantable constriction device may further comprise a second pressure sensor configured to sense the pressure in the supporting operable hydraulic constriction element.

The implantable constriction device may in any of the embodiments herein further comprise an implantable controller configured to control at least one of the first hydraulic pump, on the basis of input from the first pressure sensor, and the second hydraulic pump, on the basis of input from the second pressure sensor.

The first reservoir conduit may in any of the embodiments herein comprise an electrically operable valve, and the second reservoir conduit may comprise an electrically operable valve. The controller may be configured to control at least one of the electrically operable valve on the first reservoir conduit, on the basis of input from the first pressure sensor, and the electrically operable valve on the second reservoir conduit, on the basis of input from the second pressure sensor.

At least one of the first reservoir conduit and the second reservoir conduit may further comprise a check valve.

In one embodiment, the implantable constriction device further comprises a first injection port in fluid connection with the first reservoir for injecting fluid into the first reservoir when the first reservoir is implanted.

The implantable constriction device may further comprise a second injection port in fluid connection with the second reservoir, for injecting fluid into the second reservoir when the second reservoir is implanted. At least one of the first and second injection port may be placed subcutaneously, and the implantable constriction device further comprises a first and/or second injection port conduit fluidly connecting the first injection port to the first reservoir and/or fluidly connecting the second injection port to the second reservoir.

In one embodiment, the supporting operable hydraulic constriction element has a length in the axial direction of the urethra, when implanted, and the first operable hydraulic constriction element has a length in the axial direction of the urethra. The length of the first operable hydraulic constriction element may be longer than the length of the supporting operable hydraulic constriction element.

In one embodiment, the implantable constriction device comprises a first operable hydraulic constriction element configured to be inflated to exert a pressure on the urethra in a first direction to constrict a first portion of the urethra for restricting the flow of urine therethrough, a second operable hydraulic constriction element configured to be inflated to exert a pressure on the urethra in a second direction to constrict the first portion of the urethra for restricting the flow of urine therethrough, and a first hydraulic system in fluid connection with the first operable hydraulic constriction element, and a second hydraulic system in fluid connection with the second operable hydraulic constriction element. The first and second operable hydraulic constriction elements are adjustable independently from each other. In one embodiment, the second direction is substantially opposite to the first direction.

In one embodiment, the first hydraulic systems comprise a first hydraulic pump and the second hydraulic systems comprises a second hydraulic pump. Each of the first and second hydraulic systems may comprise a reservoir for holding hydraulic fluid and the first and second hydraulic systems may be connected to a reservoir for holding hydraulic fluid.

Each of the first and second hydraulic systems may comprise an injection port for injecting hydraulic fluid into the respective first and second hydraulic systems. The injection ports may be configured to be placed subcutaneously, and the implantable constriction device may further comprise injection port conduits fluidly connecting the injection ports to the first and second hydraulic systems.

In one embodiment, the first operable hydraulic constriction element lacks a fluid connection to the second operable hydraulic constriction element. In such embodiments the two hydraulic systems may be completely separated, which increases the redundancy.

The implantable constriction device may further comprise a first pressure sensor configured to sense the pressure in the first operable hydraulic constriction element and/or a second pressure sensor configured to sense the pressure in the second operable hydraulic constriction element.

The implantable constriction device may further comprise a controller configured to receive a pressure sensor signal from at least one of the first and second pressure sensor and control at least one of: the first hydraulic pump and the second hydraulic pump on the basis of the received pressure sensor signal.

The implantable constriction device may comprise a surrounding structure having a periphery surrounding the urethra when implanted and the surrounding structure may be substantially rigid.

An implantable constriction device for constricting a urethra of a patient is further provided. The implantable constriction device comprises an operable hydraulic constriction element configured to be inflated to exert a pressure on the urethra, a hydraulic reservoir for holding a hydraulic fluid and a hydraulic pump for pumping fluid from the hydraulic reservoir to the operable hydraulic constriction element. The implantable constriction device may further comprise a first fluid conduit creating a fluid connection between the hydraulic reservoir and the hydraulic pump and a second fluid conduit creating a fluid connection between the hydraulic pump and the operable hydraulic constriction element. The implantable constriction device may further comprise an injection port for injecting and removing hydraulic fluid from the implantable constriction device, when implanted, and a third fluid conduit creating a fluid connection between the injection port and at least one of the second fluid conduit and the operable hydraulic constriction element, such that hydraulic fluid can be removed from the operable hydraulic constriction element through the injection port.

One advantage of having the injection ports being directly in fluid connection with the first and supporting operable hydraulic constriction elements is that the injection ports can be used as a safety system through which the hydraulic fluid can be removed from the first and supporting operable hydraulic constriction elements in case there is a malfunction to the pumps of the electrically operable valves. I.e. if there is a malfunction to the pumps or valves, an injection needle can be inserted into the injection ports and fluid withdrawn from the first and supporting operable hydraulic constriction elements such that the urethra is left unrestricted such that the patient can urinate even if the constriction device does not function.

In one embodiment, the implantable constriction device further comprises a supporting operable hydraulic constriction element configured to be inflated to support the first operable hydraulic constriction element in constricting the urethra for restricting the flow of urine therethrough.

The implantable constriction device may further comprise a second hydraulic reservoir for holding a hydraulic fluid, a second hydraulic pump for pumping fluid from the hydraulic reservoir to the supporting operable hydraulic constriction element, a fourth fluid conduit creating a fluid connection between the second hydraulic reservoir and the second hydraulic pump, and a fifth fluid conduit creating a fluid connection between the second hydraulic pump and the supporting operable hydraulic constriction element. The implantable constriction device may further comprise a second injection port for injecting and removing hydraulic fluid from the implantable constriction device, when implanted, and a sixth fluid conduit creating a fluid connection between the second injection port and at least one of the second fluid conduit and the supporting operable hydraulic constriction element, such that hydraulic fluid can be removed from the supporting operable hydraulic constriction element through the second injection port.

The supporting operable hydraulic constriction element may in any of the embodiments herein be connected to the first operable hydraulic constriction element.

The supporting operable hydraulic constriction element may be less resilient than the first operable hydraulic constriction element.

In one embodiment of the implantable constriction device, the first operable hydraulic constriction element comprises a lumen surrounded by a resilient wall and the supporting operable hydraulic constriction element comprises a lumen surrounded by a resilient wall. A portion of the resilient wall of the supporting operable hydraulic constriction element is thicker than a portion of the resilient wall of the first operable hydraulic constriction element. A portion of the resilient wall of the supporting operable hydraulic constriction element may be more than 1.5 times as thick as a portion of the resilient wall of the first operable hydraulic constriction element.

In one embodiment, the first operable hydraulic constriction element comprises a lumen surrounded by a resilient wall, and the supporting operable hydraulic constriction element comprises a lumen surrounded by a resilient wall. A portion of the resilient wall of the first operable hydraulic constriction element comprises a first material, and a portion of the resilient wall of the supporting operable hydraulic constriction element comprises a second material. The second material may have a modulus of elasticity which is higher than a modulus of elasticity of the first material. In one embodiment, the modulus of elasticity of the second material is more than 1.5 times higher than the modulus of elasticity of the first material.

In one embodiment, the implantable constriction device could further comprise a first pressure sensor configured to sense the pressure in the first operable hydraulic constriction element and/or a second pressure sensor configured to sense the pressure in the supporting operable hydraulic constriction element.

The implantable constriction device may further comprise an implantable controller configured to control at least one of the first hydraulic pump on the basis of input from the first pressure sensor, and the second hydraulic pump on the basis of input from the second pressure sensor.

At least one of the first reservoir conduit and the second reservoir conduit may comprise an electrically operable valve. The controller may be configured to control at least one of the electrically operable valve on the first reservoir conduit, on the basis of input from the first pressure sensor, and the electrically operable valve on the second reservoir conduit, on the basis of input from the second pressure sensor.

The implantable constriction device may further comprise an implantable controller and the implantable controller may be configured to provide a feedback signal to the patient if the pressure in at least one of the operable hydraulic constriction element and the supporting operable hydraulic constriction element exceeds a threshold value.

At least one of the first injection port and the second injection port may be configured to be placed subcutaneously.

In one embodiment, the supporting operable hydraulic constriction element has a length in the axial direction of the urethra U, when implanted, and the first operable hydraulic constriction element has a length in the axial direction of the urethra. The length of the first operable hydraulic constriction element may be longer than the supporting operable hydraulic constriction element.

The implantable constriction device may comprise a surrounding structure having a periphery surrounding the urethra when implanted, which may be substantially rigid.

In one embodiment, the implantable constriction device comprises an operable hydraulic constriction element configured to be inflated to exert a pressure on the urethra and a hydraulic reservoir for holding a hydraulic fluid. The implantable constriction device further comprises a hydraulic pump for pumping fluid from the hydraulic reservoir to the operable hydraulic constriction element, a first fluid conduit creating a fluid connection between the hydraulic reservoir and the hydraulic pump, and an electrode arrangement configured to be arranged between the implantable constriction device and the urethra and to engage and electrically stimulate muscle tissue of the urethra to exercise the muscle tissue to improve the conditions for long term implantation of the implantable constriction device.

The electrode arrangement may be arranged on an outer surface of the operable hydraulic constriction element.

In one embodiment, the electrode arrangement comprises a plurality of electrode elements, each of which being configured to engage and electrically stimulate tissue of the urethra.

In one embodiment, the electrode arrangement comprises a coiled wire for increasing a contact surface between the electrode arrangement and the tissue of the urethra and for allowing the electrode arrangement to follow contraction and relaxation of the tissue of the urethra.

The electrode arrangement may comprise a bare electrode portion configured to form a metal-tissue interface with the tissue of the urethra, thereby allowing faradaic charge transfer to the be predominant charge transfer mechanism over said interface.

In one embodiment, the electrode arrangement comprises an electrode portion at least partly covered by a dielectric material configured to form a dielectric-tissue interface with the tissue of the urethra, thereby allowing for a faradaic portion of the charge transfer mechanism over said interface to be reduced.

The electrode arrangement may further comprise at least two electrode elements configured to be arranged on opposing sides of the urethra.

The implantable constriction device may further comprise a stimulation controller configured to be operably connected to the electrode arrangement for controlling the electrical stimulation of the tissue of the urethra. The stimulation controller may be configured to control the electrical stimulation such that the tissue of the urethra is stimulated by a series of electrical pulses.

In one embodiment, the stimulation controller may be configured to control the electrical stimulation such that a pulse of a first polarity is followed by a pulse of a second, reversed polarity.

The stimulation controller may further be configured to generate a pulsed electrical stimulation signal comprising a pulse frequency of 0.01-150 Hz and may comprises a pulse duration of 0.01-100 ms and may comprise a pulse amplitude of 1-15 mA.

In one embodiment, the electrical stimulation signal may comprise a pulse frequency of 0.15-0.25 Hz, a pulse duration of 20-30 ms and a pulse amplitude of 3-10 mA.

In one embodiment, the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

In one embodiment, the stimulation controller is configured to receive input from a wireless remote control. The implantable constriction device may further comprise an implantable sensor configured to sense actions potentials generated by pacemaker cells of the tissue of the urethra, and the stimulation controller may be configured to control the electrical simulation based at least partly on the sensed action potentials.

In one embodiment, the stimulation controller may be configured to generate electrical pulses amplifying the sensed action potentials.

In one embodiment, the implantable constriction device may comprise a surrounding structure having a periphery surrounding the urethra when implanted and the electrode arrangement may be connected to the surrounding structure.

The surrounding structure may comprise at least one cushioning element, and at least one electrode element of the electrode arrangement may be placed on the surface of the cushioning element.

In one embodiment, the implantable constriction device may comprise a first operable hydraulic constriction element configured to be inflated to exert a pressure on the urethra, and a second operable hydraulic constriction element configured to be inflated to exert a pressure on the urethra. The implantable constriction device may further comprise a first hydraulic pump for pumping fluid to the operable hydraulic constriction element, a second hydraulic pump for pumping fluid to the operable hydraulic constriction element, and a motor M. The motor may be mechanically connected to the first and second hydraulic pump for propelling the first and second hydraulic pump. The motor M could for example be an electrical motor, such as a brushless implantable DC motor.

In one embodiment, the implantable constriction device further comprises a gear system placed between the motor and the first and second hydraulic pump. The gear system is configured to reduce the velocity and increase the force of the movement generated by the motor for propelling the first and second hydraulic pump with a mechanical force with a lower velocity and a greater force.

In one embodiment, the motor is configured to generate a rotating force and propel the first and second hydraulic pump with a rotating mechanical force. A rotating force output of the motor may be connected to a force input of the gear system, and a rotating force output of the gear system, may be connected to the first and second hydraulic pump.

The at least one first and second hydraulic pump may comprise a gear pump, a peristaltic pump, a gerotor pump or a pump comprising at least one compressible hydraulic reservoir.

In one embodiment, the first hydraulic pump comprises a first gerotor pump, the second hydraulic pump comprises a second gerotor pump and the implantable constriction device further comprises a common rotating shaft mechanically connected to the motor. An inner rotor of the first gerotor pump may be mechanically connected to the common rotating shaft, and an inner rotor of the second gerotor pump may be mechanically connected to the common rotating shaft, such that the motor propels the first and second gerotor pump. At least one of the first and second hydraulic pump may be connected to the implantable reservoir.

In one embodiment, the implantable constriction device further comprises a first implantable reservoir and a second implantable reservoir, and the first hydraulic pump is connected to the first implantable reservoir, and the second hydraulic pump is connected to the second implantable reservoir.

In one embodiment, the implantable constriction device further comprises an implantable reservoir and the first and second hydraulic pump may be connected to the implantable reservoir, for pumping hydraulic fluid from the first reservoir to the first operable hydraulic constriction element and from the second reservoir to the second operable hydraulic constriction element.

In one embodiment, the first operable hydraulic constriction element is configured to be inflated and thereby expand in a first direction towards the urethra to constrict a first portion of the urethra for restricting the flow of urine therethrough, and the second operable hydraulic constriction element is a supporting operable hydraulic constriction element configured to be inflated and thereby expand in the first direction d1 towards the urethra to support the first operable hydraulic constriction element in constricting the first portion of the urethra for restricting the flow of urine therethrough. The supporting operable hydraulic constriction element may be connected to the first operable hydraulic constriction element and the supporting operable hydraulic constriction element may be less resilient than the first operable hydraulic constriction element.

In one embodiment, the first operable hydraulic constriction element comprises a lumen surrounded by a resilient wall and the supporting operable hydraulic constriction element comprises a lumen surrounded by a resilient wall. A portion of the resilient wall of the supporting operable hydraulic constriction element is thicker than a portion of the resilient wall of the first operable hydraulic constriction element.

In one embodiment, the implantable constriction device may further comprise a first pressure sensor configured to sense the pressure in the first operable hydraulic constriction element and/or a second pressure sensor configured to sense the pressure in the second operable hydraulic constriction element.

In one embodiment, the implantable constriction device may further comprise an implantable controller configured to control at least one of the first hydraulic pump on the basis of input from the first pressure sensor, and the second hydraulic pump on the basis of input from the second pressure sensor.

In one embodiment, the implantable constriction device may further comprise a first and/or a second implantable injection port in fluid connection with the first operable hydraulic constriction element.

In one embodiment, the second operable hydraulic constriction element has a length in the axial direction of the urethra, when implanted, and the first operable hydraulic constriction element has a length in the axial direction of the urethra. The length of the first operable hydraulic constriction element is longer than the length of the second operable hydraulic constriction element.

In one embodiment, the implantable constriction device comprises an operable hydraulic constriction element configured to be inflated to exert a pressure on the urethra, a pressure sensor configured to sense the pressure in the operable hydraulic constriction element, a hydraulic pump for pumping a hydraulic fluid to the operable hydraulic constriction element, and a controller configured to receive pressure sensor input from the pressure sensor and control the hydraulic pump on the basis of the received pressure sensor input. The pressure sensor may comprises a diaphragm in fluid connection with the hydraulic fluid in the operable hydraulic constriction element and connected to a pressure sensing element of the pressure sensor, such that the pressure sensing element is separated from the hydraulic fluid in the operable hydraulic constriction element by the diaphragm.

The pressure sensor may comprise a strain gauge-based pressure sensor, which may be a piezoresistive or piezoelectric strain gauge-based pressure sensor, or an optical strain gauge-based pressure sensor.

In the alternative, the pressure sensor may comprise a capacitive pressure sensor, which may be an electromagnetic pressure sensor.

In one embodiment, the diaphragm is in connection with an enclosed lumen configured to hold a gaseous fluid, and the pressure sensing element is configured to sense the pressure of the gaseous fluid.

The implantable constriction device may further comprise an electrically controllable valve connected to the controller, and the controller may be configured to control the electrically controllable valve on the basis of the received pressure sensor input.

In one embodiment, the implantable constriction device may further comprise a reservoir for holding a hydraulic fluid, and the reservoir may be in fluid connection with the operable hydraulic constriction element. The electrically controllable valve may be configured to open and close the fluid connection between the reservoir and the operable hydraulic constriction element. The implantable constriction device may further comprise a second operable hydraulic constriction element and a second pressure sensor configured to sense the pressure in the second operable hydraulic constriction element.

The implantable constriction device may further comprise a second hydraulic pump for pumping hydraulic fluid to the second operable hydraulic constriction element, and the controller may be configured to receive pressure sensor input from the second pressure sensor and control the second hydraulic pump on the basis of the received pressure sensor input.

In one embodiment, the implantable constriction device further comprises a second electrically controllable valve connected to the controller, and the controller is configured to control the second electrically controllable valve on the basis of the received pressure sensor input.

In one embodiment, the implantable constriction device further comprises a second reservoir for holding a hydraulic fluid. The second reservoir may be in fluid connection with the second operable hydraulic constriction element, and the second electrically controllable valve may be configured to open and close the fluid connection between the reservoir and second the operable hydraulic constriction element.

In one embodiment, the diaphragm comprises a medical grade silicone material.

In one embodiment, the diaphragm makes up a portion of a wall of at least one of the operable hydraulic constriction elements and the reservoir.

In one embodiment, the implantable constriction device comprises an operable hydraulic constriction element configured to be inflated to exert a pressure on the urethra and a hydraulic pump for pumping a hydraulic fluid to the operable hydraulic constriction element. The hydraulic pump may comprise a compressible reservoir configured to hold a hydraulic fluid to be moved to the operable hydraulic constriction element. The implantable constriction device further comprises a motor comprising a shaft. The motor may be configured to generate force in a radial direction by rotation of the shaft. The implantable constriction device further comprises a transmission configured to transfer the force in the radial direction to a force substantially in an axial direction of the shaft for compressing the compressible reservoir. The implantable constriction device further comprises at least one bearing for the shaft, wherein the bearing is configured to withhold at least half of the force in the axial direction, for reducing the axial load on at least one of the motor and a gear system, caused by the compression of the reservoir.

The at least one bearing could comprise at least one of a ball bearing and a roller bearing, and the bearing may be placed between the gear system and the compressible reservoir for reducing the axial load on the gear system caused by the compression of the reservoir.

In one embodiment, the compressible reservoir comprises a first resilient wall portion, and the shaft may be directly or indirectly connected to the first resilient wall portion.

The compressible reservoir may comprise a first resilient wall portion and a second resilient wall portion, and the first resilient wall portion may be more resilient than the second resilient wall portion.

The implantable constriction device may further comprise a gear system connected to the motor and adapted to receive mechanical work via the shaft having a force and a velocity, and output mechanical work having a stronger force and a lower velocity.

The gear system may be placed between the motor and the transmission.

The shaft may comprise a threaded portion, and the implantable constriction device may further comprise a compression member directly or indirectly connected to the first resilient wall portion. The compression member may comprise a corresponding threaded portion such that the threaded portions of the shaft and the compression member together creates the transmission. The compression member may be integrated in the first resilient wall portion.

The implantable constriction device may further comprise a pressure sensor configured to sense the pressure in the compressible reservoir, and the pressure sensor may be integrated in a wall portion of the compressible reservoir. The pressure sensor may comprise a strain gauge-based pressure sensor.

The first resilient wall portion may comprise a convex portion configured to be compressed and thus inverted, for creating a concave portion, and the second resilient wall portion may comprise a concave portion towards the lumen of the compressible reservoir. The first resilient wall portion may be configured to be compressed and thus inverted into the concave portion of the second resilient wall portion.

The compression member may comprise a convex portion configured to engage the first resilient wall portion for facilitating the inversion of the convex portion of the first resilient wall portion. The implantable constriction device may further comprise a shaft sealing configured to engage the shaft and provide a seal between the transmission at least one of the motor and a gear system.

The implantable constriction device may further comprise an elastic element configured to exert an elastic force on the shaft sealing, such that the shaft sealing exerts a sealing force on the shaft. The shaft sealing may comprise a self-lubricating polymer material such as PTFE.

In one embodiment the implantable operable hydraulic constriction element comprises a contacting wall portion configured to engage the urethra for exerting force thereon, a withholding wall portion configured to be connected to a withholding structure for withholding the force exerted on the urethra, such that the urethra U is constricted, and a connecting wall portion, connecting the contacting wall portion to the withholding wall portion. A first portion of the connecting wall portion is connected to the contacting wall portion, a second portion of the connecting wall portion is connected to the withholding wall portion. The first portion of the connecting wall portion is more resilient than the second portion of the connecting wall portion.

In one embodiment, the first portion of the connecting wall portion has a lower average wall thickness than the average wall thickness of the second portion of the connecting wall portion.

The first portion of the connecting wall portion has an average wall thickness which is less than 0.8 times the average wall thickness of the second portion of the connecting wall portion.

In one embodiment, the first portion of the connecting wall portion comprises a first and a second sub portion and the first sub portion of the first portion is connected to the contacting wall portion, and the second portion of the connecting wall portion comprises a first and a second sub portion. The second sub portion of the second portion is connected to the withholding wall portion, the first sub portion of the first portion is more resilient than the second sub portion of the first portion.

In one embodiment, the first sub portion of the first portion has a lower average wall thickness than the average wall thickness of the second sub portion of the first portion.

The first sub portion of the first portion may have an average wall thickness which is less than 0.9 times the average wall thickness of the second sub portion of the first portion.

The first sub portion of the first portion may be more resilient than the second sub portion of the first portion.

The first sub portion of the second portion may have a lower average wall thickness than the average wall thickness of the second sub portion of the second portion, and in one embodiment, the first sub portion of the second portion has an average wall thickness which is less than 0.9 times the average wall thickness of the second sub portion of the second portion.

In one embodiment, the first portion of the connecting wall portion may comprise a first material and the second portion of the connecting wall portion may comprise a second material. The first material may have a lower modulus of elasticity than the first material. In one embodiment, the modulus of elasticity of the first material is less than 0.8 times the modulus of elasticity of the second material.

The withholding structure in any of the embodiments herein may comprise a surrounding structure configured to surround the urethra. The surrounding structure may be comprised of a first and second support element configured to be connected to each other for forming the surrounding structure, and the first and second support element may be hingedly connected to each other.

The surrounding structure may comprise at least one cushioning element configured to contact the urethra, and the cushioning element may be more resilient than the surrounding structure.

In one embodiment, the implantable constriction device comprises an operable hydraulic constriction element configured to be inflated to exert a pressure on the urethra U, a hydraulic pump for pumping a hydraulic fluid to the operable hydraulic constriction element, an implantable energy storage, a capacitor connected to the implantable energy storage unit and connected to the hydraulic pump. The capacitor is configured to be charged by the implantable energy storage unit and to provide the hydraulic pump with electrical power. By having the implantable energy storage unit charge a capacitor, an implantable energy storage unit with high energy density but low maximum output current can be used to operate a hydraulic pump requiring a relatively high current.

The implantable energy storage unit may be a re-chargeable battery, a solid-state battery and/or a thionyl chloride battery.

The implantable energy storage unit may be connected to the hydraulic pump and configured to power the hydraulic pump after it has been started using the capacitor.

The capacitor may be configured to store energy to provide a burst of energy to the hydraulic pump. The capacitor may be a start capacitor, a run capacitor, or a dual run capacitor.

In one embodiment, the implantable constriction device further comprises a second capacitor configured to be charged by the implantable energy storage unit and to provide the hydraulic pump with electrical power.

The capacitor could for example be a supercapacitor which has a high capacitance in relation to its size, which is of importance for keeping the implant small.

In one embodiment, the hydraulic pump could comprise an electrical motor for operating a hydraulic pump and the capacitor could further be configured to provide electrical power to at least one of a device for providing electrical stimulation to a tissue portion of the body of the patient, a CPU for encrypting information, a transmitting and/or receiving unit for communication with an external unit, a measurement unit or a sensor, a data collection unit, a solenoid, a piezo-electrical element and/or a memory metal unit.

In one embodiment, the capacitor is further configured to provide electrical power to a valve.

The capacitor may further be configured to provide electrical power to a control unit for controlling at least a part of the medical implant.

The implantable constriction device may further comprise an external energy storage unit configured be arranged outside of the patient's body and configured to provide energy to the implantable energy storage unit and an implantable energy receiver configured to be electrically connected to the implantable energy storage unit and enable charging of the implantable energy storage unit by the external energy storage unit.

In one embodiment, the implantable constriction device further comprises a temperature sensor for sensing a temperature of the implantable energy storage unit and/or a temperature sensor for sensing a temperature of the capacitor.

In one embodiment, the implantable constriction device comprises an operable hydraulic constriction element configured to be inflated to exert a pressure on the urethra, a hydraulic pump for pumping a hydraulic fluid to the operable hydraulic constriction element, and an internal control unit configured to control the hydraulic pump. The internal control unit may comprise a sensor adapted to detect a magnetic field and a processing unit having a sleep mode and an active mode. By having a sleep mode, the internal control unit could consume very little energy when not active.

The external control unit may be adapted to be arranged outside of the patient's body and may comprise a first coil adapted to create a magnetic field detectable by the internal sensor. The internal control unit may further be configured to, in response to a detected magnetic field exceeding a predetermined value, setting the processing unit in an active mode.

In one embodiment, the sensor may be one of: a hall effect sensor, a fluxgate sensor, an ultra-sensitive magnetic field sensor or a magneto-resistive sensor.

The frequency of the magnetic field generated by the coil may be 9-315 kHz.

In one embodiment, the frequency of the magnetic field generated by the coil is less than or equal to 125 kHz, preferably less than 58 kHz.

In embodiment, the internal control unit comprises a receiver unit, and the internal control unit and the external control unit are configured to transmit and/or receive data via the receiver unit and the first coil via magnetic induction.

In one embodiment, the receiver unit comprises a high-sensitivity magnetic field detector.

In one embodiment, the receiver unit comprises a second coil.

In one embodiment, the implantable constriction device further comprises an implantable energy storage unit electrically connected to the receiver unit, and the implantable energy storage unit is adapted to be charged by the external control unit via the receiver unit.

The implantable energy storage unit may be configured to be charged via magnetic induction between the first and the second coils.

The receiver unit may be configured to control the charging of the implantable energy storage unit by controlling the receipt of electrical power from the external control unit at the internal receiver.

The internal receiver unit may be configured to control the charging of the implantable energy storage unit by controlling a transmission of electrical power from the external control unit to the receiver unit.

In one embodiment, the implantable constriction device further comprises a sensation generator adapted to generate a sensation detectable by a sense of the patient, the sensation generator being connected to the internal control unit or the external control unit, and being configured to, upon request, generate the sensation when implanted in a patient.

In one embodiment, the sensation generator is configured to receive the request from the internal control unit or the medical implant, and the sensation generator may be configured to receive the request from an external device.

In one embodiment, the sensation generator may be configured to create the sensation comprising a plurality of sensation components. The sensation generator may be configured to create the sensation or sensation components by at least one of: vibration of the sensation generator, producing a sound providing a photonic signal, providing a light signal, providing an electric signal, and a heat signal.

In one embodiment, the sensation generator may be adapted to be implanted in the patient and in another embodiment the sensation generator is configured to be worn in contact with the skin of the patient. The sensation generator may be configured to generate the sensation without being in physical contact with the patient.

The external control unit may comprise a wireless remote control and the wireless remote control may comprise an external signal transmitter. The internal receiver may further be configured to receive a signal transmitted by the external signal transmitter and to control an operation of the apparatus based on said signal, when the processing unit is in the active state.

The signal may in any of the embodiment be selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

A method of implanting the implantable constriction device in any of the embodiment herein is further provided. The method comprises the steps of placing at least two laparoscopic trocars in the body of a patient suffering from urinary incontinence, inserting a dissecting tool through the trocars and dissecting an area of the urethra or urine bladder in the abdominal or pelvic or retroperitoneal surroundings, placing the implantable constriction device in the dissected area engaging the urethra. The method may further comprise the step of adjusting the implantable constriction device to normally restrict the urine passageway in the urethra or urine bladder, and adjusting the implantable constriction device to open the urine passageway when the patient wants to relieve himself or herself.

The method may further comprise implanting a source of energy in the patient and providing a controller for controlling the source of energy from outside the patient's body to supply energy for the adjustment of the implantable constriction device.

A method of implanting the implantable constriction device in any of the embodiment herein is further provided. The method comprises the steps of making an incision in the abdomen of the patient, for accessing the sub peritoneal space and thus the urethra, dissecting a portion of the urethra, inserting an implantable constriction device according to any one of the embodiments herein into the body of the patient, placing the implantable constriction device around the urethra of the patient, which in some embodiments includes closing a locking or fixation device of the implantable constriction device around the urethra to position and fixate the implantable constriction device to the urethra of the patient, optionally securing the implantable constriction device additionally for example by means of sutures, stapler or a tissue growth promoting structure, such as a mesh configured to cover a part of the implantable constriction device such that the growth of fibrotic tissue fixates the implantable constriction device. In one embodiment, the method further comprises inserting an implantable controller, fixated to or fixable to the implantable constriction device, into the body of the patient and fixating the implantable controller to tissue or bone in the body of the patient. In one embodiment, the method further comprises the step of inserting an operation device, fixated to or fixable to the implantable constriction device. The operation device may comprise at least one implantable hydraulic pump and/or at least one implantable valve, fixating the implantable operation device to tissue or bone in the body of the patient. In one embodiment, the controller may be integrated in the operation device. The method may further comprise the step of implanting and fixating at least one injection port in fluid connection with the operation device. The step of fixating at least one injection port may include fixating the injection port subcutaneously. The method may further comprise at least one of the steps of calibrating the fluid level in the implantable constriction device, calibrating the pressure exerted by the implantable constriction device on the urethra, which may include calibrating the controller to control the pumps and/or valves accordingly, calibrate the time during which implantable constriction device is to remain open after activation, calibrate the time during which implantable constriction device is to remain open after activation before bed time, calibrate the speed with which the implantable constriction device should constrict the urethra, calibrate the pressure exerted on the urethra relative to the blood pressure if the patient, which may include calibrating the pressure exerted on the urethra relative to the systolic blood pressure and/or relative to the diastolic blood pressure, calibrating the pressure exerted on the urethra by the implantable constriction device by means of a pressure sensitive catheter, placing the implantable constriction device in a fully open catheter mode, testing the feedback function by providing sensory feedback to the patient, placing the implantable constriction device in a post-operative mode for enabling healing and/or growth of fibrotic tissue, testing and/or calibrating the electrical stimulation of the tissue of the urethra.

An implantable operation device for operating a hydraulic constriction element configured to exert a force on a urethra of a patient is further provided. The implantable operation device comprising: a housing comprising a first and a second chamber separated from each other. The first chamber comprises a first liquid and the second chamber comprises a second liquid, and wherein the second liquid is a hydraulic liquid configured to transfer force to the hydraulic constriction element configured to exert the force on the body portion of the patient.

According to one embodiment, the implantable operation device comprises a motor housed in the first chamber, the motor is configured for transforming electrical energy to mechanical work. The implantable operation device may further comprise a hydraulic pump configured to pump the hydraulic liquid from the operation device to the hydraulic constriction element configured to exert the force on the urethra of the patient. The hydraulic pump may comprise a gear pump, a peristaltic pump, a pump comprising at least one compressible hydraulic reservoir, or a gerotor pump.

The implantable operation device may further comprise a transmission coupled between the motor and the hydraulic pump. The transmission may be configured to transfer a week force with a high velocity into a stronger force with lower velocity and/or configured to transfer a rotating force into a linear force. The transmission may comprise a gear system. A fluid chamber of the hydraulic pump forms a portion of the second chamber.

According to one embodiment, the implantable operation device may further comprise an implantable energy storage unit housed in the first chamber.

According to one embodiment, the implantable operation device further comprising a controller housed in the first chamber.

A wall portion of the first chamber may be resilient to allow an expansion of the first chamber, the wall portion may comprise a resilient membrane.

According to one embodiment, the first liquid is a non-conductive liquid.

According to one embodiment, the first liquid is a lubricating liquid.

According to one embodiment, the first liquid is an oil-based liquid, such as a mineral oil or a silicone oil.

According to one embodiment, the second liquid is an isotone liquid.

According to one embodiment, the housing comprises a metallic material, such as titanium.

According to one embodiment, the implantable operation device further comprising a conduit for electrical transfer between the first and a second chamber.

A wall separating the first chamber from the second chamber may comprise a portion comprising an electrically insulating material, and a conduit may pass from the first chamber to the second chamber through the portion comprising the electrically insulating material. The electrically insulating material comprises a ceramic material.

An implantable device for exerting a force on a body portion of the patient is further provided. The implantable device comprises the implantable operation device according to any one of the embodiments herein and a hydraulic constriction element configured to exert a force on a urethra of the patient.

An implantable operation device for operating a hydraulic constriction element configured to exert a force on a urethra of a patient is further provided. The implantable operation device comprising a housing comprising a first and a second chamber separated from each other, a motor housed in the first chamber, wherein the motor is configured for transforming electrical energy to mechanical work. The implantable operation device further comprising an actuator housed in the second chamber. The actuator is connected to the hydraulic constriction element configured to exert a force on a urethra of a patient. The implantable operation device further comprises a magnetic coupling for transferring mechanical work from the motor to the actuator through a barrier separating the first chamber from the second chamber.

According to one embodiment, the housing comprises a metallic material such as titanium.

The actuator may in any of the embodiments be a hydraulic pump configured to transfer mechanical force to hydraulic force. The hydraulic pump may comprise a gear pump, a peristaltic pump, a pump comprising at least one compressible hydraulic reservoir, or a gerotor pump.

The actuator may be a mechanical actuator configured to transfer mechanical force from the magnetic coupling to the hydraulic constriction element to exert a force on a urethra of a patient. The mechanical actuator may be configured to transfer a rotating force into a linear force.

According to one embodiment, the magnetic coupling comprises a first coupling part comprising magnets or magnetic material and being comprised in the first chamber, connected to the motor, and configured to perform a rotating movement. The magnetic coupling may further comprise a second coupling part comprising magnets or magnetic material being comprised in the second chamber, connected to the actuator, and configured to be propelled by the rotating movement of the first coupling part.

The first coupling part may comprise magnets or magnetic material being placed radially along an outer periphery of the first coupling part, and the second coupling part comprises magnets or magnetic material being placed radially, such that the radially placed magnets or magnetic material of the first coupling part magnetically connects to the radially placed magnets or magnetic material of the second coupling part.

According to one embodiment, the first coupling part comprises magnets or magnetic material being placed axially on a surface of the first coupling part, and the second coupling part comprises magnets or magnetic material being placed axially on a surface of the first coupling part, such that the axially placed magnets or magnetic material of the first coupling part magnetically connects to the axially placed magnets or magnetic material of the second coupling part.

According to one embodiment, the implantable operation device according to any one of the preceding claims further comprises a transmission coupled between the motor and the magnetic coupling, the transmission being configured to transfer a week force with a high velocity into a stronger force with lower velocity. The transmission may comprise a gear system.

A hydraulic constriction element for exerting a force on a body portion of the patient is further provided. The hydraulic constriction element comprises the implantable operation device according to any one of the embodiments herein, and a hydraulic constriction element configured to exert a force on a urethra of the patient.

An implantable hydraulic force transfer device is further provided. The implantable hydraulic force transfer device comprises a first chamber configured to house a first fluid, the first chamber comprising a first fluid connection for fluidly connecting the first chamber to an implantable operation device, and at least one movable wall portion for varying the size of the first chamber. The implantable hydraulic force transfer device further comprises a second chamber configured to house a second fluid, the second chamber comprising a second fluid connection for fluidly connecting the second chamber to a hydraulic constriction element configured to exert a force on a urethra of the patient, and at least one movable wall portion for varying the size of the second chamber. The implantable hydraulic force transfer device may be configured to transfer hydraulic force from the implantable operation device to the hydraulic constriction element configured to exert a force on a urethra of the patient without mixing the first and second fluids.

According to one embodiment, the implantable hydraulic force transfer device may comprise a common movable wall portion, and at least a portion of the movable wall of the first chamber comprises the common movable wall portion, and at least a portion of the movable wall of the second chamber comprises the common movable wall portion.

The at least one of the movable wall portions may comprise a piston, and a first side of the piston may be facing the first chamber and a second side of the piston may be facing the second chamber.

According to one embodiment, at least one of the movable wall portions comprises a flexible wall portion, which may be an elastic wall portion and/or a pleated wall portion.

According to one embodiment, at least one of the first and second chambers comprises a bellows.

According to one embodiment, the first chamber is configured to house an oil-based fluid.

According to one embodiment, the second chamber is configured to house an isotone fluid.

An implantable constriction device for constricting the urethra to restrict the flow of urine therethrough is further provided. The implantable device may comprise an implantable operation device and a hydraulic constriction element configured to exert a force on a body portion of the patient. The implantable device may further comprise the implantable hydraulic force transfer device according to any one of embodiments herein, a first fluid conduit configured to fluidly connect the implantable operation device to the first chamber of the implantable hydraulic force transfer device, and a second fluid conduit configured to fluidly connect the hydraulic constriction element configured to exert a force on a body portion of the patient to the second chamber of the implantable hydraulic force transfer device.

According to one embodiment, the operation device comprises a hydraulic pump for pumping hydraulic fluid from the operation device to the first chamber of the implantable hydraulic force transfer device. The implantable hydraulic constriction device in any of the embodiments herein may comprise an implantable hydraulic constriction device for constricting the urethra of the patient.

The implantable device according to any one of the embodiments may further comprise a first fluid configured to be transferred between the operation device and the first chamber of the implantable hydraulic force transfer device and a second different fluid configured to be transferred between the second chamber and the hydraulic constriction element configured to exert a force on a urethra of the patient.

An implantable controller for an implantable constriction device for constricting the urethra to restrict the flow of urine therethrough is further provided. The controller is configured to control an operation device configured to operate at least one implantable element configured to exert a force on a urethra of a patient. The implantable controller is further configured to receive a first input signal being at least one of a sensor input signal related to a physiological parameter of the patient from an implantable sensor. The implantable controller is further configured to receive a control signal from an implanted or external source, and control the operation device to adjust the force exerted on the urethra in response to the first input signal, and receive a second input signal from the implantable sensor related to the physiological parameter of the patient, and control the operation device to further adjust the force exerted on the urethra in response to the second input signal.

The physiological parameter may in any of the embodiments herein comprise a parameter related to an oxygenation of a tissue portion of the patient, related to a pulse of the patient, or related to a blood pressure of the patient.

A method of calibrating an implantable constriction device for constricting the urethra to restrict the flow of urine therethrough is further provided. The implantable constriction device comprises at least one hydraulic constriction element configured to exert a force on a body portion of a patient, an operation device for operating the hydraulic constriction element and a controller for controlling the operation device. The method comprises receiving, at the controller, a first input signal comprising at least one of: a sensor input signal related to a physiological parameter of the patient from an implantable sensor, and a control signal from an implanted or external source. The method further comprises the step of controlling, by the controller, the operation device to adjust the force exerted on the urethra, in response to the first input signal, and receiving, at the controller, a second input signal from the implantable sensor related to the physiological parameter of the patient, and controlling, by the controller, the operation device to further adjust the force exerted on the body portion of a patient, in response to the second input signal. The step of controlling the operation device to adjust the force exerted on the urethra of a patient comprises adjusting the constriction of the urethra to adjust the restriction of a flow of urine.

According to one embodiment, the step of receiving, at the controller, a first input signal may comprise a signal related to an input from the patient or an input from a different unit in the controller or from another controller, e.g. a time signal. The step of receiving, at the controller, a first input signal may comprise a signal from another sensor, which may be a motion sensor in an external device.

An implantable controller for controlling an operation device for operating a hydraulic constriction element configured to exert a force on a urethra of a patient, is further provided. The implantable controller comprises an electrical switch, and the electrical switch may be a switch being mechanically connected to the hydraulic constriction element configured to exert a force on a urethra portion of a patient and being configured to be switched as a result of the force exerted on the body portion of a patient exceeding a threshold value. The switch may also be as switch being electrically connected to the operation device and being configured to be switched as a result of the current supplied to the operation device exceeding a threshold value.

The operation device may in any of the embodiments herein comprise a motor, and the switch may be electrically connected to the motor and configured to be switched as a result of the current supplied to the motor exceeding a threshold value. The switch may be configured to cut the power to the operation device or may be configured to generate a control signal to a processor of the implantable controller.

An implantable constriction device for exerting a force on a body portion of the patient is further provided. The implantable constriction device comprises an implantable operation device, a hydraulic constriction element configured to exert a force on a urethra of the patient, and the implantable controller according to any one of the embodiments herein.

The operation device may comprise a motor, and wherein the switch may be electrically connected to the motor and configured to be switched as a result of the current supplied to the motor exceeding a threshold value.

The implantable device may further comprise a transmission coupled between the motor and the implantable element configured to exert a force on a body portion of the patient, the transmission may be configured to transfer a week force with a high velocity into a stronger force with lower velocity. The transmission may comprise a gear system.

According to one embodiment, the operation device comprises a hydraulic pump for pumping hydraulic fluid from the operation device to the implantable element configured to exert a force on a body portion of the patient. The hydraulic pump may comprise a gear pump, a peristaltic pump, a pump comprising at least one compressible hydraulic reservoir or a gerotor pump.

The implantable hydraulic constriction device may comprise an implantable hydraulic constriction device for constricting the urethra of the patient.

Any embodiment, part of embodiment, method, or part of method may be combined in any applicable way.

An implantable controller for controlling an operation device for operating an implantable constriction device for constricting the urethra to restrict the flow of urine therethrough, the implantable constriction device comprises a hydraulic constriction element configured to exert a force on a urethra is further provided. The implantable controller comprises an electrical switch, and the electrical switch comprises at least one of: a switch being mechanically connected to the hydraulic constriction element to exert a force on a body portion of a patient and being configured to be switched as a result of the force exerted on the body portion of a patient exceeding a threshold value, switch being electrically connected to the operation device and being configured to be switched as a result of the current supplied to the operation device exceeding a threshold value, and a switch being electrically connected to the operation device and being configured to be switched as a result of a temperature exceeding a threshold value.

According to one embodiment, the electrical switch is configured to be switched as a result of the pressure in the hydraulic constriction element exceeding a threshold value.

According to one embodiment, the operation device comprises a motor, and the switch is electrically connected to the motor and configured to be switched as a result of the current supplied to the motor exceeding a threshold value.

According to one embodiment, the switch is configured to cut the power to the operation device.

In one embodiment, the switch is configured to generate a control signal to a processor of the implantable controller.

An implantable constriction device for exerting a force on a urethra of the patient is further provided. The implantable operation device comprises an hydraulic constriction element configured to exert a force on a urethra of the patient, and the implantable controller according to any one of the embodiments herein.

In one embodiment, the operation device comprises a motor, and the switch is electrically connected to the motor and configured to be switched as a result of the current supplied to the motor exceeding a threshold value.

The implantable device may further comprise a transmission coupled between the motor and the hydraulic constriction element configured to exert a force on a urethra of the patient, the transmission is configured to transfer a week force with a high velocity into a stronger force with lower velocity. The transmission may comprise a gear system.

The operation device may comprise a hydraulic pump for pumping hydraulic fluid from the operation device to the hydraulic constriction element to exert a force on a urethra of the patient. The hydraulic pump may comprise a gear pump and/or a peristaltic pump and/or a pump comprising at least one compressible hydraulic reservoir and/or a gerotor pump.

An implantable controller for an energized implant is further provided. The controller is configured to control an operation device configured to operate at least one hydraulic constriction element configured to exert a force on a body portion of a patient. The implantable controller is further configured to receive a first input signal being related to a pressure in the hydraulic constriction element configured to exert a force on a body portion of a patient, receive a second input signal being related to an atmospheric pressure, and control the operation device on the basis of the received first and second input signals.

The implantable controller may be configured to receive the second input signal related to the atmospheric pressure from a signal transmitter configured to be located outside the body of the patient, or may be configured to receive the second input signal related to the atmospheric pressure from an implantable pressure sensor, and the implantable controller may be configured to control the force exerted on the body of the patient on the basis of the received first and second input signals.

According to one embodiment, the implantable controller is configured to create an absolute pressure by subtracting the atmospheric pressure from the pressure in the hydraulic constriction element, and the implantable controller may be configured to control the operation device on the basis of the absolute pressure.

An energized implant is further provided. The energized implant comprises the implantable controller according to any one of the embodiment described herein, and at least one hydraulic constriction element configured to exert a force on a urethra of a patient, and an operation device configured to operate the at least one hydraulic constriction element.

The energized implant may further comprise a pressure sensor configured to sense the pressure in the hydraulic constriction element and the atmospheric pressure. In one embodiment, the energized implant further comprises a membrane, and the pressure sensor is configured to sense the pressure in the hydraulic constriction element on a first side of the membrane and the atmospheric pressure on a second side of the membrane. A portion of a wall in fluid connection with the at least one hydraulic constriction element configured to exert a force on a body portion of a patient may comprise the membrane.

The sensor may be configured to derive an absolute pressure in the implantable element by comparing a pressure in the hydraulic constriction element with the atmospheric pressure, in the alternative, the sensor may be configured to derive the pressure in the hydraulic constriction element by comparing a pressure in the hydraulic constriction element with vacuum.

The pressure sensor may comprise at least one of: a strain gauge-based pressure sensor, a piezoresistive or piezoelectric pressure sensor, an optical pressure sensor, a capacitive pressure sensor, and an electromagnetic pressure sensor.

In one embodiment, the energized implant further comprises a first pressure sensor configured to sense the pressure in the hydraulic constriction element, and a second pressure sensor configured to sense the atmospheric pressure. The first pressure sensor may be connected to the at least one hydraulic constriction element implantable element configured to exert a force on a body portion of a patient.

The second pressure sensor may be an implantable sensor placed in or connected to the energized implant.

The hydraulic constriction element configured to exert a force on a urethra of the patient may in any of the embodiments herein comprise a hydraulically operable implantable element, which may comprise a hydraulic pump.

A method in an implantable controller, for controlling an operation device of an implantable constriction device for constricting the urethra to restrict the flow of urine therethrough is further provided. The method comprises receiving a first input signal, at the implantable controller, the first input signal being related to a pressure in the hydraulic constriction element configured to exert a force on a body portion of a patient, receiving a second input signal, at the implantable controller, the second input signal being related to an atmospheric pressure, and controlling, by the controller, the operation device on the basis of the received first and second input signals.

According to one embodiment, the step of receiving a second input signal comprises receiving the second input signal from a signal transmitter located outside the body of the patient.

According to one embodiment, the step of receiving a second input signal from a signal transmitter located outside the body of the patient comprises receiving the second input signal in connection with the patient using, activating or controlling the implantable constriction device.

According to one embodiment, the step of receiving a second input signal from a signal transmitter located outside the body of the patient comprises receiving the second input signal wirelessly.

The step of receiving a second input signal may comprise receiving the second input signal from an implantable pressure sensor.

The step of controlling the operation device may comprise controlling the force exerted on the urethra of the patient by the hydraulic constriction element on the basis of the received first and second input signals.

The method may further comprise the step of creating, in the controller, an absolute pressure by subtracting the atmospheric pressure from the pressure in the implantable element, and the step of controlling the operation device may comprise controlling the operation device on the basis of the absolute pressure.

A method in an implantable controller for controlling an operation device of an implantable constriction device for constricting the urethra to restrict the flow of urine therethrough is further provided. The method comprising releasing the pressure in an implantable hydraulic constriction element such that substantially no pressure is exerted on the urethra, measuring the pressure in the implantable hydraulic constriction element, when substantially no pressure is exerted on the urethra, and increasing the pressure in the implantable hydraulic constriction element to a defined level, such that the urethra is constricted.

According to one embodiment, the step of measuring the pressure in the implantable hydraulic constriction element when substantially no pressure is exerted on the urethra, further comprises comparing the measured pressure with the atmospheric pressure.

According to one embodiment, the step of comparing the measured pressure with the atmospheric pressure comprises measuring the atmospheric pressure using a pressure sensor connected to a signal transmitter located outside the body of the patient.

According to one embodiment, the step of increasing the pressure in the implantable hydraulic constriction element to a defined level, such that the urethra is constricted, comprises constricting the urethra to a defined cross-sectional distance.

According to one embodiment, the method further comprises measuring the pressure in the implantable hydraulic constriction element when the pressure in the implantable hydraulic constriction element has been increased.

According to one embodiment, the step of steps of: measuring the pressure in the implantable hydraulic constriction element, when substantially no pressure is exerted on the urethra, and measuring the pressure in the implantable hydraulic constriction element when the pressure in the implantable hydraulic constriction element has been increased, are performed using the same pressure sensor.

According to one embodiment, the method further comprises the step of creating, in the controller, an absolute pressure by subtracting the pressure in the implantable hydraulic constriction element, when substantially no pressure is exerted on the urethra, from the pressure in the hydraulic constriction element, when the pressure in the implantable hydraulic constriction element has been increased, and wherein the step of controlling the operation device comprises controlling the operation device on the basis of the absolute pressure.

A controller for controlling the pressure in an implantable constriction device for constricting the urethra is further provided, the controller comprises pressure sensor for measuring the pressure in the implantable hydraulic constriction element, and a computing unit. The computing unit is configured to create an absolute pressure by subtracting the pressure in the implantable hydraulic constriction element, when substantially no pressure is exerted on the urethra, from the pressure in the hydraulic constriction element, when the pressure in the implantable hydraulic constriction element has been increased.

According to one embodiment, the computing unit is further configured to compare the measured pressure with the atmospheric pressure.

According to one embodiment, the controller is further configured to receive a pressure signal from a pressure sensor located outside of the body of the patient and compare the measured pressure with a pressure received in the pressure signal.

According to one embodiment, the controller is configured to increase the pressure in the implantable hydraulic constriction element on the basis of the measured pressure.

According to one embodiment, the controller is configured to increase the pressure in the implantable hydraulic constriction element to a defined cross-sectional distance.

In any of the embodiments, the pressure applied to the reservoir and/or hydraulic constriction element can be controlled either by controlling the actual pressure, or by controlling the volume of fluid pumped and/or by controlling the cross-sectional distance of the constricted urethra. I.e. if the pressure is continuously calibrated it can be established that a certain fluid level or distance leads to a specific pressure, which could make control of the device easier then control using constant pressure measurement. In embodiments in which the fluid level or cross-sectional distance of the urethra is used as control value, the pressure may be used as a back-up or safety system, e.g. the pressure sensor can be set to give an alarm signal or take a specific action if the pressure increases over a set value (threshold).

Any embodiment, part of embodiment, method, or part of method may be combined in any applicable way.

BRIEF DESCRIPTION OF THE DRAWINGS

The invention is now described, by way of example, with reference to the accompanying drawing, in which:

FIG. 3a shows an embodiment of an implantable constriction device for constricting the urethra of a patient, in an embodiment in which a portion of the surrounding structure is replaceable.

FIG. 3b shows an embodiment of a portion of the surrounding structure.

FIG. 3c shows an embodiment of a portion of the surrounding structure.

FIG. 3d shows an embodiment of a portion of the surrounding structure.

FIG. 3e shows an embodiment of a portion of the surrounding structure.

FIG. 3f shows an embodiment of an implantable constriction device for constricting the urethra of a patient, in an embodiment in which a portion of the surrounding structure is replaceable.

FIG. 11f shows an embodiment of an implantable constriction device for constricting the urethra of a patient in a sectional view, in its un-constricted state.

FIG. 12a shows a plain view of an embodiment of a hydraulic pump for an implantable constriction device.

FIG. 12b shows a side view of the hydraulic pump of FIG. 12a, for an implantable constriction device.

DETAILED DESCRIPTION

Figure 1A:
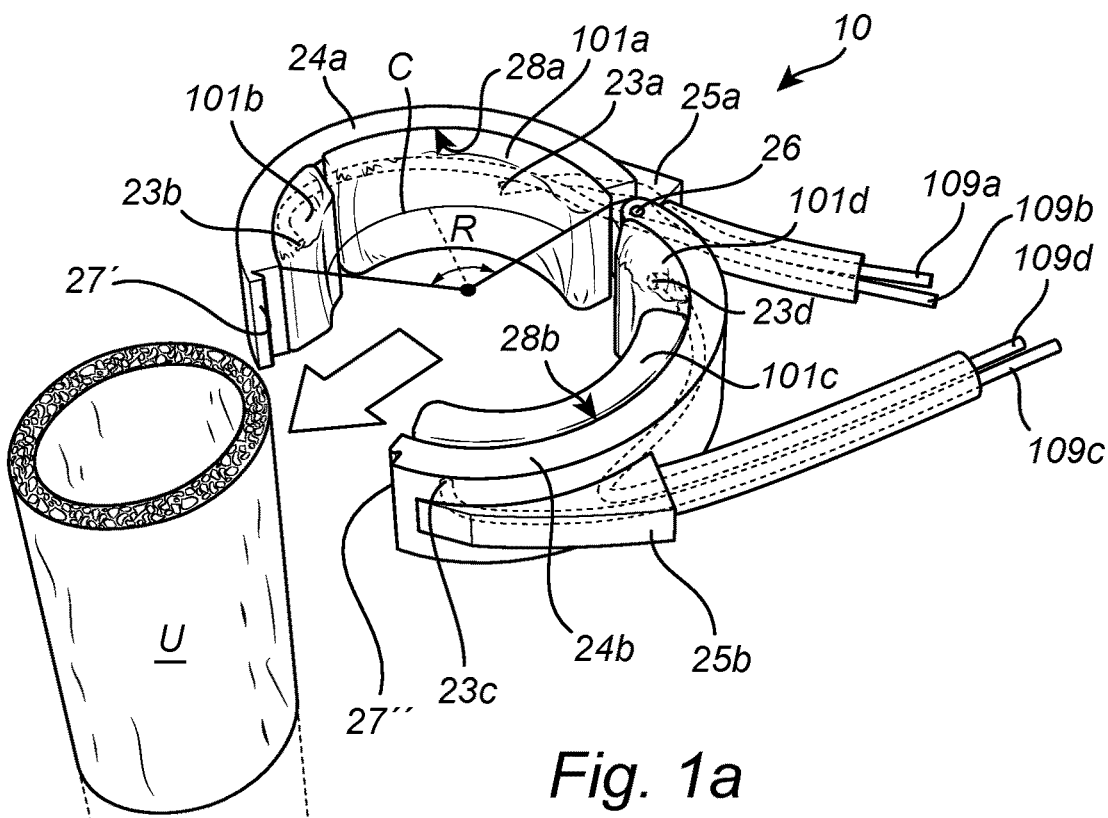
FIG. 1a shows an embodiment of an implantable constriction device for constricting the urethra of a patient, in an elevated view when being placed around the urethra.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

Restriction of the urethra is to be understood as any operation decreasing a cross-sectional area of the urethra. The restriction may decrease the flow of matter in the lumen or may completely close the lumen such that no matter can pass.

A controller is to be understood as any implantable unit capable of controlling the restriction device. A controller could include a motor and/or pump or another operation device for operating the implantable hydraulic restriction device or could be separate from the operation device and only be adapted to control the operation thereof. A control signal is to be understood as any signal capable of carrying information and/or electric power such that the restriction device can be directly or indirectly controlled.

Implantable operation device is to be understood as any device or system capable of operating an active implant. An operation device could for example be an actuator such as a hydraulic actuator such as a hydraulic pump or a hydraulic cylinder, or a mechanical actuator, such as a mechanical element actuating an implant by pressing or pulling directly or indirectly on the implant, or an electro-mechanical actuator such as an electrical motor or solenoid directly or indirectly pressing or pulling on the implant.

A gear system is to be understood as any system capable of providing transmission such that work of a first form can be transmission into work of a second form. The form of the work could for example include the velocity, the force and/or the direction of the work.

Inflatable is to be understood as possible to fill with a fluid, which may be a liquid, or gaseous fluid, or a plurality of solid structures suspended in a fluid, for the purpose of expanding the inner volume of a luminary device.

FIG. 1a shows an embodiment of an implantable constriction device 10 for constricting the urethra U of a patient. The implantable constriction device comprises a surrounding structure having a periphery surrounding the urethra U when implanted. The surrounding structure comprises two support elements 24a, 24b connected to each other for forming the surrounding structure. The first support element 24a is configured to support a first operable hydraulic constriction element 101a and a second operable hydraulic constriction element 101b. The second support element 24b is configured to support a third operable hydraulic constriction element 101c and a fourth operable hydraulic constriction element 101d. The first, second, third and fourth operable hydraulic constriction elements 101a, 101b, 101c and 101d are configured to constrict the urethra U for restricting the flow of urine therethrough and configured to release the constriction of the urethra U for enabling the patient to urinate.

The first and second support elements 24a, 24b each comprises a curvature C adapted for the curvature of the urethra U such that the implantable constriction device 10 fits snuggly around the urethra U such that the distance that the operable hydraulic constriction elements 101a, 101c needs to expand to constrict the urethra U is kept at a minimum. In the embodiment shown in FIG. 1a, the curvature C has a radius R of about 10 mm. However, it is conceivable that the radius R of the curvature C is anywhere in the range 5 mm-30 mm.

In the embodiment shown in FIG. 1a, the first and second support elements 24a, 24b are hingedly connected to each other such that a periphery of the surrounding structure is possible to open, such that the surrounding structure can be placed around the urethra U. a first end of the first and second support elements 24a, 24b comprises a hinge 26, whereas the other ends of the first and second support elements 24a, 24b comprises portions of a locking member 27', 27" which are configured to be interconnected to lock the surrounding structure around the urethra U. In the embodiment shown in FIG. 1a, the locking ends of the first and second support elements 24a, 24b comprises portions of locking members 27', 27" each comprising protruding snap-lock locking members 27', 27" materially integrated in the first second support elements 24a, 24b and configured to be snapped together for closing the periphery of the surrounding structure, such that the surrounding structure completely encircles the urethra U.

In the embodiment shown in FIG. 1a, each of the first and second support elements 24a,24b comprises fluid conduits 109a, 109b, 109c, 109d partially integrated in the support elements 24a, 24b. In the first support element 24a, a first conduit 109a comprises a first portion in the form of a first tubing which enters a tubing fixation portion 25a fixated to, or materially integrated with, the first support element 24a. In the tubing fixation portion 25a the fluid conduit 109a is transferred into a first integrated channel 23a in the first support element 24a. The first integrated channel 23a is drilled, milled or casted into the material of the first support element 24a. The first support element 24a comprises an inner surface 28a which is directed towards the urethra U, when the implantable constriction device 10 is implanted. The inner surface 28a of the first support element 24a comprises a fixation surface for fixating the first and second operable hydraulic constriction elements 101a, 101b. The fixation surface also comprises an outlet from the first integrated channel 23a into the first operable hydraulic constriction element 101a, such that fluid can be transferred from the first tubing to the first integrated channel 23a and into the first operable hydraulic constriction element 101a for expanding the first operable hydraulic constriction element 101a. A second tubing of the second fluid conduit 109b also enters the tubing fixation portion 25a fixated to, or materially integrated with, the first support element 24a. In the tubing fixation portion 25a the second fluid conduit 109b is transferred into a second integrated channel 23b in the first support element 24a. The second integrated channel 23b is also drilled, milled or casted into the material of the first support element 24a. The fixation surface also comprises an outlet from the second integrated channel 23b into the second operable hydraulic constriction element 101b, such that fluid can be transferred from the second tubing to the second integrated channel 23b and into the second operable hydraulic constriction element 101b for expanding the second operable hydraulic constriction element 101b.

In the second support element 24b, a third conduit 109c comprises a first portion in the form of a third tubing which enters a tubing fixation portion 25b fixated to, or materially integrated with, the second support element 24b. In the tubing fixation portion 25b the fluid conduit 109c is transferred into a third integrated channel 23c in the second support element 24b. The third integrated channel 23c is drilled, milled or casted into the material of the second support element 24b. The second support element 24b comprises an inner surface 28b which is directed towards the urethra U, when the implantable constriction device 10 is implanted. The inner surface 28b of the second support element 24b comprises a fixation surface for fixating the third and fourth operable hydraulic constriction elements 101c,101d. The fixation surface also comprises an outlet from the third integrated channel 23c into the third operable hydraulic constriction element 101c, such that fluid can be transferred from the first tubing to the third integrated channel 23c and into the third operable hydraulic constriction element 101c for expanding the third operable hydraulic constriction element 101c. A tubing portion of the fourth fluid conduit 109d also enters the tubing fixation portion 25b fixated to, or materially integrated with, the second support element 24b. In the tubing fixation portion 25b the fourth fluid conduit 109d is transferred into a fourth integrated channel 23d in the second support element 24b. The fourth integrated channel 23d is also drilled, milled or casted into the material of the second support element 24b. The fixation surface also comprises an outlet from the fourth integrated channel 23d into the fourth operable hydraulic constriction element 101d, such that fluid can be transferred from the fourth tubing to the fourth integrated channel 23d and into the fourth operable hydraulic constriction element 101d for expanding the fourth operable hydraulic constriction element 101d. The tubing portion of the fluid conduits 109a, 109b, 109c, 109d is preferably made from a biocompatible material such as silicone and/or polyurethane.

Integrating the fluid conduit(s) in the support element(s) enables the fluid entry to the operable hydraulic constriction elements 101a, 101b, 101c, 101d to be protected and encapsulated by the support element(s) which reduces the space occupied by the operable hydraulic constriction element 10 and reduces the amount of protruding portions thus reducing the risk of damaging the urethra U.

Figure 1B:
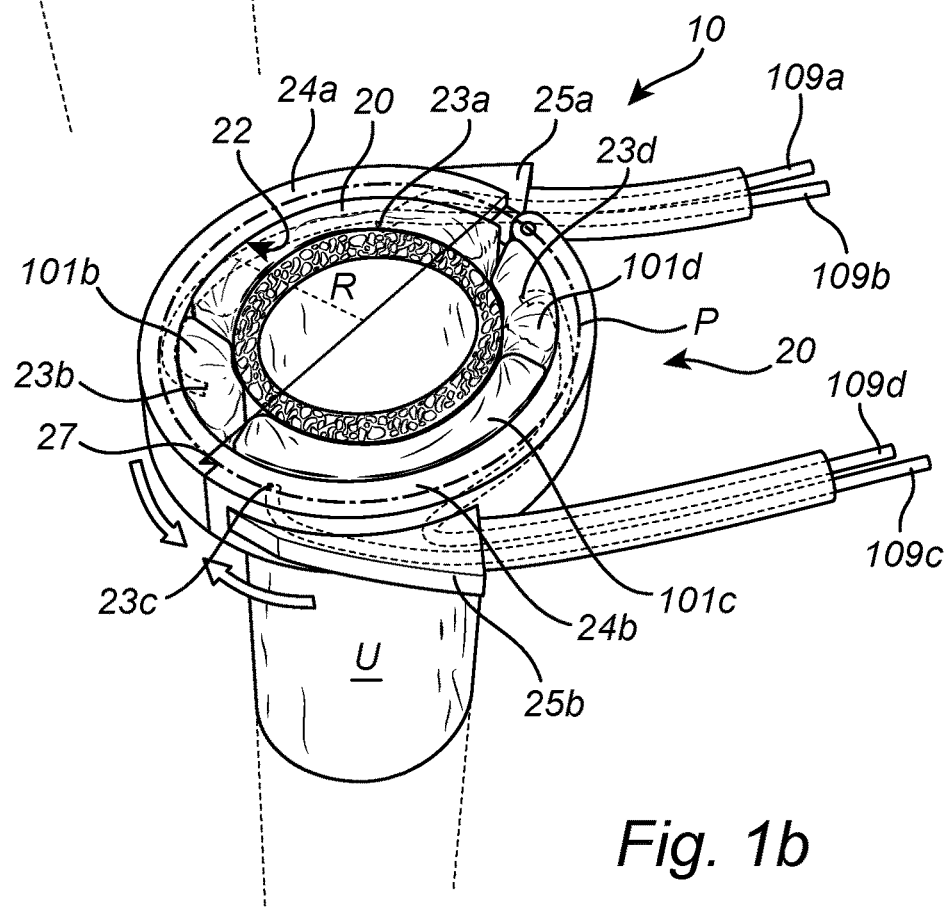
FIG. 1b shows an embodiment of an implantable constriction device for constricting the urethra of a patient, in an elevated view when placed around the urethra.

FIG. 1b shows the implantable constriction device 10 of the embodiment shown in FIG. 1a when the first and second support elements have been connected and closed such that a periphery P of the surrounding structure 20 surrounds a cross section of the urethra U perpendicularly in relation to the axial direction of the urethra U. The locking member 27 has been closed and locked. In FIG. 1b, the implantable constriction device 10 is illustrated in its open, unrestricted state, i.e. the state in which the implantable constriction device 10 is placed when the patient should urinate. In the open, unrestricted state, the first operable hydraulic constriction element 101a and the third operable hydraulic constriction element 101c is deflated for providing room for the urethra U, while the second and fourth operable hydraulic constriction elements 101b, 101d are inflated for assisting the urethra U assuming its normal substantially circular cross section. As such, hydraulic fluid is pumped from the first and third operable hydraulic constriction element 101a, 101c via the fluid conduits 109a,109c and hydraulic fluid is pumped into the second and fourth operable hydraulic constriction elements 101b,101d.

The first and second operable hydraulic constriction element 101a,101b may be connected to a shared first hydraulic system, such that the hydraulic fluid can be pumped from the first operable hydraulic constriction element 101a to the second operable hydraulic constriction element 101b for releasing the constriction of the urethra U for restoring the flow of urine therethrough, and pumped from the second operable hydraulic constriction element 101b to the first operable hydraulic constriction element 101a for constricting the urethra U and restricting the flow of urine therethrough.

The third and fourth operable hydraulic constriction element 101c, 101d may be connected to a shared second hydraulic system, such that the hydraulic fluid can be pumped from the third operable hydraulic constriction element 101c to the fourth operable hydraulic constriction element 101d for releasing the constriction of the urethra U for restoring the flow of urine therethrough, and pumped from the fourth operable hydraulic constriction element 101d to the third operable hydraulic constriction element 101c for constricting the urethra U and restricting the flow of urine therethrough.

The shared first and second hydraulic systems may be separate from each other and thus without fluid communication. The advantage of having the first and third operable hydraulic constriction element 101a, 101c connected to separate hydraulic systems is that the first and third operable hydraulic constriction element 101a, 101c may be filled the same amount of hydraulic fluid irrespective of the amount of resistance from the urethra U that the respective first and third operable hydraulic constriction element 101a, 101c encounters. This means that the urethra U will always be centered in the implantable constriction device 10 which reduced the risk of tissue damage to the urethra U.

The first, second, third and fourth operable hydraulic constriction element 101a, 101b, 101c, 101d may be connected to a shared hydraulic system, such that the hydraulic fluid can be pumped from the first and third operable hydraulic constriction element 101a, 101c to the second and fourth operable hydraulic constriction element 101b, 101d for releasing the constriction of the urethra U for restoring the flow of urine therethrough, and pumped from the second and fourth operable hydraulic constriction element 101b, 101d to the first and third operable hydraulic constriction element 101a, 101c for constricting the urethra U and restricting the flow of urine therethrough.

Figure 1C:
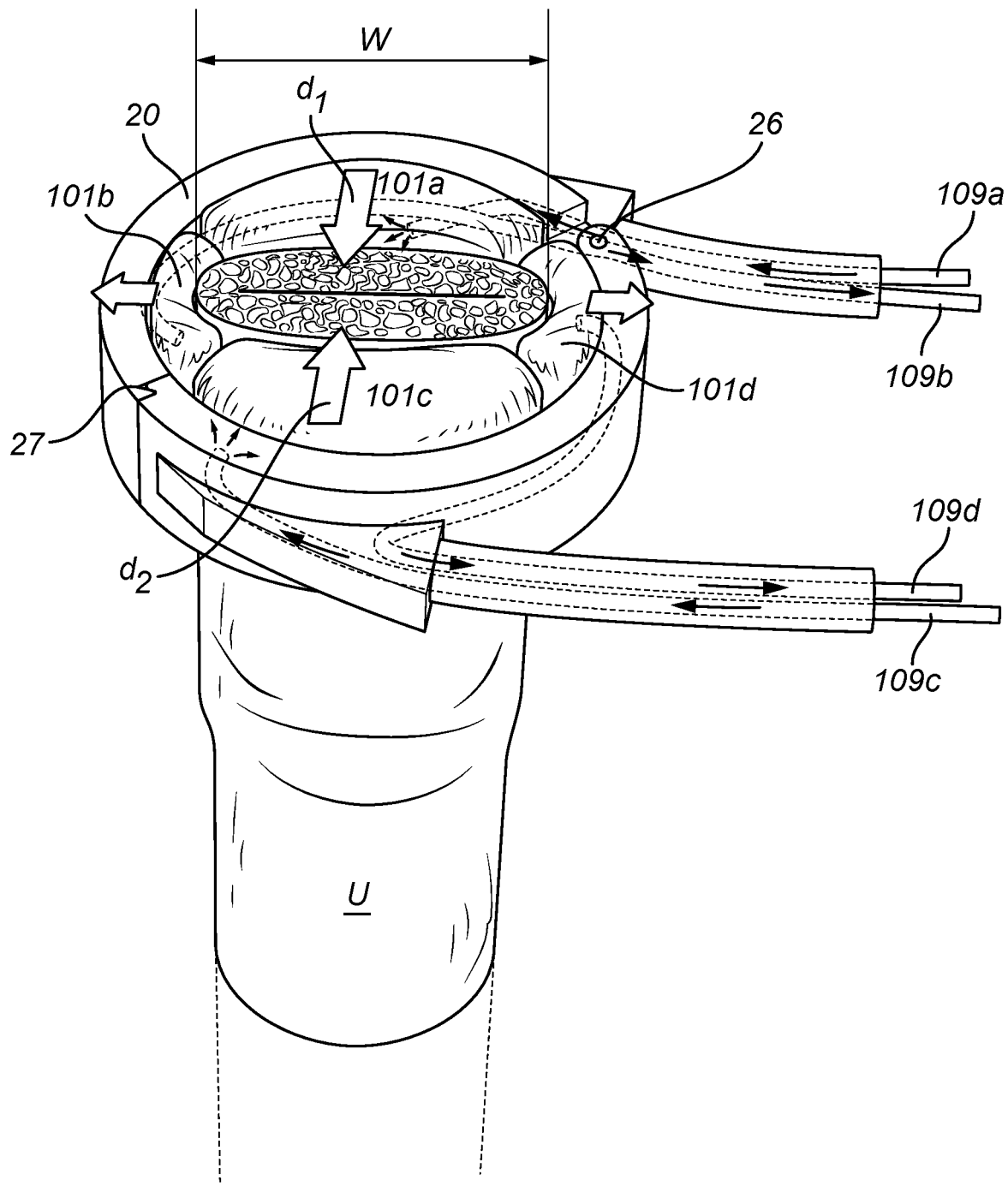
FIG. 1c shows an embodiment of an implantable constriction device for constricting the urethra of a patient, in an elevated view when placed around the urethra, in the state when the implantable constriction device constricts the urethra.

The first and third operable hydraulic constriction element 101a, 101c have larger volumes than the second and fourth operable hydraulic constriction element 101b, 101d. In the embodiment of FIG. 1a-1c, the first and third operable hydraulic constriction element 101a, 101c have a volume which is more than 1.5 times as large as the volume of the second and fourth operable hydraulic constriction element 101b, 101d, however it is also conceivable the that the first and third operable hydraulic constriction element 101a, 101c have a volume which is more than 2 times as large as the volume of the second and fourth operable hydraulic constriction element 101b, 101d.

When closed, the surrounding structure 20 is substantially rigid and has a modulus of elasticity (E), radially, in the range 0.2 GPa-1000 GPa or in the range 1 GPa-400 GPa. I.e. the modulus of elasticity calculated as the elastic deformation of an area of the inner surface 22 of the surrounding structure 20 causing an elongation in the radius R at that area when a force is applied to that area from the center of the surrounding structure 20. In the embodiment shown in FIG. 1b, the surrounding structure has a major portion, i.e. a portion making up more than half of the periphery P of the surrounding structure having a modulus of elasticity (E), in the extension of the periphery P of the surrounding structure, in the range 0.2 GPa-1000 GPa or in the range 1 GPa-400 GPa.

FIG. 1c shows the implantable constriction device 10 of the embodiment shown in FIGS. 1a-1c when the first and third operable hydraulic constriction elements 101a, 101c have been inflated with hydraulic fluid for compressing and restricting the urethra U and the second and fourth operable hydraulic constriction element 101b, 101d have been deflated to make room for the expansion of the width W of the urethra U that follows from the compression of the urethra U. The first and third operable hydraulic constriction element 101a, 101c expands against the withholding force from the rigid surrounding structure 20.

Figure 1D:
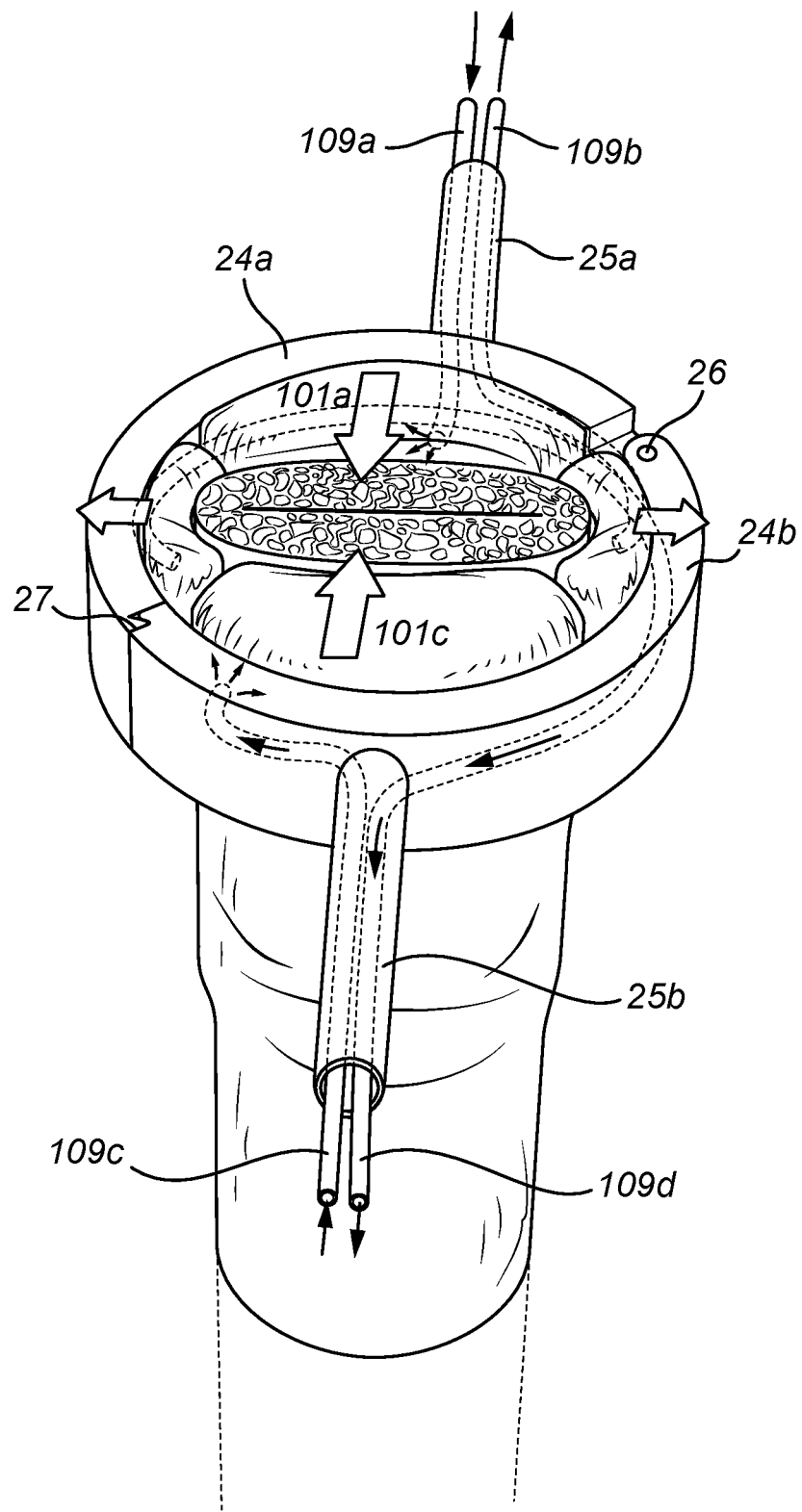
FIG. 1d shows an embodiment of an implantable constriction device for constricting the urethra of a patient, in an elevated view when placed around the urethra, in the state when the implantable constriction device constricts the urethra.

FIG. 1d shows an embodiment of the implantable constriction device 10 when in its constricted state. The embodiment of the implantable constriction device 10 shown in FIG. 1d is identical to the embodiment shown in FIGS. 1a-1c, the only difference being that the tubing fixation portions 25a, 25b enters the first and second support elements 24a, 24b perpendicularly into the first and second support elements 24a, 24b such that the fluid conduits 109a,109b,109c,109d enters the support elements 24a,24b perpendicularly, after which the fluid conduits is transferred over to the integrated channels in the support elements 24a,24b.

Figure 1E:
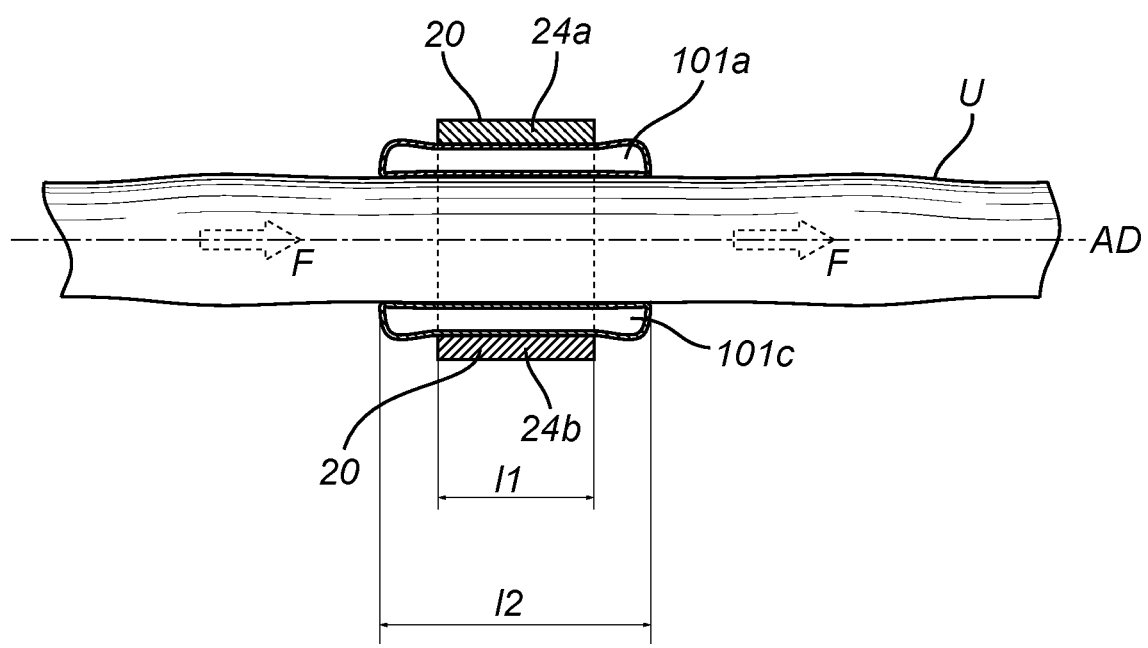
FIG. 1e shows an embodiment of an implantable constriction device for constricting the urethra of a patient, in a cross-sectional view.

FIG. 1e shows the embodiment of the implantable constriction device 10 described with reference to FIGS. 1a-1c in a cross sectional view when implanted and placed surrounding the urethra U, such that the flow F of urine can be restricted by a constriction substantially perpendicular to the axial direction AD of the urethra U. The support elements 24a,24b making up the surrounding structure 20 has a length l1 in the direction of the axial direction AD of the urethra U. The first 101a and third 101c operable hydraulic constriction elements has a length l2 in the axial direction AD of the urethra U. The length l2 of the first and third operable hydraulic constriction elements 101a, 101c is longer than the length of the support elements 24a, 24b and thereby than the length of the surrounding structure 20. In the embodiment shown in FIGS. 1 1a-1c the first and third first and third operable hydraulic constriction elements 101a, 101c are 1.2 times as long as the surrounding structure 20 but in alternative embodiments, the constriction elements may be as little as 1.1 times as long as the surrounding structure 20 or as much as 1.5 or 2 times as long as the surrounding structure 20. By the first and third operable hydraulic constriction elements 101a, 101c extending beyond the surrounding structure 20 both upstream and downstream in the axial direction AD of the urethra U. The first and third operable hydraulic constriction elements 101a, 101c can deform by flexing upwards and downwards to cover the rigid edges of the surrounding structure 20, such that the urethra U does not come in contact with the surrounding structure 20, which reduces the risk of damages to the urethra U. In the embodiment shown in FIG. 1e a major portion of the surrounding structure 20 is made from a rigid material, and a major portion of the first and third operable hydraulic constriction elements 101a, 101c are made from a resilient material, and the resilient material is more than 2 times as elastic as the rigid material.

Figure 2A:
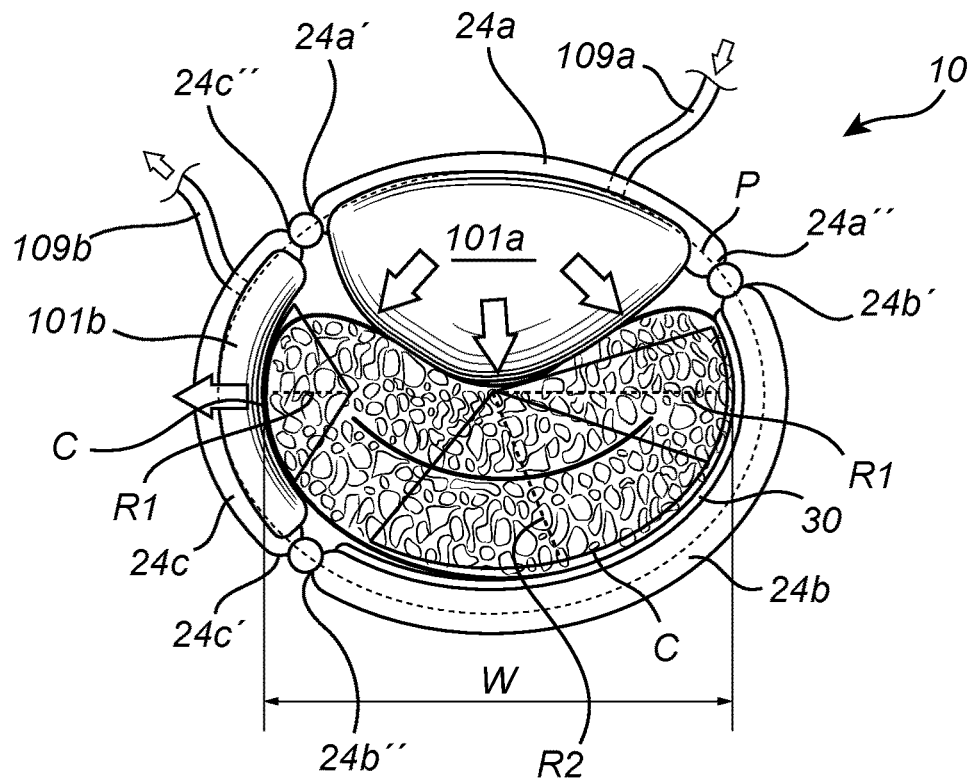
FIG. 2a shows an embodiment of an implantable constriction device for constricting the urethra of a patient when placed around the urethra, in the state when the implantable constriction device constricts the urethra.

FIG. 2a shows an embodiment of the implantable constriction device 10 in which the surrounding structure 20 is made from three support elements 24a, 24b, 24c and in which the implantable constriction device 10 comprises a first, second and third urethra contacting element. The first support element 24a comprises a urethra contacting element in the form of a first operable hydraulic constriction elements 101a configured to be inflated to constrict the urethra U and thereby restrict the flow F of urine therethrough. The first support element 24a comprises a first and second connection portion 24a', 24a''. The second connection portion 24a'' is connected to the second support element 24b which comprises a urethra contacting element in the form of a cushioning element 30 which is more resilient than the support element 24b and thereby provides a less damaging contacting surface against the urethra U, such that damage to the urethra U is minimized. The first connecting portion 24a' of the first support element 24a, and the second connecting portion 24b'' of the second support element 24b are connected to first and second connecting portions 24c', 24c'' of the third support element 24c. The third support element 24c comprises a second urethra contacting element in the form of a second operable hydraulic constriction element 101b. When the first, second and third support elements 24a, 24b, 24c are connected, a periphery P of the surrounding structure 20 surrounds a cross section of the urethra U perpendicularly in relation to the axial direction of the urethra U.

The first, second and third support elements 24a, 24b, 24c each comprises a curvature C adapted for the curvature of the urethra U such that the implantable constriction device 10 fits snuggly around the urethra U such that the distance that the operable hydraulic constriction elements 101a, 101c needs to expand to constrict the urethra U is kept at a minimum. In the embodiment shown in FIG. 2a, a curvature C of the second support element 24b has a radius R2 of about 10 mm and a curvature C of the third support element 24c has a radius R1 of about 7 mm as the surrounding structure 20 in the embodiment of FIGS. 2a and 2b has an oval cross-section and periphery P, perpendicular to the axial direction of the urethra U. In the embodiment of FIG. 2a, the second support structure 24b comprises a first and a second curvature C wherein the first curvature has a first radius R1 and the second curvature has a second radius R2 and wherein the first radius R1 is smaller than the second radius R2. However, it is conceivable that the radii R1, R2 of the curvatures C are anywhere in the range 5 mm-30 mm, and the second radius R2 may be at least 1.1 or at least 1.2 times as large as the first radius R1. In alternative embodiments it is conceivable that the surrounding structure has a circular cross-section perpendicular to the axial direction of the urethra U, such as shown in the embodiment of FIG. 3f, in which case the radii R1, R2 of the curvatures C of the first (curvature not shown), second and third support elements 24a, 24b, 24c are the same.

In FIG. 2a, the implantable constriction device 10 is shown in the state in which the first operable hydraulic constriction element 101a has been inflated with hydraulic fluid for compressing and restricting the urethra U and the second operable hydraulic constriction element 101b has been deflated to make room for the expansion of the width W of the urethra U that follows from the compression of the urethra U. The first and third operable hydraulic constriction element 101a, 101c expands against the withholding force from the rigid surrounding structure 20.

Figure 2B:
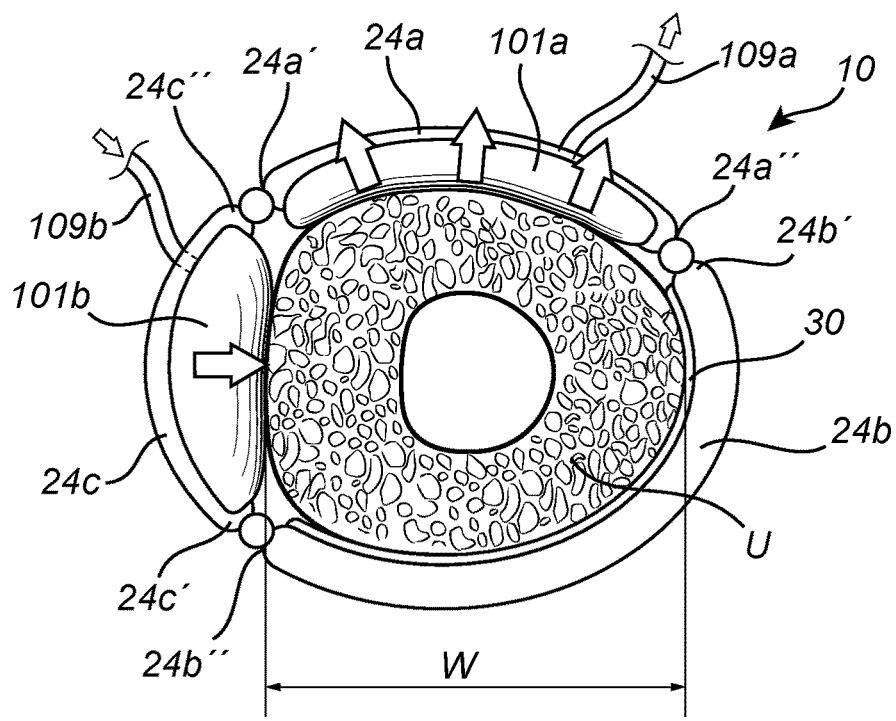
FIG. 2b shows an embodiment of an implantable constriction device for constricting the urethra of a patient when placed around the urethra, in the state when the constriction of the urethra is released.

In FIG. 2b, the implantable constriction device 10 is illustrated in its open, unrestricted state, i.e. the state in which the implantable constriction device 10 is placed when the patient should urinate. In the open, unrestricted state, the first operable hydraulic constriction element 101a is deflated for providing room for the urethra U, while the second operable hydraulic constriction element 101b is inflated for assisting the urethra U assuming its normal substantially circular cross section. As such, hydraulic fluid is pumped from the first operable hydraulic constriction element 101a via the fluid conduit 109a and hydraulic fluid is pumped into the second operable hydraulic constriction element 101b.

In the embodiment of FIGS. 2a and 2b the hydraulic fluid conduits 109a, 109b, and thereby the operable hydraulic constriction elements 101a, 101b are connected to a hydraulic pump and control system (not shown), such as any the hydraulic pump and control systems disclosed with reference to FIGS. 5-9. The controller of the hydraulic pump and control system is configured to control the flow of fluid from a hydraulic pump, such that the first operable hydraulic constriction element 101a is inflated, and the second operable hydraulic constriction element 101b is deflated, for constricting the urethra U for restricting the flow of urine therethrough (as shown in FIG. 2a). The controller of the hydraulic pump and control system is further configured to control the flow of fluid from a hydraulic pump such that the first operable hydraulic constriction element 101a is deflated, and the second operable hydraulic constriction element 101b is inflated for releasing the constriction of the urethra U for restoring the flow of urine therethrough (as shown in FIG. 2b). The first and second operable hydraulic constriction element 101a, 101b may be connected to a shared hydraulic system, such that the hydraulic fluid can be pumped from the first operable hydraulic constriction element 101a to the second operable hydraulic constriction element 101b for releasing the constriction of the urethra U for restoring the flow of urine therethrough, and pumped from the second operable hydraulic constriction element 101b to the first operable hydraulic constriction element 101a for constricting the urethra U and restricting the flow of urine therethrough.

FIG. 3a shows an overview of an implantable constriction device 10 when the implantable constriction device 10 is assembled from a kit for forming the surrounding structure 20. The surrounding structure 20 having a periphery P surrounding the urethra U when implanted. The kit comprising a first, second, third and fourth support element 24a, 24b, 24c, 24d. The second, third and fourth support elements 24b, 24c, 24d are all configured to be connected to the first support element 24a for forming the surrounding structure 20. By having a kit of exchangeable support elements, the surrounding structure can be made to match the urethra of the particular patient. In the embodiment shown in FIG. 3a, the second support 24b element has a curvature C having the same radius R1 as a curvature C of the first support element 24a. The third support element 24c is adapted for a larger urethra and has a more U-shaped cross section perpendicular to the axial direction of the urethra U and thus has a curvature C having a smaller radius R3. The fourth support element 24d is adapted for a smaller urethra and has a shallower cross-section perpendicular to the axial direction of the urethra U and thus has a curvature C having a larger radius R3 than the radii R1 and R2. The first support element 24a comprises a first operable hydraulic constriction element 101a configured to be inflated with a hydraulic fluid entering the first operable hydraulic constriction element 101a through a first hydraulic fluid conduit 109a via a tubing fixation portion 25a for constricting a portion of the tissue wall of the urethra and thereby restrict the flow of urine therethrough. The second, third and fourth support elements 24b, 24c, 24d all comprise a second operable hydraulic constriction element 101b configured to be inflated with a hydraulic fluid entering the second operable hydraulic constriction element 101b through a second hydraulic fluid conduit 109b via a tubing fixation portion 25b for constricting a portion of the tissue wall of the urethra and thereby restrict the flow of urine therethrough. The first, second, third and fourth support elements 24a, 24b, 24c, 24d all comprises connecting portions 24a', 24b', 24c', 24d', 24a", 24b",24c",24d" for connecting the first support element 24a to the second, third and fourth support elements 24b,24c,24d respectively. The connections could be hinged connections or fixed connections.

The first operable hydraulic constriction element 101a is connected to a first hydraulic system and the second operable hydraulic constriction element 101b is connected to a second hydraulic system separate from the first hydraulic system. The advantage of having the first and second operable hydraulic constriction element 101a,101b connected to separate hydraulic systems is that the first and second operable hydraulic constriction element 101a,101d may be filled the same amount of hydraulic fluid irrespective of the amount of resistance from the urethra U that the respective first and second operable hydraulic constriction element 101a,101b encounters. This means that the urethra U will always be centered in the implantable constriction device 10 which reduced the risk of tissue damage to the urethra U.

FIG. 3b shows an alternative embodiment of the supporting element 24c. The supporting element 24c has an identical curvature and connecting portions 24c',24c", the difference is that the supporting element 24c of the embodiment shown in FIG. 3b does not comprise an operable hydraulic constriction element, instead the supporting element 24c comprises a cushioning element 30 configured to contact the urethra. The cushioning element 30 is fixated to the inner surface of the support element 24c by means of an adhesive and is more resilient than the support element 24c. The cushioning element 30 is made from a solid medical grade silicone or polyurethane material.

FIG. 3c shows an alternative embodiment of the supporting element 24d. The supporting element 24d has an identical curvature and connecting portions 24d',24d", the difference is that the supporting element 24d of the embodiment shown in FIG. 3c does not comprise an operable hydraulic constriction element, instead the supporting element 24d comprises a cushioning element 30 configured to contact the urethra. The cushioning element 30 is fixated to the inner surface of the support element 24d by means of an adhesive and is more resilient than the support element 24d. The cushioning element 30 is made from a solid medical grade silicone or polyurethane material.

FIG. 3d shows an alternative embodiment of the supporting element 24c. The supporting element of FIG. 3d has an identical curvature but is in turn divided into a second and third support elements 24b, 24c such that the surrounding structure will be comprised of three support elements 24a(of FIG. 3a), 24b, 24c together having a periphery encircling the urethra. The second and third support elements 24b, 24c each comprises connecting portions 24b', 24b", 24c', 24c" such that a first connecting portion 24b' of the second support element 24b can be connected to the first support element and a second connecting portion 24b" of the second support element 24b can be connected to the first connecting portion 24c' of the third support element 24c and a second connecting portion 24c" of the third support element 24c can be connected to the first support element. The second and third support elements 24b, 24c each comprises cushioning elements 30a, 30b configured to contact the urethra. The cushioning elements 30a, 30b are fixated to the inner surface of the support elements 24b, 24c by means of an adhesive and is more resilient than the support elements 24b, 24c. The cushioning elements 30a, 30b are made from a solid medical grade silicone or polyurethane material.

FIG. 3e shows an alternative embodiment of the supporting element 24d. The supporting element of FIG. 3e has an identical curvature but is in turn divided into a second and third support elements 24b, 24c such that the surrounding structure will be comprised of three support elements 24a(of FIG. 3a), 24b, 24c together having a periphery encircling the urethra. The second and third support elements 24b, 24c each comprises connecting portions 24b', 24b", 24c', 24c" such that a first connecting portion 24b' of the second support element 24b can be connected to the first support element and a second connecting portion 24b" of the second support element 24b can be connected to the first connecting portion 24c' of the third support element 24c and a second connecting portion 24c" of the third support element 24c can be connected to the first support element. The second and third support elements 24b, 24c each comprises cushioning elements 30a, 30b configured to contact the urethra. The cushioning elements 30a, 30b are fixated to the inner surface of the support elements 24b, 24c by means of an adhesive and is more resilient than the support elements 24b, 24c. The cushioning elements 30a, 30b are made from a solid medical grade silicone or polyurethane material.

FIG. 3f shows an embodiment similar to the combination of the first and second support element 24a, 24b of FIG. 3a. The difference being that the lower portion, equivalent to the second support element 24b of FIG. 3a, is divided into a second and third support element 24b, 24c, such that the surrounding structure will be comprised of three support elements 24a, 24b, 24c together having a circular periphery P encircling the urethra. The first, second and third support elements 24a, 24b, 24c each comprises connecting portions 24a', 24a", 24b', 24b", 24c', 24c" such that a first connecting portion 24b' of the second support element 24b can be connected to a second connecting portion 24a" of the first support element 24a and a second connecting portion 24b" of the second support element 24b can be connected to the first connecting portion 24c' of the third support element 24c and a second connecting portion 24c" of the third support element 24c can be connected to a first connecting portion 24a' of the first support element 24a. The first, second and third support elements 24a, 24b, 24c all comprise operable hydraulic constriction elements 101a, 101b, 101c configured to be inflated with a hydraulic fluid entering the operable hydraulic constriction elements 101a, 101b, 101c through a first, second and third hydraulic fluid conduit 109, 109b, 109c via a tubing fixation portions 25a, 25b, 25c for constricting a portion of the tissue wall of the urethra and thereby restrict the flow of urine therethrough. In the embodiment of FIG. 3f, the first support element 24a has a first length la extending along a portion of the periphery P of the surrounding structure 20. The second and third support element 24b, 24c have a second and third length lb, lc, respectively, extending along a portion of the periphery P of the surrounding structure 20. In the embodiment of FIG. 3f, the second and third lengths lb, lc are equally long and the first length la is more than 1.2 times as long as the second and third lengths.

A major portion of the all the support elements of the embodiments of FIGS. 1a-3f can be made of a substantially rigid material, such that the resulting surrounding structure becomes substantially rigid. The material of the major portion may comprise a material having a modulus of elasticity (E), in the range 0.2 GPa-1000 GPa or in the range 1 GPa-400 GPa. The material could for example be a biocompatible metallic material, such as titanium or a medical grade metal alloy, such as medical grade stainless steel. In the alternative, material could be a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The support elements could also comprise at least one composite material, such as any combination of metallic/ceramic and polymer materials or a polymer material reinforced with organic or inorganic fibers, such as carbon or mineral fibers.

In the embodiments of FIGS. 1a-3f, the hydraulic fluid conduits, and thereby the operable hydraulic constriction elements are configured to be connected to a hydraulic pump and control system, such as any the hydraulic pump and control systems disclosed with reference to FIGS. 5-9.

Figure 4:
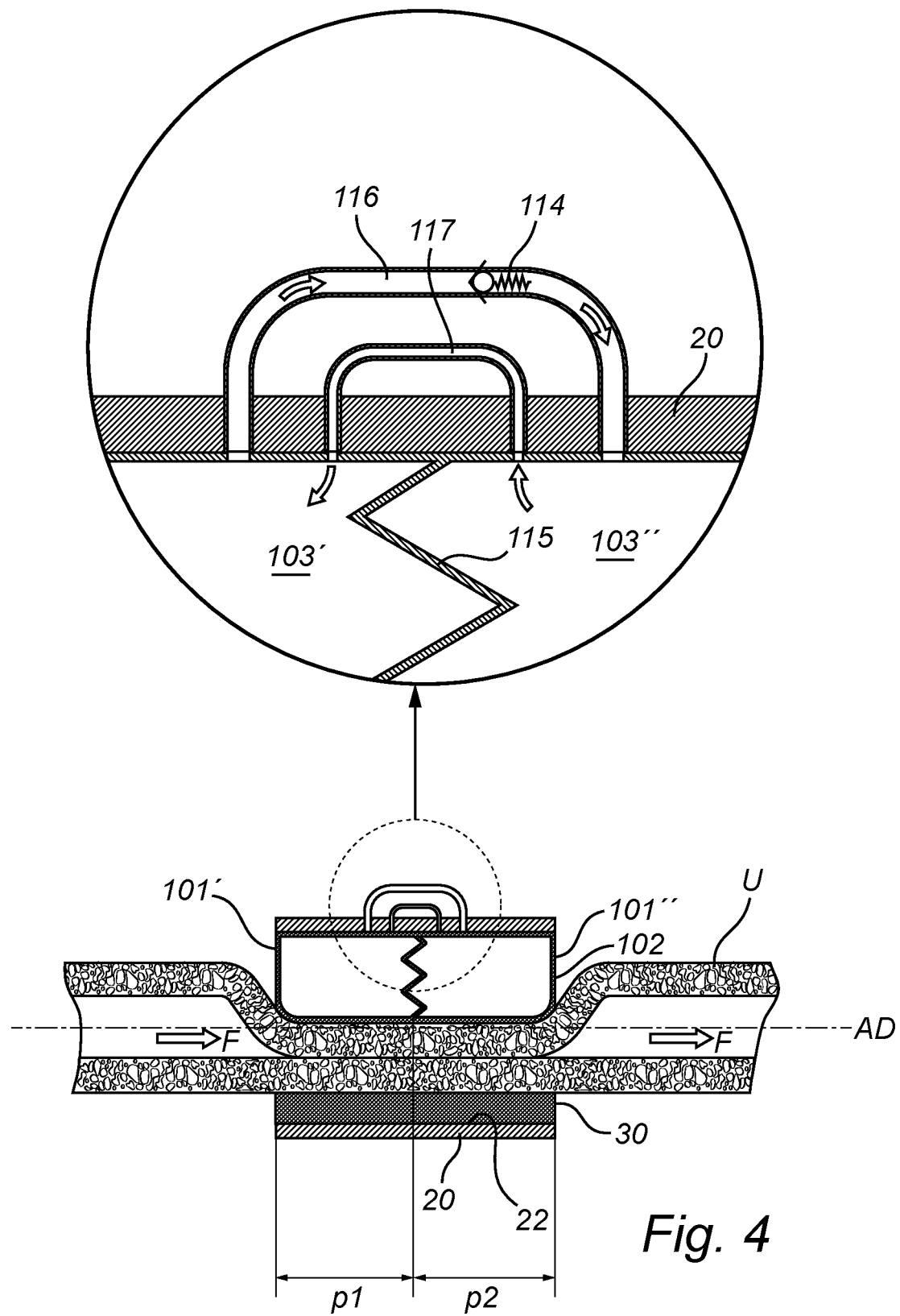
FIG. 4 shows an embodiment of an implantable constriction device for constricting the urethra of a patient in a sectional side view, in its constricted state.
Figure 5:
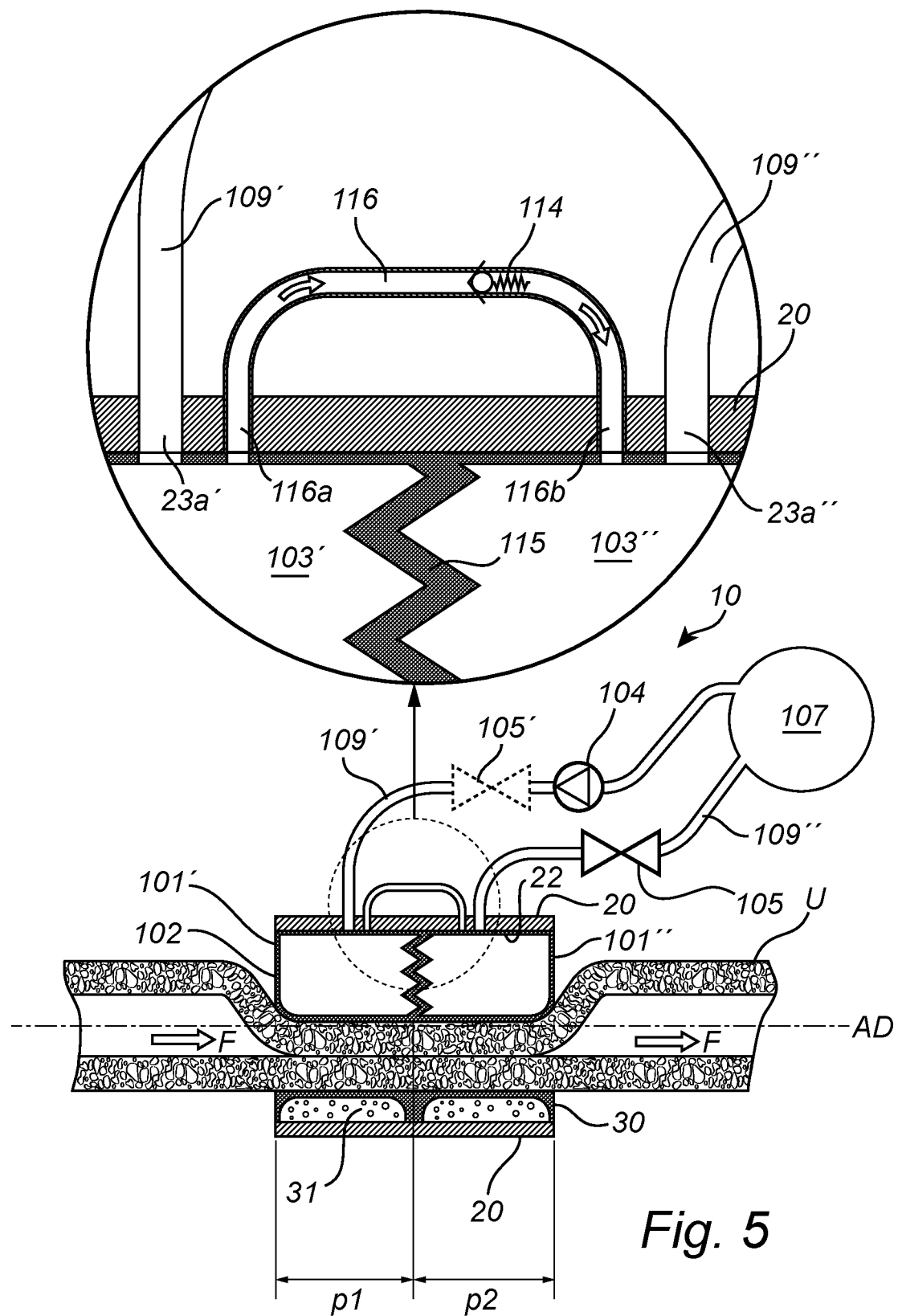
FIG. 5 shows an embodiment of an implantable constriction device for constricting the urethra of a patient in a sectional side view, in its constricted state.

FIG. 4 shows a schematic view of an embodiment of an implantable constriction device 10 for constricting a urethra U of a patient. In the embodiment of FIG. 5 the implantable constriction device 10 comprises a first operable hydraulic constriction element 101' configured to be inflated to constrict the urethra U for restricting the flow of urine therethrough, and a second operable hydraulic constriction element 101" configured to be inflated to constrict the urethra U for restricting the flow of urine therethrough. The first and second operable hydraulic constriction elements 101', 101" are configured to be connected to a hydraulic pump and control system, such as any the hydraulic pump and control systems disclosed with reference to FIGS. 5-9.

The first operable hydraulic constriction element 101' is configured to be placed at a first portion p1 of the urethra U for constricting the first portion p1 of the urethra U for restricting the flow of urine therethrough, and the second operable hydraulic constriction element 101" is configured to be placed at a second portion p2 of the urethra U, downstream the first portion p1, for constricting the second portion p2 of the urethra U for restricting the flow of urine therethrough.

The lumen 103' of the first operable hydraulic constriction element 101' is connected to the lumen 103" of the second operable hydraulic constriction element 101" by means of an interconnecting fluid conduit 116, and as such, the first operable hydraulic constriction element 101' is in fluid connection with the second operable hydraulic constriction element 101". The fluid connection is configured to conduct fluid from the first operable hydraulic constriction element 101' to the second operable hydraulic constriction element 101" when the pressure increases in the first operable hydraulic constriction element 101', such that second operable hydraulic constriction element constricts 101" the second portion p2 of the urethra U further.

In the embodiment shown in FIG. 4, the first and second operable hydraulic constriction elements 101',101" are of the same size. It is however equally conceivable that the first and second operable hydraulic constriction elements 101', 101" have different sizes, such as for example described with reference to FIG. 9.

When a patient is resting, the pressure on the urinary sphincter from the urinary bladder is typically about 50 cm H2O. However, when the patient is moving, running, jumping, laughing, or sneezing, this pressure may increase to about 100 cm H2O. If an artificial urinary sphincter is configured to exert a continuous pressure high enough to handle these pressure spikes, the blood flow to the tissue of the urethra U will be hampered, which in the long term could lead to damage of the urethra U and in the worst cases necrosis. The implantable constriction device 10 of the embodiment of FIG. 4 solves this problem by having a first and a second operable hydraulic constriction element 101', 101" placed sequentially along the axial direction AD of the urethra U, such that the first and second operable hydraulic constriction elements 101', 101" can exert a constant moderate force on the urethra U which the tissue of the urethra U can endure long term. However, when the pressure temporarily increases in the urethra U, the pressure first increases in the first operable hydraulic constriction element 101', as the first operable hydraulic constriction element 101' is positioned upstream in relation to the direction of the flow F of urine, and thereby closest to the urinary bladder. The increased pressure in the first operable hydraulic constriction element 101' causes fluid to be conducted from the first operable hydraulic constriction element 101', through the interconnecting fluid conduit 116 into the second operable hydraulic constriction element 101". The flow of fluid into the second operable hydraulic constriction element 101" increases the pressure in the second operable hydraulic constriction element 101" causing the second operable hydraulic constriction element 101" to exert a higher pressure on the second portion p2 of the urethra U further constricting the urethra U and thereby preventing leakage through the implantable constriction device 10 during the pressure increase. The interconnecting fluid conduit 116 comprises a check valve 114 which means that the fluid in the second operable hydraulic constriction element 101" cannot return to the first operable hydraulic constriction element 101' through the interconnecting fluid conduit 116.

In the embodiment of FIG. 4, the implantable constriction device 10 comprises a second interconnecting fluid conduit 117 fluidly connecting the first operable hydraulic constriction element 101' to the second operable hydraulic constriction element 101". A cross section of a tubular lumen of the second interconnecting fluid conduit 117 has an area which is less than 0.5 times a cross section area of a tubular lumen of the first interconnecting fluid conduit 116. In the alternative, the second interconnecting fluid conduit 117 could comprise a hydraulic restrictor valve restricting the flow over the valve allowing a small leakage over the valve, which means that the pressures in the first operable hydraulic constriction element 101' and the second operable hydraulic constriction element 101" will reach an equilibrium over time. That time may be in the interval 1-10 minutes, or may be more than 10 seconds, or may be between 10 seconds and 1 hour or may be less than one hour.

As an increased pressure is to be present in the second operable hydraulic constriction element 101" for a longer time than it is to be present in the first operable hydraulic constriction element 101', the second operable hydraulic constriction element 101" may be configured to hold a higher pressure than the first operable hydraulic constriction element 101'. A wall of the second operable hydraulic constriction element 101" may be thicker than a wall of the first operable hydraulic constriction element 101', e.g. the wall of the second operable hydraulic constriction element may be more than 1.5 times as thick as the wall of the first operable hydraulic constriction element. In the alternative, or as a combination, the material of the wall of the second operable hydraulic constriction element 101" may be more durable than the material of the wall of the first operable hydraulic constriction element 101'. The material of the wall of the second operable hydraulic constriction element 101" may be made from a material which is less elastic than the material of the wall of the first operable hydraulic constriction element 101', e.g. the material of the wall of the first operable hydraulic constriction element 101' may be more than 1.2 times as elastic as the material of the wall of the second operable hydraulic constriction element 101".

The lumens 103', 103" of the first and second operable hydraulic constriction elements 101', 101" are divided by a resilient division wall 115, which in the embodiment of FIG. 4 is a wall made from the same medical grade silicone as the other walls 102 of the first and second operable hydraulic constriction elements 101',101" and concurrently made in the same molding process, which means that the resilient division wall 115 is materially integrated with the other walls 102 of the first and second operable hydraulic constriction elements 101',101". In the embodiment shown in FIG. 4 the division wall 115 is pleated such that the division wall 115 can accordion fold when the first and second operable hydraulic constriction elements 101',101" are compressed.

In the embodiment of FIG. 4, the implantable constriction device 10 further comprises a surrounding structure 20 having a periphery surrounding the urethra U when implanted. The surrounding structure 20 is substantially rigid and a major portion of the surrounding structure 20 could for example comprise a biocompatible metallic material, such as titanium or a medical grade metal alloy, such as medical grade stainless steel. In the alternative, the surrounding structure 20 could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The surrounding structure 20 could also comprise at least one composite material, such as any combination of metallic/ceramic and polymer materials or a polymer material reinforced with organic or inorganic fibers, such as carbon or mineral fibers. In the embodiment shown in FIG. 4, the material of the major portion of the surrounding structure 20 has a modulus of elasticity (E) in the range 0.2 GPa-1000 GPa or more specifically in the range 1 GPa-400 GPa. The major portion of the surrounding structure 20 being made from a stiff material results in that the surrounding structure 20 has a modulus of elasticity (E), radially, in the range 0.2 GPa-1000 GPa or more specifically in the range 1 GPa-400 GPa, which means that the supporting structure 20 only expands an insignificant distance when the operable hydraulic constriction devices are expanded to close the urethra U, which means that it can be established with high precision that the fluid pumped into the operable hydraulic constriction devices are used for exerting a closing force on the urethra U.

The surrounding structure 20 comprises an inner surface 22 configured to face the urethra U, when implanted. The portion of the wall of the first and second operable hydraulic constriction elements 101',101" facing the inner surface 22 of the surrounding structure 20 is configured to be fixated to the inner surface 22 of the surrounding structure 20 e.g. by means of an adhesive.

In the embodiment shown in FIG. 4, the implantable constriction device 10 further comprises at least one cushioning element 30 configured to contact the urethra U. The cushioning element is fixated to the inner surface 22 of the surrounding structure 20 by means of an adhesive and is more resilient than the surrounding structure 20. The cushioning element 30 is made from a solid medical grade silicone or polyurethane material.

In the embodiment shown in FIG. 4, the two fluid connections 116a, 116b to the interconnecting fluid conduit 116 and the two fluid connections 117a, 117b to the second interconnecting fluid conduit 117 runs through the surrounding structure 20 by means of channels in the form of through-holes running through, and being integrated in, the surrounding structure 20.

FIG. 5 shows an overview of an embodiment of an implantable constriction device 10 for constricting the urethra U of a patient. In the embodiment of FIG. 5 the implantable constriction device 10 comprises a first operable hydraulic constriction element 101' configured to be inflated to constrict the urethra U for restricting the flow of urine therethrough, and a second operable hydraulic constriction element 101" configured to be inflated to constrict the urethra U for restricting the flow F of urine therethrough.

The first operable hydraulic constriction element 101' is configured to be placed at a first portion p1 of the urethra U for constricting the first portion p1 of the urethra U for restricting the flow F of urine therethrough, and the second operable hydraulic constriction element 101" is configured to be placed at a second portion p2 of the urethra U, downstream the first portion p1, for constricting the second portion p2 of the urethra U for restricting the flow F of urine therethrough.

A first portion 109' of a first reservoir conduit 109 is connected to the lumen 103' of the first operable hydraulic constriction element 101' and a second portion 109" of the first reservoir conduit 109 is connected to the lumen 103" of the second operable hydraulic constriction element 101". The lumen 103' of the first operable hydraulic constriction element 101' is connected to the lumen 103" of the second operable hydraulic constriction element 101" by means of an interconnecting fluid conduit 116, and as such, the first operable hydraulic constriction element 101' is in fluid connection with the second operable hydraulic constriction element 101". The fluid connection is configured to conduct fluid from the first operable hydraulic constriction element 101' to the second operable hydraulic constriction element 101" when the pressure increases in the first operable hydraulic constriction element 101', such that second operable hydraulic constriction element constricts 101" the second portion p2 of the urethra U further. In the embodiment shown in FIG. 5 the lumen 103' of the first operable hydraulic constriction element 101' has the same volume as the lumen 103" of the second operable hydraulic constriction element 101"

The lumens 103',103" of the first and second operable hydraulic constriction elements 101',101" are divided by a resilient division wall 115, which in the embodiment of FIG. 5 is a wall made from the same medical grade silicone as the other walls 102 of the first and second operable hydraulic constriction elements 101',101" and concurrently made in the same molding process, which means that the resilient division wall 115 is materially integrated with the other walls 102 of the first and second operable hydraulic constriction elements 101',101". In the embodiment shown in FIG. 5 the division wall 115 is pleated such that the division wall 115 can accordion-fold when the first and second operable hydraulic constriction elements 101',101" are compressed.

In the embodiment shown in FIG. 5, a pump 104 is placed on the first portion of the reservoir conduit 109', such that the pump 104 can pump a hydraulic fluid from the reservoir 107 to the first operable hydraulic constriction element 101'. The pump 104 may be of any of the types of hydraulic pumps disclosed herein.

In the embodiment shown in FIG. 5, an electrically operable valve 105 is placed on the second portion of the reservoir conduit 109", to open a fluid communication between the second operable hydraulic constriction element 101" and the reservoir 107. The electrically operable valve 105 may in any of the embodiments herein be an electrically operable ball valve, butterfly valve, swing valve, diaphragm valve, pinch valve, needle valve or gate valve, and the valve may be electrically operable by means of a solenoid.

The pump 104 moves fluid from the reservoirs 107 to the first operable hydraulic constriction element 101' and further via the interconnecting fluid conduit 116 to the second operable hydraulic constriction element 101" for expanding the first and second operable hydraulic constriction elements 101',101" for restricting the urethra U and thereby hindering the flow of urine though the urethra U. When the patient would like to urinate, the patient activates the pump 104 for moving fluid in the opposite direction, i.e. from the first operable hydraulic constriction element 101 to the reservoir 107, and opens the electrically operable valve 105 for allowing the fluid to flow from the second operable hydraulic constriction element 101" to the reservoir 107. This connects the first and second operable hydraulic constriction elements 101',101" and releases the restriction of the urethra U for allowing the flow of urine therethrough.

Depending on which type of pump it is, there may be a need to have an electrically operable valve 105' also connected in series with the hydraulic pump 104 to enable closure of the fluid communication between the first hydraulic constriction element 101' and the reservoir 107. However, in embodiments in which the hydraulic pump 104 is of a leak-free type that hinders leakage through the pump and/or hinders elasticity in the pump 104 and/or reservoir 107, such as for example a peristaltic pump, the electrically operable valve 105' may be omitted.

When a patient is resting, the pressure on the urinary sphincter from the urinary bladder is typically about 50 cm H2O. However, when the patient is moving, running, jumping, laughing, or sneezing, this pressure may increase to about 100 cm H2O. If an artificial urinary sphincter is configured to exert a continuous pressure high enough to handle these pressure spikes, the blood flow to the tissue of the urethra U will be hampered, which in the long term could lead to damage of the urethra U and in the worst cases necrosis. The implantable constriction device 10 of the embodiment of FIG. 5 solves this problem by having a first and a second operable hydraulic constriction element 101', 101" placed sequentially along the axial direction AD of the urethra U, such that the first and second operable hydraulic constriction elements 101', 101" can exert a constant moderate force on the urethra U which the tissue of the urethra U can endure long term. However, when the pressure temporarily increases in the urethra U, the pressure first increases in the first operable hydraulic constriction element 101', as the first operable hydraulic constriction element 101' is positioned upstream in relation to the direction of the flow F of urine, and thereby closest to the urinary bladder. The increased pressure in the first operable hydraulic constriction element 101' causes fluid to be conducted from the first operable hydraulic constriction element 101', through the interconnecting fluid conduit 116 into the second operable hydraulic constriction element 101". The flow of fluid into the second operable hydraulic constriction element 101" increases the pressure in the second operable hydraulic constriction element 101" causing the second operable hydraulic constriction element 101" to exert a higher pressure on the second portion p2 of the urethra U further constricting the urethra U and thereby preventing leakage through the implantable constriction device 10 during the pressure increase. The interconnecting fluid conduit 116 comprises a check valve 114 which means that the fluid in the second operable hydraulic constriction element 101" cannot return to the first operable hydraulic constriction element 101' through the interconnecting fluid conduit 116. The increased pressure in the second operable hydraulic constriction element 101" can then be contained for as long as it is considered necessary, after which fluid can be returned to the reservoir 107 by the opening of the electrically operable valve 105 such that a pressure equilibrium is achieved between the first and second operable hydraulic constriction elements 101', 101".

The electrically operable valve 105 may be replaced by a hydraulic restrictor valve restricting the flow over the valve allowing a small leakage over the valve, which means that the pressures in the first operable hydraulic constriction element 101' and the second operable hydraulic constriction element 101" will reach an equilibrium over time. That time may be in the interval 1-10 minutes, or may be more than 10 seconds, or may be between 10 seconds and 1 hour or may be less than one hour.

In the embodiment of FIG. 5, the implantable constriction device 10 further comprises a surrounding structure 20 having a periphery surrounding the urethra U when implanted. The surrounding structure 20 is substantially rigid and a major portion of the surrounding structure 20 could for example comprise a biocompatible metallic material, such as titanium or a medical grade metal alloy, such as medical grade stainless steel. In the alternative, the surrounding structure 20 could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The surrounding structure 20 could also comprise at least one composite material, such as any combination of metallic/ceramic and polymer materials or a polymer material reinforced with organic or inorganic fibers, such as carbon or mineral fibers. In the embodiment shown in FIG. 5, the material of the major portion of the surrounding structure 20 has a modulus of elasticity (E) in the range 0.2 GPa-1000 GPa or more specifically in the range 1 GPa-400 GPa. The major portion of the surrounding structure 20 being made from a stiff material results in that the surrounding structure 20 has a modulus of elasticity (E), radially, in the range 0.2 GPa-1000 GPa or more specifically in the range 1 GPa-400 GPa, which means that the supporting structure 20 only expands an insignificant distance when the operable hydraulic constriction devices are expanded to close the urethra U, which means that it can be established with high precision that the fluid pumped into the operable hydraulic constriction devices are used for exerting a closing force on the urethra U.

The surrounding structure 20 comprises an inner surface 22 configured to face the urethra U, when implanted. The portion of the wall of the first and second operable hydraulic constriction elements 101',101" facing the inner surface 22 of the surrounding structure 20 is configured to be fixated to the inner surface 22 of the surrounding structure 20 e.g. by means of an adhesive.

In the embodiment shown in FIG. 5, the implantable constriction device 10 further comprises at least one cushioning element 30 configured to contact the urethra U. The cushioning element is fixated to the inner surface 22 of the surrounding structure 20 by means of an adhesive and is more resilient than the surrounding structure 20. The cushioning element 30 is made from a medical grade silicone material and is filled with a biocompatible gel 31 which enables the cushioning element 30 to be shaped to suit the urethra U which reduces the risk that the contact with the urethra U damages the urethra U. In alternative embodiments, it is conceivable that the cushioning element 30 comprises a solid resilient material, such as a soft medical grade silicone of polyurethane material.

In the embodiment shown in FIG. 5, the first and second portions 109',109" of the first reservoir conduit 109 and the two fluid connections to the interconnecting fluid conduit 116 runs through the surrounding structure 20 by means of channels 116a, 116b, 23a', 23a" in the form of through-holes running through, and being integrated in, the surrounding structure 20.

Figure 6A:
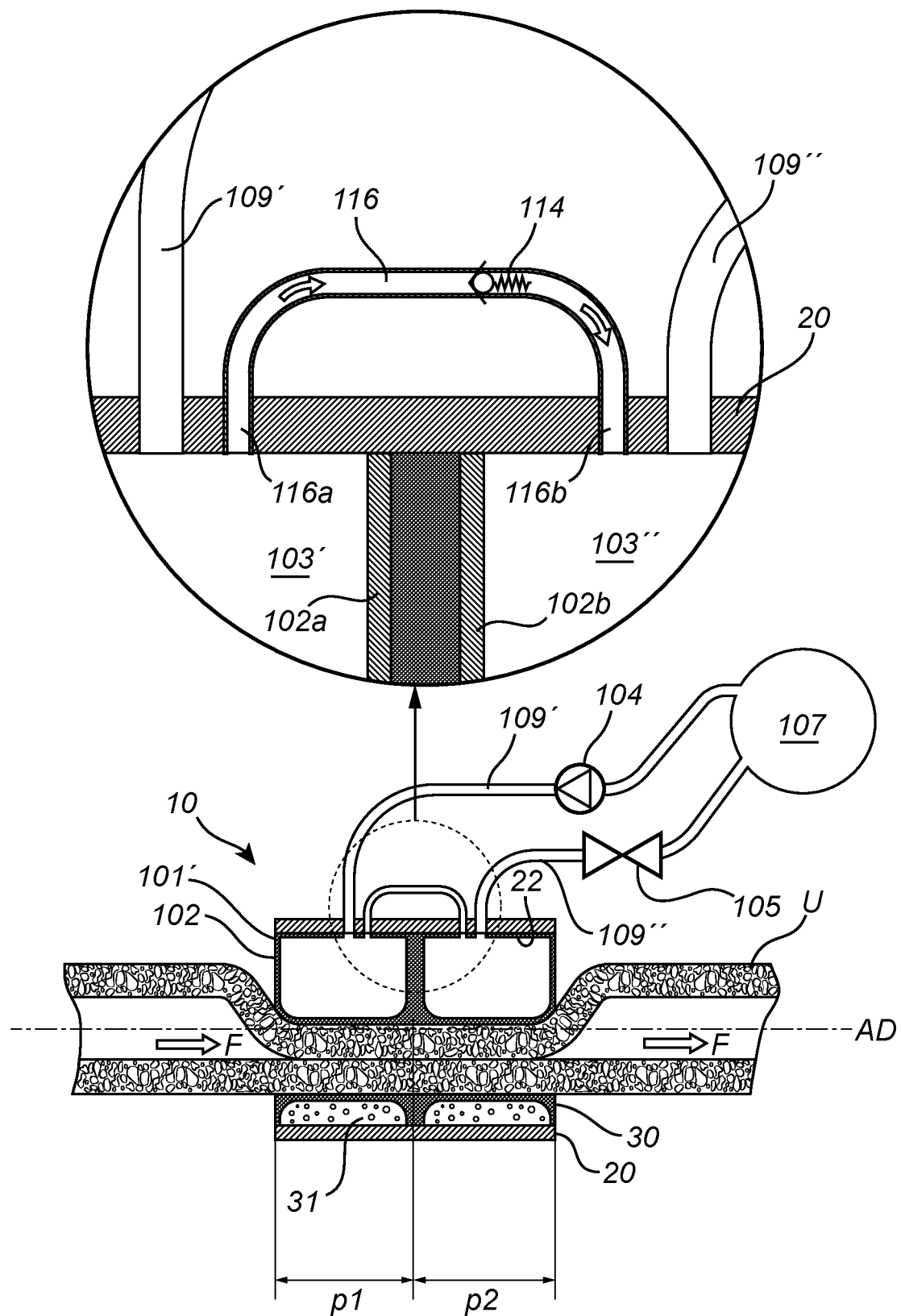
FIG. 6a shows an embodiment of an implantable constriction device for constricting the urethra of a patient in a sectional side view, in its constricted state.

FIG. 6a shows an overview of an embodiment of an implantable constriction device 10 for constricting a urethra U of a patient which is identical to the system described with reference to FIG. 5. The only difference is that the first and second operable hydraulic constriction elements 101', 101" are not materially integrated with each other. Instead, the implantable constriction device 10 in the embodiment of FIG. 6a comprises a first and second operable hydraulic constriction element 101', 101" that are separated from each other and placed with a small distance between a first wall portion 102a of the first operable hydraulic constriction element 101' and a first wall portion 102b of the second operable hydraulic constriction element. The first wall portions 102a, 102b are facing each other. Having the first and second operable hydraulic constriction elements 101', 101" separated from each other means that they can move individually and independently from each other. Fixating wall portions of the first and second operable hydraulic constriction element 101', 101" facing the inner surface 22 of the surrounding structure 20 are fixated to the inner surface 22 of the surrounding structure 20 by means of an adhesive. In the embodiment shown in FIG. 6, the first and second operable hydraulic constriction elements 101', 101" are of the same size. It is however equally conceivable that the first and second operable hydraulic constriction elements 101', 101" have different sizes, such as for example described with reference to FIG. 9. As an increased pressure is to be present in the second operable hydraulic constriction element 101" for a longer time than it is to be present in the first operable hydraulic constriction element 101', the second operable hydraulic constriction element 101" may be configured to hold a higher pressure than the first operable hydraulic constriction element 101'. The wall 102b of the second operable hydraulic constriction element 101" may be thicker than the wall 102a of the first operable hydraulic constriction element 101', e.g. the wall 102b of the second operable hydraulic constriction element 101" may be more than 1.5 times as thick as the wall 102a of the first operable hydraulic constriction element 101'. In the alternative, or as a combination, the material of the wall 102b of the second operable hydraulic constriction element 101" may be more durable than the material of the wall 102a of the first operable hydraulic constriction element 101'. The material of the wall 102b of the second operable hydraulic constriction element 101" may be made from a material which is less elastic than the material of the wall 102a of the first operable hydraulic constriction element 101', e.g. the material of the wall of the first operable hydraulic constriction element 101' may be more than 1.2 times as elastic as the material of the wall of the second operable hydraulic constriction element 101".

Figure 6B:
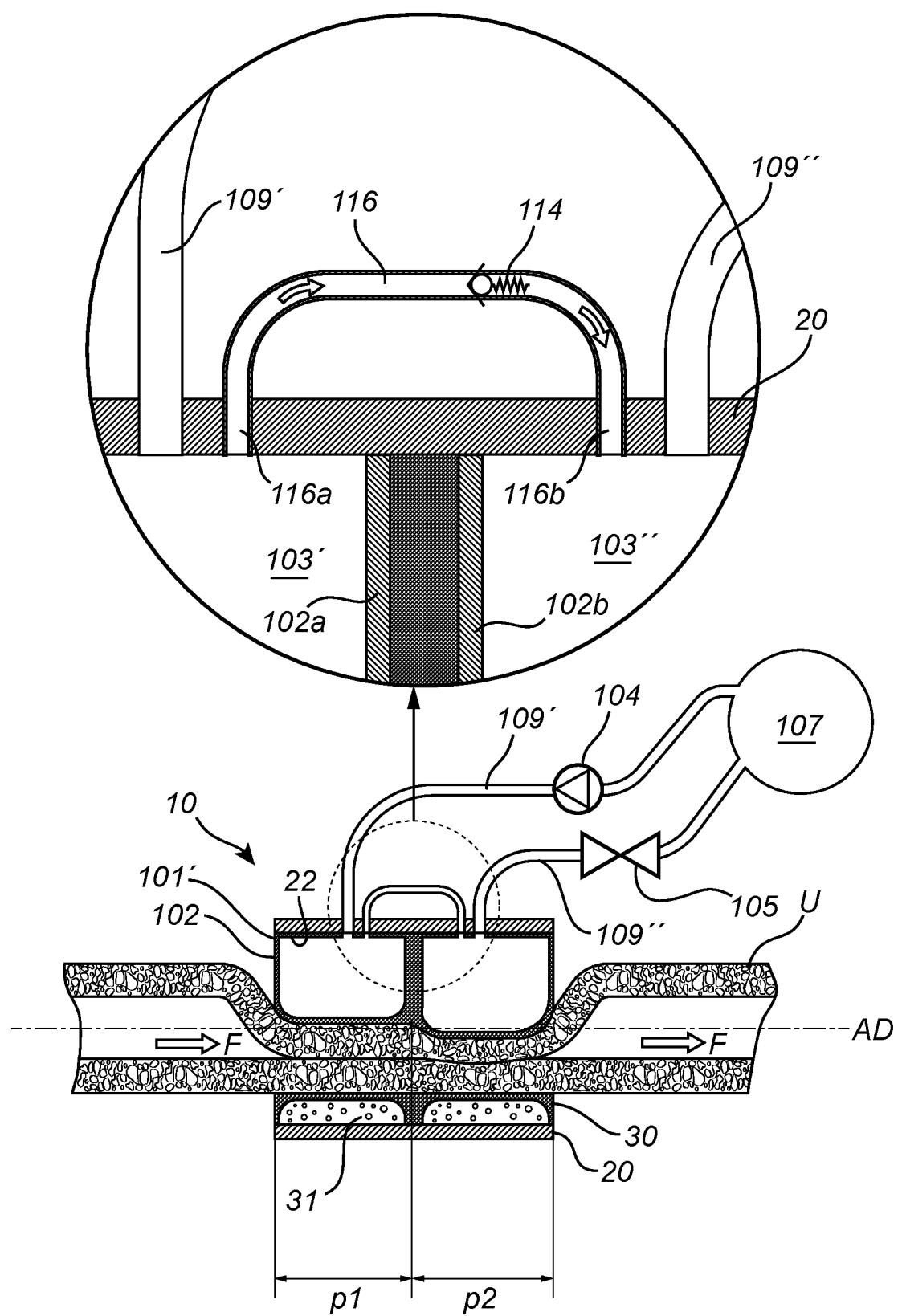
FIG. 6b shows an embodiment of an implantable constriction device for constricting the urethra of a patient in a sectional side view, in its constricted state.

FIG. 6b shows an overview of the embodiment of the implantable constriction device 10 for constricting the urethra U of a patient described with reference to FIG. 6a. In FIG. 6b, the implantable constriction device 10 is in the state in which the pressure in the urinary bladder and thus in the portion of the urethra U located upstream the implantable constriction device 10 has temporarily increased. The increase in pressure is e.g. a result of the patient moving, running, jumping, laughing, sneezing, or bending over causing the pressure in the urethra to increase to about 100 cm H2O. In increase in pressure in the urethra U causes the pressure to also increase in the first operable hydraulic constriction element 101' which forces hydraulic fluid to flow from the lumen 103' of the first operable hydraulic constriction element 101', through the interconnecting fluid conduit 116 and into the lumen 103" of the second operable hydraulic constriction element 101" causing the second operable hydraulic constriction element 101" to expand further and thus press harder on the second portion p2 of the urethra U for further constricting the urethra and thus preventing the leakage of urine through the implantable constriction device 10. The pressure in the second operable hydraulic constriction element 101" will increase to substantially the same pressure as in the urethra U and as the fluid cannot return to the first operable hydraulic constriction element 101' as the check valve 114 closes the flow of fluid from the second to the first operable hydraulic constriction element 101', 101" through the interconnecting fluid conduit 116. As such, the increased pressure in the second operable hydraulic constriction element 101" will remain until the pressure is released back to the reservoir 107 by the opening of the electrically operable valve 105.

Figure 7:
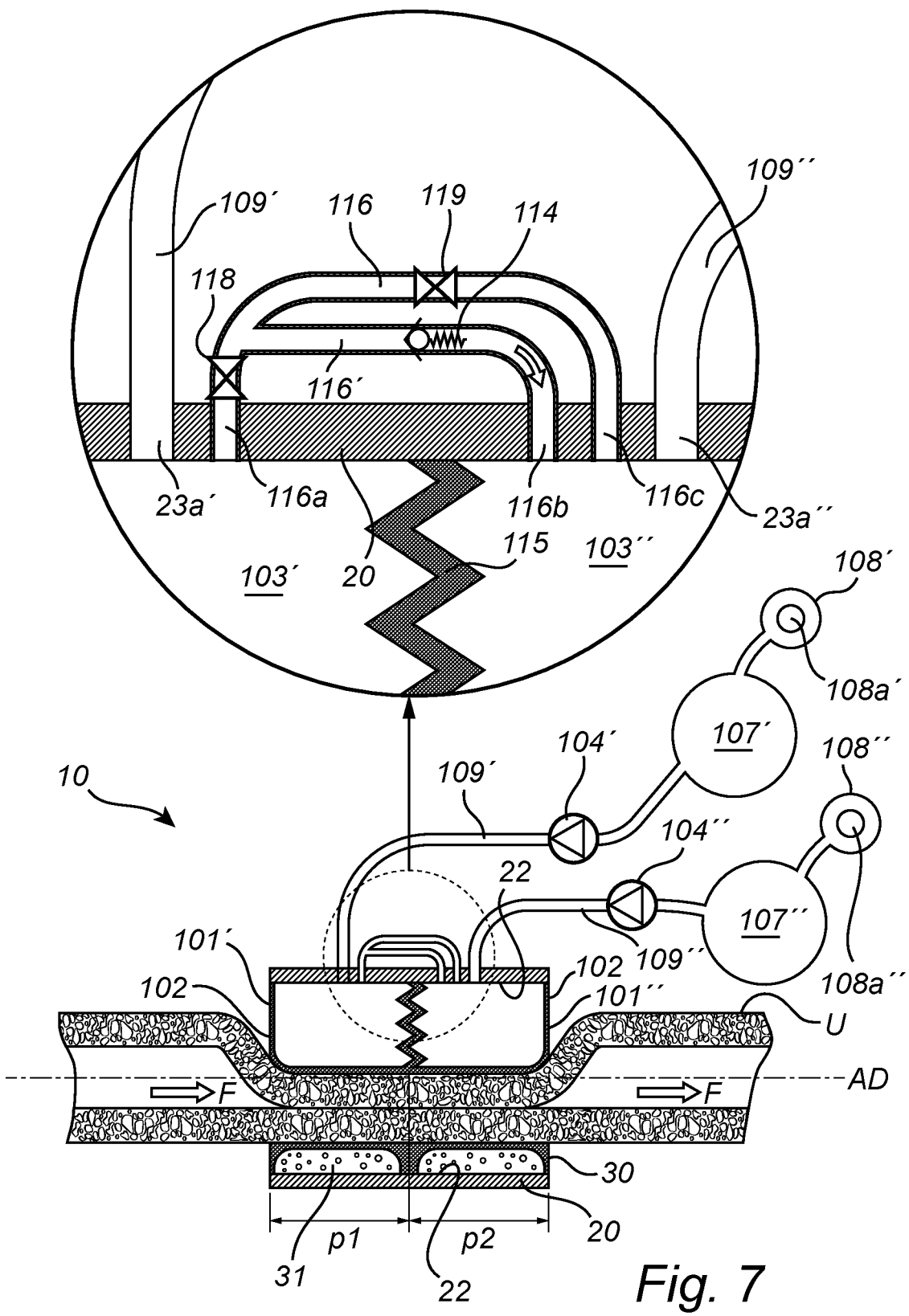
FIG. 7 shows an embodiment of an implantable constriction device for constricting the urethra of a patient in a sectional side view, in its constricted state.

FIG. 7 shows an overview of an embodiment of an implantable constriction device 10 for constricting a urethra U of a patient. In the embodiment of FIG. 7 the implantable constriction device 10 comprises a first operable hydraulic constriction element 101' configured to be inflated to constrict the urethra U for restricting the flow of urine therethrough, and a second operable hydraulic constriction element 101" configured to be inflated to constrict the urethra U for restricting the flow of urine therethrough.

The first operable hydraulic constriction element 101' is configured to be placed at a first portion p1 of the urethra U for constricting the first portion p1 of the urethra U for restricting the flow of urine therethrough, and the second operable hydraulic constriction element 101" is configured to be placed at a second portion p2 of the urethra U, downstream the first portion p1, for constricting the second portion p2 of the urethra U for restricting the flow of urine therethrough.

A first portion 109' of a first reservoir conduit 109 is connected to the lumen 103' of the first operable hydraulic constriction element 101' and a second portion 109" of the first reservoir conduit 109 is connected to the lumen 103" of the second operable hydraulic constriction element 101". The lumen 103' of the first operable hydraulic constriction element 101' is connected to the lumen 103" of the second operable hydraulic constriction element 101" by means of an interconnecting fluid conduit 116, and as such, the first operable hydraulic constriction element 101' is in fluid connection with the second operable hydraulic constriction element 101". The fluid connection is configured to conduct fluid from the first operable hydraulic constriction element 101' to the second operable hydraulic constriction element 101" when the pressure increases in the first operable hydraulic constriction element 101', such that second operable hydraulic constriction element constricts 101" the second portion p2 of the urethra U further. In the embodiment shown in FIG. 7 the lumen 103' of the first operable hydraulic constriction element 101' has the same volume as the lumen 103" of the second operable hydraulic constriction element 101"

The lumens 103', 103" of the first and second operable hydraulic constriction elements 101', 101" are divided by a resilient division wall 115, which in the embodiment of FIG. 7 is a wall made from the same medical grade silicone as the other walls 102 of the first and second operable hydraulic constriction elements 101', 101" and concurrently made in the same molding process, which means that the resilient division wall 115 is materially integrated with the other walls 102 of the first and second operable hydraulic constriction elements 101', 101". In the embodiment shown in FIG. 7 the division wall 115 is pleated such that the division wall 115 can accordion fold when the first and second operable hydraulic constriction elements 101', 101" are compressed.

In the embodiment shown in FIG. 7, a pump 104' is placed on the first portion of the reservoir conduit 109'. The pump 104' may be of any of the types of hydraulic pumps disclosed herein. The pump 104' is fluidly connected to the first operable hydraulic constriction element 101'. Another pump 104" is placed on the second portion of the reservoir conduit 109". The pump 104" may also be of any of the types of hydraulic pumps disclosed herein. The pump 104" is fluidly connected to the second operable hydraulic constriction element 101".

The pumps 104', 104" moves fluid from the reservoirs 107', 107" to the first and second operable hydraulic constriction elements 101', 101", respectively, for expanding the first and second operable hydraulic constriction elements 101', 101" for restricting the urethra U and thereby hindering the flow of urine though the urethra U. When the patient would like to urinate, the patient activates the pumps 104 for moving fluid in the opposite direction, i.e. from the first and second operable hydraulic constriction elements 101', 101" to the reservoirs 107', 107", which contracts the first and second operable hydraulic constriction elements 101', 101" and releases the restriction of the urethra U for allowing the flow of urine therethrough.

Depending on which type of pumps it is, there may be a need to have electrically operable valves connected in series with the hydraulic pumps 104', 104" to enable closure of the fluid communication between the first and second operable hydraulic constriction elements 101', 101" and the first reservoirs 107', 107". However, in embodiments in which the hydraulic pumps 104', 104" are of a type that hinders leakage through the pumps and/or hinders elasticity in the pumps 104', 104" and/or reservoirs 107', 107", such as for example a peristaltic pump, an electrically operable valve may be omitted.

When a patient is resting, the pressure on the urinary sphincter is typically about 50 cm H2O. However, when the patient is moving, running, jumping, laughing, or sneezing, this pressure may increase to about 100 cm H2O. If an artificial urinary sphincter is configured to exert a continuous pressure high enough to handle these pressure spikes, the blood flow to the tissue of the urethra U will be hampered, which in the long term could lead to damage of the urethra U and in the worst cases necrosis. The implantable constriction device 10 of the embodiment of FIG. 7 solves this problem by having a first and a second operable hydraulic constriction element 101', 101" placed sequentially along the axial direction AD of the urethra U, such that the first and second operable hydraulic constriction elements 101', 101" can exert a constant moderate force on the urethra U which the tissue of the urethra U can endure long term. However, when the pressure temporarily increases in the urethra U, the pressure first increases in the first operable hydraulic constriction element 101', as the first operable hydraulic constriction element 101' is positioned upstream in relation to the direction of the flow F of urine, and thereby closest to the urinary bladder. The increased pressure in the first operable hydraulic constriction element 101' causes fluid to be conducted from the first operable hydraulic constriction element 101', through a first portion of an interconnecting fluid conduit 116' into the second operable hydraulic constriction element 101". The flow of fluid into the second operable hydraulic constriction element 101" increases the pressure in the second operable hydraulic constriction element 101" causing the second operable hydraulic constriction element 101" to exert a higher pressure on the second portion p2 of the urethra U further constricting the urethra and thereby preventing leakage through the implantable constriction device 10 during the pressure increase. The first portion of the interconnecting fluid conduit 116' comprises a check valve 114 which means that the fluid in the second operable hydraulic constriction element 101" cannot return to the first operable hydraulic constriction element 101' through the first portion of the interconnecting fluid conduit 116'. In the embodiment shown in FIG. 7, the implantable constriction device 10 comprises a second portion of the interconnecting fluid conduit 116" for creating a second route for fluid to be conducted from the first operable hydraulic constriction element 101' to the second operable hydraulic constriction element 101'. The second portion of the interconnecting fluid conduit 116" comprises an electrically operable valve 119 which is closed in normal operation but enables the return of fluid from the second operable hydraulic constriction element 101" to the first operable hydraulic constriction element 101' when the pressure in the second operable hydraulic constriction element 101" does not need to be increased any longer. I.e. the system shown in FIG. 7 enables the pressure to increase in the second operable hydraulic constriction element 101" when the pressure increases in the urethra. The increased pressure in the second operable hydraulic constriction element 101" can then be contained for as long as it is considered necessary, after which fluid can be returned to the first operable hydraulic constriction element 101' by the opening of the electrically operable valve 119 such that a pressure equilibrium is achieved between the first and second operable hydraulic constriction elements 101', 101". In the embodiment shown in FIG. 7, the joint portion of the interconnecting fluid conduit 116 also comprises an electrically operable valve 118 such that the fluid connection between the first and second operable hydraulic constriction elements 101', 101" can be closed entirely.

The electrically operable valve 119 may be replaced by a hydraulic restrictor valve restricting the flow over the valve allowing a small leakage over the valve, which means that the pressures in the first operable hydraulic constriction element 101' and the second operable hydraulic constriction element 101" will reach an equilibrium over time. That time may be in the interval 1-10 minutes, or may be more than 10 seconds, or may be between 10 seconds and 1 hour or may be less than one hour.

The implantable constriction device 10 shown in FIG. 7 further comprises a first injection port 108' in fluid connection with the first reservoir 107', for injecting fluid into the first reservoir 107 when the first reservoir 107 is implanted. The implantable constriction device 10 further comprises a second injection port 108" in fluid connection with the second reservoir 107", for injecting fluid into the second reservoir 107" when the second reservoir 107" is implanted. In the embodiments shown in FIG. 7, the first and second injection ports 108', 108" are configured to be placed subcutaneously and comprises self-sealing injection port membranes 108a', 108a" for example made from a medical grade hard silicone, such that an injection needle can be inserted through the skin of the patient and through the self-sealing membranes 108a', 108a" and be removed substantially without the occurrence of any leakage.

The injection ports 108', 108" enables the fluid level in the hydraulic restriction device 10 to be calibrated. The calibration could enable the calibration of the amount of fluid in the reservoirs 107', 107", the pressure in the reservoirs 107', 107" and/or the amount of fluid in the first and second operable hydraulic constriction element 101', 101", for calibrating the amount of pressure which could be exerted on the urethra U. The injection ports 108', 108" could also be used to re-fill the system in case of leakage in the hydraulic restriction device 10, or in case some of the hydraulic fluid diffuses through a material of the hydraulic restriction device 10, or in case some part of the hydraulic restriction device 10 distends as a result of material fatigue.

In the embodiment of FIG. 7, the implantable constriction device 10 further comprises a surrounding structure 20 having a periphery surrounding the urethra U when implanted. The surrounding structure 20 is substantially rigid and a major portion of the surrounding structure 20 could for example comprise a biocompatible metallic material, such as titanium or a medical grade metal alloy, such as medical grade stainless steel. In the alternative, the surrounding structure 20 could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The surrounding structure 20 could also comprise at least one composite material, such as any combination of metallic/ceramic and polymer materials or a polymer material reinforced with organic or inorganic fibers, such as carbon or mineral fibers. In the embodiment shown in FIG. 7, the material of the major portion of the surrounding structure 20 has a modulus of elasticity (E) in the range 0.2 GPa-1000 GPa or more specifically in the range 1 GPa-400 GPa. The major portion of the surrounding structure 20 being made from a stiff material results in that the surrounding structure 20 has a modulus of elasticity (E), radially, in the range 0.2 GPa-1000 GPa or more specifically in the range 1 GPa-400 GPa, which means that the supporting structure 20 only expands an insignificant distance when the operable hydraulic constriction devices are expanded to close the urethra U, which means that it can be established with high precision that the fluid pumped into the operable hydraulic constriction devices are used for exerting a closing force on the urethra U.

The surrounding structure 20 comprises an inner surface 22 configured to face the urethra U, when implanted. The inner surface 22 of the surrounding structure 20 forms one portion of the wall of the first and second operable hydraulic constriction element 101',101". The resilient wall of the first and second operable hydraulic constriction element 101', 101" is fixated to the support structure by means of an adhesive.

In the embodiment shown in FIG. 7, the implantable constriction device 10 further comprises at least one cushioning element 30 configured to contact the urethra U. The cushioning element is fixated to the inner surface 22 of the surrounding structure 20 by means of an adhesive and is more resilient than the surrounding structure 20. The cushioning element 30 is made from a medical grade silicone material and is filled with a biocompatible gel 31 which enables the cushioning element 30 to be shaped to suit the urethra U which reduces the risk that the contact with the urethra U damages the urethra U. In alternative embodiments, it is conceivable that the cushioning element 30 comprises a solid resilient material, such as a soft medical grade silicone of polyurethane material.

In the embodiment shown in FIG. 7, the first and second reservoir conduits 109', 109" and the three fluid connections 116a, 116b, 116c to the interconnecting fluid conduit 116, 116', 116" runs through the surrounding structure 20 by means of channels in the form of through-holes running through, and being integrated in, the surrounding structure 20.

The surrounding structure 20 and the integrated channels shown in FIG. 7 may be replaced by the surrounding structures described with reference to FIGS. 1a-3f.

Figure 8A:
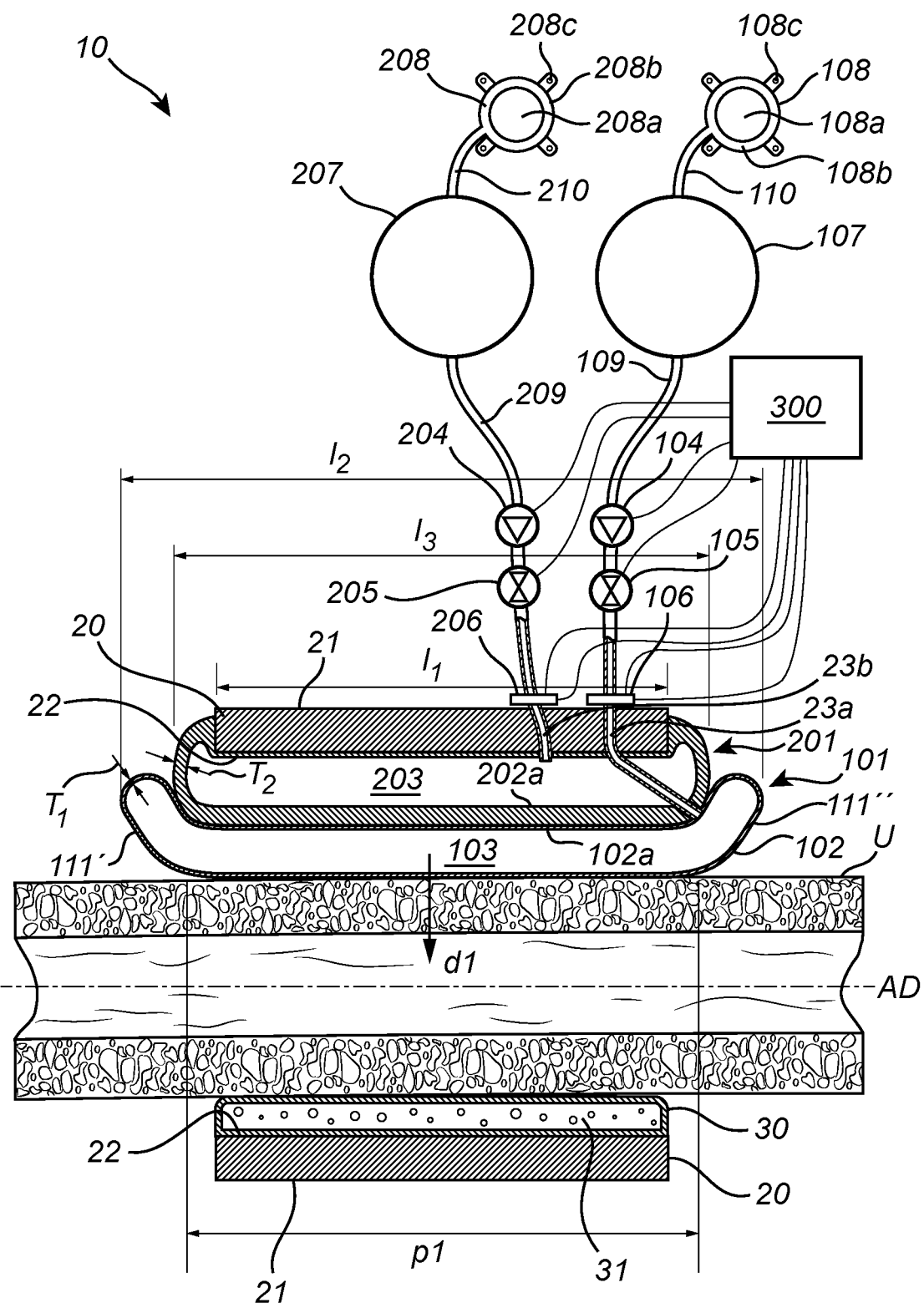
FIG. 8a shows an embodiment of an implantable constriction device for constricting the urethra of a patient in a sectional side view, in its un-constricted state.

FIG. 8a shows an overview of an embodiment of an implantable constriction device 10 for constricting a urethra U of a patient. The urethra U is a luminary organ or tube that connects the urinary bladder to the urinary meatus for the removal of urine from the body. In males, the urethra U is on average 18 to 20 centimeters and in females the urethra U is on average about 4 centimeters. The urethra U comprises the urethral sphincters which are two muscles that in normal function control the exit of urine from the urinary bladder through the urethra U. The urethra U has a substantially circular cross section and is elongated in an axial direction AD from the urinary bladder to the urinary meatus.

The implantable constriction device 10 comprises a first operable hydraulic constriction element 101 configured to be inflated and thereby expand in a first direction d1 towards the urethra U to constrict a first portion p1 of the urethra U for restricting the flow of urine therethrough. The first operable hydraulic constriction element 101 comprises a lumen 103 surrounded by a resilient wall 102 made from a biocompatible material such as a medical grade silicone or a medical grade polyurethane-based material.

The implantable constriction device 10 further comprises a supporting operable hydraulic constriction element 201 configured to be inflated and thereby expand in the first direction d1 towards the urethra U to support the first operable hydraulic constriction element 101 in constricting the first portion p1 of the urethra U for restricting the flow of urine therethrough. The supporting operable hydraulic constriction element 201 comprises a lumen 203 surrounded by a resilient wall 202 made from a biocompatible material such as a medical grade silicone or a medical grade polyurethane-based material. The supporting operable hydraulic constriction element 201 is connected to the first operable hydraulic constriction element 101 at the contacting walls 102a, 202a of the first operable hydraulic constriction element 101 and the supporting operable hydraulic constriction element 201. The connection may be realized simply by abutment or by friction or by an adhesive or by the contacting walls 102a, 202a of the first operable hydraulic constriction element 101 and the supporting operable hydraulic constriction element 201 being materially integrated with each other by concurrent manufacturing or by subsequent thermal bonding.

In the embodiment shown in FIG. 8a, the supporting operable hydraulic constriction element 201 is less resilient than the first operable hydraulic constriction element 101 which means that the supporting operable hydraulic constriction element 201 is more rigid and less prone to change its size and/or location by external forces pushing on the supporting operable hydraulic constriction element 201. For example, the supporting operable hydraulic constriction element 201 is more stable along the axial direction of the urethra U, which means that the supporting operable hydraulic constriction element 201 will retain its position along the axial direction AD of the urethra U, such that the force exerted on the urethra U in the first direction d1 is exerted on the first portion p1 of the urethra U. In the embodiment shown in FIG. 8a, the supporting operable hydraulic constriction element 201 is more rigid than the first operable hydraulic constriction element 101 by the wall 202 of the supporting operable hydraulic constriction element 201 having a thickness T2 being thicker than the thickness T1 of the wall 102 of the first operable hydraulic constriction element 101. In the embodiment shown in FIG. 8a, the resilient wall 202 of the supporting operable hydraulic constriction element 201 is more than 1.5 times thicker than a portion of the wall 102 of the first operable hydraulic constriction element 101. In alternative embodiments, it is equally conceivable that the wall 202 of the supporting operable hydraulic constriction element 201 is more than 2 times thicker than a portion of the wall 102 of the first operable hydraulic constriction element 101 for further increasing the stability of the supporting operable hydraulic constriction element 202.

In an alternative embodiment, which could be combined with the difference in thickness describe with reference to FIG. 8a, the supporting operable hydraulic constriction element 201 could be made more rigid than the first operable hydraulic constriction element 101 by at least a portion of the resilient wall 102 of the first operable hydraulic constriction element 101 comprising a first material, and at least a portion of the resilient wall 202 of the supporting operable hydraulic constriction element 201 comprising a second material. The second material has a modulus of elasticity which is higher than a modulus of elasticity of the first material. As an example, the first material could be a medical grade silicone material, and the second material could be another, less elastic medical grade silicone. According to one embodiment, the modulus of elasticity of the second material is more than 1.5 times higher than the modulus of elasticity of the first material. According to another embodiment, the modulus of elasticity of the second material is more than 2 times higher than the modulus of elasticity of the first material.

In the embodiment shown in FIG. 8a, the implantable constriction device 10 further comprises a first hydraulic pump 104, a second hydraulic pump 204, a first reservoir 107 for holding hydraulic fluid and a second reservoir for holding hydraulic fluid 207. The implantable constriction device 10 further comprises a first reservoir conduit 109, fluidly connecting the first reservoir 107 to the first operable hydraulic constriction element 101, and a supporting reservoir conduit 209, fluidly connecting the second reservoir 207 to the supporting operable hydraulic constriction element 201. The first hydraulic pump 104 is configured to pump fluid from the first reservoir 107 to the first operable hydraulic constriction element 101 through the first reservoir conduit 109, for constricting the urethra U. The second hydraulic pump 204 is configured to pump fluid from the second reservoir 207 to the supporting operable hydraulic constriction element 201 through the supporting reservoir conduit 209, for assisting in the constriction of the urethra U.

The implantable constriction device according to the embodiment of FIG. 8a further comprises a first pressure sensor 106 positioned on the first reservoir conduit 109 and configured to sense the pressure in the first operable hydraulic constriction element 101, and a second pressure sensor 206 on the supporting reservoir conduit 209 configured to sense the pressure in the supporting operable hydraulic constriction element 201. The pressure sensors may in alternative embodiments be positioned differently, for example in or directly on the first operable hydraulic constriction element 101 and in or on the supporting operable hydraulic constriction element 201 respectively, or in direct or indirect connection with the lumens 103, 203 of the first operable hydraulic constriction element 101 and the supporting operable hydraulic constriction element 201, respectively.

The first and second hydraulic pumps 104, 204 could be a type of hydraulic pump disclosed herein. Depending on which type of pump it is, there may be a need to have electrically operable valves 105, 205 connected in series with the hydraulic pumps 104, 204 to enable closure of the fluid communication between the first operable hydraulic constriction element 101 and the first reservoir 107 and between the supporting operable hydraulic constriction element 201 and the second reservoir 207, respectively. However, in embodiments in which the hydraulic pumps are of a type that hinders leakage through the pump and/or hinders elasticity in the pump and/or reservoir, such as for example a peristaltic pump, the electrically operable valves 105, 205 may be omitted.

The implantable constriction device 10 shown in FIG. 8a further comprises an implantable controller 300 configured to control the first and second hydraulic pump 104, 204, and the electrically operable valve 105, 205. The implantable controller is further configured to receive input from the first and second pressure sensor 106, 206. The input from the first and/or second pressure sensor 106, 206 may be used as input for the control of the first and/or second pump 104, 204 and/or for the control of the electrically operable valves 105, 205 for ultimately controlling the pressure in the first operable hydraulic constriction element 101 and/or the supporting operable hydraulic constriction element 201 for controlling the force exerted on the urethra U.

The implantable constriction device 10 shown in FIG. 8a further comprises a first injection port 108 in fluid connection with the first reservoir 107, via a first injection port conduit 110, for injecting fluid into the first reservoir 107 when the first reservoir 107 is implanted. The implantable constriction device 10 further comprises a second injection port 208 in fluid connection with the second reservoir 207, via a second injection port conduit 210, for injecting fluid into the second reservoir 207 when the second reservoir 207 is implanted. In the embodiments shown in FIG. 8a, the first and second injection ports 108, 208 are configured to be placed subcutaneously. The injection ports 108, 208 each comprises a housing 108b, 208b which supports self-sealing injection port membranes 108a, 208a for example made from a medical grade hard silicone, such that an injection needle can be inserted through the skin of the patient and through the self-sealing membranes 108a, 208a and be removed substantially without the occurrence of any leakage. The injection ports 108, 208 further comprises fixation portions 108c, 208c enabling the fixation of the injection ports 108, 208 subcutaneously to for example muscular fascia and/or at least one bone fascia and/or at least one cortical bone layer and/or at least one muscular layer and/or fibrotic tissue and/or any part of the abdominal wall and/or any part of the subcutaneous space and its surroundings in the body. The fixation is for example realized by means of sutures through the small holes in the fixation portions 108c, 208c.

The injection ports 108, 208 enables the fluid level in the hydraulic restriction device 10 to be calibrated. The calibration could enable the calibration of the amount of fluid in the reservoirs 107, 207, the pressure in the reservoirs 107, 207 and/or the amount of fluid in the first and/or supporting operable hydraulic constriction element 101, 201, for calibrating the amount of pressure which could be exerted on the urethra U. The injection ports 108, 208 could also be used to re-fill the system in case of leakage in the hydraulic restriction device 10, or in case some of the hydraulic fluid diffuses through a material of the hydraulic restriction device 10, or in case some part of the hydraulic restriction device 10 distends as a result of material fatigue.

In an alternative embodiment, the injection port may be an integrated portion of the reservoir, such that for example a portion of the wall of the medical device may comprise the self-sealing membrane injection port membrane such that additional hydraulic fluid can be injected directly into the reservoir.

Turning again to the first and/or supporting operable hydraulic constriction elements 101, 201. The supporting operable hydraulic constriction element 201 has a length l3 in the axial direction AD of the urethra U, when implanted. The first operable hydraulic constriction element 101 has a length l2 in the axial direction AD of the urethra U. In the embodiment shown in FIG. 8a the length l2 of the first operable hydraulic constriction element 101 is longer than the length l3 of the supporting operable hydraulic constriction element 201. In the embodiment shown in FIG. 8a, the first operable hydraulic constriction element 101 is more than 1.1 times longer than the length l3 of the supporting operable hydraulic constriction element 201. As the first operable hydraulic constriction element 101 is more resilient than the supporting operable hydraulic constriction element 201, the first operable hydraulic constriction element 101 provides a softer contacting surface against the urethra U, which reduces the risk that the urethra U is injured. As the first operable hydraulic constriction element 101 is longer than the supporting operable hydraulic constriction element 201, the supporting operable hydraulic constriction element 201 is never placed in contact with the urethra U.

In the embodiment shown in FIG. 8a, the end portions 111', 111" of the first operable hydraulic constriction element 101 are directed upwards, away from the urethra U, which creates a smooth rounded surface in contact with the urethra U which reduces the risk of damage to the urethra U. By the end portions 111', 111" of the first operable hydraulic constriction element 101 being directed upwards, a void is created between the end portions 111', 111" of the first operable hydraulic constriction element 101 and the urethra U, when the first operable hydraulic constriction element 101 is in its non-expanded state.

In the embodiment of FIG. 8a, the implantable constriction device 10 further comprises a surrounding structure 20 having a periphery surrounding the urethra U when implanted. The surrounding structure 20 is substantially rigid and a major portion of the surrounding structure could for example comprise a biocompatible metallic material, such as titanium or a medical grade metal alloy, such as medical grade stainless steel. In the alternative, the surrounding structure could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The surrounding structure could also comprise at least one composite material, such as any combination of metallic/ceramic and polymer materials or a polymer material reinforced with organic or inorganic fibers, such as carbon or mineral fibers. In the embodiment shown in FIG. 8, the material of the major portion of the surrounding structure has a modulus of elasticity (E) in the range 0.2 GPa-1000 GPa or more specifically in the range 1 GPa-400 GPa. The major portion of the surrounding structure being made from a stiff material results in that the surrounding structure has a modulus of elasticity (E), radially, in the range 0.2 GPa-1000 GPa or more specifically in the range 1 GPa-400 GPa, which means that the supporting structure only expands an insignificant distance when the operable hydraulic constriction devices are expanded to close the urethra U, which means that it can be established with high precision that the fluid pumped into the operable hydraulic constriction devices are used for exerting a closing force on the urethra U.

In the embodiment shown in FIG. 8a, the surrounding structure 20 is a band-like structure having a rectangular cross-section and being made from a metallic material. The surrounding structure is divided into two portions and is configured to be possible to open such that it can be placed around the intact urethra U of a patient. The surrounding structure 20 comprises an inner surface 22 configured to face the urethra U, when implanted, and an outer surface 21 configured to face away from the urethra U, when implanted. The supporting operable hydraulic constriction device 201 is fixated to the inner surface 22 of the surrounding structure 20, such that the supporting operable hydraulic constriction device 201 can use the surrounding structure 20 as support for constricting the urethra U.

In the embodiment shown in FIG. 8a, the surrounding structure further comprises at least one cushioning element 30 configured to contact the urethra U. In the embodiment shown in FIG. 8a, the cushioning element is fixated to the inner surface 22 of the surrounding structure 20 and is more resilient than the surrounding structure 20. The cushioning element 30 is made from a medical grade silicone material and is filled with a biocompatible gel which enables the cushioning element 30 to be shaped to suit the urethra U which reduces the risk that the contact with the urethra U damages the urethra U. In alternative embodiments, it is conceivable that the cushioning element 30 comprises a solid resilient material, such as a soft medical grade silicone or polyurethane material.

In the embodiment shown in FIG. 8a, the first reservoir conduit 109 and the supporting reservoir conduit 209 enters the first operable hydraulic constriction element 101 and the supporting operable hydraulic constriction element 201 through the surrounding structure 20, by means of channels 23',23" in the form of through-holes running through, and being integrated in, the surrounding structure 20.

Figure 8B:
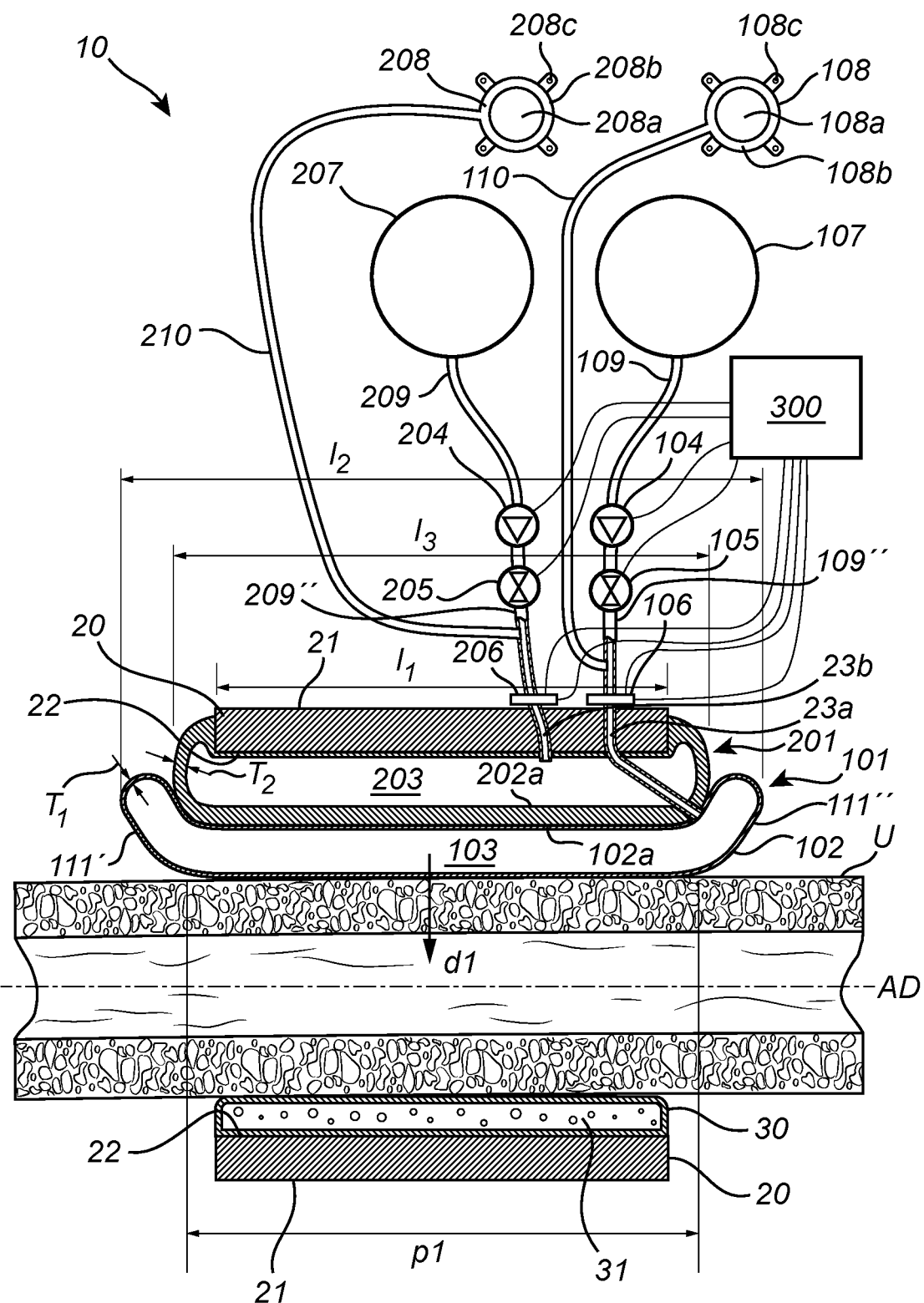
FIG. 8b shows an embodiment of an implantable constriction device for constricting the urethra of a patient in a sectional side view, in its un-constricted state.

FIG. 8b shows an overview of an embodiment of an implantable constriction device 10 for constricting a urethra U of a patient identical to that described with reference to FIG. 8a, with the exception of the placement of the first and second injection ports 108,208. In the embodiment shown in FIG. 8b, the first injection port 108 is connected to the first injection port conduit 110 which creates a fluid connection between the first injection port 108 and a second portion 109" of the first reservoir conduit 109, which is placed between the electrically operable valve 105 and the first operable hydraulic constriction element 101, such that hydraulic fluid can be removed from the first operable hydraulic constriction element 101 through the first injection port 108. The second injection port 208 is connected to the second injection port conduit 210 which creates a fluid connection between the second injection port 208 and a second portion 209" of the supporting reservoir conduit 209, which is placed between the electrically operable valve 205 and second operable hydraulic constriction element 201, such that hydraulic fluid can be removed from the supporting operable hydraulic constriction element 201 through the second injection port 208.

One advantage of having the injection ports 108, 208 being directly in fluid connection with the first and supporting operable hydraulic constriction elements 101, 201 is that the injection ports can be used as a safety system through which the hydraulic fluid can be removed from the first and supporting operable hydraulic constriction elements 101, 201 in case there is a malfunction to the pumps 104, 204 of the electrically operable valves 105, 205. I.e. if there is a malfunction to the pumps 104, 204 or valves 105, 205, an injection needle can be inserted into the injection ports 108, 208 and fluid withdrawn from the first and supporting operable hydraulic constriction elements 101, 201 such that the urethra U is left unrestricted such that the patient can urinate even if the constriction device does not function.

The controller 300 is in the embodiment shown in FIG. 8b configured to receive a pressure signal from a first and second pressure sensor 106, 206 and status signals from the first and second pumps 104, 204 and from the first and second electrically operable valves 105, 205. The controller 300 is further configured to communicate the status of the implantable constriction device 10 and/or the pressure to an external device. If the pressure in the hydraulic system and/or the first and supporting operable hydraulic constriction elements 101, 201 is too high and the implantable constriction device 10 does not function to lower the pressure, an emergency signal is sent to the external device such that the patient or a doctor could lower the pressure to manually removing fluid from the first and supporting operable hydraulic constriction elements 101, 201 through the injection ports 108, 208.

Figure 8C:
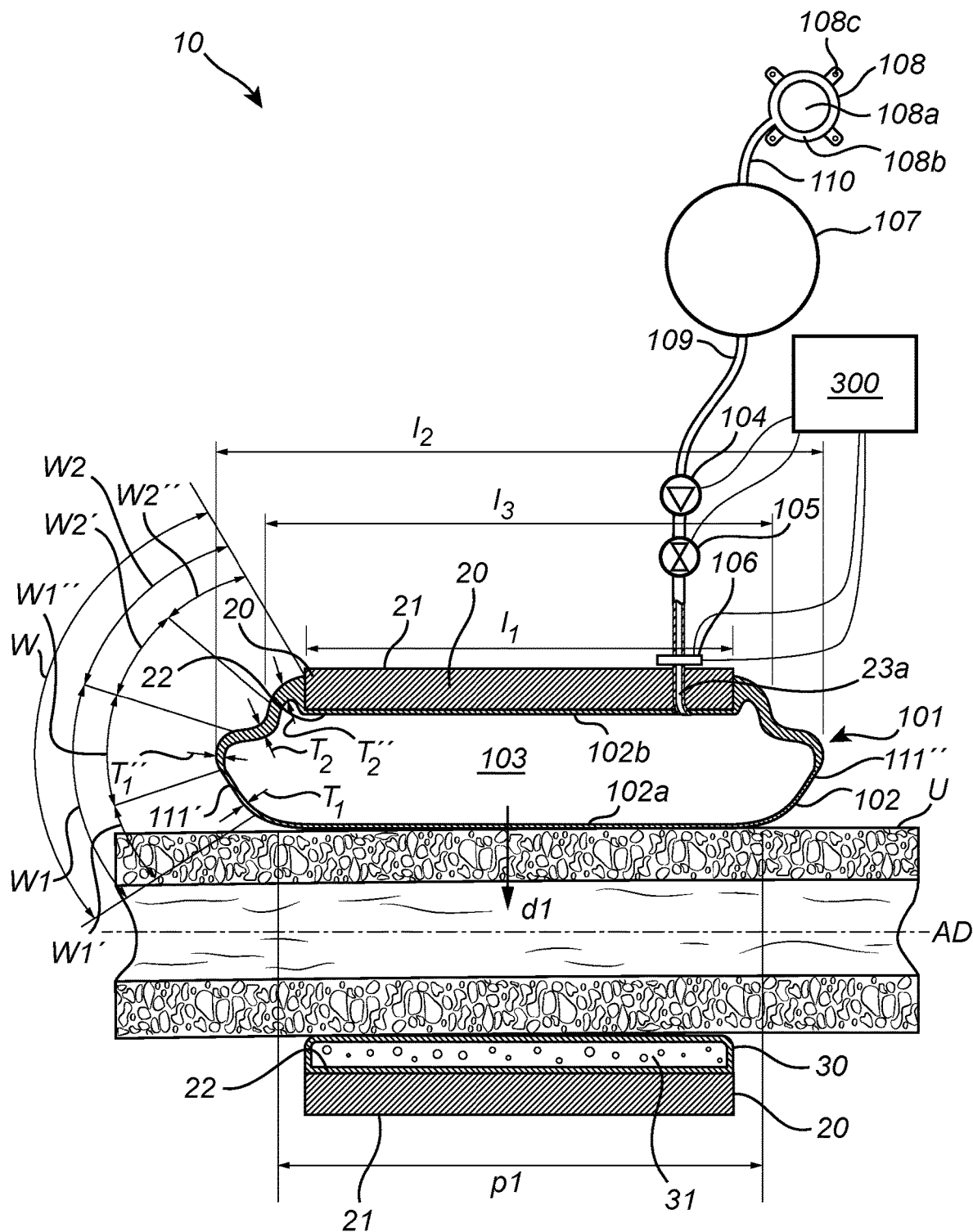
FIG. 8c shows an embodiment of an implantable constriction device for constricting the urethra of a patient in a sectional side view, in its un-constricted state.

FIG. 8c shows an overview of an embodiment of an implantable constriction device 10 for constricting a urethra U of a patient similar to that shown in FIGS. 8a and 8b. The difference from the embodiment shown in FIG. 8a is that the embodiment of FIG. 8c comprises a single implantable operable hydraulic constriction element 101 configured to be inflated to exert a pressure on a urethra U of a patient for constricting the urethra U and thereby restrict the flow of urine therethrough. The implantable operable hydraulic constriction element 101 of FIG. 8c comprises a contacting wall portion 102a configured to engage the urethra U for exerting force on the urethra in the direction d1 for constricting the urethra U. The implantable operable hydraulic constriction element 101 further comprises a withholding wall portion 102b configured to be connected to a withholding structure 20 for withholding the force exerted on the urethra U, such that the urethra U is constricted. The implantable operable hydraulic constriction element 101 further comprises a connecting wall portion W, connecting the contacting wall portion 102a to the withholding wall portion 102b. The contacting wall portion 102a, the withholding wall portion 102b and the connecting wall portion W are all wall portions involved in enclosing a lumen 103 of the implantable operable hydraulic constriction element 101. The lumen 103 is configured to receive a hydraulic fluid such that the implantable operable hydraulic constriction element 101 is inflated for exerting force on the urethra U. A first portion W1 of the connecting wall portion W is connected to the contacting wall portion 102a and a second portion W2 of the connecting wall portion W is connected to the withholding wall portion 102b. In the embodiment shown in FIG. 8c, the first portion W1 of the connecting wall portion W is more resilient than the second portion W2 of the connecting wall portion W, by the first portion W1 of the connecting wall portion W having a lower average wall thickness T1 than the average wall thickness T2 of the second portion W2 of the connecting wall portion W.

In the embodiment shown in FIG. 8c, the withholding structure is a surrounding structure 20, which is further disclosed with reference to FIGS. 8a-9c. The surrounding structure is comprised of a first and second support element configured to be connected to each other for forming the surrounding structure. The first and second support element may be are hingedly connected to each other, such as further disclosed with reference to FIGS. 1a-3f and 10a-11f. In the embodiment shown in FIG. 8c, the withholding structure 20, being a surrounding structure 20, comprises a cushioning element 30 configured to contact the urethra U, the cushioning element 30 being more resilient than the surrounding structure 20.

The surrounding structure 20 and the integrated channels shown in FIGS. 8a-8c may be replaced by the surrounding structures described with reference to FIGS. 1a-3f.

That the first portion W1 of the connecting wall portion W is more resilient than the second portion W2 means that the second portion W2 is more rigid and less prone to change its size and/or location by external forces pushing on the operable hydraulic constriction element 101. That the first portion W1 of the connecting wall portion W is more resilient than the second portion W2 further means that the first wall portion is more adaptable and follows the contours of the urethra U better as the operable hydraulic constriction element 101 is inflated and deflated which reduces the risk that the urethra is damaged by the contact with the operable hydraulic constriction element 101. The combination of a more rigid second wall portion W2 and a more resilient first wall portion W1 creates an operable hydraulic constriction element 101 which is stable along the axial direction AD of the urethra U, which means that the operable hydraulic constriction element 101 will retain its position along the axial direction AD of the urethra U, such that the force exerted on the urethra U in the first direction d1 is exerted on the first portion p1 of the urethra U, while at the same time being resilient enough not to injure the urethra U.

In the embodiment shown in FIG. 8c, the first portion W1 of the connecting wall portion W has an average wall thickness T1 which is less than 0.8 times the average wall thickness T2 of the second portion W2 of the connecting wall portion W. However, in alternative embodiments, the first portion W1 of the connecting wall portion W may have an average wall thickness T1 which is less than 0.6 times the average wall thickness T2 of the second portion W2 of the connecting wall portion W, or an average wall thickness Ti which is less than 0.4 times the average wall thickness T2 of the second portion W2 of the connecting wall portion W.

In the embodiment shown in FIG. 8c the first portion W1 of the connecting wall portion W comprises a first and a second sub portion W1', W1". The first sub portion W1' of the first portion W1 is connected to the contacting wall portion 102a, and the second sub portion W1" of the first portion W1 is connected to the second portion W2 of the connecting wall portion W. In the embodiment shown in FIG. 8c, the second portion W2 of the connecting wall portion W also comprises a first and a second sub portion W2', W2". The first sub portion W2' of the second portion W2 is connected to the second sub portion W1" of the first portion W1 and the second sub portion W2" of the second portion W2 is connected to the withholding wall portion 102b. In the embodiment shown in FIG. 8c the first sub portion W1' of the first portion W1 is more resilient than the second sub portion W1" of the first portion W1 and the first sub portion W2' of the first portion W2 is more resilient than the second sub portion W2" of the first portion W2. In the embodiment in FIG. 8c, the difference in resilience is due to the first sub portion W1' of the first portion W1 having a lower average wall thickness T1 than the average wall thickness T1" of the second sub portion W1" of the first portion W1 and the first sub portion W2' of the second portion W2 having a lower average wall thickness T2 than the average wall thickness T2" of the second sub portion W2" of the second portion W2.

In the embodiment shown in FIG. 8c, the first sub portion W1' of the first portion W1 has an average wall thickness T1 which is less than 0.9 times the average wall thickness T1" of the second sub portion W1" of the first portion W1 and the first sub portion W2' of the second portion W2 has an average wall thickness T2 which is less than 0.9 times the average wall thickness T2" of the second sub portion W2" of the second portion W2.

The varying resilience of the wall of the connecting wall means that the implantable operable hydraulic constriction element 101 will be more resilient closest to the urethra U and more stable at a distance from the urethra U. This will ensure that the implantable operable hydraulic constriction element 101 can maintain its shape even in its expanded state, in which the distance from the withholding structure 20 to the urethra is relatively large, also when the pressure in the urethra U presses on the implantable operable hydraulic constriction element 101 in the axial direction AD of the urethra U. At the same time, the more resilient portions art of the connecting wall W, together with the more resilient contacting wall portion 102a ensures that the implantable operable hydraulic constriction element 101 does minimal harm to the urethra U.

In alternative embodiments, the difference in resilience could come from the different portions of the connecting wall comprising different materials. In embodiments in which the different portions of the connecting wall comprise different materials, the different wall portions may have the same average wall thickness. It is also conceivable that the difference in resilience comes from a combination of wall thickness and material, i.e. portions of the connecting wall close to the urethra may have both a lower average wall thickness and comprise a more resilient material and portions of the connecting wall further from the urethra may have both a higher average wall thickness and comprise a less resilient material.

In one alternative embodiment, the first portion W1 of the connecting wall portion W may comprise a first material and the second portion W2 of the connecting wall portion W may comprise a second material, and wherein the first material has a lower modulus of elasticity than the first material. In the alternative embodiment, the modulus of elasticity of the first material is less than 0.8 times the modulus of elasticity of the second material, and in another embodiment the modulus of elasticity of the first material is less than 0.8 times the modulus of elasticity of the second material. In the alternative embodiment, the first material is a medical grade silicone material and the second material is a less elastic medical grade silicone material.

In any of the embodiments, the pressure applied to the reservoir and/or hydraulic constriction element can be controlled either by controlling the actual pressure, or by controlling the volume of fluid pumped and/or by controlling the cross-sectional distance of the constricted urethra. I.e. if the pressure is continuously calibrated it can be established that a certain fluid level or distance leads to a specific pressure, which could make control of the device easier then control using constant pressure measurement. In embodiments in which the fluid level or cross-sectional distance of the urethra is used as control value, the pressure may be used as a back-up or safety system, e.g. the pressure sensor can be set to give an alarm signal or take a specific action if the pressure increases over a set value (threshold).

Figure 9A:
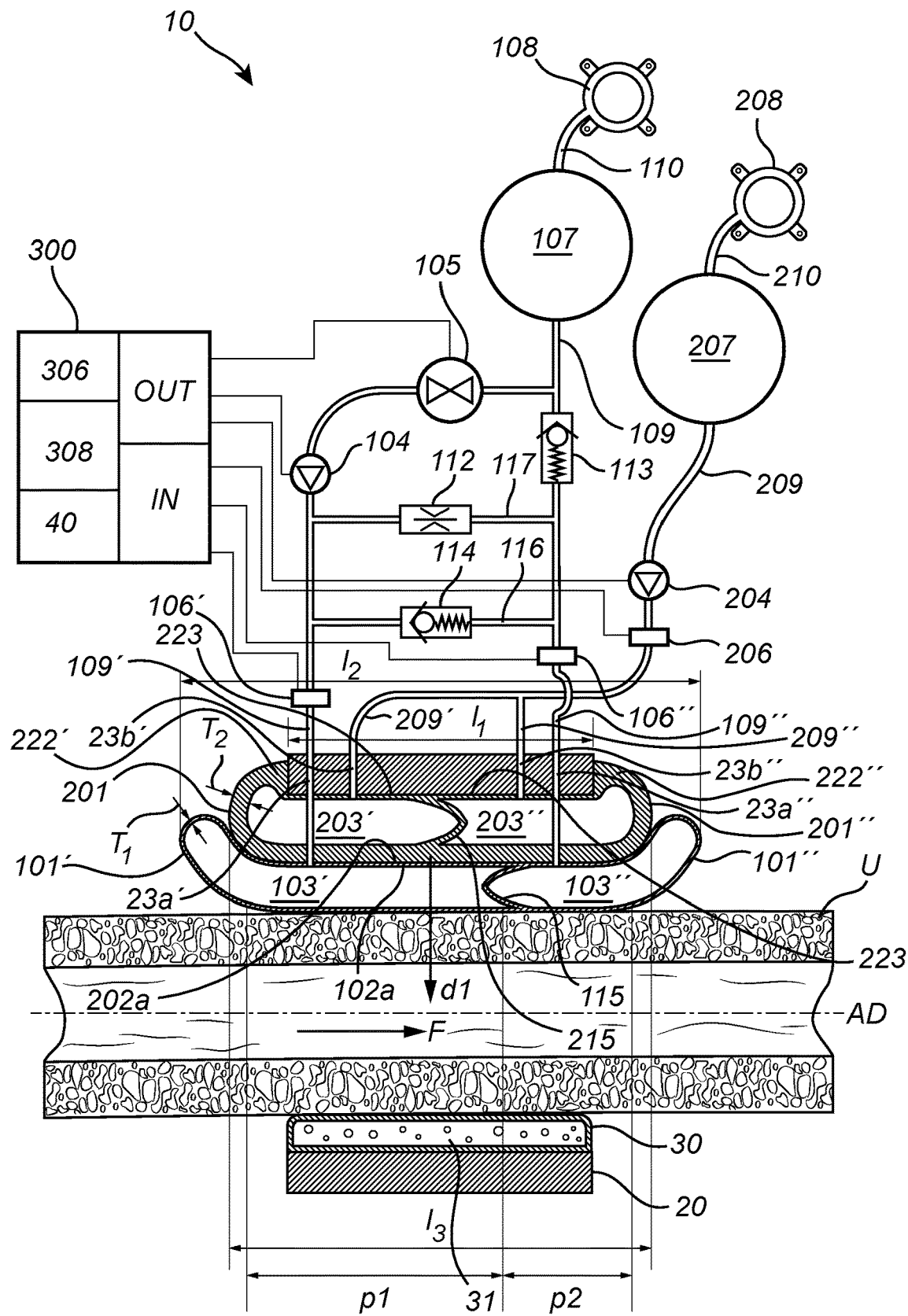
FIG. 9a shows an embodiment of an implantable constriction device for constricting the urethra of a patient in a sectional side view, in its un-constricted state.

FIG. 9a shows an overview of an embodiment of an implantable constriction device 10 for constricting a urethra U of a patient. The embodiment of FIG. 9a is very similar to the embodiment shown in FIG. 8. The difference between the embodiment of FIG. 8 and the embodiment of FIG. 9a is that in the embodiment of FIG. 9a the implantable constriction device 10 comprises a first operable hydraulic constriction element 101' configured to be inflated to constrict the urethra U for restricting the flow of urine therethrough, and a second operable hydraulic constriction element 101" configured to be inflated to constrict the urethra U for restricting the flow of urine therethrough.

The first operable hydraulic constriction element 101' is configured to be placed at a first portion p1 of the urethra U for constricting the first portion p1 of the urethra U for restricting the flow of urine therethrough, and the second operable hydraulic constriction element 101" is configured to be placed at a second portion p2 of the urethra U, downstream the first portion p1, for constricting the second portion p2 of the urethra U for restricting the flow of urine therethrough.

A first portion 109' of the first reservoir conduit 109 is connected to the lumen 103' of the first operable hydraulic constriction element 101' and a second portion 109" of the first reservoir conduit 109 is connected to the lumen 103" of the second operable hydraulic constriction element 101". The first portion 109' of the first reservoir conduit 109 is connected to the second portion 109" of the first reservoir conduit 109 by means of a first interconnecting fluid conduit 116, and as such, the first operable hydraulic constriction element is in fluid connection with the second operable hydraulic constriction element. The fluid connection is configured to conduct fluid from the first operable hydraulic constriction element 101' to the second operable hydraulic constriction element 101" when the pressure increases in the first operable hydraulic constriction element 101', such that second operable hydraulic constriction element constricts 101" the second portion p2 of the urethra U further.

The first operable hydraulic constriction element 101' has a larger volume than the second operable hydraulic constriction element 101", i.e. the lumen 103' of the first operable hydraulic constriction element 101' is larger than the lumen 103" of the second operable hydraulic constriction element 101". This means that a compression of the first operable hydraulic constriction element 101' leads to a larger expansion of the first operable hydraulic constriction element 101" by the fluid connection 109',109",116.

The lumens 103', 103" of the first and second operable hydraulic constriction elements 101', 101" are divided by a resilient division wall 115, which in the embodiment of FIG. 9a is a wall made from the same medical grade silicone as the other walls of the first and second operable hydraulic constriction elements 101', 101" and concurrently made in the same molding process which means that the resilient division wall 115 is materially integrated with the other walls of the first and second operable hydraulic constriction elements 101', 101". When the first and second operable hydraulic constriction elements 101', 101" are compressed, the resilient division wall 115 bends to the left in the figure.

In the embodiment shown in FIG. 9a, the implantable constriction device 10 also comprises a supporting operable hydraulic constriction element, being less resilient than the first and second operable hydraulic constriction elements 101', 101". However, in the embodiment shown in FIG. 9a, the supporting operable hydraulic constriction element is also divided into a first and second supporting operable hydraulic constriction element 201', 201". The first and second supporting operable hydraulic constriction element 201', 201" are configured to be inflated and thereby expand in the first direction d1 towards the urethra U to support the first and second operable hydraulic constriction elements 101', 101" in constricting the first and second portions p1,p2 of the urethra U for restricting the flow of urine therethrough. The two supporting operable hydraulic constriction elements 201', 201" each comprises a lumen 203', 203" surrounded by a resilient wall made from a biocompatible material such as a medical grade silicone or a medical grade polyurethane-based material. The supporting operable hydraulic constriction elements 201', 201" are connected to the first and second operable hydraulic constriction elements 101', 101" at the contacting walls 102a, 202a of the first and second operable hydraulic constriction elements 101', 101" and supporting operable hydraulic constriction elements 201', 201". The connection may be realized simply by abutment or by friction or by an adhesive or by the contacting walls 102a, 202a of the first operable hydraulic constriction elements 101', 101" and the supporting operable hydraulic constriction elements 201', 201" being materially integrated with each other by concurrent manufacturing or by subsequent thermal bonding.

The lumens 203', 203" of the first and second supporting operable hydraulic constriction elements 201', 201" are divided by a resilient division wall 215, which in the embodiment of FIG. 9a is a wall made from the same medical grade silicone as the other walls of the first and second supporting operable hydraulic constriction elements 201', 201" and concurrently made in the same molding process which means that the resilient division wall 215 is materially integrated with the other walls of the first and second operable hydraulic constriction elements 201', 201". When the first and second operable hydraulic constriction elements 201', 201" are compressed, the resilient division wall 215 bends to the right in the figure.

Similarly to FIG. 8a, the supporting operable hydraulic constriction elements 201', 201" of FIG. 9a are less resilient than the first and second operable hydraulic constriction elements 101', 101" which means that the supporting operable hydraulic constriction elements 201', 201" are more rigid and less prone to change size and/or location by external forces pushing on the supporting operable hydraulic constriction elements 201', 201". For example, the supporting operable hydraulic constriction elements 201', 201" are more stable along the axial direction of the urethra U, which means that the supporting operable hydraulic constriction elements 201', 201" will retain its position along the axial direction AD of the urethra U, such that the force exerted on the urethra U in the first direction d1 is exerted on the first and second portions p1, p2 of the urethra U, respectively. In the embodiment shown in FIG. 9a, the supporting operable hydraulic constriction elements 201', 201" are more rigid than the first operable hydraulic constriction elements 101', 101" by the wall of the supporting operable hydraulic constriction elements 201', 201" having a thickness T2 being thicker than the thickness T1 of the wall of the first and second operable hydraulic constriction elements 101', 101". In the embodiment shown in FIG. 9a, the resilient wall of the supporting operable hydraulic constriction elements 201', 201" is more than 1.5 times thicker than a portion of the wall of the first and second operable hydraulic constriction elements 101', 101". In alternative embodiments, it is equally conceivable that the wall of the supporting operable hydraulic constriction elements 201', 201" is more than 2 times thicker than a portion of the wall of the first and second operable hydraulic constriction elements 101', 101" for further increasing the stability of the supporting operable hydraulic constriction elements 201', 201".

The first and second supporting operable hydraulic constriction elements 201', 201" are connected to a second reservoir 207 though a supporting reservoir conduit 209. A second hydraulic pump 204 is provided on the supporting reservoir conduit 209 for moving fluid from the second reservoir 207 to the first and second supporting operable hydraulic constriction elements 201', 201".

In normal operation, the implantable constriction device 10 in the embodiment of FIG. 9a has substantially the same function as the implantable constriction device in the embodiment of FIG. 8. A first pump 104 is placed on the first reservoir conduit 109. The pump 104 may just as in the embodiment disclosed in FIG. 8 be of any of the hydraulic pumps disclosed herein. The pump 104 is fluidly connected to both the first and second operable hydraulic constriction elements 101', 101" by means of the two interconnecting fluid conduits 116, 117, connecting the first portion 109' of the first reservoir conduit to the second portion 109" of the reservoir conduit 109. The pump moves fluid from the reservoir 107 to the first and second operable hydraulic constriction elements 101', 101" for expanding the first and second operable hydraulic constriction elements 101', 101" for restricting the urethra U and thereby hindering the flow of urine though the urethra U. When the patient would like to urinate, the patient activates the pump 104 for moving fluid in the opposite direction, i.e. from the first and second operable hydraulic constriction elements 101',101" to the reservoir 107, which contracts the first and second operable hydraulic constriction elements 101',101" and releases the restriction of the urethra U for allowing the flow of urine therethrough. The second hydraulic pump 204 operates in conjunction with the first hydraulic pump such that the first and second supporting operable hydraulic constriction elements 201', 201" operates to support the first and second operable hydraulic constriction elements 101', 101" such that all four operable hydraulic constriction elements 101', 101", 201', 201" basically operates as a single operable hydraulic constriction element for restricting and releasing the restriction of the urethra U.

Depending on which type of pump it is, there may be a need to have electrically operable valve 105 connected in series with the hydraulic pump 104 to enable closure of the fluid communication between the first and second operable hydraulic constriction elements 101', 101" and the first reservoir 107. However, in embodiments in which the hydraulic pump 104 is of a type that hinders leakage through the pump and/or hinders elasticity in the pump and/or reservoir 107, such as for example a peristaltic pump, the electrically operable valve 105 may be omitted.

When a patient is resting, the pressure on the urinary sphincter is typically about 50 cm H2O. However, when the patient is moving, running, jumping, laughing, or sneezing, this pressure may increase to about 100 cm H2O. If an artificial urinary sphincter is configured to exert a continuous pressure high enough to handle these pressure spikes, the blood flow to the tissue of the urethra U will be hampered, which in the long term could lead to damage of the urethra U and in the worst cases necrosis. The implantable constriction device 10 of the embodiment of FIG. 9a solves this problem by having a first and a second operable hydraulic constriction element 101', 101" placed sequentially along the axial direction AD of the urethra U, such that the first and second operable hydraulic constriction elements 101', 101" can exert a constant moderate force on the urethra U which the tissue of the urethra U can endure long term. However, when the pressure temporarily increases in the urethra U the pressure first increases in the first operable hydraulic constriction element 101', as the first operable hydraulic constriction element 101' is positioned upstream in relation to the direction of the flow F of urine, and thereby closest to the urinary bladder. The increased pressure in the first operable hydraulic constriction element 101' causes fluid to be conducted from the first operable hydraulic constriction element 101', through the first portion 109' of the first reservoir conduit 109, through the interconnecting fluid conduit 116, and further through the second portion 109" of the first reservoir conduit 109 and into the second operable hydraulic constriction element 101". The flow of fluid into the second operable hydraulic constriction element 101" increases the pressure in the second operable hydraulic constriction element 101" causing the second operable hydraulic constriction element 101" to exert a higher pressure on the second, smaller, portion p2 of the urethra U further constricting the urethra and thereby preventing leakage through the implantable constriction device 10 during the pressure increase. The interconnecting fluid conduit 116 comprises a check valve 114 which means that the fluid in the second operable hydraulic constriction element 101" cannot return to the first operable hydraulic constriction element 101' through the interconnecting fluid conduit 116. The second portion 109" of the first reservoir conduit 109 also comprises a check valve 113 such that fluid cannot flow from the second operable hydraulic constriction element 101" to the reservoir 107, which means that the elasticity of the reservoir 107 does not reduce the increase of pressure in the second operable hydraulic constriction element 101". The first and second portion 109', 109" of the first reservoir conduit 109 are further connected by means of a second interconnecting conduit 117. The second interconnecting conduit 117 comprises a hydraulic restrictor valve 112, which restricts the flow over the valve by the valve having a smaller cross-sectional area than the tubular lumen of the second interconnecting conduit 117. The restrictor valve 112 allows a small leakage over the valve, which means that the pressures in the first operable hydraulic constriction element 101' and the second operable hydraulic constriction element 101" will reach an equilibrium over time. In the embodiment shown in FIG. 9a, that time is in the interval 1-10 minutes, however, in alternative embodiments that time may be more than 10 seconds, between 10 seconds and 1 hour or less than one hour. In alternative embodiments, the restrictor valve 112 may be replaced by an electrically operable valve, such as a solenoid valve, which could control the flow from the first operable hydraulic constriction element 101' to the second operable hydraulic constriction element 101".

In the embodiment shown in FIG. 9a, the first operable hydraulic constriction element 101' has a volume which is more than 1.5 times larger than the volume of the second operable hydraulic constriction element 101".

The embodiment of FIG. 9a also comprises injection ports 108, 208 of the same type and for the same purpose as the injection ports described in the embodiment of FIG. 8. In an alternative embodiment, the injection ports 108, 208 may be connected to the hydraulic system in the same way as described with reference to FIG. 8b, i.e. such that the first injection port conduit 110 creates a fluid connection between the first injection port 108 and the first and/or second portion 109', 109" of the first reservoir conduit 109, which are placed between the pump 104 and the first operable hydraulic constriction element 101, such that hydraulic fluid can be removed from the first operable hydraulic constriction element 101 through the first injection port 108. The second injection port 208 is connected to the second injection port conduit 210 which creates a fluid connection between the second injection port 208 and the first and/or second portions 209', 209" of the supporting reservoir conduit 209, which is placed between the pump 204 and supporting operable hydraulic constriction element 201, such that hydraulic fluid can be removed from the supporting operable hydraulic constriction element 201 through the second injection port 208.

In the embodiment shown in FIG. 9a, the implantable constriction device 10 further comprises a first pressure sensor 106' configured to sense the pressure in the first operable hydraulic constriction element 101', and a second pressure sensor 106" configured to sense the pressure in the second operable hydraulic constriction element 101", and a third pressure sensor 206 configured to sense the pressure in the supporting operable hydraulic constriction elements 201', 201".

The embodiment shown in FIG. 9a further comprises a controller 300 having an input unit IN and an output unit OUT. The controller is configured to receive input at the input unit IN from the pressure sensors 106', 106", 206 in the form of a pressure sensor signals, and deliver output in the form of control signals from the output unit OUT to the hydraulic pumps 104, 204 and the electrically controllable valve 105, such that the operation of the hydraulic pumps 104, 204 and/or the electrically controllable valve 105 can be controlled on the basis of input from the pressure sensors 106', 106", 206.

The controller 300 further comprises an energy storage unit 40 which may be a battery, a chargeable battery or a capacitor by means of which energy can be stored in the body of the patient. The controller 300 further comprises an internal computing unit 306 for handling the control of the restriction device. The computing unit 306 could comprise a single central processing unit or could comprise two or more processing units. The processing unit could comprise a general-purpose microprocessor and/or an instruction set processor and/or related chips sets and/or special purpose microprocessors such as ASICs (Application Specific Integrated Circuit). The computing unit 306 comprises an internal memory configured to store programs thereon. The controller 300 could be adapted to keep track of the lapsed time with specific pressures such that the average and min/max pressures exerted by the implantable constriction device 10 can be logged. The controller 300 further comprises a transceiver 308 for receiving and/or transmitting wirelessly signals to/from outside the body. The transceiver 308 can enable programming the controller 300 form outside of body of the patient such that the implantable constriction device 10 can be programmed to function optimally. The optimal function of the implantable constriction device 10 could in many instances be a mediation between optimal restriction of the urethra U and restriction with causes the least damage.

As an example, the controller 300 could comprise a pressure threshold value stored in memory, and be configured to open the electrically operable valve 105 to allow fluid to flow back to the reservoir 107 if the received pressure sensor signal from the first pressure sensor 106' exceeds the pressure threshold value.

The controller 300 is enclosed by an enclosure such that the controller 300 is protected from bodily fluids. The enclosures may be an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass. In any instance the enclosure should be made from a material with low permeability, such that migration of fluid through the walls of the enclosure is prevented.

In the embodiment of FIG. 9a, the combined first and second supporting operable hydraulic constriction elements 201', 201" has a length l3 in the axial direction AD of the urethra U, when implanted. The first and second operable hydraulic constriction elements 101',101" has a combined length l2 in the axial direction AD of the urethra U, and the combined length l2 of the first and second operable hydraulic constriction elements 101',101" is longer than the combined length l3 of the supporting operable hydraulic constriction elements 201',202".

In the embodiment of FIG. 9a, the implantable constriction device 10 further comprises a surrounding structure 20 having a periphery surrounding the urethra U when implanted. The surrounding structure 20 is substantially rigid and a major portion of the surrounding structure 20 could for example comprise a biocompatible metallic material, such as titanium or a medical grade metal alloy, such as medical grade stainless steel. In the alternative, the surrounding structure 20 could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The surrounding structure 20 could also comprise at least one composite material, such as any combination of metallic/ceramic and polymer materials or a polymer material reinforced with organic or inorganic fibers, such as carbon or mineral fibers. In the embodiment shown in FIG. 9a, the material of the major portion of the surrounding structure 20 has a modulus of elasticity (E) in the range 0.2 GPa-1000 GPa or more specifically in the range 1 GPa-400 GPa. The major portion of the surrounding structure 20 being made from a stiff material results in that the surrounding structure 20 has a modulus of elasticity (E), radially, in the range 0.2 GPa-1000 GPa or more specifically in the range 1 GPa-400 GPa, which means that the supporting structure 20 only expands an insignificant distance when the operable hydraulic constriction devices are expanded to close the urethra U, which means that it can be established with high precision that the fluid pumped into the operable hydraulic constriction devices are used for exerting a closing force on the urethra U.

The surrounding structure 20 comprises an inner surface 22 configured to face the urethra U, when implanted. The supporting operable hydraulic constriction devices 201',

201" is fixated to the inner surface 22 of the surrounding structure 20, such that the supporting operable hydraulic constriction devices 201', 201" can use the surrounding structure 20 as support for constricting the urethra U. In the embodiment shown in FIG. 9, the wall portion 223 of the supporting operable hydraulic constriction devices 201', 201" which faces the inner surface 22 of the supporting structure 20 is bonded to the supporting structure 20 by means of an adhesive. The side portions 222', 222" of the supporting operable hydraulic constriction devices 201', 201" are bonded to the sides of the surrounding structure 20 by means of an adhesive. By bonding the sides portions 222', 222" of the supporting operable hydraulic constriction devices 201', 201" to the surrounding structure 20, the supporting operable hydraulic constriction devices 201', 201" becomes more stable along the axial direction AD of the urethra U, which means that the supporting operable hydraulic constriction elements 201', 201" will retain its position along the axial direction AD of the urethra U, such that they are less prone to change size and/or location by external forces pushing on the supporting operable hydraulic constriction elements 201', 201". For example, the supporting operable hydraulic constriction elements 201', 201" is more stable along the axial direction AD of the urethra U, which means that the supporting operable hydraulic constriction element 201 will retain its position along the axial direction AD of the urethra U, such that the force exerted on the urethra U in the first direction d1 is exerted on the first and second portions p1, p2 of the urethra U.

In the embodiment shown in FIG. 9a, the implantable constriction device 10 further comprises at least one cushioning element 30 configured to contact the urethra U. The cushioning element is fixated to the inner surface 22 of the surrounding structure 20 by means of an adhesive and is more resilient than the surrounding structure. The cushioning element 30 is made from a medical grade silicone material and is filled with a biocompatible gel which enables the cushioning element 30 to be shaped to suit the urethra U which reduces the risk that the contact with the urethra U damages the urethra U. In alternative embodiments, it is conceivable that the cushioning element 30 comprises a solid resilient material, such as a soft medical grade silicone of polyurethane material.

In the embodiment shown in FIG. 9a, the first and second reservoir conduits 109',109" and the first and second supporting reservoir conduits 209', 209" enters the first and second operable hydraulic constriction elements 101', 101" and the supporting operable hydraulic constriction elements 201', 201" through the surrounding structure 20, by means of channels 23a', 23a", 23b1, 23b" in the form of through-holes running through, and being integrated in, the surrounding structure 20.

The surrounding structure 20 and the integrated channels shown in FIG. 9a may be replaced by the surrounding structures described with reference to any of the FIGS. 1a-3f.

Figure 9B:
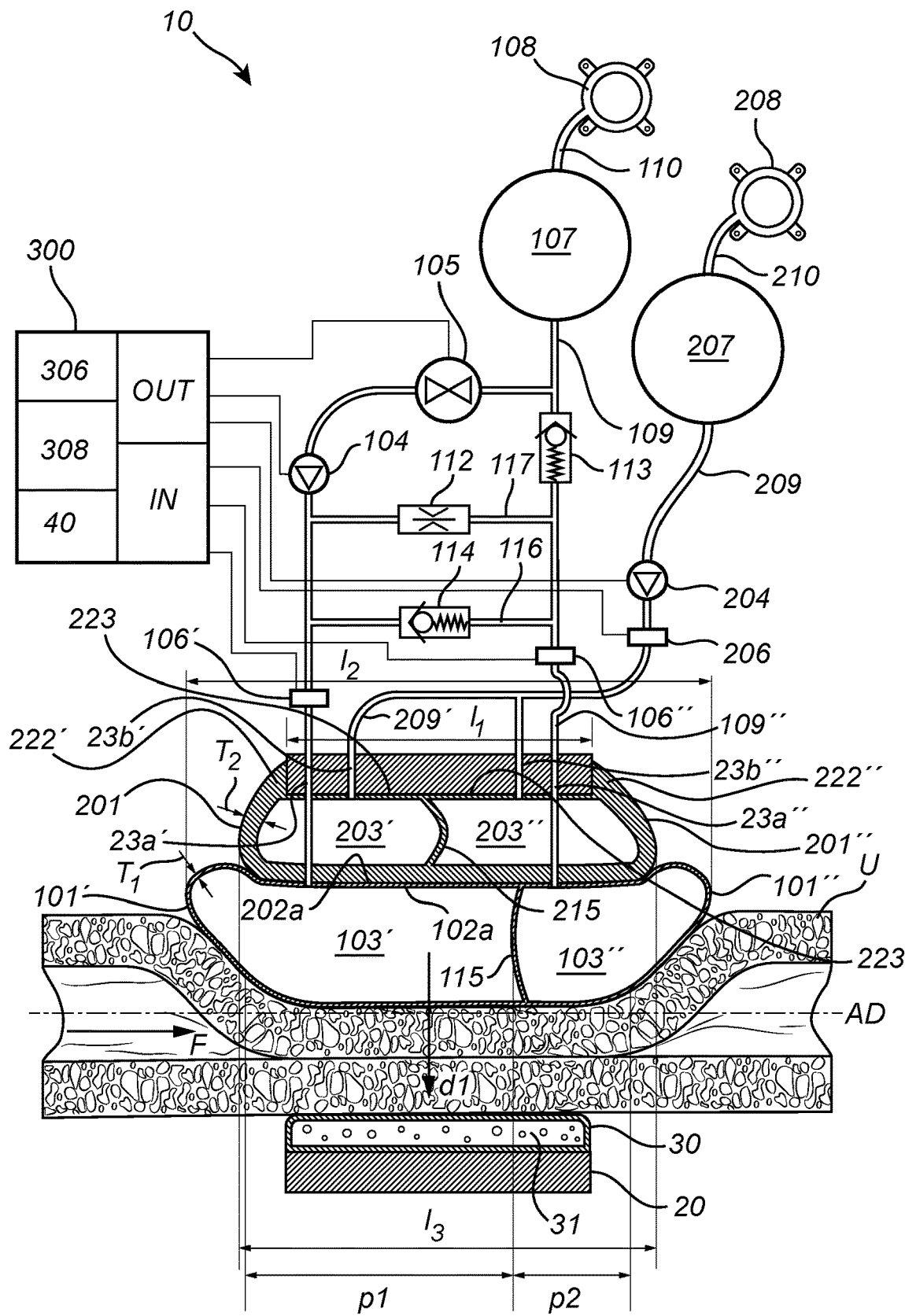
FIG. 9b shows an embodiment of an implantable constriction device for constricting the urethra of a patient in a sectional side view, in its constricted state.

FIG. 9b shows the implantable constriction device 10 described with reference to FIG. 9a in its closed state, when fluid has been pumped from the reservoir 107 to the first and second operable hydraulic constriction elements 101', 101" by the hydraulic pump 104 and to the supporting operable hydraulic constriction elements 201', 201" from the second reservoir 207 by the second hydraulic pump 204, such that the implantable constriction device 10 constricts the urethra U and restricts the flow of urine therethrough. The pressure in the supporting operable hydraulic constriction elements 201', 201" is sensed by the third pressure sensor 206 which is connected to the controller 300. The pressure in the first operable hydraulic constriction element 101' is sensed by a first pressure sensor 106' connected to the controller 300 an the pressure in the second operable hydraulic constriction element 101" is sensed by a second pressure sensor 106" also connected to the controller 300. The controller 300 is configured to deliver output in the form of control signals from the output unit OUT to the hydraulic pumps 104, 204 and the electrically controllable valve 105, such that the operation of the hydraulic pumps 104, 204 and/or the electrically controllable valve 105 can be controlled on the basis of input from the pressure sensors 106', 106", 206. As such, the pressure exerted on the urethra U can be constantly monitored to make sure that the pressure does not hamper the blood flow through the tissue wall of the urethra U for a period of time which makes such pressure damaging to tissue of the urethra U. The optimal function of the implantable constriction device 10 is a mediation between restriction of the urethra U which ensures that no leakage can occur, and restriction with causes the least damage.

Figure 9C:
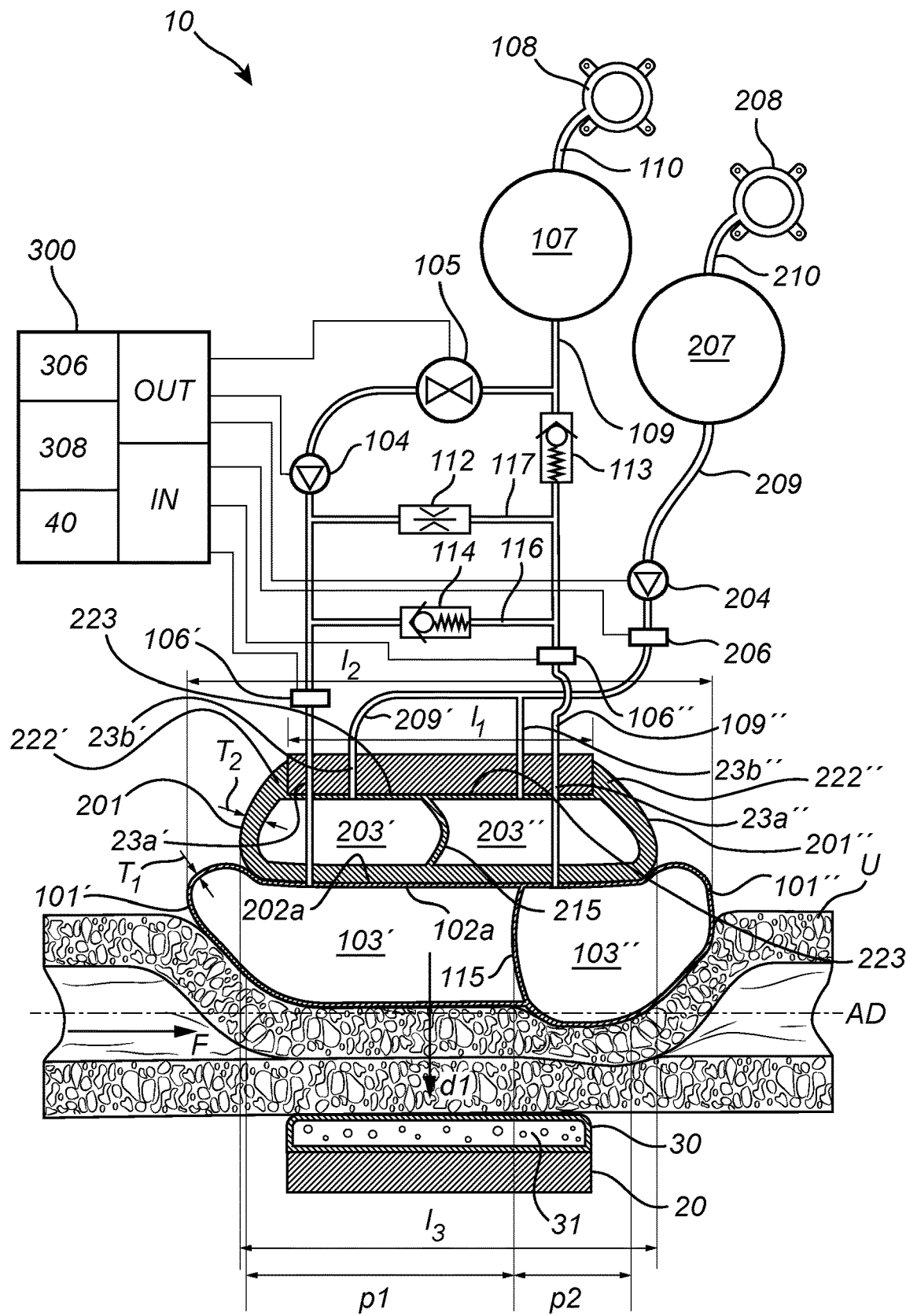
FIG. 9c shows an embodiment of an implantable constriction device for constricting the urethra of a patient in a sectional side view, in its constricted state.

FIG. 9c shows the implantable constriction device 10 described with reference to FIGS. 9a and 9b. In FIG. 9c, the implantable constriction device 10 is in the state in which the pressure in the urinary bladder and thus in the portion of the urethra U located upstream the implantable constriction device 10 has temporarily increased. The increase in pressure is e.g. a result of the patient moving, running, jumping, laughing, sneezing, or bending over causing the pressure in the urethra to increase to about 100 cm H2O. In increase in pressure in the urethra U causes the pressure to also increase in the first operable hydraulic constriction element 101' which forces hydraulic fluid to flow from the lumen 103' of the first operable hydraulic constriction element 101', through the interconnecting fluid conduit 116 and into the lumen 103" of the second operable hydraulic constriction element 101" causing the second operable hydraulic constriction element 101" to expand further and thus press harder on the second portion p2 of the urethra U for further constricting the urethra and thus preventing the leakage of urine through the implantable constriction device 10. The pressure in the second operable hydraulic constriction element 101" will increase to substantially the same pressure as in the urethra U and as the fluid cannot return to the first operable hydraulic constriction element 101' as the check valve 114 closes the flow of fluid from the second to the first operable hydraulic constriction element 101', 101" through the interconnecting fluid conduit 116. A further check valve 113 hinders fluid from flowing from the second operable hydraulic constriction element 101" to the reservoir 107 which also ensures that the elasticity in the reservoir does not affect the ability of the second operable hydraulic constriction element 101' to withhold the force from the increased pressure in the urethra U. The second operable hydraulic constriction element 101" is further in fluid connection with a hydraulic restrictor valve 112 which allows a small fluid flow through the second interconnecting fluid conduit 117 such that the pressure in the second operable hydraulic constriction element 101" will return to normal such that a pressure equilibrium between the first and second operable hydraulic constriction elements 101', 101" will be reached in time. In the embodiment shown in FIG. 9c, that time is in the interval 1-10 minutes, however, in alternative embodiments that time may be more than 10 seconds, between 10 seconds and 1 hour or less than one hour. In alternative embodiments, the restrictor valve 112 may be replaced by an electrically operable valve, such as a solenoid valve, which could control the flow from the first operable hydraulic constriction element 101' to the second operable hydraulic constriction element 101".

Figure 10A:
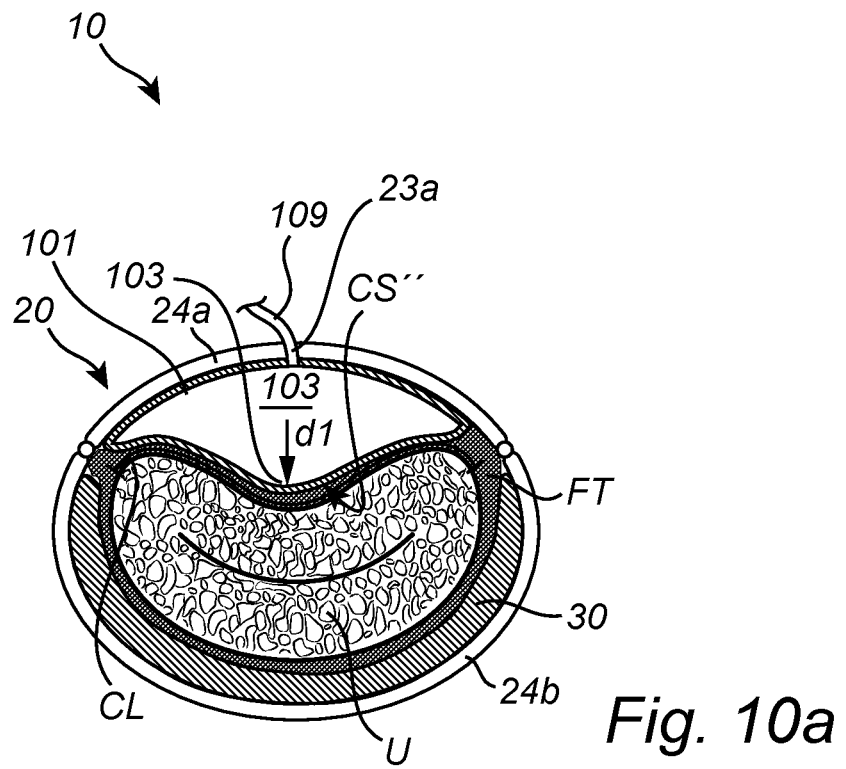
FIG. 10a shows an embodiment of an implantable constriction device for constricting the urethra of a patient in a sectional view, in its constricted state.
Figure 10B:
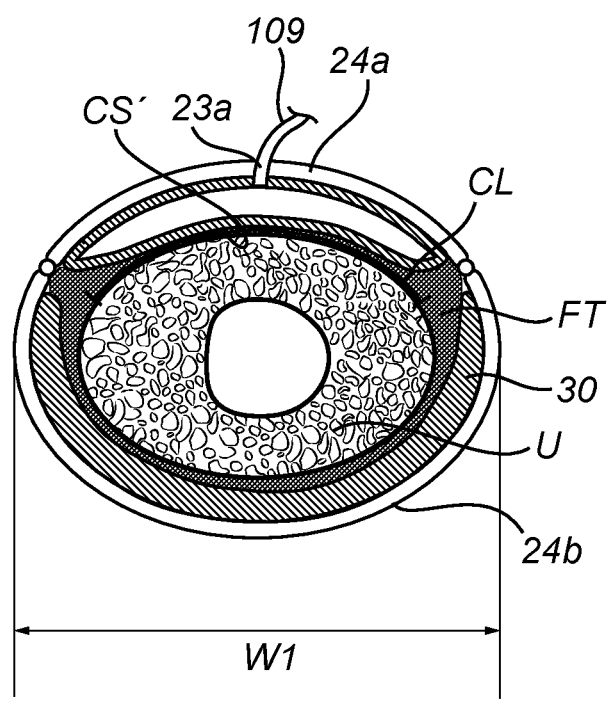
FIG. 10b shows an embodiment of an implantable constriction device for constricting the urethra of a patient in a sectional view, in its un-constricted state.

FIG. 10*a* shows an embodiment of the implantable constriction device 10 in a cross-sectional view in a state in which the implantable constriction device 10 is constricting the urethra U and thereby restricts the flow of urine through the urethra U, and FIG. 10*b* shows the embodiment of FIG. 10*a* in a state in which the constriction of the urethra U has been released to allow the flow of urine through the urethra U. The embodiment of FIG. 10*a* is similar to the embodiment shown in FIG. 8*c*. In the embodiment shown in FIG. 10*a*, the implantable constriction device 10 comprises a surrounding structure 20 having a periphery surrounding the urethra U when implanted. The surrounding structure 20 comprises two support elements 24*a*, 24*b* connected to each other for forming the surrounding structure 20. The first support element 24*a* is configured to support a first operable hydraulic constriction element 101. The first operable hydraulic constriction element 101 is configured to constrict the urethra U for restricting the flow of urine therethrough and configured to release the constriction of the urethra U for enabling the patient to urinate. The first and second support elements 24*a*, 24*b* each comprises a curvature adapted for the curvature of the urethra U such that the implantable constriction device 10 fits snuggly around the urethra U such that the distance that the operable hydraulic constriction elements 101, 201 needs to expand to constrict the urethra U is kept at a minimum.

The first operable hydraulic constriction element 101 is configured to be inflated and thereby expand in a first direction d1 towards the urethra U to constrict a portion of the urethra U for restricting the flow of urine therethrough. The first operable hydraulic constriction element 101 comprises a lumen 103 surrounded by a resilient wall 102 made from a biocompatible material such as a medical grade silicone or a medical grade polyurethane-based material.

In the embodiment shown in FIGS. 10*a* and 10*b*, the first operable hydraulic constriction element 101 has a shape such that the first operable hydraulic constriction element 101 expands and extends the furthest in the center of the urethra U. Having an additional pressure on the central part of the urethra U improves the sealing capabilities of the implantable constriction device 10 and thus reduces the risk of leakage.

The second support element 24*b* comprises a cushioning element 30 configured to contact the urethra U. The cushioning element 30 is fixated to the inner surface of the second support element 24*b* by means of an adhesive and is more resilient than the second support element 24*b*. The cushioning element 30 is made from a soft medical grade silicone or polyurethane material.

All foreign matter implanted into the human body inevitably causes an inflammatory response. In short, the process starts with the implanted medical device immediately and spontaneously acquiring a layer of host proteins. The blood protein-modified surface enables cells to attach to the surface enabling monocytes and macrophages to interact on the surface of the medical implant. The macrophages secrete proteins that modulate fibrosis and in turn developing the fibrosis capsule around the foreign body. In practice, a fibrosis capsule is a dense layer of excess fibrous connective tissue. On a medical device implanted in the abdomen, the fibrotic capsule typically grows to a thickness of about 0.5 mm-2 mm, and is substantially inelastic and dense. In the embodiment of FIGS. 10*a* and 10*b*, the fibrotic tissue is shown as FT covering all surfaces of the implantable constriction device 10 and as such is formed between the cushioning element 30 and the urethra U and between the first operable hydraulic constriction element 101 and the urethra U. As the fibrotic tissue is substantially inelastic, this means that the first operable hydraulic constriction element 101 needs a shape such that it is substantially unaffected by the formation of an inelastic layer of fibrotic tissue FT on its surface. In the embodiment shown in FIGS. 10*a*, 10*b* this means that the expansion and exertion of pressure on the urethra U cannot be dependent on elastic expansion of the first operable hydraulic constriction element 101, but rather on a shape change that is possible to make inelastically. In the embodiment shown in FIGS. 10*a*-11*d*, this substantially inelastic shape change is achieved by the first operable hydraulic constriction element 101 going from having concave surface contacting the urethra U, as shown e.g. in FIG. 10*b*, to having a convex surface contacting the urethra U, as shown e.g. in FIG. 10*a*. With this movement, the fibrotic tissue FT can follow the contacting surface of the first operable hydraulic constriction element 101 and the fibrotic tissue can have a contacting length CL being the same when the contacting surface is a concave contacting surface CS' and a convex contacting surface CS".

In the embodiment of FIGS. 10*a* and 10*b* the first operable hydraulic constriction element 101 is connected to a first hydraulic fluid conduit 109 which enters the first operable hydraulic constriction element 101 through a first integrated channel 23*a* in the first support element 24*a*. The first fluid conduit 109, and thereby the operable hydraulic constriction element 101, is connected to a hydraulic pump and control system (not shown), such as any the hydraulic pump and control systems disclosed with reference to FIGS. 5-9. The controller of the hydraulic pump and control system is configured to control the flow of fluid from a hydraulic pump, such that the first operable hydraulic constriction element 101 is inflated for constricting the urethra U for restricting the flow of urine therethrough (as shown in FIG. 10*a*).

Figure 10C:
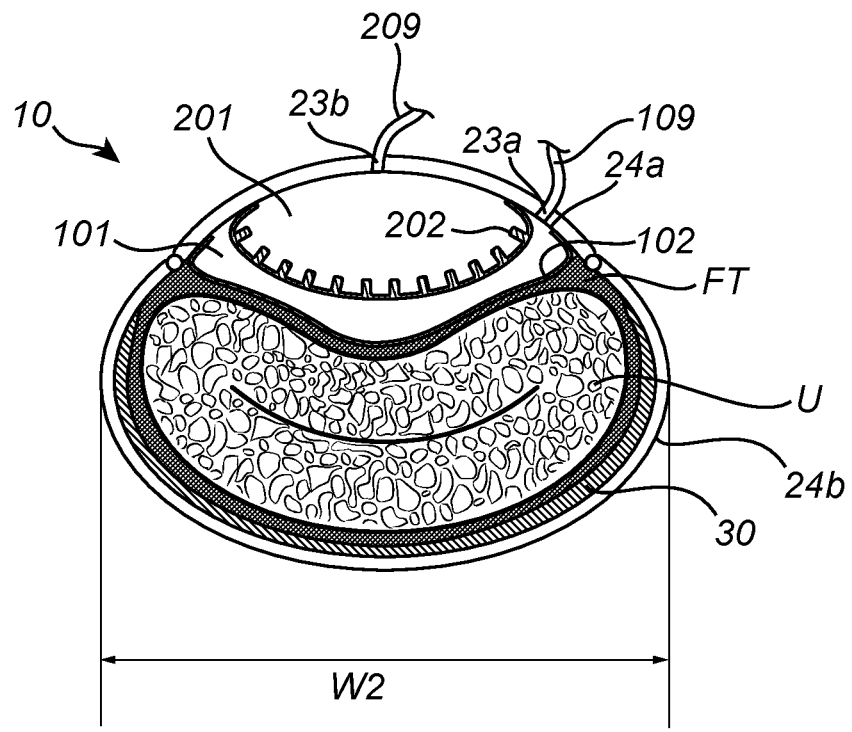
FIG. 10c shows an embodiment of an implantable constriction device for constricting the urethra of a patient in a sectional view, in its constricted state.

FIG. 10*c* shows an embodiment of the implantable constriction device 10 in a cross-sectional view in a state in which the implantable constriction device 10 is constricting the urethra U and thereby restricts the flow of urine through the urethra U. The embodiment of FIG. 10 is similar to the embodiment shown in FIG. 8*a* with the major difference being the design of the wall 202 of the supporting hydraulic operable constriction element 201. In the embodiment shown in FIG. 10*c*, the second support element 24*b* is configured for a urethra U with a larger cross-sectional area than in the embodiment shown in FIGS. 10*a*, 10*b*. Having different second support elements 24*b* makes it possible to adapt the implantable constriction device 10 to urethras of different size while maintaining the same first support element 24*a*, in which the operable hydraulic constriction elements 101, 201 are fixated. As such, a kit which can be combined in different ways can be created, with the more complex part (first support element 24*a*) being the same can be created. This is further described with reference to FIGS. 3*a*-3*e*, which is based on the same basic concept. The surrounding structure 20 has a periphery surrounding the urethra U when implanted. The first and supporting operable hydraulic constriction element 101, 201 are configured to constrict the urethra U for restricting the flow of urine therethrough and configured to release the constriction of the urethra U for enabling the patient to urinate. The first and second support elements 24*a*, 24*b* each comprises a curvature adapted for the curvature of the urethra U such that the implantable constriction device 10 fits snuggly around the urethra U such that the distance that the operable hydraulic constriction elements 101, 201 needs to expand to constrict the urethra U is kept at a minimum.

The first support element 24a is configured to support a first operable hydraulic constriction element 101 and a supporting operable hydraulic constriction element 201. The first and supporting operable hydraulic constriction element 101, 201 are configured to constrict the urethra U for restricting the flow of urine therethrough and configured to release the constriction of the urethra U for enabling the patient to urinate. The first and second support elements 24a, 24b each comprises a curvature adapted for the curvature of the urethra U such that the implantable constriction device 10 fits snuggly around the urethra U such that the distance that the operable hydraulic constriction elements 101, 201 needs to expand to constrict the urethra U is kept at a minimum.

Both the first and supporting operable hydraulic constriction element 101, 201 are configured to be inflated and thereby expand in a first direction d1 towards the urethra U to constrict a portion of the urethra U for restricting the flow of urine therethrough. The first operable hydraulic constriction element 101 comprises a lumen 103 surrounded by a resilient wall 102 made from a biocompatible material such as a medical grade silicone or a medical grade polyurethane-based material. The supporting operable hydraulic constriction element 201 comprises a lumen 203 surrounded by a resilient wall 202 made from a biocompatible material such as a medical grade silicone or a medical grade polyurethane-based material. The supporting operable hydraulic constriction element 201 is placed between the first operable hydraulic constriction element 101 and the support element 24a.

Figure 10D:
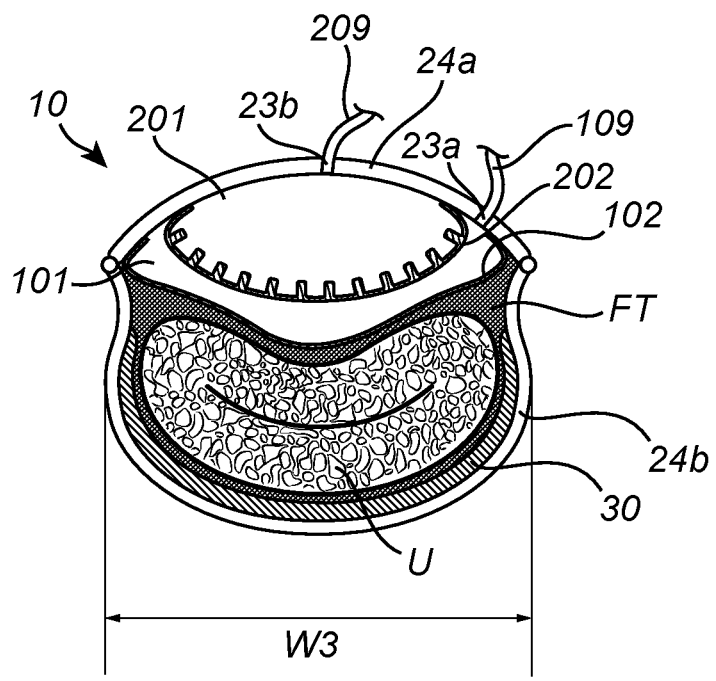
FIG. 10d shows an embodiment of an implantable constriction device for constricting the urethra of a patient in a sectional view, in its constricted state.

In the embodiment shown in FIGS. 10c and 10d, the first operable hydraulic constriction element 101 has a shape such that the first operable hydraulic constriction element 101 expands and extends the furthest in the center of the urethra U. Having an additional pressure on the central part of the urethra U improves the sealing capabilities of the implantable constriction device 10 and thus reduces the risk of leakage.

In the embodiment shown in FIGS. 10c and 10d, the supporting operable hydraulic constriction element 201 is less resilient than the first operable hydraulic constriction element 101 which means that the supporting operable hydraulic constriction element 201 is more rigid and less prone to change its size and/or location by external forces pushing on the supporting operable hydraulic constriction element 201. For example, the supporting operable hydraulic constriction element 201 is more stable along the axial direction of the urethra U, which means that the supporting operable hydraulic constriction element 201 will retain its position along the axial direction of the urethra U, such that the force exerted on the urethra U in the first direction d1 is exerted on the intended portion of the urethra U. In the embodiment shown in FIGS. 10c and 10d, the supporting operable hydraulic constriction element 201 is more rigid than the first operable hydraulic constriction element 101 by the wall 202 of the supporting operable hydraulic constriction element 201 being enforced by thicker portions having a thickness T2" being more than 2 times as the thickness T2' of other portions of the wall 202 of the supporting operable hydraulic constriction element 201. The thicker portions make up at least ⅕ of the area of the wall of the supporting operable hydraulic constriction element 201, and it may make up at least ⅓ of the area of the wall 202 of the supporting operable hydraulic constriction element 201 for further increasing the stability of the supporting operable hydraulic constriction element 201.

The portions of the wall 202 of the supporting operable hydraulic constriction element 201 could be made from the same material as the rest of the wall of the supporting operable hydraulic constriction element 201 or could in the alternative be made from a second different, more rigid material. The second material could have a modulus of elasticity which is higher than a modulus of elasticity of the first material. As an example, the first material could be a medical grade silicone material, and the second material could be another, less elastic medical grade silicone. According to one embodiment, the modulus of elasticity of the second material is more than 1.5 times higher than the modulus of elasticity of the first material. According to another embodiment, the modulus of elasticity of the second material is more than 2 times higher than the modulus of elasticity of the first material.

The supporting operable hydraulic constriction element 201 is connected to a second hydraulic fluid conduit 209 which enters the supporting operable hydraulic constriction element 201 through a second integrated channel 23b in the first support element 24a. The first and second fluid conduits 109, 209, and thereby the operable hydraulic constriction elements 101, 201, are connected to a hydraulic pump and control system (not shown), such as any the hydraulic pump and control systems disclosed with reference to FIGS. 5-9. The controller of the hydraulic pump and control system is configured to control the flow of fluid from a hydraulic pump, such that the first and supporting operable hydraulic constriction elements 101, 201 are inflated for constricting the urethra U for restricting the flow of urine therethrough (as shown in FIG. 10a).

FIG. 10d shows an embodiment of the implantable constriction device 10 in a cross-sectional view in a state in which the implantable constriction device 10 is constricting the urethra U and thereby restricts the flow of urine through the urethra U. The embodiment of FIG. 10d is identical to the embodiment shown in FIG. 10c, with the exception that the second support element 24b is configured for a urethra U with a smaller cross sectional area than in the embodiment shown in FIGS. 10a, 10b and 10c. The second support elements of FIGS. 10b,10c and 10d makes up a kit of second support members, or a surrounding structure kit together with the first support element of FIG. 10a. In FIG. 10b, the second support element 24b has a width W1 at the widest place which is 0.9 times the width W2 of the second support element 24b of FIG. 10c at the widest place, and 1.1 times the width W3 of the second support element 24b of FIG. 10d at the widest place. In alternative embodiments, it is conceivable that a kit of second support elements 24b comprises one second support element which has a width W1 at the widest place which is 0.8 times the width W2 of another second support element 24b in the kit, at the widest place, and 1.2 times the width W3 of yet another support element 24b of the kit, at the widest place.

Figure 11A:
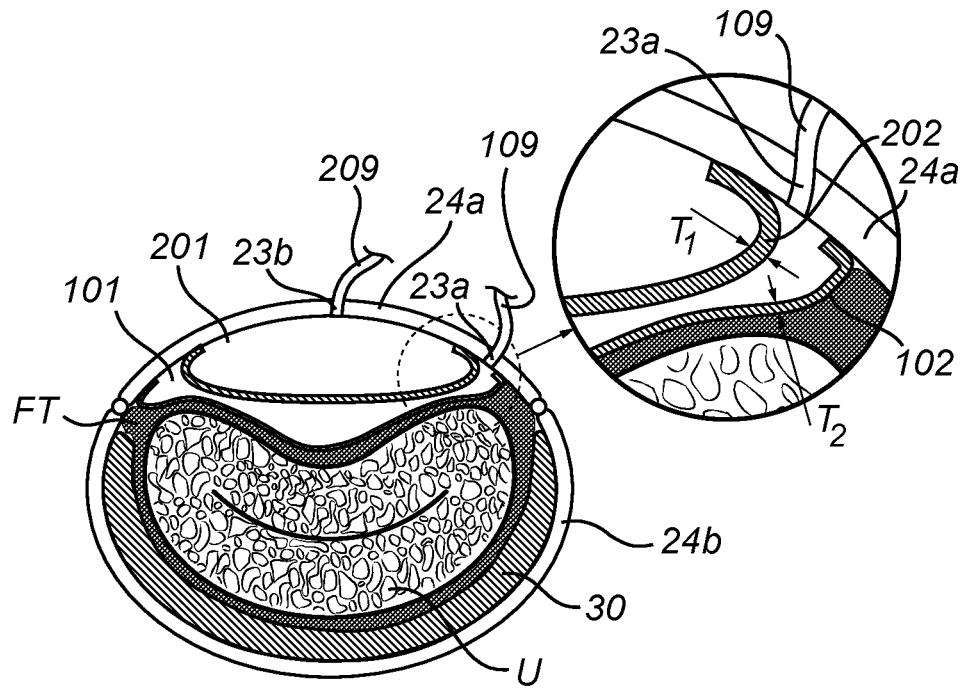
FIG. 11a shows an embodiment of an implantable constriction device for constricting the urethra of a patient in a sectional view, in its constricted state.
Figure 11B:
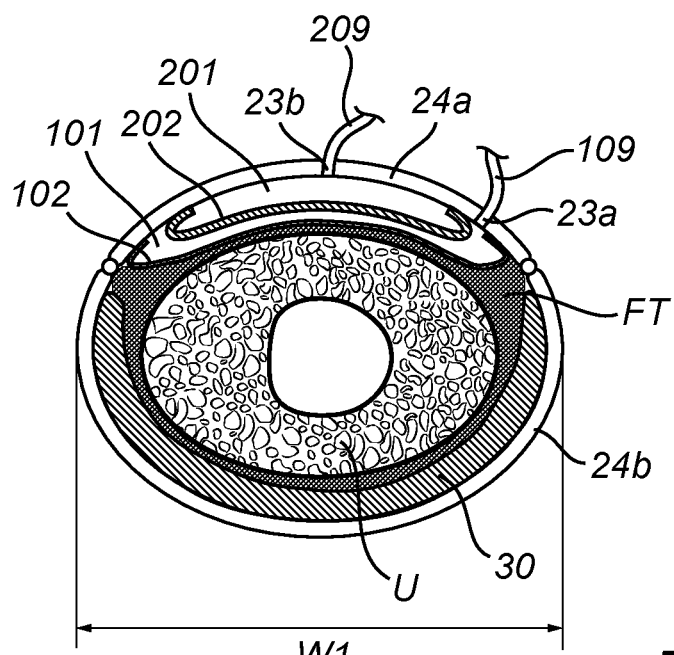
FIG. 11b shows an embodiment of an implantable constriction device for constricting the urethra of a patient in a sectional view, in its un-constricted state.

FIGS. 11a shows an embodiment of the implantable constriction device 10 in a cross-sectional view in a state in which the implantable constriction device 10 is constricting the urethra U and thereby restricts the flow of urine through the urethra U, and FIG. 11b shows the embodiment of FIG. 11a in a state in which the constriction of the urethra U has been released to allow the flow of urine through the urethra U. In the embodiment of FIGS. 11a and 11b, the supporting operable hydraulic constriction element 201 is more rigid than the first operable hydraulic constriction element 101 by the wall 202 of the supporting operable hydraulic constriction element 201 having a thickness T2 being thicker than the thickness T1 of the wall 102 of the first operable hydraulic constriction element 101. In the embodiment shown in FIGS. 11a,11b the resilient wall 202 of the supporting operable hydraulic constriction element 201 is more than 1.5 times thicker than a portion of the wall 102 of the first operable hydraulic constriction element 101. In alternative embodiments, it is equally conceivable that the wall 202 of the supporting operable hydraulic constriction element 201 is more than 2 times thicker than a portion of the wall 102 of the first operable hydraulic constriction element 101 for further increasing the stability of the supporting operable hydraulic constriction element 202. The increased rigidity of the supporting operable hydraulic constriction element 201 could also be a combination of increase wall thickness and that at least a portion of the resilient wall 102 of the first operable hydraulic constriction element 101 comprises a first material, and at least a portion of the resilient wall 102 of the supporting operable hydraulic constriction element 201 comprises a second material. The second material has a modulus of elasticity which is higher than a modulus of elasticity of the first material. As an example, the first material could be a medical grade silicone material, and the second material could be another, less elastic medical grade silicone. According to one embodiment, the modulus of elasticity of the second material is more than 1.5 times higher than the modulus of elasticity of the first material. According to another embodiment, the modulus of elasticity of the second material is more than 2 times higher than the modulus of elasticity of the first material.

Figure 11C:
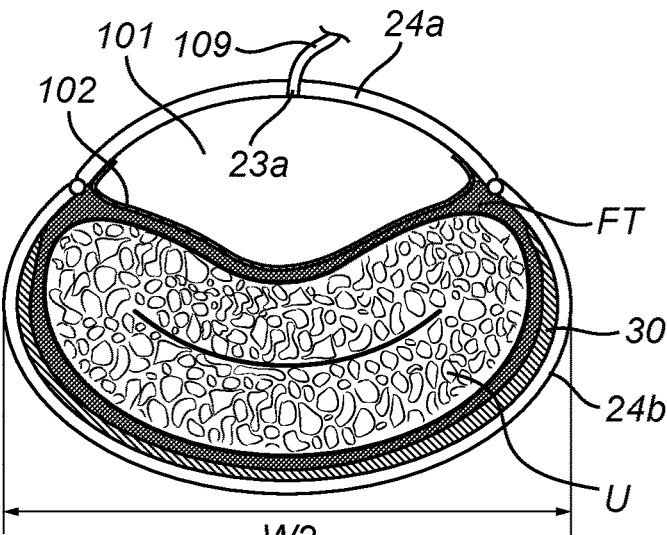
FIG. 11c shows an embodiment of an implantable constriction device for constricting the urethra of a patient in a sectional view, in its constricted state.

FIG. 11c shows an embodiment of the implantable constriction device 10 in a cross-sectional view in a state in which the implantable constriction device 10 is constricting the urethra U and thereby restricts the flow of urine through the urethra U. In the embodiments shown in FIGS. 11c-11e, the operable hydraulic constriction element is a single operable hydraulic constriction element 101, i.e. the FIGS. 11c-11e does not comprise a supporting operable hydraulic constriction element. The embodiment of FIG. 11c also differs from the embodiment shown in FIGS. 11a and 11b in that the second support element 24b is configured for a urethra U with a larger cross sectional area than in the embodiment shown in FIGS. 11a, 11b. Having different second support elements 24b makes it possible to adapt the implantable constriction device 10 to urethras of different size while maintaining the same first support element 24a, in which the operable hydraulic constriction elements 101, 201 are fixated. As such, a kit which can be combined in different ways can be created, with the more complex part (first support element 24a) being the same can be created. This is further described with reference to FIGS. 3a-3e, which is based on the same basic concept.

Figure 11D:
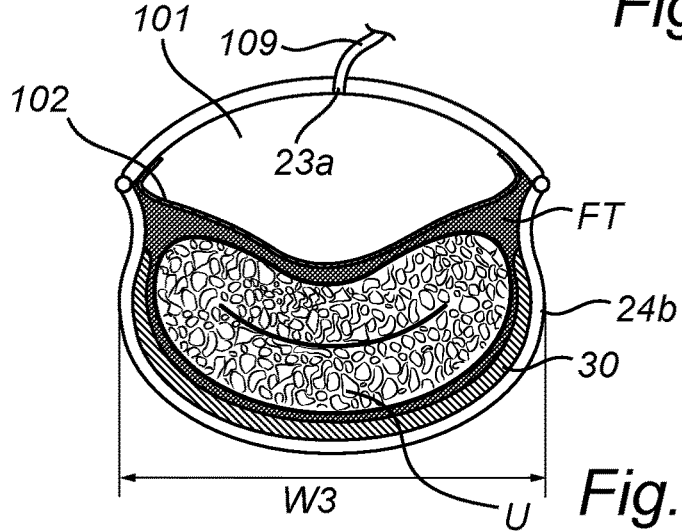
FIG. 11d shows an embodiment of an implantable constriction device for constricting the urethra of a patient in a sectional view, in its constricted state.

FIG. 11d shows an embodiment of the implantable constriction device 10 in a cross-sectional view in a state in which the implantable constriction device 10 is constricting the urethra U and thereby restricts the flow of urine through the urethra U. The embodiment of FIG. 11d is identical to the embodiment shown in FIG. 11c, with the exception that the second support element 24b is configured for a urethra U with a smaller cross sectional area than in the embodiment shown in FIGS. 11a, 11b and 11c. The second support elements 24b of FIGS. 11b, 11c and 11d makes up a kit of second support members 24b, or a surrounding structure kit together with the first support element of FIG. 11a. In FIG. 11b, the second support element 24b has a width W1 at the widest place which is 0.9 times the width W2 of the second support element 24b of FIG. 11c at the widest place, and 1.1 times the width W3 of the second support element 24b of FIG. 11d at the widest place. In alternative embodiments, it is conceivable that a kit of second support elements 24b comprises one second support element 24b which has a width W1 at the widest place which is 0.8 times the width W2 of another second support element 24b in the kit, at the widest place, and 1.2 times the width W3 of yet another support element 24b of the kit, at the widest place.

Figure 11E:
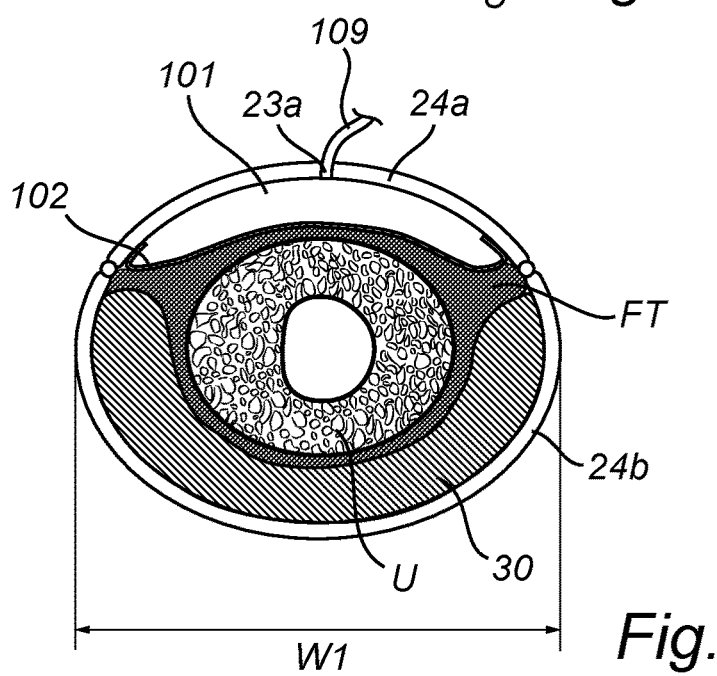
FIG. 11e shows an embodiment of an implantable constriction device for constricting the urethra of a patient in a sectional view, in its un-constricted state.

FIG. 11e shows an embodiment of the implantable constriction device 10 in a cross-sectional view in a state in which the constriction of the urethra U has been released to allow the flow of urine through the urethra U. In the embodiment of FIG. 11e the cushioning element 30 is configured for a urethra U with a smaller cross-sectional area than in the embodiment shown in FIGS. 11a and 11b. As such, a kit made up of a first support element 24a and a plurality of second support elements 24b with the same curvature etc. but with different thickness of the cushioning element 30 can be made. In the embodiment shown in FIG. 11e, the cushioning element 30 is made from a solid medical grade silicone or polyurethane material.

FIG. 11f shows an embodiment of the implantable constriction device 10 in a cross-sectional view in a state in which the constriction of the urethra U has been released to allow the flow of urine through the urethra U. The embodiment of FIG. 11f is identical to the embodiment shown in FIG. 11e, with the exception that the cushioning element 30 is inflatable with a fluid or a semi-solid or gel like substance 31. In the embodiment shown in FIG. 11f, the cushioning element 30 is divided into a plurality of individually inflatable cells 33', 33", 33''', 33'''' such that the shape of the cushioning element 30 can be further adapted to the urethra U of the specific patient. Each cell 33', 33", 33''', 33'''' may be filled with different amounts of substance 31 for adapting the cushioning element 30 to the anatomy of the urethra U of the specific patient. Each cell 33', 33", 33''', 33'''' comprises a self-sealing membrane 32 through which a syringe can be inserted to inject the substance 31 into the specific cell 33',33",33''',33''''. The self-sealing membrane 32 may be accessible through a hole or recess in the second support element, or axially from the side of the implantable constriction device 10 facing upstream or downstream the urethra U. In alternative embodiments, the cushioning element 30 may consist of a single inflatable cell.

FIG. 12a shows an embodiment of a hydraulic pump 104 which may be used in any of the embodiments of the implantable constriction device. In the embodiment of FIG. 12a, the hydraulic pump 104 is a peristaltic hydraulic pump shown in cross-section. The implantable peristaltic pump 104 comprises a deflectable hollow member 401 for fluid transportation, in form of a tubing made from a resilient material, such as an elastomeric polymer material, such as silicone, Parylene® coated silicone, NBR, Hypalon, Viton, PVC, EPDM, Polyurethane or Natural Rubber. The deflectable hollow member 401 is placed between a first portion of a fluid conduit 109' at the inlet of the hydraulic pump 104 and a second portion of a fluid conduit 109" at the outlet of the hydraulic pump 104. The deflectable hollow member 401 is adapted to be deflected by operable compression members 402 or "wipers", adapted to engage and compress the hollow member 401, and thus transport the hydraulic fluid. The compression member 402 is propelled by the motor M via a gear system G. The hollow member 401 is placed inside a peristaltic pump housing 403, such that the hollow member 401 is compressed between the operable compression member 402 and the housing 403. The peristaltic pump 104 is a sealed pump which means that fluid will not leak through the pump even at standstill. As the peristaltic pump is a sealed pump no additional valve is needed to keep the fluid through the fluid conduits 109',109" closed.

The deflectable hollow member 401 is connected to or integrated with fluid conduits 109'109", which in turn are a part of the hydraulic system in any of the embodiments described herein. When the compression member 402 is propelled in a counterclockwise direction, it creates a peristaltic wave which presses hydraulic fluid through the hollow member 401 and further through the second portion of the fluid conduit 109". When the compression member 402 is propelled in a clockwise direction, it creates a peristaltic wave which presses hydraulic fluid through the hollow member 401 and further through the first fluid conduit 109'. By using a peristaltic pump 104 of the embodiment of FIG. 12a, the construction of the embodiment of FIG. 2b, the implantable constriction device can be opened and closed by operating the motor in a first and second direction and thereby altering the direction of movement of the compression member 402.

FIG. 12b shows the peristaltic pump in accordance with the embodiment of FIG. 12a in a side view in which the electrical motor M and gear system G for propelling the compression member 402 is shown. The electrical motor M is adapted to transform electrical energy to mechanical work. The electrical motor M may receive electrical energy from a receiving unit receiving wireless energy transmitted from an energy transmitting unit external to the body of the patient or may receive electrical energy stored in an implantable battery. The electrical motor M in the embodiment of FIGS. 12a and 12 is a brush-less direct current electrical motor M, but in alternative embodiment the electrical motor could be an electrical motor M selected from an alternating current (AC), a linear electrical motor, an axial electrical motor, a piezo-electric motor, a multiple phase motor, such as a three-phase motor, a bimetal motor, and a memory metal motor.

The force output of the electrical motor M is in connection with a force input of a gear system G adapted to receive mechanical work having a first force and first velocity, and output mechanical work having a different second force and a different second velocity, such that the high velocity movement supplied by the electrical motor M is transformed to low velocity movement with increased force.

The gear system G may for example comprise a gear system having the configuration such as the gear system G described with reference to FIGS. 13a and 13b. In alternative embodiments, it is conceivable that the gear system G comprises a transmission system of some other configuration, such as a conventional gear wheel system, a worm gear system, or a belt transmission system.

Figure 13A:
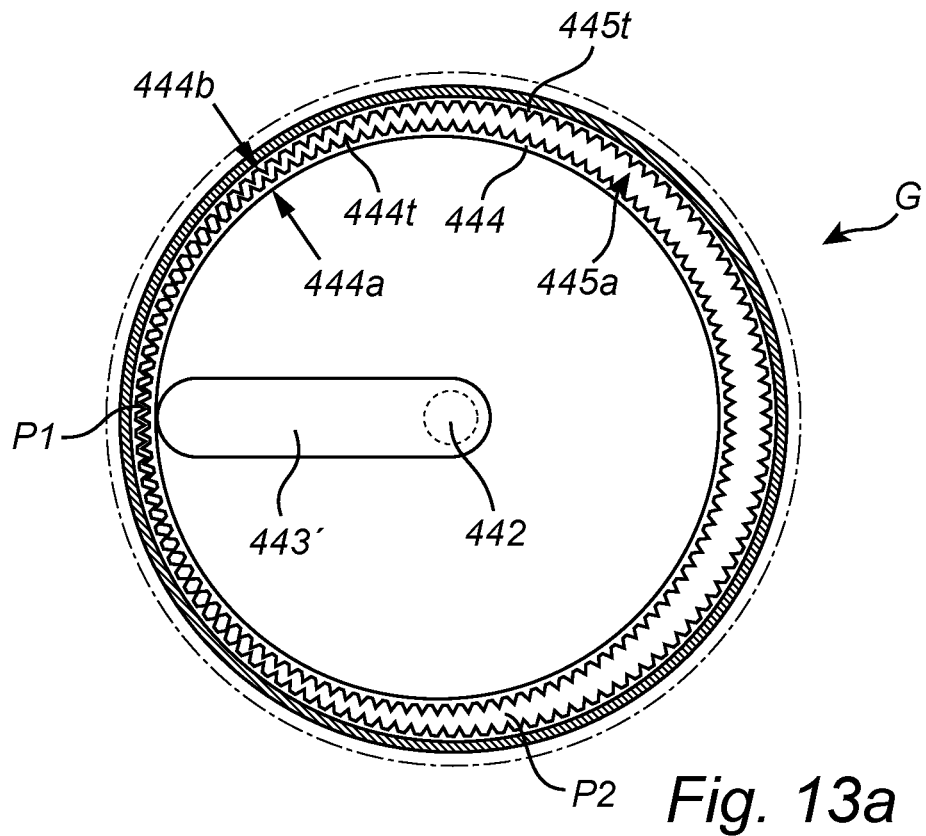
FIG. 13a shows a top view of a gear system for an implantable constriction device.

FIG. 13a shows an embodiment of an implantable gear system G adapted to receive mechanical work having a first force and first velocity, and output mechanical work having a second, different force and a second different velocity. The gear system G comprises a force input 442 connected to an operable element 443' adapted to engage a first gear 444 having the shape of a hollow cylinder, comprising a first number of teeth 444t, for example 160, on the peripheral outside thereof, and a second gear 445 having the shape of a hollow cylinder, comprising a greater number of teeth 445t than the first gear, for example 462, on the inside surface thereof. The operable element 443' is adapted to engage the inside 444a of the first gear 444, such that the outside 444b of the first gear 444 is pressed against the inside 445a of the second gear 445 such that the teeth 444t of the first gear 444 are interengaged with the teeth 445t of the second gear 445 in position $P_1$ interspaced by positions (for example the position $P_2$) at which the teeth are not interengaged. The operation of the operable element 443' advances the position $P_1$ and thereby causes relative rotation between the first gear 444 and the second gear 445. In the embodiment shown in FIG. 13a, the second gear 445 comprises two more teeth 445t than the first gear 444, resulting in the first gear 444 rotating 2/160 or 1/80 of a revolution for each revolution that the operable element 443' performs, which results in a transmission of 80 times, i.e. the force output (449 of FIG. 13b) provides a force with 1/80 of the velocity and 80 times the force, thus increasing the force which can be exerted on a urethra U by the electrical motor, 80 times. In the embodiment shown in FIG. 13a the operable element 443' slides radially against the inner surface of the first gear 444. For reducing the friction a lubricating fluid may be present in the gear system G, it is further conceivable that the operable element 443' or the surface against which the operable implant 443' slides may comprise a self-lubricating material, such as Graphalloy, Nyloil® or PTFE.

Figure 13B:
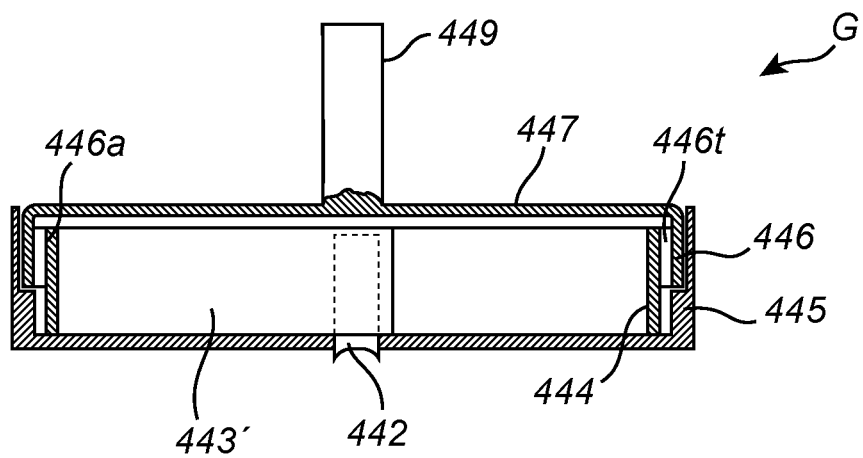
FIG. 13b shows a partially sectional side view of a gear system for an implantable constriction device.

FIG. 13b shows the gear system G in a sectional side view, in an embodiment in which the gear system G comprises a third gear 446 having an inside 446a comprising the same amount of teeth 446t as the outside 444b of the first gear 444. The teeth 446t of the third gear 446 are adapted to interengage with the teeth of the first gear 444 such that the third gear 446 rotates in relation to the second gear 445, along with the interengaged position ($P_1$ of FIG. 2a). The third gear 446 is in connection with a force output 449 of the gear system 440 by means of a radially extending connecting structure 447 for transferring force from the third gear 446 to the force output 449.

The gear system G of FIGS. 13a and 13b could for example be made of a metallic material, plastic material, or ceramic material. In one embodiment, the gear system is made from non-metallic and/or non-magnetic material, such that the gear system G does not affect the energy transfer to an implantable energy receiver. The gear system G may be lubricated with a biocompatible lubricant, such as hyaluronic acid, and may, for that purpose, be placed inside a reservoir adapted to hold a hydraulic fluid, which also may serve as a lubricant. The gear system G may be encapsulated by an enclosure for preventing bodily fluids from affecting the gear system G and/or the in-growth of human tissue in the gear system and/or the leakage of hydraulic and/or lubricating fluids. The enclosure may be a non-metallic and/or non-magnetic enclosure, such that the material of the enclosure does not affect the ability of transferring wireless energy to a wireless energy receiver of the operable implant. The gear system may be encapsulated separately or may be encapsulated along with an electrical motor (such as shown in FIGS. 12a,12b) or alongside additional components (such as shown in FIGS. 14a,14b).

Figure 14:
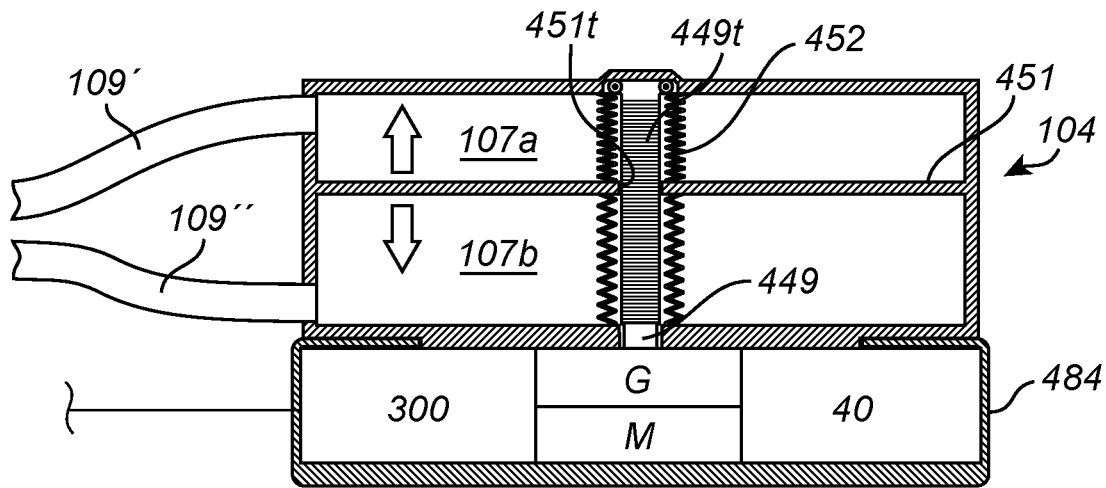
FIG. 14 shows a sectional side view of an embodiment of a hydraulic pump for an implantable constriction device.

FIG. 14 shows a cross-sectional view of an electrical motor M in combination with a gear system G for propulsion of a hydraulic pump 104. The electrical motor M is connected to the controller 300 (which may have the features and capabilities described with reference to FIG. 9) which in turn is connected to an energy storage unit 40. The energy storage unit 40 may be a battery, a chargeable battery or a capacitor by means of which energy can be stored in the body of the patient. The controller 300 further comprises a processing unit 306 for handling the control of the restriction device. The processing unit 306 could be a single central processing unit or could comprise two or more processing units. The processing unit 306 could comprise a general-purpose microprocessor and/or an instruction set processor and/or related chips sets and/or special purpose microprocessors such as ASICs (Application Specific Integrated Circuit). The processing unit 306 may also comprise memory for storing instruction and/or data. The controller 300 further comprises a transceiver 308b for receiving and/or transmitting wirelessly signals to/from outside the body. The transceiver can enable programming the controller 300 form outside of body of the patient such that the implantable constriction device can be programmed to function optimally. The optimal function of the implantable constriction device could in many instances be a mediation between optimal restriction of the urethra U and restriction with causes the least damage.

The controller 300, the energy storage unit 40 and the motor M and gear system G may be enclosed by a housing 484 such that the controller 300 is protected from bodily fluids. The housing 484 may be an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass. In any instance the enclosure should be made from a material with low permeability, such that migration of fluid through the walls of the enclosure is prevented.

Turning now to the hydraulic pump 104 shown in FIG. 14. In the embodiment shown in FIG. 14, the force output 449 of the gear system G is threaded 449t and engages a correspondingly threaded portion 451t of the movable wall 451 such that the rotating force created by the motor M and gear system G is transferred to a linear force moving the movable wall 451. The threaded force output 449 is enclosed by pleated bellows portions 452 both above and below the movable wall 451 such that the threaded force output 449 is protected from the fluid in the lumens of the reservoirs 107a, 107b. The reservoirs 107a, 107b has a common moveable wall 451 for changing the volume of the implantable fluid reservoirs 107a, 107b and thereby increasing fluid in the first fluid reservoir 107a simultaneously with decreasing fluid in the second fluid reservoir 107b and vice versa. The peristaltic pump is a sealed pump which means that fluid will not leak through the pump even at standstill. As the peristaltic pump is a sealed pump no additional valve is needed to keep the fluid through the fluid conduits 109',109" closed. The movable wall pump 104 of FIG. 14 is a sealed pump which means that fluid will not leak through the pump even at standstill. As the movable wall pump 104 is a sealed pump, no additional valve is needed to keep the fluid through the fluid conduits 109',109" closed.

Figure 15A:
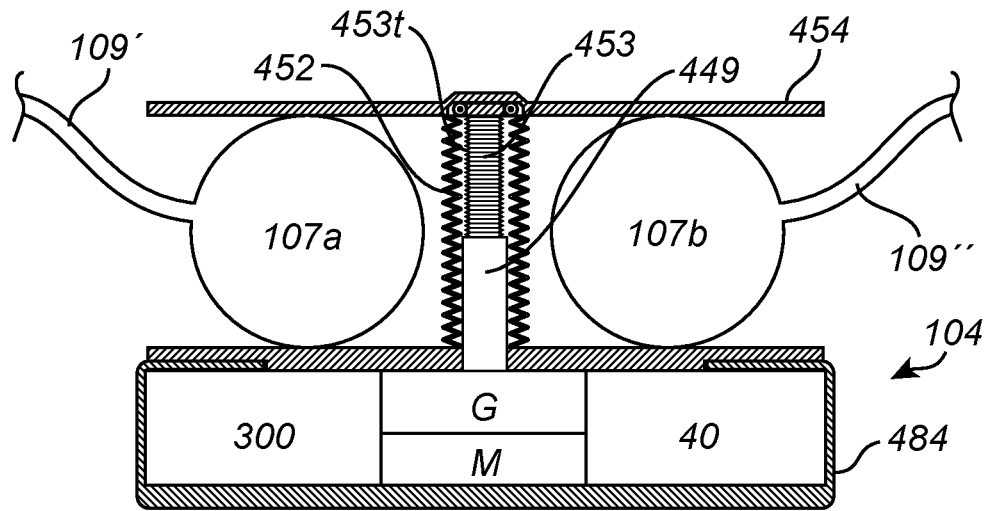
FIG. 15a shows a sectional side view of an embodiment of a hydraulic pump for an implantable constriction device.

FIG. 15a shows a cross-sectional view of a hydraulic pump comprising two expandible reservoirs 107a,107b. The hydraulic pump 104 comprises an encapsulated motor M, gear system G, controller 300 and energy storage unit 40 being identical to that described with reference to FIG. 14. Turning to the hydraulic pump 104, the force output 449 is, in the embodiment described in FIG. 15 a hollow shaft equipped with inner threads (not shown) adapted to engage outer threads 453t of a threaded member 453, such that the interaction between the hollow shaft 449 and the threaded member 453 transforms the radially rotating force generated by the motor M and the gear system G, to a linear force. The threaded member 453 is connected to a radially extending engaging member 454 adapted to engage the first and second reservoirs 107a,107b containing a hydraulic fluid. The reservoirs 107a, 107b may be fixated to the radially extending engaging members 454, for example by means of an adhesive, such that the reservoirs 107a,107b are forced to expand when the radially extending engaging member 454 is moved upwards in the expanding direction of the reservoirs 107a, 107b. The first reservoir 107a is connected to a first fluid conduit and the second reservoir 107b is connected to a second fluid conduit 109". The embodiment shown in FIG. 15a further comprises a pleated bellows portions 452 for encapsulating and protecting the force output 449 and the threaded member 453 from bodily fluids. The reservoirs 107a, 107b are preferably made from medical grade implantable silicone or Parylene® coated medical grade implantable silicone but may in alternative embodiments be made from another resilient material such as NBR, Hypalon, Viton, PVC, EPDM, Polyurethane or Natural Rubber. When the reservoirs 107a, 107b are compressed and expanded they function as hydraulic pumps for moving fluid to and from the operable hydraulic constriction elements in any of the embodiments herein.

Figure 15B:
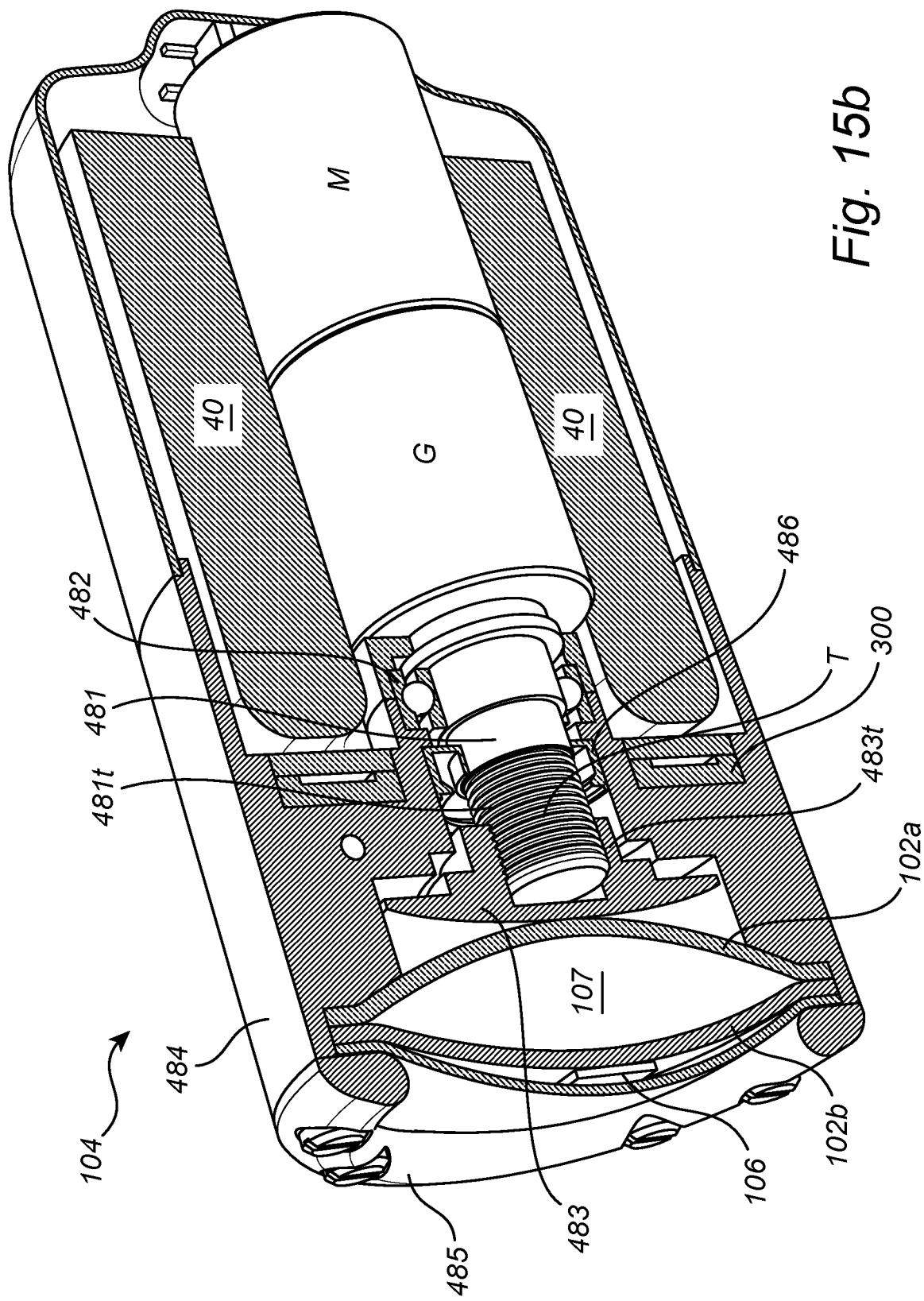
FIG. 15b shows a partially sectional perspective view from the left of an embodiment of a hydraulic pump for an implantable constriction device.

FIG. 15b shows a cross-sectional view of a hydraulic pump 104 similar to the hydraulic pump or the embodiment of FIG. 15a. In the embodiment of FIG. 15b, the hydraulic pump 104 comprises one expandible reservoir 107. The hydraulic pump 104 comprises an encapsulated motor M, gear system G, controller 300 and energy storage unit 40. The motor M is configured to generate force in a radial direction by rotation of the force output in the form of a shaft 481. The shaft 481 is equipped with outer threads 481t adapted to engage inner threads 483t of a compression member 483, such that the interaction between the threaded shaft 481, 481t and the threaded portion 483t of the compression member 483 transforms the radially rotating force generated by the motor M and the gear system G, to a linear force acting in the axial direction of the shaft 481, and thus makes up a transmission T. The axial force acts on the compression member 483 which engages a first resilient wall 102a of the compressible reservoir 107 for compressing the compressible reservoir 107 and thus increasing the pressure on a hydraulic fluid in the compressible reservoir 107. The compression member 483 may be fixated to the first resilient wall portion 102a by means of an adhesive, such that the reservoir 107 is forced to expand when the compression member 483 moves in the expanding direction of the reservoir 107. The reservoir 107 is connected to a fluid conduit (not shown) for conducting hydraulic fluid from the compressible reservoir to the and from the reservoir 107. The reservoir 107 is preferably made from medical grade implantable silicone or Parylene® coated medical grade implantable silicone but may in alternative embodiments be made from another resilient material such as NBR, Hypalon, Viton, PVC, EPDM, Polyurethane or Natural Rubber. When the reservoir 107 is compressed and expanded it functions as hydraulic pump for moving hydraulic fluid to and from the operable hydraulic constriction elements in any of the embodiments herein.

The hydraulic pump 104 further comprises at least one bearing 482 for the shaft 481 placed between the gear system G and the compressible reservoir 107. The bearing 482 is configured to withhold at least half of the force in the axial direction, for reducing the axial load on the motor M and the gear system G which is caused by the compression of the reservoir 107. In the embodiment shown in FIG. 15b, the bearing 482 is a ball bearing, but in other embodiments the bearing may comprise a roller bearing or a plain bearing preferably including a self-lubricating material such as PTFE or HDPE.

The gear system G is connected to the motor M, and placed between the motor M and transmission T and adapted to receive mechanical work via the shaft 481 having a force and a velocity, and output mechanical work having a stronger force and a lower velocity. The compressible reservoir 107 comprises a first resilient wall portion 102*a* and a second resilient wall portion 102*b*, wherein the first resilient wall portion 102*a* is more resilient than the second resilient wall portion 102*b*.

In alternative embodiments, the compression member 483 may be directly connected to the first resilient wall portion 102*a*, and in such embodiments, the threaded portion 483*t* may be integrated in the first resilient wall portion 102*a*.

In the embodiment shown in FIG. 15*b*, the hydraulic pump 104 further comprises a pressure sensor 106 connected to the compressible reservoir 107 and configured to sense the pressure in the compressible reservoir 107. The pressure sensor 106 is integrated in, and placed on the outside of, the second resilient wall portion 102*b* of the compressible reservoir 107. The pressure sensor 106 comprises a strain gauge-based pressure sensor 106 such as for example described with reference to FIG. 17.

The compressible reservoir 107 in the embodiment shown in FIG. 15*b* comprises a first and second resilient wall portion 102*a*, 102*b* in the form of a first and second circular diaphragm 102*a*, 102*b*. The first resilient wall portion 102*a* has a convex shape facing the compression member 483, and the second resilient wall portion 102*b* has a convex shape facing away from the compression member 483 and a lumen is formed between the two diaphragms 102*a*, 102*b*, and being enclosed by the concave surfaces of the diaphragms 102*a*, 102*b*. The first resilient wall portion 102*a* is configured to be compressed and thus inverted, such that the part of the first resilient wall portion 102*a* facing the compression member 483 assumes a concave shape facing the compression member 483, and as such, a convex shape is formed towards the lumen of the compressible reservoir 107. The inverted, convex, portion of the first resilient wall portion 102*a* thus enters the concave shape of the second resilient wall portion 102*b*. The portion of the compression member 483 configured to engage the first resilient wall portion 102*a* comprises a convex portion for facilitating the inversion of the convex portion of the first resilient wall portion 102*a*. In the embodiment shown in FIG. 15*b*, the first resilient wall portion 102*a* is more resilient than the second resilient wall portion 102*b* such that the compressible reservoir 107 can create a suction when the compression member 483 moves in the direction away from the compressible reservoir 107 thus enabling the compressible reservoir 107 to expand. In the embodiment shown in FIG. 15*b*, a major portion of the first resilient wall portion is made from a material having a modulus of elasticity (E) which is less than 70% or the modulus of elasticity (E) of the material of a major portion of the second resilient wall portion 102*b*. In alternative embodiments, it is conceivable that the first and second resilient wall portions 102*a*, 102*b* are made from the same material, but with the second resilient wall portion 102*b* being more than 1.5 times as thick as the first resilient wall portion 102*a*. In the embodiment shown in FIG. 15*b*, the two diaphragms 102*a*, 102*b* are pressed against each other, for creating the sealed lumen between the first and second diaphragm, by means of a fixation ring 485, which is screwed into the housing 484.

In the embodiment shown in FIG. 15*b*, the hydraulic pump further comprises a shaft sealing 486, which is a sealing engaging the shaft and thus creating a seal between the portion of the pump housing 484 comprising the motor M, gear system G, energy storage unit 40 and controller 300, and the portion of the pump housing 484 comprising the compressible reservoir 107. The seal reduces the risk that hydraulic fluid that may leak from the compressible reservoir 107 will come in contact with any of the motor M, gear system G, energy storage unit 40 and/or controller 300. In the embodiment shown in FIG. 15*b*, the shaft sealing comprises a spring-loaded PTFE sealing 486. A spring engages the housing 484 of the hydraulic pump 104 and the PTFE sealing for creating a constant elastic pressure between the sealing and the shaft 481 which ensures a self-lubricating tight seal. In alternative embodiments, the spring may be replaced by a different type of elastic element, such as an elastic element made from an elastomer. In alternative embodiment, the shaft sealing 486 could be a shaft sealing made from another self-lubricating material such as HDPE.

The hydraulic pump 104 of FIG. 15*b* is enclosed by a pump housing 484, which in the embodiment shown in FIG. 15*b* is a titanium housing 484. In alternative embodiments, the housing could be made from a another medical grade metal alloy, such as medical grade stainless steel or could comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The housing could also comprise at least one composite material, such as any combination of metallic/ceramic and polymer materials or a polymer material reinforced with organic or inorganic fibers, such as carbon or mineral fibers.

Figure 15C:
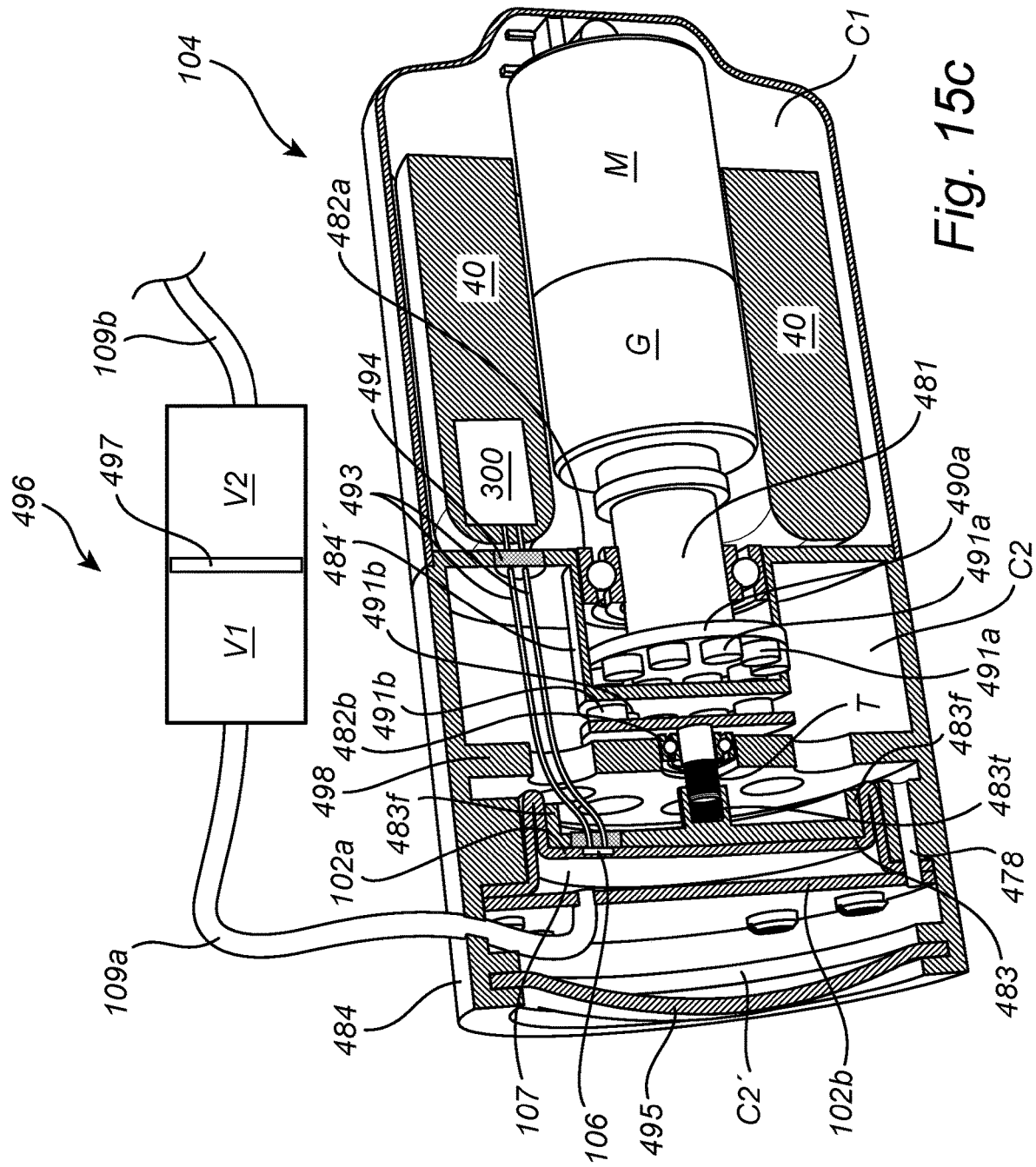
FIG. 15c shows a partially sectional perspective view from the left of an embodiment of a hydraulic pump for an implantable constriction device.

FIG. 15*c* shows a cross-sectional view of a hydraulic pump 104 similar to the hydraulic pump of the embodiment of FIG. 15*b*. In the embodiment of FIG. 15*c*, the hydraulic pump comprises one expandable reservoir 107. The hydraulic pump 104 comprises a housing 484 comprising a first and a second chamber C1, C2 separated from each other by a barrier 484'. Just as in the embodiment of FIG. 15*c*, the first chamber C1 comprises the motor M configured for transforming electrical energy to mechanical work and the gear system gear system G adapted to receive mechanical work having a first force and first velocity, and output mechanical work having a different second force and a different second velocity, such that the high velocity movement supplied by the electrical motor M is transformed to low velocity movement with increased force. The output mechanical work having the different second force and different second velocity acts on a shaft 481 which transfers the force to a magnetic coupling 490*a*, 490*b* for transferring mechanical work from the motor M to an actuator in the form of a compression member 483 for compressing the expandable reservoir 107 for pressing a hydraulic fluid through the conduit 109*a*. The magnetic coupling 490*a*, 490*b* comprises a first disc shaped member 490*a* mounted to the shaft 481 such that the first disc shaped member 490*a* rotates along with the shaft 481. The shaft 481 is supported by ball bearings 482 assisting in the centering of the shaft 481.

In any of the embodiments, the pressure applied to the reservoir and/or hydraulic constriction element can be controlled either by controlling the actual pressure, or by controlling the volume of fluid pumped and/or by controlling the cross-sectional distance of the constricted urethra. I.e. if the pressure is continuously calibrated it can be established that a certain fluid level or distance leads to a specific pressure, which could make control of the device easier then control using constant pressure measurement. In embodiments in which the fluid level or cross-sectional distance of the urethra is used as control value, the pressure may be used as a back-up or safety system, e.g. the pressure sensor can be set to give an alarm signal or take a specific action if the pressure increases over a set value (threshold).

The first disc shaped member 490a comprises magnets (or a material susceptible to magnetic fields) 491 evenly distributed axially in a circular formation on the distal surface of the first disc shaped member 490a.

The barrier 484' separates the first chamber C1 of the housing 484 from the second chamber C2 of the housing. In the embodiment shown in FIG. 15c, the barrier 484' is made from the same material as the outer wall of the housing 484, i.e. medical grade titanium. In the embodiment shown in FIG. 15c the barrier is materially integrated with the portion of the outer wall of the housing 484 enclosing the second chamber C2. However, in other embodiments it is equally conceivable that the barrier is materially integrated with the portion of the outer wall of the housing 484 enclosing the first chamber C1. In any event, the purpose is the both the first and second chambers C2 should be hermetically enclosed and separated from each other.

The second part of the magnetic coupling comprises a second disc shaped member 490b positioned in the second chamber C2 and held in place by a ball bearing 482b being fixated to the inside of the wall of the housing 484 enclosing the second chamber C2 by means of an internal wall portion 498. The second disc shaped member 490b comprises magnets (or a material susceptible to magnetic fields) 491b evenly distributed in a circular formation axially on the distal surface of the first disc shaped member 490b. The magnets 490b of the second disc shaped member 490b are configured to be magnetically connected to the magnets 491a of the first disc shaped member 490a such that the second disc shaped member 490b is dragged by the first disc shaped member 490a by means of the magnetic connection. As such, force from the motor M is transferred from the first hermetically enclosed chamber C1 to the second hermetically enclosed chamber C2.

The second disc shaped member 490b comprises a threaded shaft which is configured to be placed in and engage with a sleeve of a compression member 483. The sleeve of the compression member 483 comprises inside threads 483t for creating a transmission T that transforms the radially rotating force generated by the motor M and the gear system G, to a linear force acting in the axial direction of the shaft 481, and thus makes up a transmission T.

The compression member 483 is a disc shaped element having a distal surface engaging a first resilient wall portion 102a of the reservoir 107 for moving the first resilient wall portion 102a and thereby compressing the reservoir 107. The periphery of the compression member 483 comprises a flange 483f extending towards the first chamber C1 in the proximal direction creating a lateral surface area towards the housing 484. The lateral surface of the flange 483f is configured to engage the first resilient wall portion 102a for creating a rolling crease of the first resilient wall portion 102a. The disc shaped compression member 483 is rigid and made from titanium, just as the rest of the housing 484. That the compression member 483 is rigid makes the reservoir 107 stiff which ensures that the fluid amount in the hydraulic constriction element connected to the reservoir 107 remains the same even as the pressure exerted on the hydraulic constriction element increases.

The reservoir 107 is further enclosed by a second wall portion 102b which is a rigid titanium wall portion through which the conduit 109a enters the reservoir 107. Compression of the reservoir 107 thus forces the fluid from the reservoir through the conduit 109a. The housing 484 further comprises a transfer channel 478 creating a fluid connection between the second chamber C2 and a portion of the second chamber C2' placed more distally. The transfer channel ensures that the pressure is the same in the second chamber C2 and distal portion of the second chamber C2'. The distal portion C2' of the second chamber C2 comprises a expansion portion comprising a resilient membrane 495 configured to move to alter the volume of the distal portion C2' of the second chamber C2 for compensating for the changes to the volume of the reservoir 107 which is created by the movement of the first resilient wall portion 102a of the reservoir 107. As such, the pressure in the second chamber C2 will be substantially constant. The resilient membrane 495 is in the embodiment shown in FIG. 15c made from a medical grade elastic silicone material but may in alternative embodiments be made from another biocompatible polymer material, such as polyurethane.

Figure 17A:
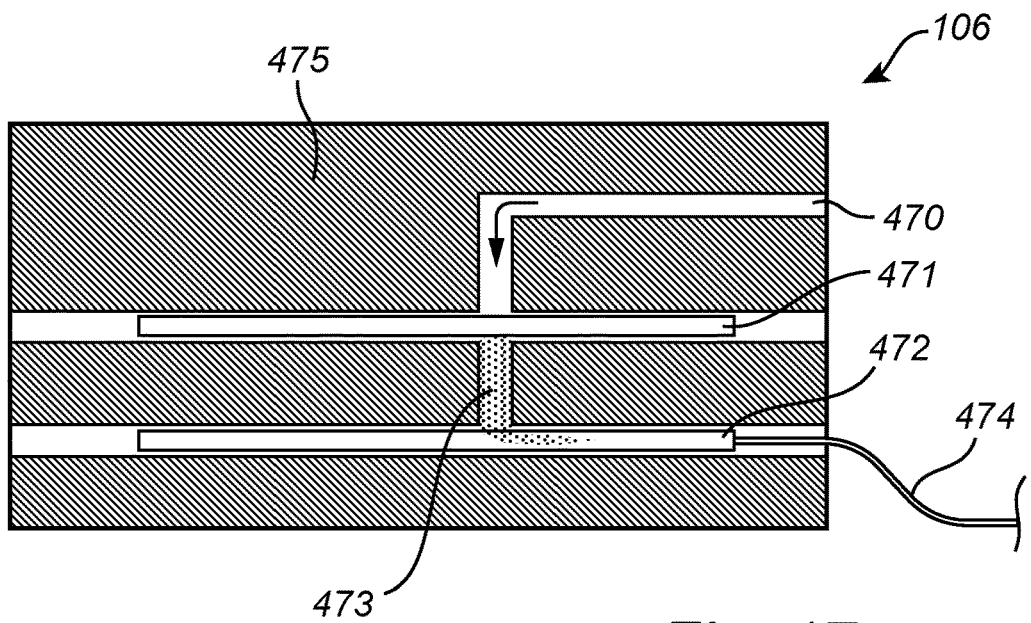
FIG. 17a shows an embodiment of a sensor for sensing the pressure in a hydraulic portion of the implantable constriction device.
Figure 17B:
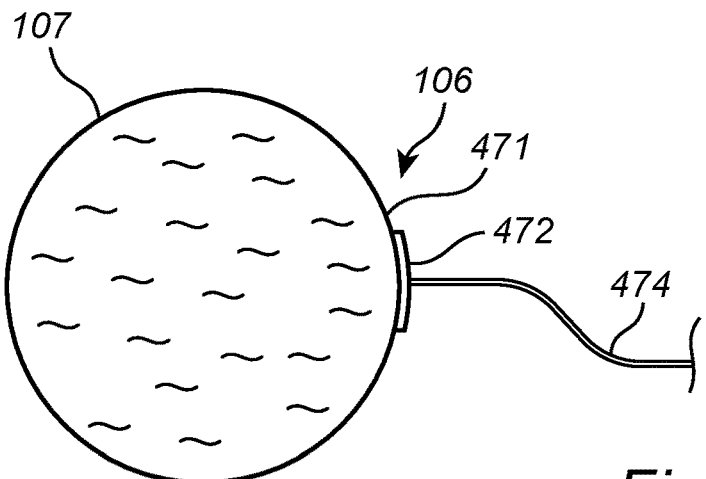
FIG. 17b shows an embodiment of a sensor for sensing the pressure in a hydraulic portion of the implantable constriction device.

The hydraulic pump of FIG. 15c further comprises a pressure sensor 106 placed on the first resilient wall portion 102a of the chamber 107 for sensing the pressure in the chamber 107. The sensor 106, which may be a pressure sensor of the types described with reference to FIGS. 17a, 17b, is connected to electrical conduits 493 for transferring an electrical sensor signal from the pressure sensor 106 to the controller 300. The electrical conduits 493 passes from the second chamber C2 to the first chamber C1 through an electrically insulating ceramic grommet 494 integrated in the barrier 484' wall such that the conduits 493 can pass the barrier 484' without being further insulated which enables the conduits 493 to pass through the barrier 484' whilst the barrier hermetically separates the first chamber C1 from the second chamber C2.

A first portion 109a of the fluid conduit is connected to an implantable hydraulic force transfer device 496 comprising a first chamber V1 configured to house a first fluid, and as such the first portion 109a of the fluid conduit forms a fluid inlet into the first chamber V1. The first chamber V1 is in connection with a movable wall portion 497 for varying the size of the first chamber V1. The movable wall portion 497 is in turn connected to a second chamber V2 configured to house a second fluid. The second chamber comprises an outlet formed by a second portion 109b of the fluid conduit. The second portion 109b of the fluid conduit fluidly connects the second chamber C2 to the implantable hydraulic constriction element in any of the embodiments described herein, such that the implantable hydraulic constriction element can be operated for restricting and releasing the restriction of the urethra. As such, the implantable hydraulic force transfer device 496 transfers hydraulic force from the hydraulic pump 104 to the implantable hydraulic constriction element without mixing the first and second fluids.

In the embodiment shown in FIG. 15c, the implantable hydraulic force transfer device 496 comprises a cylinder-shaped housing in which the piston-like movable wall portion 497 moves linearly. The piston-like movable wall portion 497 seals against the inner side of the wall of the cylinder-shaped housing such that the first and second chambers V1, V2 remains separated. The implantable hydraulic force transfer device 496 enables the system to have a first fluid in the compressible reservoir 107 and in the first chamber V1 of the implantable hydraulic force transfer device 496. This part of the system may be hermetically sealed in such a way that leakage is highly improbable, which enables this part of the system to use a fluid which cannot be allowed to escape into the body, such as an oil based fluid, such as a silicone oil. The second part of the system, comprising the second chamber C2 of the implantable hydraulic force transfer device 496, the second portion 109*b* of the fluid conduit, and the implantable hydraulic constriction element (not shown) will have a second fluid which must be a biocompatible fluid as some level of leakage or diffusion may be hard to avoid. In the second part of the system the fluid could for example be an isotone aqueous fluid, such as a saline solution.

In the embodiment shown in FIGS. 15*a*-15*f*, the housing 484 and the housing of the implantable hydraulic force transfer device 496 is a titanium housing. However, it is equally conceivable that the housing is made from another biocompatible material such as a medical grade metal alloy, such as medical grade stainless steel or a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA).

In alternative embodiments, the magnetic coupling described with reference to FIGS. 15*c* and 15*d* could be used in connection with another type of pumps, such as the pumps described with reference to FIGS. 12*a*, 12*b*, 14 and 16. In the alternative, the magnetic coupling could be used in connection with a gear pump. It is also conceivable that the magnetic coupling could be used in connection with a mechanical actuator configured to transfer mechanical force from the magnetic coupling to an implantable element configured to exert a force on a body portion of a patient. The mechanical actuator could be an actuator configured to transfer a rotating force into a linear force, such as the transmission (T) described with reference to FIGS. 14-15*f*.

Figure 15D:
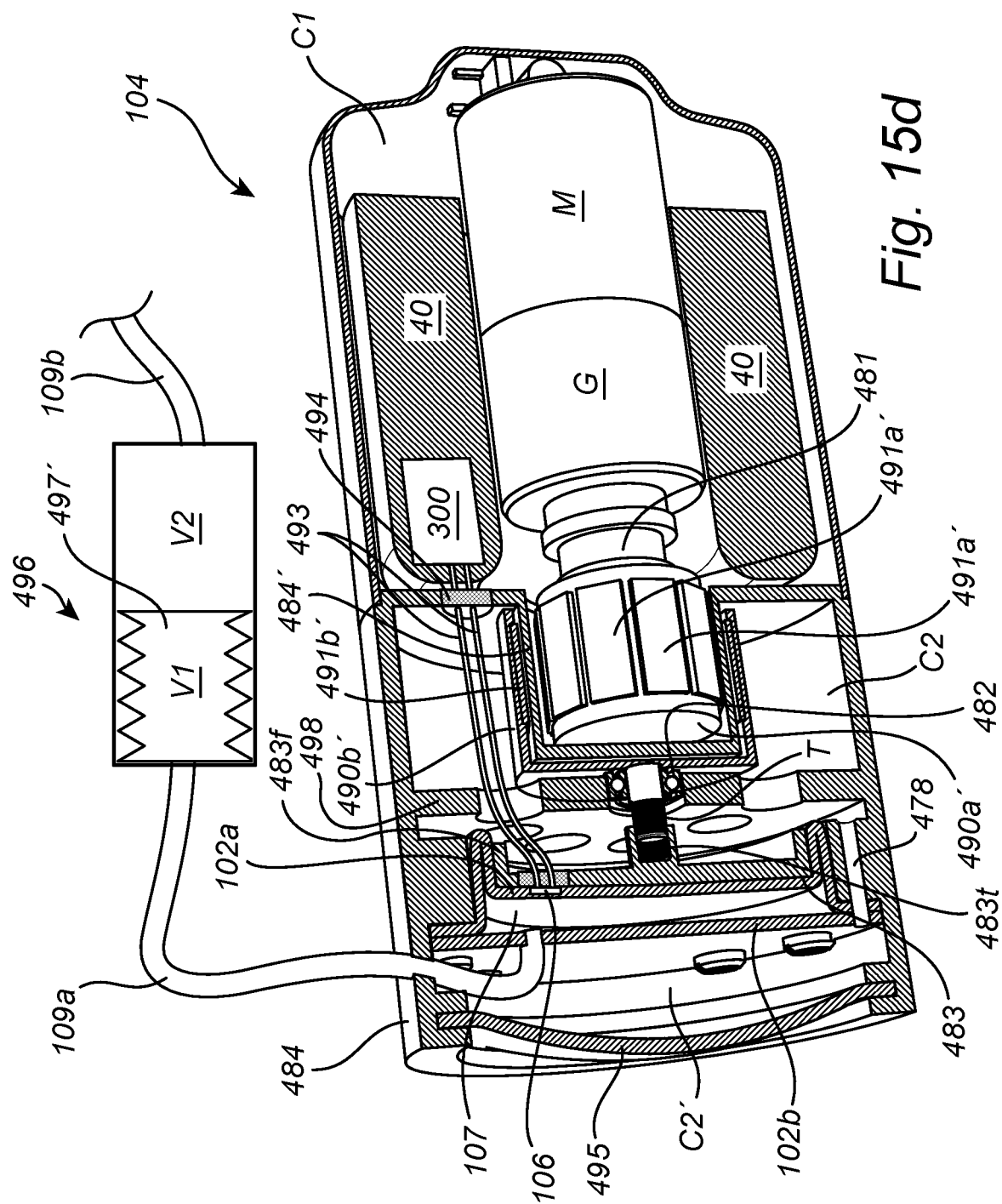
FIG. 15d shows a partially sectional perspective view from the left of an embodiment of a hydraulic pump for an implantable constriction device.

FIG. 15*d* shows a hydraulic pump in an embodiment similar to the embodiment shown in FIG. 15*c*. One difference with the embodiment of FIG. 15*d* in comparison to the embodiment of FIG. 15*c* is that the first coupling part 490*a*' comprises magnets 491*a*' or material susceptible to magnetic fields which are placed radially along an outer periphery, on the lateral surface, of the cylinder-like first coupling part 490*a*'. The magnets 491*a*' of the first coupling part 490*a*' are magnetically connected to magnets 491*b*' placed radially on the inner lateral surface of the cylinder-shaped second coupling part 490*b*'. The magnets 491*a*',491*b*' of the first and second coupling parts 490*a*', 490*b*' are separated from each other by the barrier 484'. The second coupling part 490*b*' is connected to a rotatable shaft which is supported by ball bearings 482*b* being fixated to the inside of the wall of the housing 484 enclosing the second chamber C2 by means of an internal wall portion 498. The rotatable shaft comprises a threaded portion which is configured to be placed in and engage with a sleeve of a compression member 483. The sleeve of the compression member 483 comprises inside threads 483*t* for creating a transmission T that transforms the radially rotating force generated by the motor M and the gear system G, to a linear force acting in the axial direction of the shaft 481, and thus makes up a transmission T.

Another difference between the embodiment shown in FIG. 15*c* and the embodiment shown in FIG. 15*d* is in the implantable hydraulic force transfer device 496. In the embodiment shown in FIG. 15*d*, the implantable hydraulic force transfer device 496 comprises a movable wall portion 497' in the form of a bellows with a pleated flexible wall portion which can be compressed and expanded. The material of the flexible wall portion could be an elastic material, such as an elastic polymer material or a substantially inelastic material such as a metal material forming a metal bellows which is mainly flexible due to its shape. In an alternative embodiment, the flexible wall portion can be purely elastic and thus be without the pleats, which means that the expansion and contraction of the reservoir is done purely based on the elasticity of the material in the flexible wall. The flexible movable wall portion 497' encloses the first chamber V1 and keeps the chamber V1 completely separated from the chamber V2. The implantable hydraulic force transfer device 496 enables the system to have a first fluid in the compressible reservoir 107 and in the first chamber V1 of the implantable hydraulic force transfer device 496. This part of the system may be hermetically sealed in such a way that leakage is highly improbable, which enables this part of the system to use a fluid which cannot be allowed to escape into the body, such as an oil based fluid, such as a silicone oil. The second part of the system, comprising the second chamber C2 of the implantable hydraulic force transfer device 496, the second portion 109*b* of the fluid conduit, and the implantable hydraulic constriction element (not shown) will have a second fluid which must be a biocompatible fluid as some level of leakage or diffusion may be hard to avoid. In the second part of the system the fluid could for example be an isotone aqueous fluid, such as a saline solution.

Figure 15E:
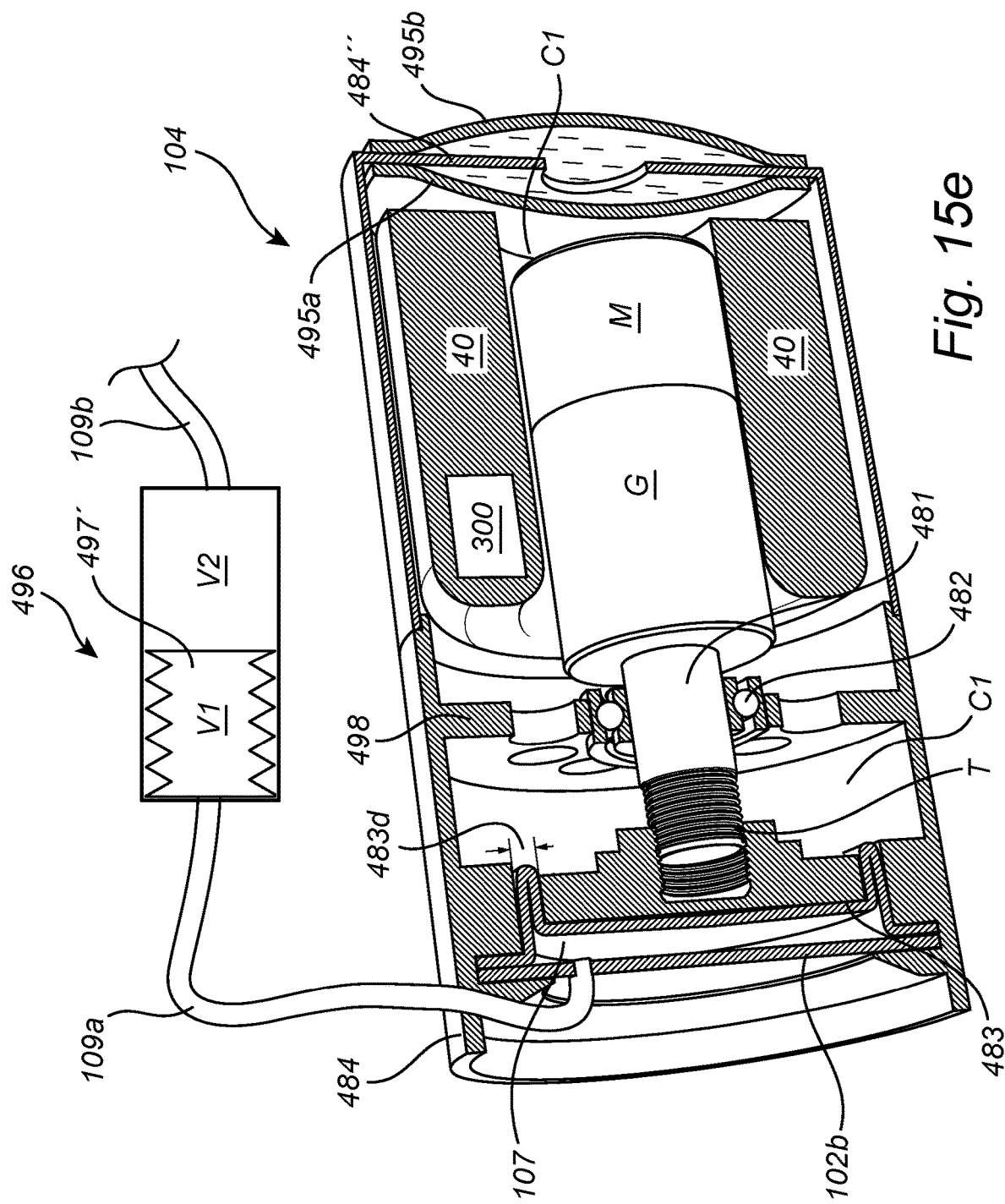
FIG. 15e shows a partially sectional perspective view from the left of an embodiment of a hydraulic pump for an implantable constriction device.

FIG. 15*e* shows an embodiment of a hydraulic pump 104 which is similar to the embodiment shown in FIG. 15*b*. One difference in comparison to the embodiment of FIG. 15*b* is that the compression member 483 has a flat circular surface engaging the first resilient wall portion 102*a* of the reservoir 107. The flat surface is bonded to the first resilient wall portion 102*a* such that the first resilient wall portion 102*a* moves along with the compression member 483. The compression member 483 has a diameter such that a distance 483*d* is created between the compression member 483 and the portion of the housing facing the compression member 483. The distance is slightly more than two times the thickness of the first resilient wall portion 102*a*, such that the first resilient wall portion 102*a* can be folded such that a rolling crease of the first resilient wall portion 102*a* is created which moves along with the compression member 483. The distance 483*d* is smaller than the radius (or half cross-sectional distance) of the compression member 483. The distance is 483*d* is also smaller than half the radius of the compression member 483. The first resilient wall portion 102*a*, towards the second chamber C2, being either folded or supported by the compression member means that ensures that the reservoir 107 will be substantially stiff which enables the fluid amount in the hydraulic constriction element connected to the reservoir 107 to remain the same even as the pressure exerted on the hydraulic constriction element increases.

The embodiment of FIG. 15*e* differs from the embodiment of FIGS. 15*c* and 15*d* in that it only comprises a single chamber C1. The housing 484 of the hydraulic pump 104 of FIG. 15*e* comprises an expansion portion placed in the proximal portion of the hydraulic pump 104 (on the right side of the hydraulic pump of FIG. 15*e*). The expansion portion comprises a first and second resilient membrane 495*a*, 495*b* with a silicone oil filling the space formed between the first and second resilient membranes 495*a*, 495*b*. The oil between the first and second resilient membrane 495*a*, 495*b* reduces the risk of diffusion of fluids through the expansion portion. The first and second resilient membranes 495*a*, 495*b* are placed on two sides of a portion 484" of the housing comprising a hole through which the fluid can travel as the expansion portion compensates for the changes to the volume of the reservoir 107 which is created by the movement of the first resilient wall portion 102*a* of the reservoir 107. As such, the pressure in the first chamber C1 will be substantially constant. The first and second resilient membranes 495a, 495b are in the embodiment shown in FIG. 15e made from a medical grade elastic silicone material but may in alternative embodiments be made from another biocompatible polymer material, such as polyurethane.

Another aspect of having the housings of any of the embodiments herein, is that the atmospheric pressure that the patient exists in may vary. At sea level, the air pressure is about 101 kPa, in a commercial airplane at cruising altitude, the air pressure is about 80 kPa which is about the same as in Mexico city, whereas in La Paz, the highest situated city, air pressure is only 62 kPa. This difference in air pressure affects any gaseous fluid, such as the air present in the chamber C1 in the embodiment of FIG. 15e. The reduced atmospheric air pressure means that the gaseous fluid inside of the housing needs to be able to expand if the pressure in the housing should remain the same. If the pressure in the housing would increase 20%-40%, the motor would have to operate the hydraulic constriction device against that pressure which would mean that the motor would have to be more powerful which would require more energy. As the expansion portion comprises a resilient membrane, the expansion portion allows the gaseous fluid in the housing to expand which at least reduces the pressure increase in the housing in response to a reduced atmospheric pressure.

Figure 15F:
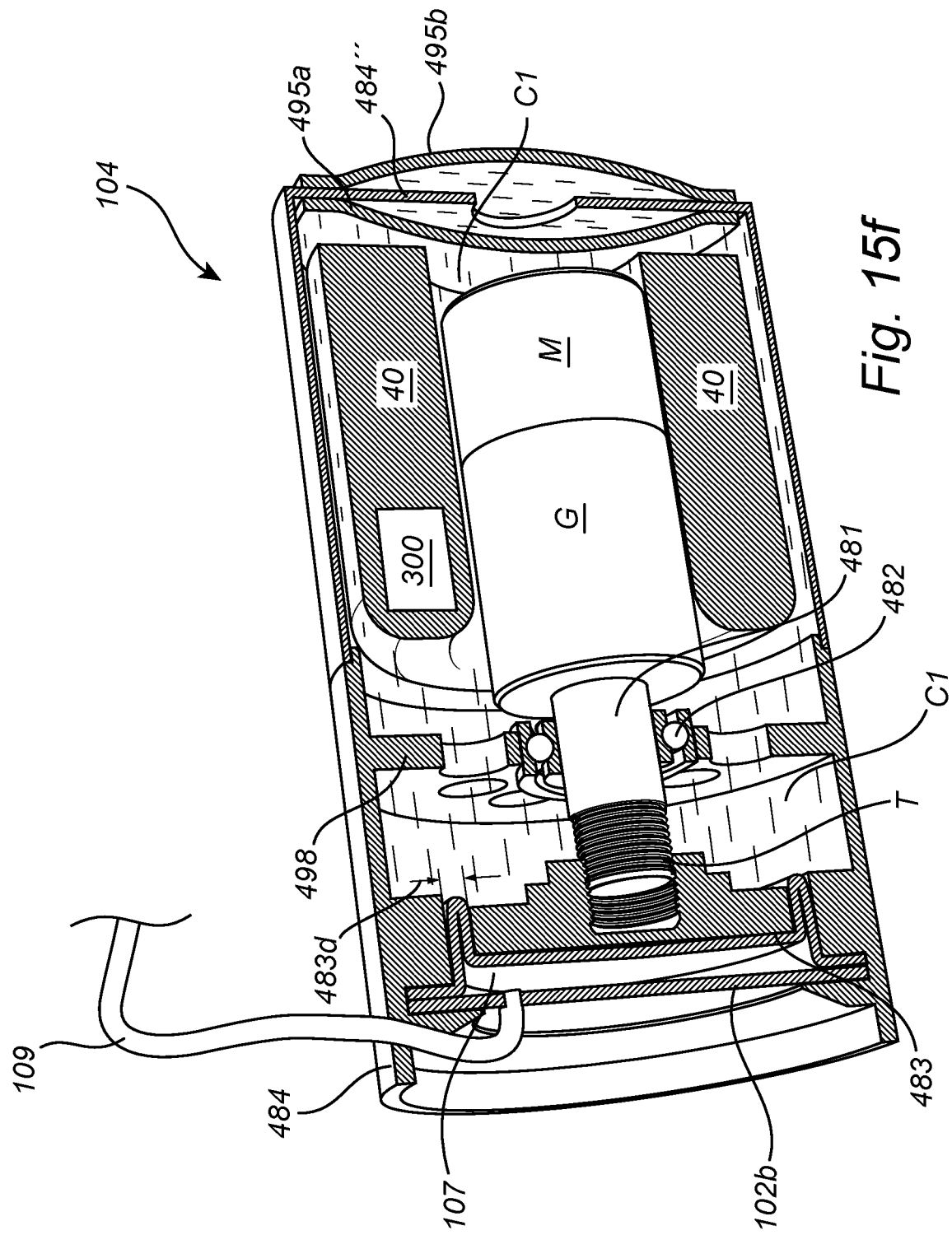
FIG. 15f shows a partially sectional perspective view from the left of an embodiment of a hydraulic pump for an implantable constriction device.

FIG. 15f differs from the embodiment of FIG. 15e only in that the chamber C1 is completely filled with a liquid dielectric silicone oil. The liquid fluid could in the alternative be a synthetic single-phase liquid dielectric fluid, such as ElectroCool EC-100, from Engineered Fluids, or a 2-phase coolant such as Fluorinert or Novec from 3M. The fluid in the chamber C1 is non-conductive and as such does not risk damaging the electrical components placed in the chamber C1, such as the energy storage unit 40. In the embodiment shown in FIG. 15f, the expandible reservoir 107, the conduit 109 and the implantable element configured to exert force on the body portion of the patient forms the second chamber and second hydraulic system configured to comprise a second liquid which is a hydraulic liquid configured to transfer force. The second liquid may be an isotone aqueous liquid, such as a saline solution.

In the embodiment shown in FIG. 15f, the first chamber comprises the motor M, the gear system G and the transmission T for transforming the rotating force generated by the motor M to a linear force for pressing on the expandible reservoir 107. Advantages with having the housing and the first chamber C1 entirely filled with a liquid fluid includes the liquid acting as a cooling agent for components that may produce heat, such as the controller 300, the energy storage unit 40, the motor M, gear system G, bearing 482 and transmission T, and as a lubricant for components that may require lubrication, such as the motor M, gear system G, bearing 482 and transmission T.

Just as in FIG. 15e, the housing 484 of the hydraulic pump 104 comprises an expansion portion 495a, 484", 495b placed in the proximal portion of the hydraulic pump 104 (on the right side of the hydraulic pump of FIG. 15f), such that the housing can expand when the expandible reservoir 107 expands.

In alternative embodiments, the liquid filled first chamber C1 could be used in connection with another type of pump, i.e. the shaft 481 could be connected to another type of pump, such as the pumps described with reference to FIGS. 12a,12b,14 and 16, or a gear pump.

Figure 15G:
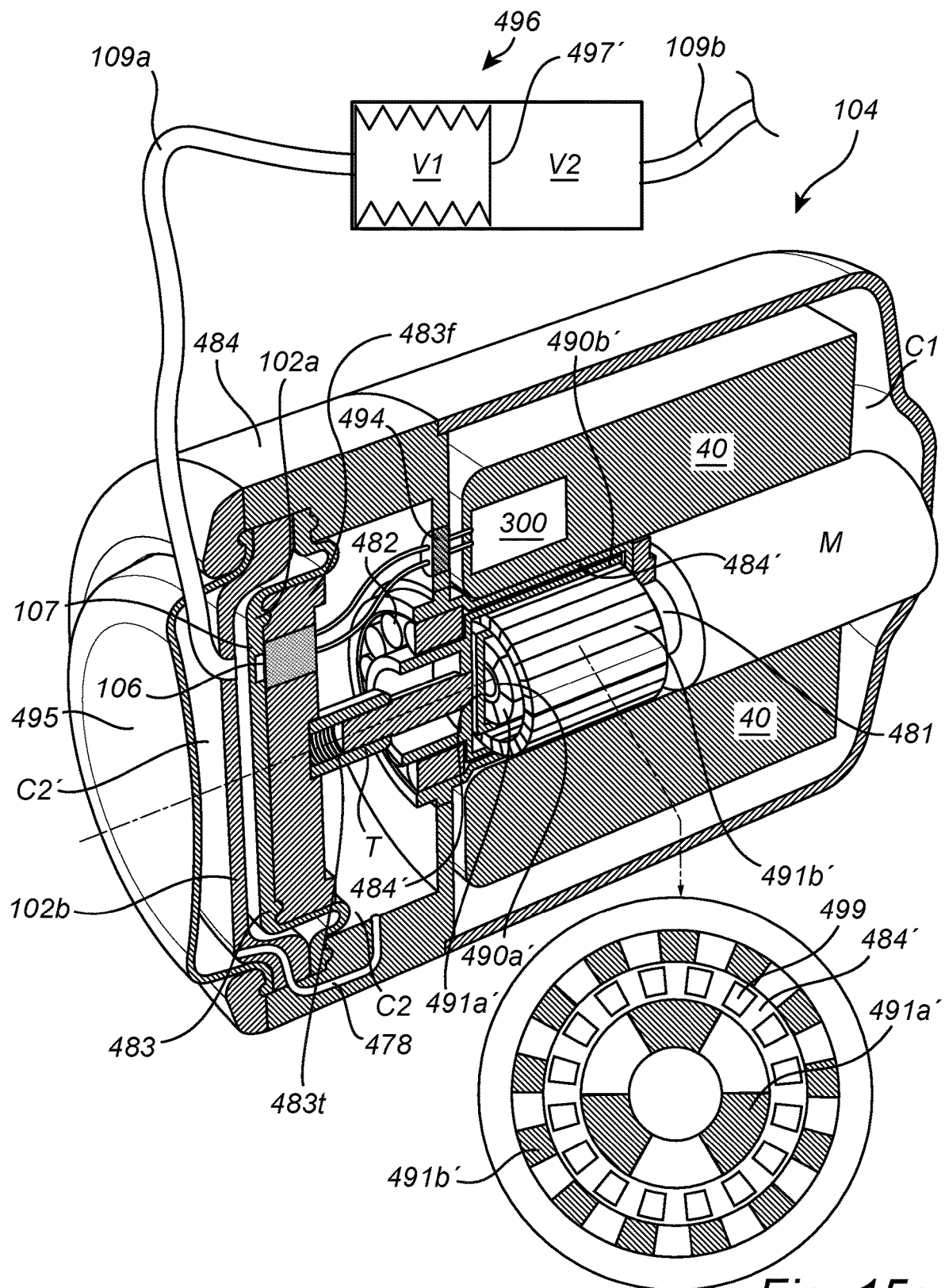
FIG. 15g shows a partially sectional perspective view from the left of an embodiment of a hydraulic pump for an implantable constriction device.

FIG. 15g shows an embodiment of a hydraulic pump 104 which is similar to the embodiment shown in FIG. 15d. The main difference with the embodiment shown in FIG. 15g is that it made more compact as the gear system is integrated in the magnetic coupling. The magnetic coupling thus comprises a magnetic gear which transfers a week force with a high velocity into a stronger force with lower velocity. The magnetic coupling/gear comprises a first coupling part 490a' fixated to the shaft 481 connected to the electrical motor M such that the first coupling part 490a' rotates along with the electrical motor M. The first coupling part 490a' comprises a first number of magnets 491a', which in the embodiment shown in FIG. 15g is 6 magnets, 3 with each polarity (3 pole pairs). The magnets are placed radially along an outer periphery, on the lateral surface, of the cylinder-like first coupling part 490a'. The second coupling part 490b' comprises a second number of magnets 491b', placed radially on the inner lateral surface of the cylinder-shaped second coupling part 490b'. In the embodiment shown in FIG. 15g the second coupling part 490b' comprises 26 magnets, 13 with each polarity. Between the first coupling part 490a' and the second coupling part 490b' there is a stationary part, which is a portion of the barrier 484'. The stationary part comprises a plurality of intermediate ferromagnetic elements 499 thus placed between the first and second coupling parts 490a', 490b'. The intermediate ferromagnetic elements 499 directs the concentration of the magnetic lines between the magnets 491a', 491b' of the first coupling part 490a' and the second coupling part 490b'. The gear ratio between the first coupling part 490a' and the second coupling part 490b' is the number of magnetic pole pairs on the second coupling part 490a' divided by the number of magnetic pole pairs on the second coupling part 490b'. In the embodiment shown in FIG. 15g, the gear ratio is 13/3. The number of intermediate ferromagnetic elements 499 is equal to the sum of pole pairs on the first and second coupling parts 490a', 490b'. In the embodiment shown in FIG. 15g this means that the number of intermediate ferromagnetic elements 499 is 16 (13+3). In operation, this set up of magnetic gear changes the direction of rotation of the coupling, which means that that in operation the second coupling part 490b' will rotate in the opposite direction and 4.33 times slower than the first coupling part 490a'. The embodiment having a magnetic gear have a number of advantages, for example, the magnetic gear is quiet, does not wear and does not need to be lubricated. In alternative embodiments it is conceivable that the magnetic gear is used in combination with a traditional gear wheel gear system or a transmission of the kind described with reference to FIGS. 13a, 13b.

The second coupling part 490b' is connected to a rotatable shaft which is supported by roller bearings 482 being fixated to the inside of the wall of the housing 484. The rotatable shaft comprises a threaded portion which is configured to be placed in and engage with a sleeve of a compression member 483. The sleeve of the compression member 483 comprises inside threads 483t for creating a transmission T that transforms the radially rotating force generated by the motor M and the gear system G, to a linear force acting in the axial direction of the shaft 481, and thus makes up a transmission T.

Figure 15H:
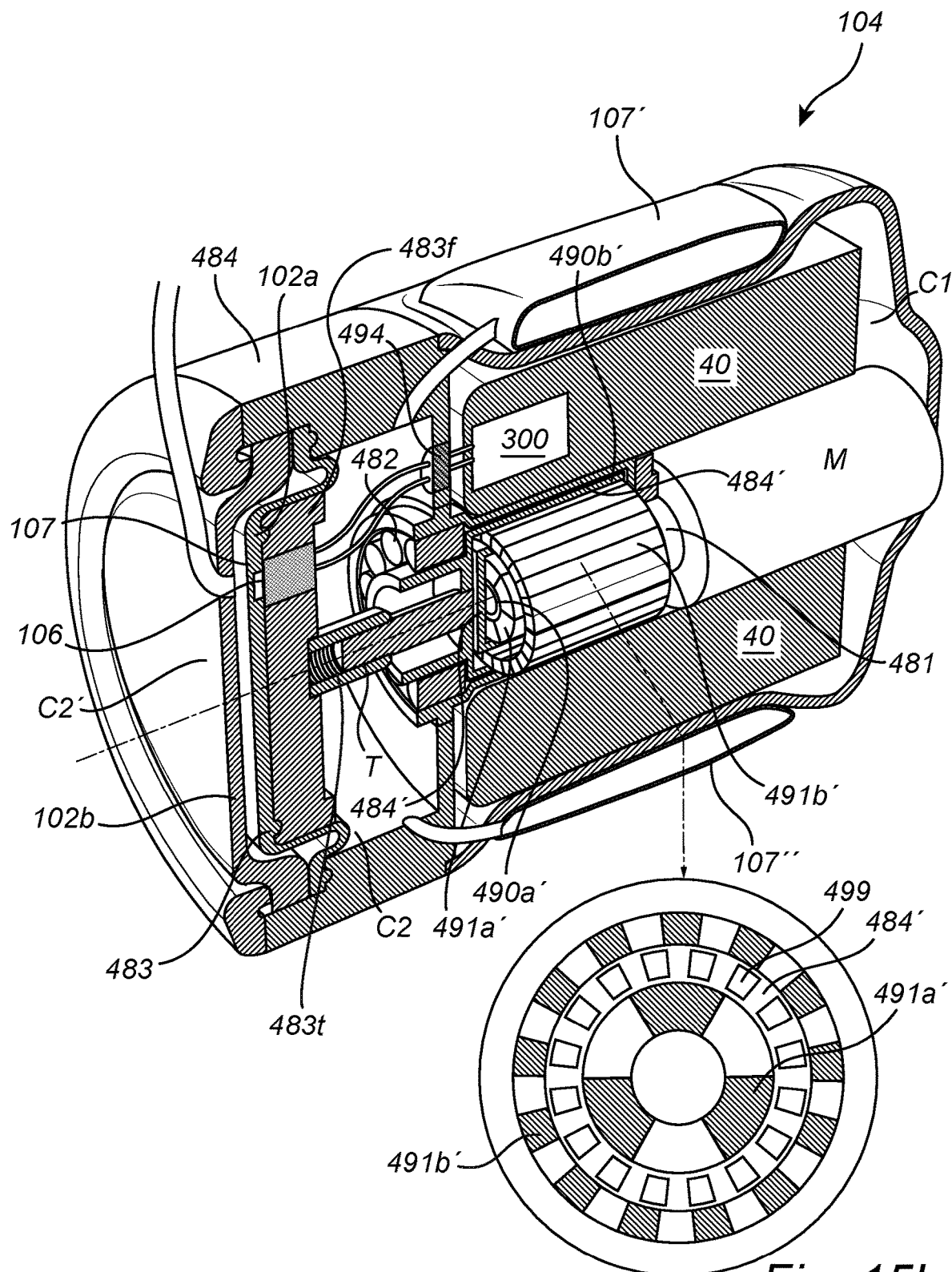
FIG. 15h shows a partially sectional perspective view from the left of an embodiment of a hydraulic pump for an implantable constriction device.

FIG. 15h shows an embodiment of a hydraulic pump 104 which is similar to the embodiment shown in FIG. 15g. The main difference with the embodiment shown in FIG. 15h is that the expansion portion is replaced with two resilient reservoirs 107',107" which are placed in indentations in the housing, on respective two opposite sides of the housing. The two resilient reservoirs 107',107" are configured to expand and contract to compensate for the changes to the volume of the reservoir 107 which is created by the movement of the first resilient wall portion 102a of the reservoir 107. As such, the pressure in the second chamber C2 will be substantially constant. The two resilient reservoirs 107',107" are made from a medical grade elastic silicone material but may in alternative embodiments be made from another biocompatible polymer material, such as polyurethane.

Figure 16:
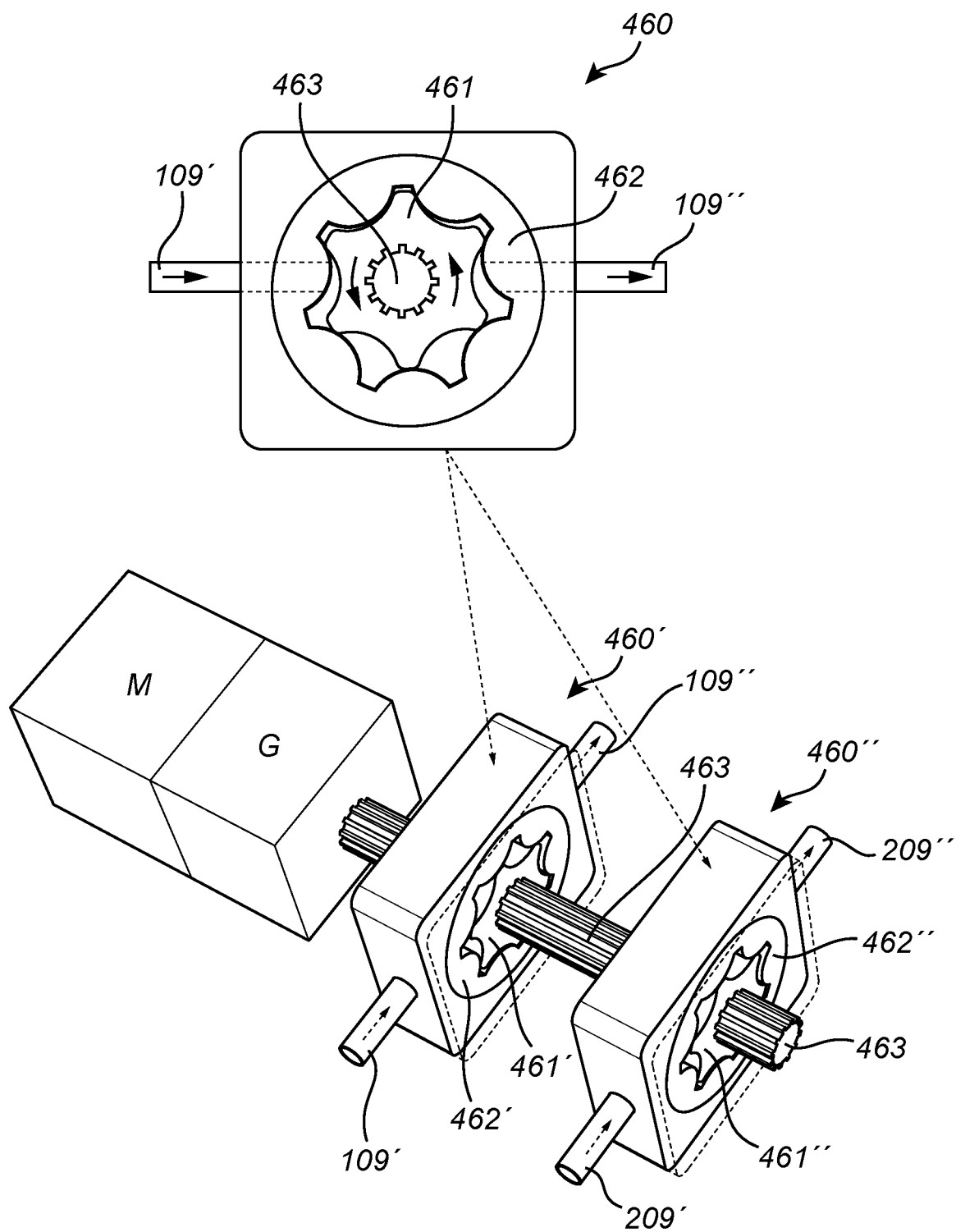
FIG. 16 shows an elevated perspective view from the left of an embodiment of a hydraulic pump for an implantable constriction device.

FIG. 16 shows and embodiment of a system comprising a motor M, gear system G and two pump 460',460" which could be implemented in any of the embodiments of implantable constriction devices shown herein, in which the implantable constriction device comprises more than one operable hydraulic constriction element. In the embodiment shown in FIG. 16, the force output of the motor M is connected to a force input of the gear system G. The gear system G is configured to reduce the velocity and increase the force of the movement generated by the motor M, such that the movement exiting the gear system G at the force output of the gear system G is a mechanical force with a lower velocity and a greater force than the movement entering the force input of the gear system G. Typically, an implantable brushless DC motor, such as the motors provided by Maxon group or Dr. Fritz Faulhaber, typically produces a rotational velocity exceeding 10 000 rpm. For such a motor to be able to mechanically operate any of the hydraulic pumps described herein, a gear system G is needed. In the embodiment shown with reference to FIG. 16, the gear system G reduces the rotational velocity 100 times, to about 100 rpm. The force output of the gear system G is mechanically connected to a common rotating shaft 463. The first hydraulic pump comprises a first gerotor pump 460' and the second hydraulic pump comprises a second gerotor pump 460". The common rotating shaft 463 is mechanically connected to an inner rotor 461' of the first gerotor pump 460' and an inner rotor 461" of the second gerotor pump, such that the motor M propels the first and second gerotor pump 460'460". A gerotor is a positive displacement pump comprising consists of an inner rotor 461 and an outer rotor 462. The inner rotor 461 has 6 teeth, while the outer rotor has 7 teeth (the importance being that the outer rotor 462 has one tooth more than the inner rotor 461. The axis of the inner rotor 461, which is the rotational center of the common rotating shaft 463, is offset from the rotational center or axis of the outer rotor 462. Both the inner and outer rotors 461, 462 rotate on their respective axes. The geometry of the two rotors 461, 462 partitions the volume between them into 6 different dynamically changing volumes. During the rotation cycle, each of these volumes changes continuously, so any given volume first increases, and then decreases. An increase creates a vacuum. This vacuum creates suction, and hence, this part of the cycle is where the inlet 109' is located. As a volume decreases compression occurs which pumps the fluid though the outlet 109".

In the embodiment shown in FIG. 16, the first gerotor pump 460' is configured to be in fluid connection with a first operable hydraulic constriction element for pumping hydraulic fluid into the first operable hydraulic constriction element for inflating the first operable hydraulic constriction element to exert a pressure on the urethra and thereby restrict the flow or urine therethrough. The second gerotor pump 460" is configured to be in fluid connection with a second operable hydraulic constriction element for pumping hydraulic fluid into the second operable hydraulic constriction element for inflating the second operable hydraulic constriction element to exert a pressure on the urethra and thereby restrict the flow or urine therethrough. The inlets 109',109" of the first and second gerotor pumps 460',460" are configured to be connected to a reservoir for holding hydraulic fluid, or in the alternative, the first inlet 109' is configured to be connected to a first implantable reservoir and the second inlet 109" is configured to be connected to a second implantable reservoir.

In alternative embodiments, the first and second hydraulic pump mechanically connected to a common rotating shaft could be pump comprising at least one compressible hydraulic reservoir (such as the pump described with reference to FIG. 15a), a pump comprising a displaceable wall (such as the pump described with reference to FIG. 14), or a peristaltic pump (such as the pump described with reference to FIGS. 12a and 12b).

The embodiment of two pumps mechanically connected to a common rotating shaft, described with reference to FIG. 16, could be implemented in any of the embodiments disclosed herein in which there are more than one operable hydraulic constriction element, in particular the embodiments disclosed with reference to FIGS. 1a-3a, 3f, 4-8a, 9a-9c, 10c, 10d, 11a, 11b, 11f and 18b.

The pump system could further comprise pressure sensor (s) for sensing the pressure in the fluid flowing to and/or from the hydraulic pumps 460', 460". The sensor(s) could for example be sensors such as the sensors described with reference to FIGS. 17a and 17b. The sensor values could be used as input to an implantable controller, such as for example described with reference to FIGS. 8a-9c and FIGS. 23a-23e which then could be used for controlling the motor M and as such the first and second pumps 460',460". The controller could use a continuous or intermittent pressure signal to compute an average pressure over a time period, such as a period of more than 20 seconds, more than 1 minute, more than 3 minutes, more than 5 minutes or more than 10 minutes, as it is the average pressure over a time period that risks creating low oxygenation in the tissue and thus risks the damaging of the tissue. It may be ok that the pressure on the tissue exceeds the diastolic bold pressure, and even the systolic blood pressure, for a shorter period but not be ok if that period exceeds 20 seconds or 1 minute or 3 minutes or 5 minutes or 10 minutes. It is conceivable that the controller measures the average pressure as the integral of pressure values over a period of time.

FIG. 17a shows an embodiment of a pressure sensor 106 which could be implemented in any of the implantable constriction devices shown herein for sensing a pressure in a hydraulic fluid in the system. Pressure is an expression of the force required to stop a fluid from expanding and is stated in terms of force per unit area. The pressure sensor 106 acts as a transducer generating a signal as a function of the pressure imposed. In FIGS. 17a and 17b, a diaphragm is used as a force collector. However, it is equally conceivable that the diaphragm is replaced by e.g. a piston, a bourdon tube, or a bellows acting as force collector.

The pressure sensor 106 comprises a sensor housing 475 which comprises integrated channels. An inlet channel 470 is configured to conduct hydraulic fluid such that the hydraulic fluid is placed in contact with a diaphragm 471. The diaphragm 471 is resilient and could for example be made from a medical grade silicone material which is elastic enough such that the pressure exerted on the diaphragm 471 is transferred to a gel-like substance 473 which in turn presses on a pressure sensing element. The pressure sensing element is thus separated from the hydraulic fluid in the implantable constriction devices by the diaphragm 471. In the embodiment shown in FIG. 17a, the pressure sensing element 472 is a strain gauge which creates an electrical pressure sensor signal which is transferred to a controller by means of a lead 474. The strain gauge could be a resistive, piezoresistive or piezoelectric strain gauge, or an optical strain gauge or a capacitive strain gauge.

A resistive strain gauge uses a pressure sensing element 472 where metal strain gauges are fixated. The resistance through the metal strain gauges is changed with the elongation which is used to create the electrical pressure signal. A piezoresistive strain gauge uses the piezoresistive effect of strain gauges to detect strain due to applied pressure, resistance increasing as pressure deforms the material. Common technology types are Silicon (Monocrystalline), Polysilicon Thin Film, Bonded Metal Foil, Thick Film, Silicon-on-Sapphire and Sputtered Thin Film. A capacitive strain gauge uses the diaphragm 471 to create a variable capacitor to detect strain due to applied pressure as the capacitance decreases as pressure deforms the diaphragm 471. Common technologies use metal, ceramic, and silicon diaphragms. Electromagnetic strain gauges measure the displacement of the diaphragm 471 by means of changes in inductance (reluctance), LVDT, Hall Effect, or by eddy current principle. An optical strain gauge uses the physical change of an optical fiber to detect strain due to applied pressure. A common example of this type utilizes Fiber Bragg Gratings. The strain gauges may be connected to form a Wheatstone bridge circuit to maximize the output of the sensor and to reduce sensitivity to errors.

The pressure sensor, when implemented in any of the implantable constriction devices shown herein is ultimately configured to measure the pressure in the operable hydraulic constriction elements which exerts pressure on the urethra for the purpose restricting the flow of urine in the urethra for treating incontinence. When a portion of the urethra U is restricted, the blood flow of that particular portion of the urethra is hampered, which creates a risk that the portion suffers from ischemia, which may cause irreversible necrosis of the restricted tissue. By measuring the pressure, the hydraulic pumps or electrically controllable valves of the system can be controlled to create optimal constriction of the urethra which in many instances is a mediation between restriction of the urethra such that no leakage occurs while making sure that the restriction does not damage the tissue of the urethra.

As an example, the pressure in the urinary bladder when the patient is resting is about 50 cm $H_2O$, which is the pressure that the urine has when leaving the ureters. As such, the pressure exerted on the urinary tract and thus on the urethra needs to exceed 50 cm $H_2O$ for no leakage to occur. The tissue wall of the urethra is oxygenized through the circulatory blood system in which the blood pressure in a normal person is about 120 mm Hg during systole and 80 mm Hg during diastole. This means that a normal person is capable if oxygenizing tissue against a pressure not exceeding 120 mm Hg. 120 mm Hg equals 163 cm $H_2O$ which means that there is no risk, in a normal person, that the tissue of the urethra will suffer from ischemia as long as the pressure exerted on the urethra is below 100 cm $H_2O$. A pressure in the range 60 cm $H_2O$-100 cm $H_2O$ is sufficient when the patient is at rest or performing limited physical activity. However, if the patient runs, jumps, coughs, laughs, or sneezes, the pressure in of the urine may exceed 100 cm $H_2O$ which means that the pressure exerted on the urethra also needs to exceed 100 cm $H_2O$. As a short hampering of the blood flow in the tissue wall of the urethra could be acceptable, but a longer could be damaging, the continuous sensing and control of the pressure exerted on the urethra is important for continuously creating an optimal constriction.

The controller, such as for example the controller described with reference to FIGS. 8-9c and FIGS. 23a-23e, may be configured to control the hydraulic pump(s) and/or electrically controllable valve(s) on the basis of the received pressure sensor input, for the purpose of controlling the pressure exerted on the urethra.

FIG. 17b shows an alternative embodiment of the pressure sensor, in which the pressure sensor 106 comprises a diaphragm 471 being an integrated part of the reservoir 107 in which the pressure is to be measured. A pressure sensing element 472 is connected to the diaphragm 471, such that the diaphragm 471 separates the pressure sensing element 472 from the hydraulic fluid. The pressure sensing element 472 comprises a strain gauge, for example a strain gauge functioning in accordance with one of the strain gauge principles described above. The strain gauge is connected to a controller (described with reference to FIGS. 8-9c and FIGS. 23a-23e) by means of a lead 474, such that the measured pressure in the reservoir could be used in the control of the system.

In alternative embodiments, the pressure sensor could be used for measuring the pressure of a gaseous fluid. In this case, the diaphragm is in connection with an enclosed lumen configured to hold a gaseous fluid, and the pressure sensing element is configured to sense the pressure of the gaseous fluid. The enclosed lumen configured to hold a gaseous fluid may then be in connection with a part of the hydraulic system holding the hydraulic fluid, such that the pressure in the hydraulic system (such as in a reservoir or in an operable hydraulic constriction element) can be measured indirectly by measuring the pressure of the gaseous fluid in the enclosed lumen.

Figure 17C:
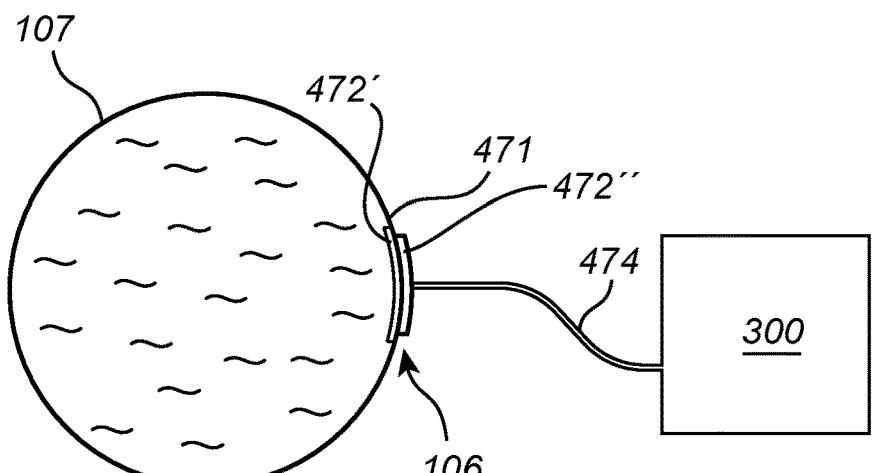
FIG. 17c shows an embodiment of a sensor for sensing the pressure in a hydraulic portion of the implantable constriction device.

FIG. 17c shows an embodiment of a pressure sensor similar to the embodiment shown in FIG. 17b, with the difference that in the embodiment of FIG. 17c, the pressure sensor 106 comprises a first 472' and second 472" pressure sensing element. The first pressure sensing element 472' is configured to measure a pressure in an implantable constriction device, by measuring the pressure in a reservoir 107 in fluid connection, or indirect fluid connection, with the implantable constriction device (described as reference numerals 101a-101d in the embodiments herein). The second pressure sensing element 472" is configured to measure the atmospheric pressure. The reservoir 107 comprises an elastic membrane 471 being integrated in the wall of the reservoir 107, and the first pressure sensing element 472' is configured to measure the pressure in the reservoir 107 on the first, inner, side of the elastic membrane 471 and the second pressure sensing element 472" is configured to measure the atmospheric pressure on the second, outer, side of the elastic membrane 471. The pressure sensor 106 is connected to a controller 300, and the controller 300 is configured to derive an absolute pressure by subtracting the atmospheric pressure from the pressure in the reservoir 107. The controller 300 (further described with reference to FIGS. 8-9c and FIGS. 23a-23e) then controls the pressure in the reservoir 107, and thus indirectly in the implantable constriction device, on the basis of the derived absolute pressure, or in the alternative on the basis of the received first and second input signals.

In the embodiment shown in FIG. 17c, the pressure sensor is configured to derive the pressure in the reservoir 107 by measuring the pressure in the reservoir relative to the atmospheric pressure. However, in alternative embodiments it is equally conceivable that the pressure sensor is configured to derive the pressure in the reservoir or in any other part of the implant connected to the implantable constriction device by comparing a pressure in the implantable element with vacuum.

Figure 17D:
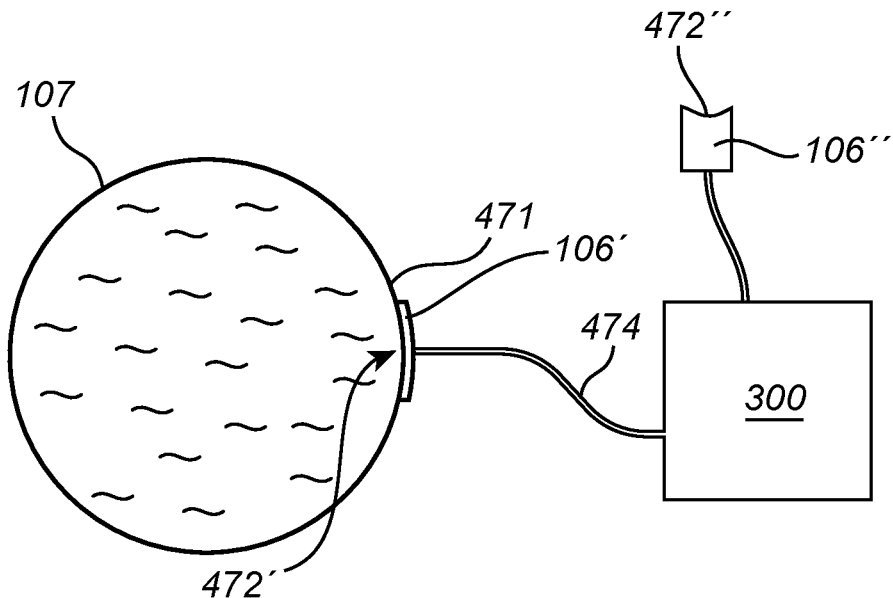
FIG. 17d shows an embodiment of a sensor for sensing the pressure in a hydraulic portion of the implantable constriction device.

FIG. 17d shows an embodiment of a pressure sensor similar to the embodiment shown in FIG. 17b, with the difference that in the embodiment of FIG. 17d, the implant comprises a second implantable pressure sensor 106" connected to the controller 300. The second implantable pressure sensor 106" is configured to sense the atmospheric pressure by means of a pressure sensing element 472". The controller 300 is as such configured to receive a second input signal related to the atmospheric pressure from the second implantable pressure sensor 106", not necessarily placed in direct connection with the reservoir 107. In the same way as in the embodiment described with reference to FIG. 17c, the controller 300 is configured to control the pressure in the reservoir 107, and thus indirectly in the implantable constriction device, on the basis of a derived absolute pressure, or in the alternative on the basis of the received first and second input signals from the first and second pressure sensors 106', 106".

Figure 17E:
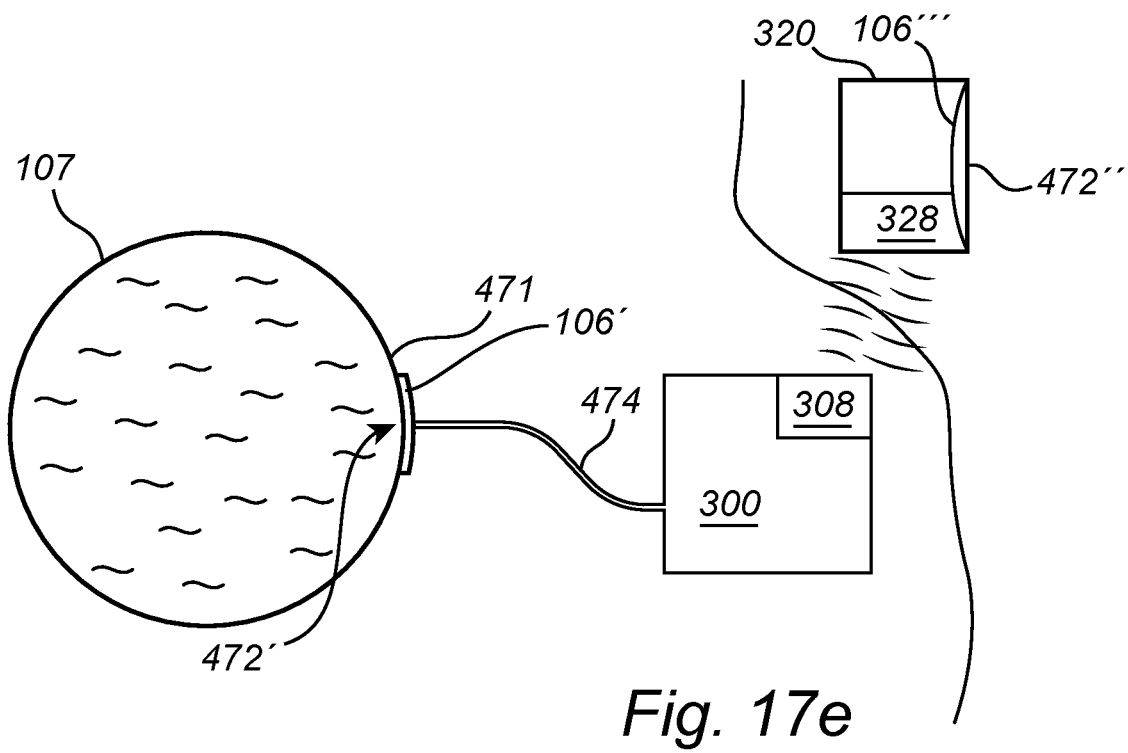
FIG. 17e shows an embodiment of a sensor for sensing the pressure in a hydraulic portion of the implantable constriction device.

FIG. 17e shows an embodiment of a pressure sensor similar to the embodiment shown in FIG. 17d, with the difference that in the embodiment of FIG. 17e the system comprises a second pressure sensor 106''' located external to the body of the patient. In the embodiment shown in FIG. 17e, the external device 320 is an external controller or communicator (further described with reference to FIGS. 23a-23e) comprising a wireless transceiver 328 configured to communicate wirelessly with an implantable transceiver of the implantable controller 300. The second pressure sensor 106''' located external to the body of the patient comprises a pressure sensing element 472" configured to sense the atmospheric pressure and communicate the atmospheric pressure to the implantable controller 300 by means of the wireless communication link 328, 308 between the external device 320 and the implantable controller 300. The external device 320 may communicate the atmospheric pressure each time the patient uses, controls, programs or adjusts the implantable constriction device, i.e. a signal related the atmospheric pressure may be sent together with the signal for operating, controlling or programming the implantable constriction device. As such, the implantable controller 300 may control the pressure in the reservoir 107, and thus indirectly in the implantable constriction device on the basis of a derived absolute pressure, or in the alternative on the basis of the received first and second input signals from the first and second pressure sensors 106', 106''', such that differences in atmospheric pressure due to weather or altitude may be considered when setting the suitable pressure in the implantable constriction device. This enables the pressure to be optimized to not create leakage and not constrict with unnecessarily high pressure to not damage tissue by for example hampering the blood flow.

In the alternative, the atmospheric pressure may be measured by means of the pressure sensor 106' connected to the reservoir, or by means of a pressure sensor connected to a hydraulic constriction element. The method of measuring the atmospheric pressure comprises releasing the pressure from the reservoir and/or the hydraulic constriction element before the pressure is measured. As no pressure is added to the reservoir and/or the hydraulic constriction element, the atmospheric pressure will be the pressure that is measures. The pressure measured when the reservoir and/or hydraulic constriction element is without added pressure can be used as a reference value against which the pressure in the reservoir and/or hydraulic constriction element can be measured. This enables both the atmospheric (reference) pressure and the pressure in the reservoir and/or hydraulic constriction element to be measured using the same pressure sensor, which creates a compact and efficient design. The measured reference could also be compared with the atmospheric pressure measured by a second, external pressure sensor 106''''. This comparison/calibration can be used to establish that there is no pressure in the reservoir and/or hydraulic constriction element when the controller has released the pressure. The pressure applied to the reservoir and/or hydraulic constriction element can be controlled either by controlling the actual pressure, or by controlling the volume of fluid pumped and/or by controlling the cross-sectional distance of the constricted urethra. I.e. if the pressure is continuously calibrated it can be established that a certain fluid level or distance leads to a specific pressure, which could make control of the device easier then control using constant pressure measurement. The controller (a computing unit of the controller) could in one embodiment create an absolute pressure by subtracting the pressure in the implantable hydraulic constriction element/reservoir, when substantially no pressure is exerted on the urethra, from the pressure in the hydraulic constriction element/reservoir, when the pressure in the implantable hydraulic constriction element has been increased. The operation device could then control the pressure in the hydraulic constriction element/reservoir on the basis of the absolute pressure. In embodiments in which the fluid level or cross-sectional distance of the urethra is used as control value, the pressure may be used as a back-up or safety system, e.g. the pressure sensor can be set to give an alarm signal or take a specific action if the pressure increases over a set value (threshold).

In all of the described sensor embodiments above, any of the pressure sensors 106 may be a strain gauge-based pressure sensor, such as a piezoresistive or piezoelectric pressure sensor, or an optical pressure sensor, a capacitive pressure sensor, or an electromagnetic pressure sensor.

As described with further reference to FIGS. 8a-9c and 23a-23e, the controller 300 references in any of FIGS. 17an-17e could be configured to control an electrically operable pump and/or valve to control the pressure in the implantable constriction device.

In the following a detailed description of a method and apparatus for electrically stimulating the tissue of the urethra for exercising the urethra and thereby improve the conditions for long term implantation will be given. The electrical electrode arrangement described and the electrical electrodes comprised in the arrangement may be implemented in any of the embodiments of the implantable constriction device described herein for the purpose of exercising the tissue wall which is in contact with the constriction device. The body tends to react to a medical implant, partly because the implant is a foreign object, and partly because the implant interacts mechanically with tissue of the body. Exposing tissue to long-term engagement with, or pressure from, an implant may deprive the cells of oxygen and nutrients, which may lead to deterioration of the tissue, atrophy and eventually necrosis. The interaction between the implant and the tissue may also result in fibrosis, in which the implant becomes at least partially encapsulated in fibrous tissue. It is therefore desirable to stimulate or exercise the cells to stimulate blood flow and increase tolerance of the tissue for pressure from the implant.

Muscle tissue is generally formed of muscle cells that are joined together in tissue that can be either striated or smooth, depending on the presence or absence, respectively, of organized, regularly repeated arrangements of myofibrillar contractile proteins called myofilaments. Striated muscle tissue is further classified as either skeletal or cardiac muscle tissue. Skeletal muscle tissue is typically subject to conscious control and anchored by tendons to bone. Cardiac muscle tissue is typically found in the heart and not subject to voluntary control. A third type of muscle tissue is the so-called smooth muscle tissue, which is typically neither striated in structure nor under voluntary control. Smooth muscle tissue can be found within the walls of organs and in for example the urethra U.

The contraction of the muscle tissue may be activated both through the interaction of the nervous system as well as by hormones. The different muscle tissue types may vary in their response to neurotransmitters and endocrine substances depending on muscle type and the exact location of the muscle.

A nerve is an enclosed bundle of nerve fibers called axons, which are extensions of individual nerve cells or neurons. The axons are electrically excitable, due to maintenance of voltage gradients across their membranes, and provide a common pathway for the electrochemical nerve impulses called action potentials. An action potential is an all-or-nothing electrochemical pulse generated by the axon if the voltage across the membrane changes by a large enough amount over a short interval. The action potentials travel from one neuron to another by crossing a synapse, where the message is converted from electrical to chemical and then back to electrical.

The distal terminations of an axon are called axon terminals and comprise synaptic vesicles storing neurotransmitters. The axonal terminals are specialized to release the neurotransmitters into an interface or junction between the axon and the muscle cell. The released neurotransmitter binds to a receptor on the cell membrane of the muscle cell for a short period of time before it is dissociated and hydrolyzed by an enzyme located in the synapse. This enzyme quickly reduces the stimulus to the muscle, which allows the degree and timing of muscular contraction to be regulated delicately.

The action potential in a normal skeletal muscle cell is similar to the action potential in neurons and is typically about −90 mV. Upon activation, the intrinsic sodium/potassium channel of the cell membrane is opened, causing sodium to rush in and potassium to trickle out. As a result, the cell membrane reverses polarity and its voltage quickly jumps from the resting membrane potential of −90 mV to as high as +75 mV as sodium enters. The muscle action potential lasts roughly 2-4 ms, the absolute refractory period is roughly 1-3 ms, and the conduction velocity along the muscle is roughly 5 m/s. This change in polarity causes in turn the muscle cell to contract.

The contractile activity of smooth muscle cells is typically influenced by multiple inputs such as spontaneous electrical activity, neural and hormonal inputs, local changes in chemical composition, and stretch. This in contrast to the contractile activity of skeletal and cardiac muscle cells, which may rely on a single neural input. Some types of smooth muscle cells are able to generate their own action potentials spontaneously, which usually occur following a pacemaker potential or a slow wave potential. However, the rate and strength of the contractions can be modulated by external input from the autonomic nervous system. Autonomic neurons may comprise a series of axon-like swellings, called varicosities, forming motor units through the smooth muscle tissue. The varicosities comprise vesicles with neurotransmitters for transmitting the signal to the muscle cell.

The muscle cells described above, i.e., the cardiac, skeletal, and smooth muscle cells are known to react to external stimuli, such as electrical stimuli applied by electrodes. A distinction can be made between stimulation transmitted by a nerve and direct electrical stimulation of the muscle tissue. In case of stimulation via a nerve, an electrical signal may be provided to the nerve at a location distant from the actual muscle tissue, or at the muscle tissue, depending on the accessibility and extension of the nerve in the body. In case of direct stimulation of the muscle tissue, the electrical signal may be provided to the muscle cells by an electrode arranged in direct or close contact with the cells. However, other tissue such as fibrous tissue and nerves may of course be present at the interface between the electrode and the muscle tissue, which may result in the other tissue being subject to the electrical stimulation as well.

In the context of the present application, the electrical stimulation discussed in connection with the various aspects and embodiments may be provided to the tissue in direct or indirect contact with the implantable constriction device. Preferably, the electrical stimulation is provided by one or several electrode elements arranged at the interface or contact surface between the implantable constriction device and the tissue. Thus, the electrical stimulation may, in terms of the present disclosure, be considered as a direct stimulation of the tissue. Particularly when contrasted to stimulation transmitted over a distance by a nerve, which may be referred to as an indirect stimulation or nerve stimulation.

Hence, an electrode arrangement comprising one or several electrode elements may be arranged in, partly in, on, or in close vicinity of the tissue that is to be exercised by means of an electrical signal. Preferably, the electrode may be arranged to transmit the electrical signal to the portions of the tissue that is affected, or risks to be affected, by mechanical forces exerted by the medical implant. Thus, the electrode element may be considered to be arranged between the implanted device and the tissue against which the device is arranged to rest when implanted.

During operation of the implantable constriction device, or the electrode arrangement, the electric signal may cause the muscle cells to contract and relax repeatedly. This action of the cells may be referred to as exercise and may have a positive impact in terms of preventing deterioration and damage of the tissue. Further, the exercise may help increasing tolerance of the tissue for pressure and mechanical forces generated by the medical implant.

The interaction between the implanted electrode element and the tissue of the urethra is to a large extent determined by the properties at the junction between the tissue and the electrode element. The active electrically conducting surface of the electrode element (in the following referred to as "metal", even though other materials is equally conceivable) can either be uncoated resulting in a metal-tissue interface, or insulated with some type of dielectric material. The uncoated metal surface of the electrode element may also be referred to as a bare electrode. The interface between the electrode element and the tissue may influence the behavior of the electrode element since the electrical interaction with the tissue is transmitted via this interface. In the biological medium surrounding the electrode element, such as the actual tissue and any electrolyte that may be present in the junction, the current is carried by charged ions, while in the material of the electrode element the current is carried by electrons. Thus, in order for a continuous current to flow, there needs to be some type of mechanism to transfer charge between these two carriers.

In some examples, the electrode element may be a bare electrode wherein the metal may be exposed to the surrounding biological medium when implanted in, or at the muscle tissue that is to be stimulated. In this case there may be a charge transfer at a metal-electrolyte interface between the electrode element and the tissue. Due to the natural strive for thermodynamic equilibrium between the metal and the electrolyte, a voltage may be established across the interface which in turn may cause an attraction and ordering of ions from the electrolyte. This layer of charged ions at the metal surface may be referred to as a "double layer" and may physically account for some of the electrode capacitance.

Hence, both capacitive faradaic processes may take place at the electrode element. In a faradaic process, a transfer of charged particles across the metal-electrolyte interface may be considered as the predominant current transfer mechanism. Thus, in a faradaic process, after applying a constant current, the electrode charge, voltage, and composition tend to go to constant values. Instead, in a capacitive (non-faradaic) process charge is progressively stored at the metal surface and the current transfer is generally limited to the amount which can be passed by charging the interface.

In some examples, the electrode element may comprise a bare electrode portion, i.e., an electrode having an uncoated surface portion facing the tissue such that a conductor-tissue interface is provided between the electrode element and the tissue when the electrode element is implanted. This allows for the electric signal to be transmitted to the tissue by means of a predominantly faradaic charge transfer process. A bare electrode may be advantageous from a power consumption perspective since a faradaic process tend to be more efficient than a capacitive charge transfer process. Hence, a bare electrode may be used to increase the current transferred to the tissue for a given power consumption.

In some examples, the electrode element may comprise a portion that is at least partly covered by a dielectric material so as to form a dielectric-tissue interface with the muscle tissue when the electrode is implanted. This type of electrode element allows for a predominantly capacitive, or non-faradaic, transfer of the electric signal to the muscle tissue. This may be advantageous over the predominantly faradaic process associated with bare electrodes since faradaic charge transfer may be associated with several problems. Example of problems associated with faradaic charge transfer include undesirable chemical reactions such as metal oxidation, electrolysis of water, oxidation of saline, and oxidation of organics. Electrolysis of water may be damaging since it produces gases. Oxidation of saline can produce many different compounds, some of which are toxic. Oxidation of the metal may release metal ions and salts into the tissue which may be dangerous. Finally, oxidation of organics in a situation with an electrode element directly stimulating tissue may generate chemical products that are toxic.

These problems may be alleviated if the charge transfer by faradaic mechanisms is reduced, which may be achieved by using an electrode at least partly covered by a dielectric material. Preferably, the dielectric material is chosen to have as high capacitance as possible, restricting the currents flowing through the interface to a predominantly capacitive nature.

Several types of electrode elements can be combined with the present disclosure. The electrode element can for example be a plate electrode, comprising a plate-shaped active part forming the interface with the tissue. In other examples, the electrode may be a wire electrode, formed of a conducting wire that can be brought in electrical contact with the tissue. Further examples may include needle- or pin-shaped electrodes, having a point at the end which can be attached to or inserted in the muscle tissue. The electrodes may for example be encased in epoxy for electrical isolation and protection and comprise gold wires or contact pads for contacting the muscle tissue. Some of these examples of electrodes, methods of stimulating using electrodes, and how the electrode arrangements can be arranged in connection with implantable constriction devices will be discussed below with reference to FIGS. 18a-22.

Figure 18A:
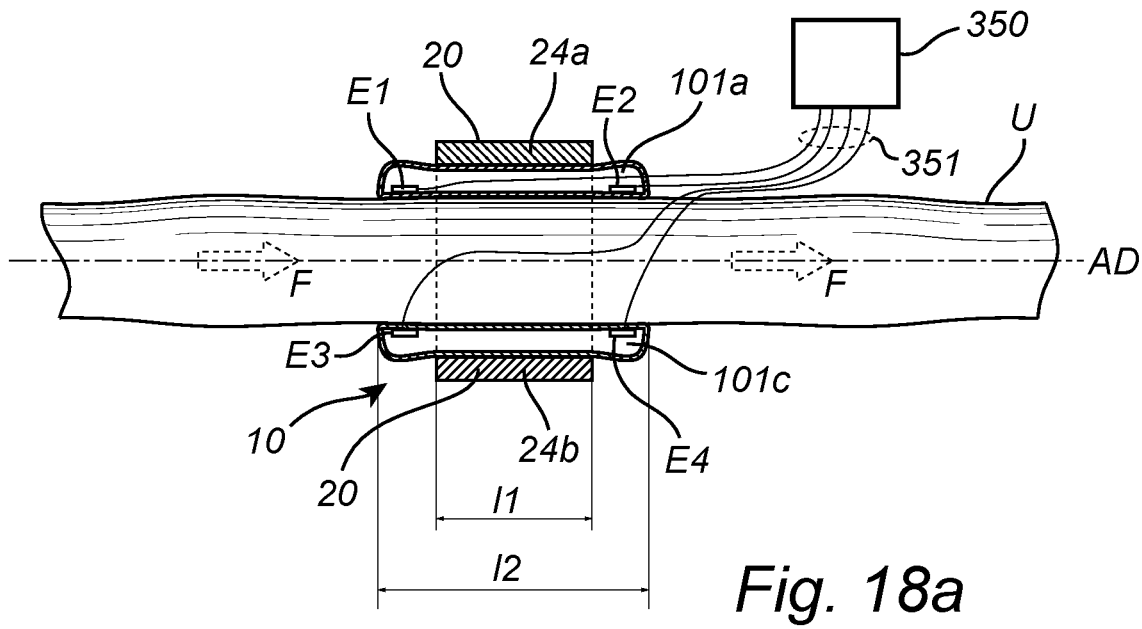
FIG. 18a shows an embodiment of an implantable constriction device in section, including an electrode arrangement for electrical stimulation, when placed on the urethra of a patient.

FIG. 18a shows an embodiment of the implantable constriction device 10 having all the elements as in the embodiment described with reference to FIGS. 1a-1c and 1e, in a cross-sectional view when implanted and placed surrounding the urethra U. The implantable constriction device 10 of FIG. 18a further comprises an electrode arrangement comprising four electrodes E1, E2, E3, E4 for electrically stimulating the tissue of the urethra U for exercising the muscle tissue to improve the conditions for long term implantation of the implantable constriction device 10. In the embodiment of FIG. 18a, the electrode arrangement is arranged on an outer surface of the operable hydraulic constriction elements 101a, 101c and thus placed in abutment and in electrical connection with the tissue of the urethra U. A first and a second electrode element E1, E2 are placed on a first side of the urethra, and a second and third electrode element E3, E4 are placed on a second, opposing side of the urethra U. Each of the four electrode elements E1, E2, E3, E4 are connected to a stimulation controller 350 by means of electrical conduits 351. The stimulation controller 350 is configured to be operably connected to the electrode arrangement for controlling the electrical stimulation of the tissue of the urethra U. In the embodiment shown in FIG. 18a, the stimulation controller 350 is configured to control the electrical stimulation such that the tissue of the urethra U is stimulated by a series of electrical pulses. In the embodiment shown in FIG. 18a, the pulses comprise a pulse of a first polarity followed by a pulse of a second, reversed polarity, and the pulsed electrical stimulation signal generated comprises a pulse frequency of 0.01-150 Hz. In the embodiment shown in FIG. 18a, the electrical stimulation signal comprises a pulse duration of 0.01-100 ms and a pulse amplitude of 1-15 mA. More specifically, in the embodiment of FIG. 18a, the electrical stimulation signal comprises a pulse frequency of 0.15-0.25 Hz, a pulse duration of 20-30 ms and a pulse amplitude of 3-10 mA. Further, in the embodiment of FIG. 18a, the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

The stimulation controller 350 of FIG. 18a is integrated in an implantable controller, such as the implantable controller described with reference to FIG. 8-9c and FIGS. 23a-23e, and the stimulation controller may be configured to receive input from a wireless remote control, directly or via a receiver of the implantable controller, for controlling the stimulation or for programming a stimulation routine for exercising the muscle tissue to improve the conditions for long term implantation of the implantable constriction device 10. The programming of a stimulation routine could for example be the programming of the frequency of the stimulation, or the current and/or voltage of the stimulation.

Figure 18B:
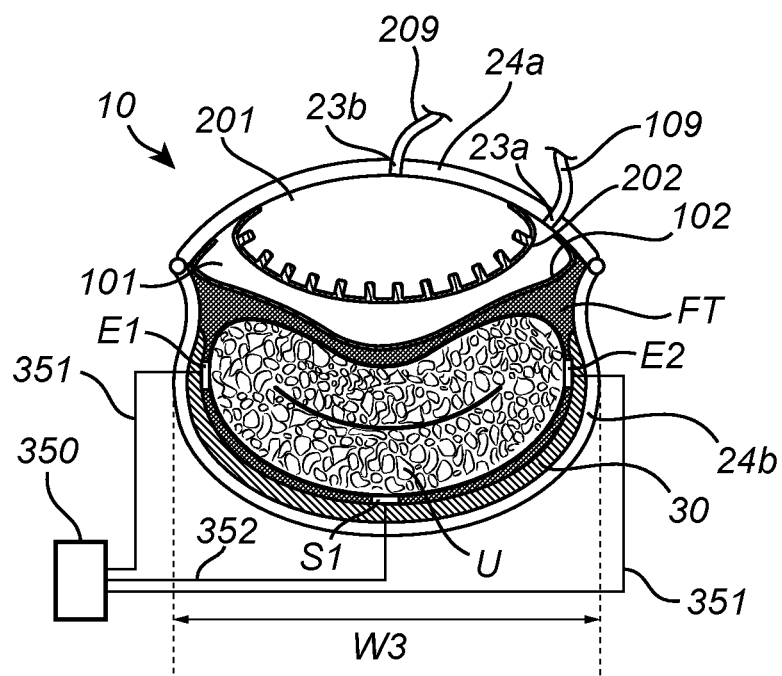
FIG. 18b shows an embodiment of an implantable constriction device for constricting the urethra of a patient in a sectional side view, including an electrode arrangement for electrical stimulation, in its constricted state.

FIG. 18b shows an embodiment of the implantable constriction device 10 comprising all of the features and elements of the embodiment described with reference to FIG. 10d. In addition, the implantable constriction device 10 of FIG. 18b further comprises an electrode arrangement comprising two electrode elements E1, E2 for electrically stimulating the tissue of the urethra U for exercising the muscle tissue to improve the conditions for long term implantation of the implantable constriction device 10. In the embodiment of FIG. 18b, the electrode arrangement is arranged on an outer surface of the cushioning element 30 which is fixated to the support element 24b making up a portion of the surrounding structure. The first and second electrode elements E1, E2 are thus placed in abutment and in electrical connection with the tissue of the urethra U. The first electrode element E1 is placed on a first side of the urethra U, and a second electrode element E2 is placed on the second, opposing side of the urethra U. Each of the electrode elements E1, E2 are connected to a stimulation controller 350 by means of electrical leads 351. The stimulation controller 350 is configured to be operably connected to the electrode arrangement for controlling the electrical stimulation of the tissue of the urethra U. The stimulation of the tissue could e.g. be performed with electrical pulses, such as described with reference to FIG. 18a, or may in the alternative be controlled as a continuous low-energy current providing a continuous stimulation of the wall.

In the embodiment shown in FIG. 18b, the implantable constriction device 10 further comprises an implantable sensor S1 configured to sense actions potentials generated by pacemaker cells of the tissue of the urethra U. The implantable sensor S1 is also connected to the cushioning element 30 and connected to the stimulation controller by means of a sensor lead 351. The stimulation controller 350 is configured to control the electrical simulation based at least partly on the sensed action potentials and is configured to generate electrical pulses amplifying the sensed action potentials. The implantable sensor may be implemented in any of the embodiments of implantable constriction device 10 for controlling the electrical stimulation by the electrode elements, which also may be implemented in any of the embodiments of implantable constriction devices described herein.

Figure 18C:
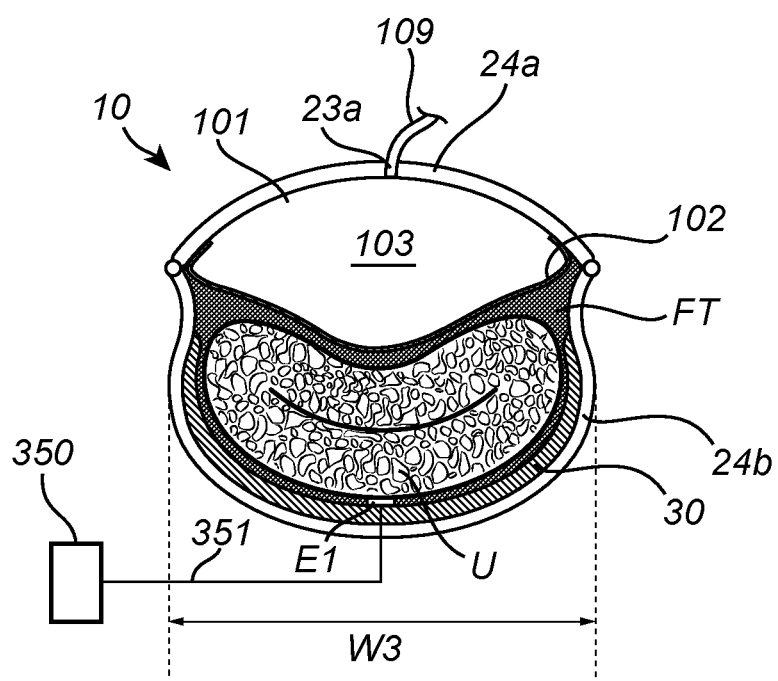
FIG. 18c shows an embodiment of an implantable constriction device for constricting the urethra of a patient in a sectional side view, including an electrode arrangement for electrical stimulation, in its constricted state.

FIG. 18c shows an embodiment of the implantable constriction device 10 very similar to the embodiment shown in FIG. 11d, with the difference that the implantable constriction device 10 of FIG. 18c comprises a single electrode element E1 for electrically stimulating the tissue of the urethra U for exercising the muscle tissue to improve the conditions for long term implantation of the implantable constriction device 10. In the embodiment of FIG. 18c, the electrode arrangement is arranged on an outer surface of the cushioning element 30 which is fixated to the support element 24b making up a portion of the surrounding structure. The electrode element E1 is thus placed in abutment and in electrical connection with the tissue of the urethra U. The electrode element E1 is connected to a stimulation controller 350 by means of an electrical lead 351. The stimulation controller 350 is configured to be operably connected to the electrode arrangement for controlling the electrical stimulation of the tissue of the urethra U. The stimulation of the tissue could e.g. be performed with electrical pulses, such as described with reference to FIG. 18a, or may in the alternative be controlled as a continuous low-energy current providing a continuous stimulation of the wall.

Figure 18D:
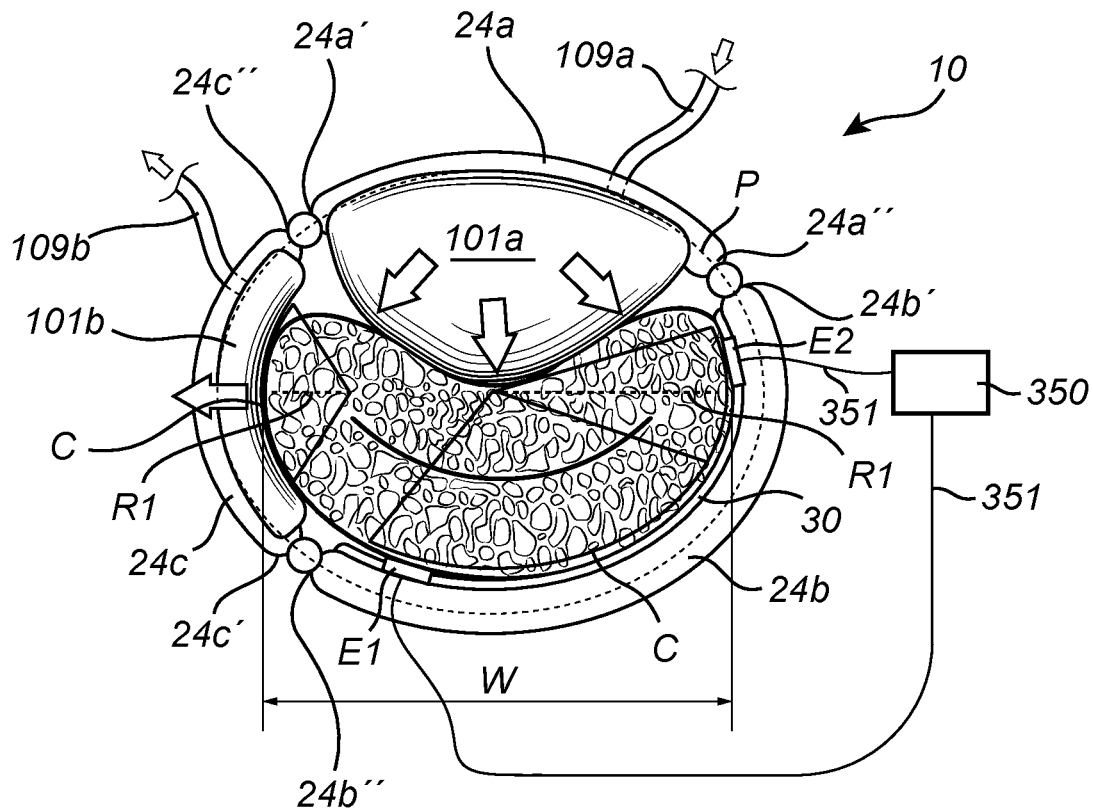
FIG. 18d shows an embodiment of an implantable constriction device for constricting the urethra of a patient in a sectional side view, including an electrode arrangement for electrical stimulation, in its constricted state.

FIG. 18d shows an embodiment of the implantable constriction device 10 comprising all of the features and elements of the embodiment described with reference to FIGS. 2a and 2b. In addition, the implantable constriction device 10 of FIG. 18d further comprises an electrode arrangement comprising two electrode elements E1, E2 for electrically stimulating the tissue of the urethra U for exercising the muscle tissue to improve the conditions for long term implantation of the implantable constriction device 10. In the embodiment of FIG. 18d, the electrode arrangement is arranged on an outer surface of the cushioning element 30 which is fixated to the support element 24b making up a portion of the surrounding structure. The first and second electrode elements E1, E2 are thus placed in abutment and in electrical connection with the tissue of the urethra U. In alternative embodiments, it is equally conceivable that a first electrode element is placed on the cushioning element 30 and a second electrode element is placed on one of the operable hydraulic constriction elements 101a, 101b. Each of the electrode elements E1, E2 are connected to a stimulation controller 350 by means of electrical leads 351. The stimulation controller 350 is configured to be operably connected to the electrode arrangement for controlling the electrical stimulation of the tissue of the urethra U. The stimulation of the tissue could e.g. be performed with electrical pulses, such as described with reference to FIG. 18a, or may in the alternative be controlled as a continuous low-energy current providing a continuous stimulation of the wall.

Figure 19A:
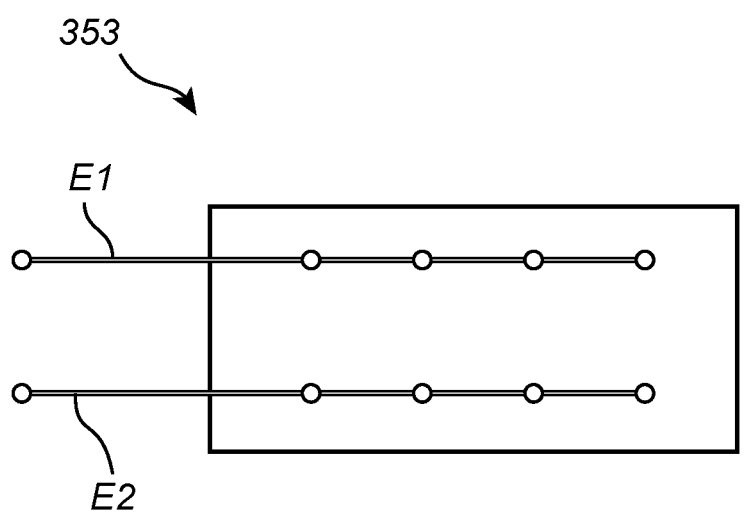
FIG. 19a shown an embodiment of an electrode arrangement, for inclusion in an implantable constriction device.

FIG. 19a is an example of a bipolar electrode arrangement, comprising a first and a second electrode element E1, E2 that can be connected to different electrical potentials. Thus, the first electrode element E1 can be operated as an anode and the second electrode element E2 can be operated as a cathode. The electrode elements E1, E2 may be attached directly to an outer surface of the implantable device, such as disclosed with reference to FIGS. 18a-18c. In some examples the electrode elements E1, E2 may be arranged on a support, such as a flexible patch, which may be configured to be attached to the implantable constriction device. The electrode arrangement 353 can be arranged between the implantable constriction device and the tissue (such as disclosed with reference to FIGS. 18a-18c) and may in some examples be provided as a separate, physically distinct item and in other examples be integrated in the implantable constriction device. The electrode arrangement 353 may comprise one or several contact pads for increasing the contact surface between the electrode and the tissue when implanted. During operation, the electrical signal may be delivered to the muscle tissue by means of the first and second electrode elements E1, E2 so as to stimulate contraction of the muscle cells.

Figure 19B:
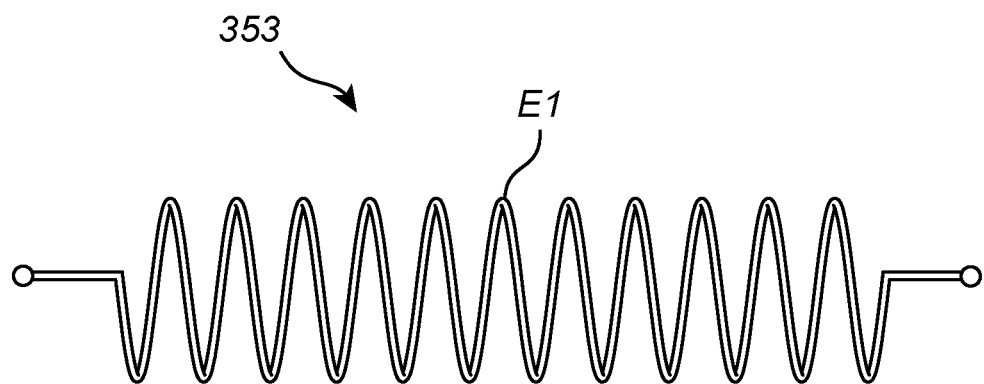
FIG. 19b shown an embodiment of an electrode arrangement, for inclusion in an implantable constriction device.

FIG. 19b is another example of an electrode arrangement 353, which in the present example may be a unipolar electrode element E1. The electrode element E1 may for example be operated as a cathode when implanted. The electrode element E1 may be formed of a flat, coiled wire for increasing the contact surface between the electrode element E1 and the tissue. Further, the coiled configuration allows for a certain mechanical flexibility of the electrode element E1 such that it can follow the muscle tissue during contraction and relaxation.

Figure 19C:
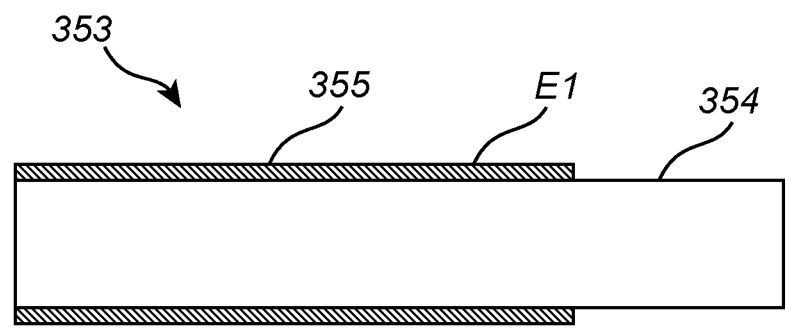
FIG. 19c shown an embodiment of an electrode arrangement, for inclusion in an implantable constriction device.

FIG. 19c illustrates the end portion of a needle- or pin-shaped electrode arrangement 353, wherein the active portion of the electrode element E1 is provided as a bare electrode surface 354 at the end of the electrode element E1, protruding from an insulation 355 covering the rest of the electrode element E1. Thus, when implanted at or in the muscle tissue, the active, bare electrode surface 354 of the electrode element E1 may form a metal-tissue interface with the muscle tissue, wherein the interface may surround the end portion of the electrode element E1 so as to provide a relatively large contact surface. The present example is advantageous in that it can be inserted into the tissue, thereby allowing for a selective stimulation at a certain depth of the tissue.

Figure 19D:
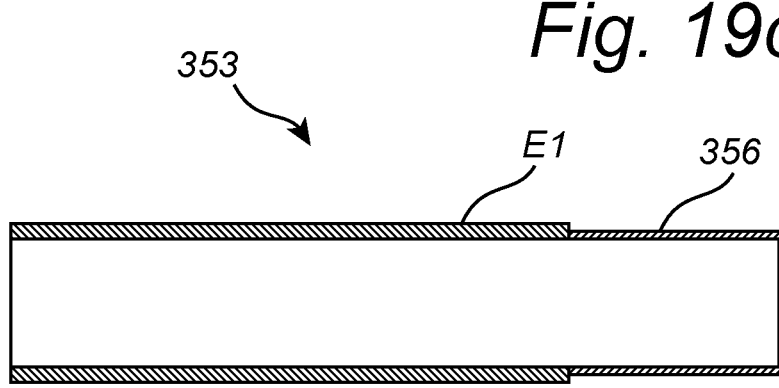
FIG. 19d shown an embodiment of an electrode arrangement, for inclusion in an implantable constriction device.

FIG. 19d shows a similar electrode element as the one in FIG. 19c, with the difference that the present electrode element E1 comprises an active portion that is covered by a dielectric material 356 so as to protect the electrode material from deterioration and to facilitate capacitive current transfer. The dielectric material 356 may for example be electrochemically deposited tantalum oxide, which allows the electrical charge to pass through the interface but reduces the risk for electrode corrosion, gas formation and metabolite reactions.

It will be appreciated that both faradaic and capacitive mechanisms may be present at the same time, irrespectively of the type of electrode used. Thus, capacitive charge transfer may be present also for a bare electrode forming a metal-tissue interface, and faradaic charge transfer may be present also for a coated electrode forming a dielectric-tissue interface. It has been found that the faradaic portion of the current delivered to the muscle tissue can be reduced or even eliminated by reducing the duration of the pulses of the electric signal. Reducing the pulse duration has turned out to be an efficient way of increasing the portion of the signal which can be passed through the interface as a capacitive current, rather than by a faradaic current. As a result, shorter pulses may produce less electrode and tissue damage.

The capacitive portion of the current may further be increased, relative to the faradaic portion, by reducing the amplitude of the current pulses of the electrical signal. Reducing the amplitude may reduce or suppress the chemical reactions at the interface between the electrode and the tissue, thereby reducing potential damage that may be caused by compounds and ions generated by such reactions.

In one example, the electrical stimulation may be controlled in such a manner that a positive pulse of the electrical signal is followed by a negative pulse (or, put differently, a pulse of a first polarity being followed by a pulse of a second, reversed polarity), preferably of the same amplitude and/or duration. Advantageously, the subsequent negative (or reversed) pulse may be used to reverse or at least moderate chemical reactions or changes taking place in the interface in response to the first, positive pulse. By generating a reversed pulse, the risk of deterioration of the electrode and/or the tissue at the interface between the electrode and the muscle tissue may be reduced.

Figure 20:
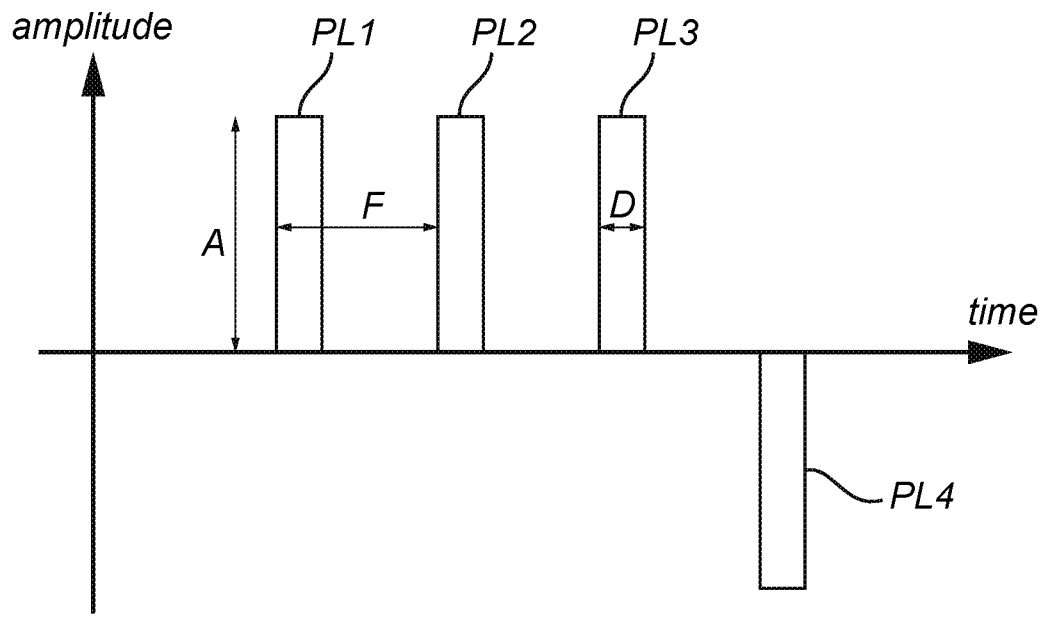
FIG. 20 shown an embodiment of a stimulation cycle for electrical stimulation of a tissue wall.

FIG. 20 shows an example of a pulsed electrical signal to be applied to an electrode for electrically stimulating muscle tissue via an electrode-tissue interface as discussed above. The electrical signal may be generated by a stimulation controller arranged outside the body or implanted in the body (as described with reference to FIGS. 18a-18c). The stimulation controller may be operatively connected to the electrode element by means of a lead, and the electrical signal shown in the present figure may either reflect the signal as generated at the stimulation controller, or the signal as delivered to the electrode element at the electrode-tissue interface. The characteristics of the electrical signal may be selected and varied determined on the electrical and properties at the electrode-tissue interface and on the actual response of the tissue. The electrical stimulation delivered to the muscle cells may depend on several factors, such as the configuration and placement of the electrode element at the tissue, the presence of fibrous material at the interface, the composition of the electrolyte in the interface, accumulation of non-conducting material on the electrode surfaces, etcetera. It is therefore suggested that the characteristics of the electric signal, as shown in the present figure, be selected and varied based on an observed or estimated response from the stimulated tissue.

In the present example, the electrical signal is a pulsed signal comprising square waves PL1, PL2, PL3, PL4. However, other shapes of the pulses may be employed as well. The pulse signal may be periodic, as shown, or may be intermittent (i.e., multiple series of pulses separated by periods of no pulses). The pulses may have an amplitude A, which may be measured in volts, ampere, or the like. Each of the pulses of the signal may have a pulse width D. Likewise, if the signal is periodic, the pulse signal may have a period F that corresponds to a frequency of the signal. Further, the pulses may be either positive or negative in relation to a reference.

The pulse frequency may for example lie within the range of 0.01-150 hertz. More specifically, the pulse frequency may lie within at least one of the ranges of 0.1-1 Hz, 1-10 Hz, 10-50 Hz and 50-150 Hz. It has been observed that relatively low pulse frequencies may be employed to imitate or enhance the slow wave potential associated with pacemaker cells of the smooth muscle tissue. Thus, it may be advantageous to use relatively low pulse frequencies, such as 0.01-0.1 Hz or frequencies below 1 Hz or a few Hz for such applications.

The pulse duration may for example lie within the range of 0.01-100 milliseconds, such as 0.1-20 milliseconds (ms), and preferably such as 1-5 ms. The natural muscle action potential has in some studies been observed to last about 2-4 ms, so it may be advantageous to use a pulse duration imitating that range.

The amplitude may for example lie within the range of 1-15 milliamperes (mA), such as 0.5-5 mA in which range a particularly good muscle contraction response has been observed in some studies.

In a preferred, specific example the electrical stimulation may hence be performed using a pulsed signal having a pulse frequency of 10 Hz, a pulse duration of 3 ms and an amplitude of 3 mA.

Figure 21:
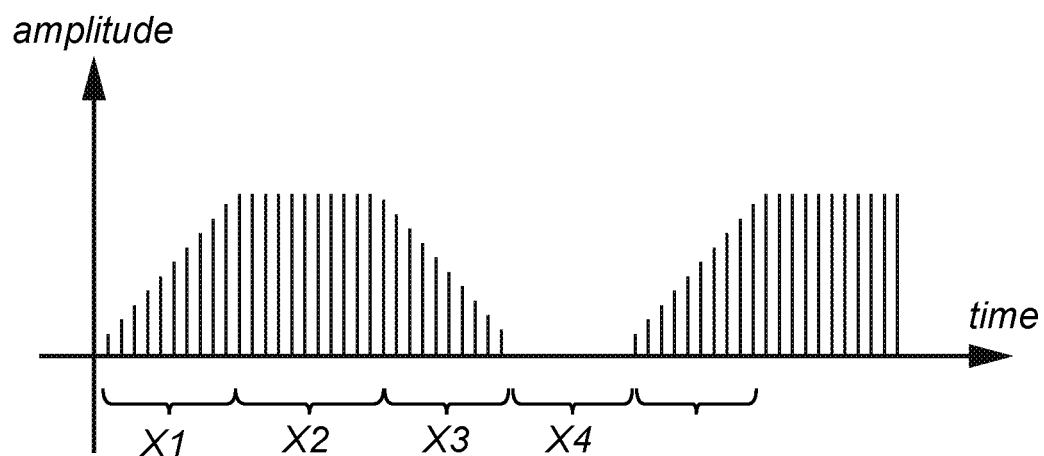
FIG. 21 shown an embodiment of a stimulation cycle for electrical stimulation of a tissue wall.

FIG. 21 shows an example of a pulsed signal, comprising build-up period X1, in which the amplitude is gradually increasing, a stimulation period X2 during which the muscle tissue is exposed to a contracting stimulation signal, a ramp down period X3 in which the amplitude is gradually decreasing, and a stimulation pause X4 before a new build-up period is initiated. The build-up period may for example be 0.01-2 seconds, the stimulation period 1-60 seconds, the ramp-down period 0.01-2 seconds, and the stimulation pause 0.01-60 seconds. The pulse frequency may for example be 1-50 Hz, the pulse duration 0.1-10 milliseconds and the amplitude during the stimulation period be 1-15 milliampere. The stimulation of skeletal muscle tissue may for example be performed using a frequency of 50 Hz and pulses having a duration of 100 µs. The current amplitude may be 1, 2.5, 7.5 or 10 mA. In particular, a desired muscle contraction response has been experimentally observed within a range of 0.5 to 5.0 mA. In the present example, a coiled electrode may be used as a cathode. Another example design is a multi-stranded wire arranged in a helical design. They can be imbricated in the muscular wall of the urinary bladder and can be stimulated in any desired pattern. The stimulus parameters may for example be biphasic pulses, 10 to 40 Hz, lasting 0.1 to 5 ms, with a current density of 3 to 5 mA/cm2.

Figure 22:
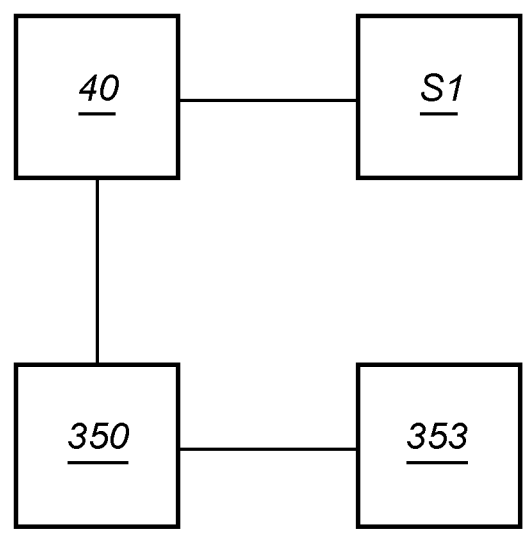
FIG. 22 is a block diagram schematically describing the function of the system for electrical stimulation of a tissue wall of the patient.

FIG. 22 is a schematic outline of a system for electrically stimulating or exercising muscle cells to increase tolerance of the tissue for pressure from the implantable constriction device. The system may be used in combination with the implantable constriction device and may in some examples be comprises in such an implantable constriction device. The system comprises an electrode arrangement 353 which may be similarly configured as the electrodes arrangements/electrode elements discussed above in connection with the previous examples, an energy storage unit 40 for providing the electrical energy required for generating the electrical signal, and a stimulation controller 350 controlling the generation of the electrical signal.

The electrode arrangement, which may comprise one or several electrode elements, such as a bare electrode or an electrode at least partly covered by a dielectric material, may be configured to be implanted in the muscle tissue to be stimulated, or to engage the muscle, so as to form an electrode-tissue interface through which the stimulating signal may be transferred. Alternatively, or additionally, the electrode element may be arranged in close vicinity to the muscle tissue such that an electrical coupling between the electrode element and the muscle tissue may be established. This may for example be the case when other tissue, such as connective tissue, is present between the implanted device and the muscle tissue.

The electrode may be electrically connected to the energy storage unit 40, for example by means of a wiring or a lead, such that the electrical signal may be transferred to the electrode-tissue interface. In some examples, the electrode may be integrated with or attached to the implantable constriction device, such that the electrode when implanted in the patient is arranged at the interface between the implantable constriction device and the muscle tissue. The electrode can thereby be used for exercising the muscle tissue that is mechanically affected by the implantable constriction device.

The energy storage unit 40 may for example be of a non-rechargeable type, such as a primary cell, or of a rechargeable type, such as a secondary cell. The energy storage unit 40 may be rechargeable by energy transmitted from outside the body, from an external energy storage unit, or be replaced by surgery. Further, the electrode arrangement 353 may be operably connected to a stimulation controller 353, which may comprise an electrical pulse generator, for generating the electrical pulse. The stimulation controller 350 may be integrated with the energy storage unit 40 or provided as a separate, physically distinct unit which may be configured to be implanted in the body or operate from the outside of the body. In case of the latter, is may be advantageous to allow the external control unit to communicate wirelessly with the stimulation controller for example by means of a communication unit of a more general controller (for example described with reference to FIGS. 8-9c and FIGS. 23a-23e.

The system may according to some examples comprise a sensor S1 that is configured to sense a physical parameter of the body and/or the implantable constriction device. The sensor S1 may for example be employed to sense or detect a bodily response to the electrical stimulation, such as for example a contraction of the stimulated muscle tissue. In an example, the sensor S1 may be configured to sense action potentials that are being sent to the muscle tissue. The action potentials may for example be generated by pacemaker cells of the muscle tissue, which may be registered by the sensor S1 and transmitted to the stimulation controller 350. The stimulation controller 350 may use the received signal when controlling the energy storage unit 40, such that the generated electrical signal amplifies the sensed action potentials.

The function and features of the controller comprised in the implantable constriction device for controlling the implantable constriction device will now described with reference to FIGS. 23a-23e. The features of the controller described with reference to FIGS. 23a-23e may be implemented and combined with any of the embodiments of implantable constriction devices disclosed herein. The features may for example be implemented in the controllers shown and described with reference to FIGS. 8a-9c and 14-15g. Any controller may comprise an internal computing unit, also called a processor, and it may comprise a communication unit and implement methods for communication, including verification, authentication, and encryption of data, as described in the following.

The controller may comprise a collection of communication related sub-units such as a wired transceiver, a wireless transceiver, energy storage unit, an energy receiver, a computing unit, a memory, or a feedback unit. The sub-units of the controller may cooperate with each other or operate independently with different purposes. The sub-units of the controller may inherit the prefix "internal". This is to distinguish these sub-units from the sub-units of the external devices as similar sub-units may be present for both the implanted controller and the external devices. The sub-units of the external devices may similarly inherit the prefix "external".

A wireless transceiver may comprise both a wireless transmitter and a wireless receiver. The wireless transceiver may also comprise a first wireless transceiver and a second wireless transceiver. In this case, the wireless transceiver may be part of a first communication system (using the first wireless transceiver) and a second communication system (using the second wireless transceiver).

In some embodiments, two communication systems may be implemented using a single wireless transceiver in e.g. the implant and a single wireless transceiver in e.g. an external device (i.e. one antenna at the implant and one antenna at the external device), but where for example the network protocol used for data transmission from the external device to the implant is different from the network protocol used for data transmission from the implant to the external device, thus achieving two separate communication systems.

Alternatively, the wireless transceiver may be referred to as either a wireless transmitter or a wireless receiver as not all embodiments of secure wireless communication discussed herein require two-way communication capability of the wireless transceiver. The wireless transceiver may transmit or receive wireless communication via wireless connections. The wireless transceiver may connect to both the implant and to external devices, i.e. devices not implanted in the patient.

The wireless connections may be based on radio frequency identification (RFID), near field charge (NFC), Bluetooth, Bluetooth low energy (BLE), or wireless local area network (WLAN). The wireless connections may further be based on mobile telecommunication regimes such as 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

A wired transceiver may comprise both a wired transmitter and a wired receiver. The wording wired transceiver aims to distinguish between it and the wireless transceiver. It may generally be considered a conductive transceiver. The wired transceiver may transmit or receive conductive communication via conductive connections. Conductive connections may alternatively be referred to as electrical connections or as wired connections. The wording wired however, does not imply there needs to be a physical wire for conducting the communication. The body tissue of the patient may be considered as the wire. Conductive connection may use the body of the patient as a conductor. Conductive connections may still use ohmic conductors such as metals to at least some extent, and more specifically at the interface between the wired transceiver and the chosen conductor.

Communication, conductive or wireless may be understood as digital or analogue. In analogue communication, the message signal is in analogue form i.e., a continuous time signal. In digital communication, usually digital data i.e., discrete time signals containing information is transmitted.

The controller may comprise a sensation generator. A sensation generator is a device or unit that generates a sensation. The sensation generated may be configured to be experienceable by the patient such that the patient may take actions to authenticate a device, connection, or communication. The sensation generator may be configured to generate a single sensation or a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm.

The sensations generated by the sensation generator may be configured to be experienceable by a sensory function or a sense of the patient from the list of tactile, pressure, pain, heat, cold, taste, smell, sight, and hearing. Sensations may be generated of varying power or force as to adapt to sensory variations in the patient. Power or force may be increased gradually until the patient is able to experience the sensation. Variations in power or force may be controlled via feedback. Sensation strength or force may be configured to stay within safety margins. The sensation generator may be connected to the implant. The sensation generator may be comprised within the implant or be a separate unit.

A motor, e.g. of the active device or unit of the implant, for controlling a physical function in the body of the patient may provide a secondary function as a sensation generator, generating a vibration or sound. Generation of vibrations or sounds of the motor may be achieved by operating the motor at specific frequencies. When functioning as to generate a sensation the motor may operate outside of its normal ranges for frequency controlling a physical function in the body. The power or force of the motor when operating to generate a sensation may also vary from its normal ranges for controlling a physical function in the body.

An external device is a device which is external to the patient in which the implant is implanted in. The external device may be also be enumerated (first, second, third, etc.) to separate different external devices from each other. Two or more external devices may be connected by means of a wired or wireless communication as described above, for example through IP (internet protocol), or a local area network (LAN). The wired or wireless communication may take place using a standard network protocol such as any suitable IP protocol (IPv4, IPv6) or Wireless Local Area Network (IEEE 802.11), Bluetooth, NFC, RFID etc. The wired or wireless communication may take place using a proprietary network protocol. Any external device may also be in communication with the implant using wired or wireless communication according to the above. Communication with implanted devices may be thus accomplished with a wired connection or with wireless radiofrequency (RF) telemetry. Other methods of wireless communication may be used to communicate with implants, including optical and ultrasound. Alternatively, the concept of intrabody communication may be used for wireless communication, which uses the conductive properties of the body to transmit signals, i.e. conductive (capacitive or galvanic) communication with the implant. Means for conductive communication between an external device and an implant may also be called "electrical connection" between an external device and an implant. The conductive communication may be achieved by placing a conductive member of the external device in contact with the skin of the patient. By doing this, the external device and/or the implant may assure that it is in direct electrical connection with the other device. The concept relies on using the inherent conductive or electrical properties of a human body. Signals may preferably be configured to affect the body or body functions minimally. For conductive communication this may mean using low currents. A current may flow from an external device to an implant or vice versa. Also, for conductive communication, each device may have a transceiver portion for transmitting or receiving the current. These may comprise amplifiers for amplifying at least the received current. The current may contain or carry a signal which may carry e.g. an authentication input, implant operation instructions, or information pertaining to the operation of the implant.

Alternatively, conductive communication may be referred to as electrical or ohmic or resistive communication.

The conductive member may be an integrated part of the external device (e.g. in the surface of a smartwatch that is intended to be in contact with the wrist of the person wearing it), or it may be a separate device which can be connected to the external device using a conductive interrace such as the charging port or the headphone port of a smartphone.

A conductive member may be considered any device or structure set up for data communication with the implant via electric conductive body tissue. The data communication to the implant may be achieved by e.g. current pulses transmitted from the conductive member through the body of the patient to be received by a receiver at the implant. Any suitable coding scheme known in the art may be employed. The conductive member may comprise an energy storage unit such as a battery or receive energy from e.g. a connected external device.

The term conductive interface is representing any suitable interface configured for data exchange between the conductive member and the external device. The conductive member may in an alternative configuration receive and transmit data to the external device through a radio interface, NFC, and the like.

An external device may act as a relay for communication between an implant and a remote device, such as e.g. second, third, or other external devices. Generally, the methods of relaying communication via an external device may be preferable for a large number of reasons. The transmission capabilities of the implant may be reduced, reducing its technical complexity, physical dimensions, and medical effects on the patient in which the implant is implanted. Communication may also be more efficient as direct communication, i.e. without a relaying device, with an implant from a remote device may require higher energy transmissions to account for different mediums and different rates of attenuation for different communication means. Remote communication with lower transmission energy may also increase the security of the communication as the spatial area or volume where the communication may be at all noticeable may be made smaller. Utilizing such a relay system further enables the use of different communication means for communication with the implant and communication with remote devices that are more optimized for their respective mediums.

An external device may be any device having processing power or a processor to perform the methods and functions needed to provide safe operation of the implant and provide the patient or other stakeholders (caregiver, spouse, employer etc.) with information and feedback from the implant. Feedback parameters could include battery status, energy level at the controller, the fluid level of the hydraulic restriction device, number of operations that the restriction device has performed, properties, version number etc. relating to functionality of the implantable constriction device. The external device may for example be a handset such as a smartphone, smartwatch, tablet etc. handled by the patient or other stakeholders. The external device may be a server or personal computer handled by the patient or other stakeholders. The external device may be cloud based or a virtual machine. In the drawings, the external device handled by the patient is often shown as a smart watch, or a device adapted to be worn by the patient at the wrist of the patient. This is merely by way of example and any other type of external device, depending on the context, is equally applicable.

Several external devices may exist such as a second external device, a third external device, or another external device. The above listed external devices may e.g. be available to and controllable by a patient, in which an implant is implanted, a caregiver of the patient, a healthcare professional of the patient, a trusted relative of the patient, an employer or professional superior of the patient, a supplier or producer of the implant or its related features. By controlling the external devices may provide options for e.g. controlling or safeguarding a function of the implant, monitoring the function of the implant, monitoring parameters of the patient, updating or amending software of the implant etc.

An external device under control by a supplier or producer of the implant may be connected to a database comprising data pertaining to control program updates and/or instructions. Such database may be regularly updated to provide new or improved functionality of the implant, or to mitigate for previously undetected flaws of the implant. When an update of a control program of an implant is scheduled, the updated control program may be transmitted from the database in a push mode and optionally routed via one or more further external devices before received by the implanted controller. In another embodiment, the update is received from the database by request from e.g. an external device under control by the patient having the implant implanted in his/her body, a pull mode.

The external device may require authentication to be operated in communication with other external devices or the implant. Passwords, multi-factor authentication, biometric identification (fingerprint, iris scanner, facial recognition, etc.) or any other way of authentication may be employed.

The external device may have a user interface (UI) for receiving input and displaying information/feedback from/to a user. The UI may be a graphical UI (GUI), a voice command interface, speaker, vibrators, lamps, etc.

The communication between external devices, or between an external device and the implant may be encrypted. Any suitable type of encryption may be employed such as symmetric or asymmetric encryption. The encryption may be a single key encryption or a multi-key encryption. In multi-key encryption, several keys are required to decrypt encrypted data. The several keys may be called first key, second key, third key, etc. or first part of a key, second part of the key, third part of the key, etc. The several keys are then combined in any suitable way (depending on the encryption method and use case) to derive a combined key which may be used for decryption. In some cases, deriving a combined key is intended to mean that each key is used one by one to decrypt data, and that the decrypted data is achieved when using the final key.

In other cases, the combination of the several key result in one "master key" which will decrypt the data. In other words, it is a form of secret sharing, where a secret is divided into parts, giving each participant (external device(s), internal device) its own unique part. To reconstruct the original message (decrypt), a minimum number of parts (keys) is required. In a threshold scheme this number is less than the total number of parts (e.g. the key at the implant and the key from one of the two external device are needed to decrypt the data). In other embodiments, all keys are needed to reconstruct the original secret, to achieve the combined key which may decrypt the data.

In should be noted that it is not necessary that the generator of a key for decryption is the unit that in the end sends the key to another unit to be used at that unit. In some cases, the generator of a key is merely a facilitator of encryption/decryption, and the working in behalf of another device/user.

A verification unit may comprise any suitable means for verifying or authenticating the use (i.e. user authentication) of a unit comprising or connected to the verification unit, e.g. the external device. For example, a verification unit may comprise or be connected to an interface (UI, GUI) for receiving authentication input from a user. The verification unit may comprise a communication interface for receiving authentication data from a device (separate from the external device) connected to the device comprising the verification unit. Authentication input/data may comprise a code, a key, biometric data based on any suitable techniques such as fingerprint, a palm vein structure, image recognition, face recognition, iris recognition, a retinal scan, a hand geometry, and genome comparison, etc. The verification/authentication may be provided using third party applications, installed at or in connection with the verification unit.

The verification unit may be used as one part of a two-part authentication procedure. The other part may e.g. comprise conductive communication authentication, sensation authentication, or parameter authentication.

The verification unit may comprise a card reader for reading a smart card. A smart card is a secure microcontroller that is typically used for generating, storing, and operating on cryptographic keys. Smart card authentication provides users with smart card devices for the purpose of authentication. Users connect their smart card to the verification unit. Software on the verification unit interacts with the keys material and other secrets stored on the smart card to authenticate the user. In order for the smart card to operate, a user may need to unlock it with a user-PIN. Smart cards are considered a very strong form of authentication because cryptographic keys and other secrets stored on the card are very well protected both physically and logically and are therefore hard to steal.

The verification unit may comprise a personal e-ID that is comparable to, for example, passport and driving license. The e-ID system comprises is a security software installed at the verification unit, and a e-ID which is downloaded from a web site of a trusted provided or provided via a smart card from the trusted provider.

The verification unit may comprise software for SMS-based two-factor authentication. Any other two-factor authentication systems may be used. Two-factor authentication requires two things to get authorized: something you know (your password, code, etc.) and something you have (an additional security code from your mobile device (e.g. a SMS, or a e-ID) or a physical token such as a smart card).

Other types of verification/user authentication may be employed. For example, a verification unit which communicate with an external device using visible light instead of wired communication or wireless communication using radio. A light source of the verification unit may transmit (e.g. by flashing in different patterns) secret keys or similar to the external device which uses the received data to verify the user, decrypt data or by any other means perform authentication. Light is easier to block and hide from an eavesdropping adversary than radio waves, which thus provides an advantage in this context. In similar embodiments, electromagnetic radiation is used instead of visible light for transmitting verification data to the external device.

Parameters relating to functionality of the implant may comprise for example a status indicator of the implant such as battery level, version of control program, properties of the implant, status of a motor of the implant, etc.

Data comprising operating instructions sent to the implant may comprise a new or updated control program, parameters relating to specific configurations of the implant, etc. Such data may for example comprise instructions how to operate the body engaging portion of the implantable constriction device, instructions to collect patient data, instructions to transmit feedback, etc.

The expressions "confirming the electrical connection between an implant and an external device" or "authenticating a connection between an implant and an external device", or similar expressions, are intended to encompass methods and processes for ensuring or be reasonably sure that the connection has not been compromised. Due to weaknesses in the wireless communication protocols, it is a simple task for a device to "listen" to the data and grab sensitive information, e.g. personal data regarding the patient sent from the implant, or even to try to compromise (hack) the implant by sending malicious commands or data to the implant. Encryption may not always be enough as a security measure (encryption schemes may be predictable), and other means of confirming or authenticating the external device being connected to the implant may be needed.

The expression "network protocol" is intended to encompass communication protocols used in computer networks. a communication protocol is a system of rules that allow two or more entities of a communications system to transmit information via any kind of variation of a physical quantity. The protocol defines the rules, syntax, semantics and synchronization of communication and possible error recovery methods. Protocols may be implemented by hardware, software, or a combination of both. Communication protocols have to be agreed upon by the parties involved. In this field, the term "standard" and "proprietary" is well defined. A communication protocol may be developed into a protocol standard by getting the approval of a standards organization. To get the approval the paper draft needs to enter and successfully complete the standardization process. When this is done, the network protocol can be referred to a "standard network protocol" or a "standard communication protocol". Standard protocols are agreed and accepted by whole industry. Standard protocols are not vendor specific. Standard protocols are often, as mentioned above, developed by collaborative effort of experts from different organizations.

Proprietary network protocols, on the other hand, are usually developed by a single company for the devices (or Operating System) which they manufacture. A proprietary network protocol is a communications protocol owned by a single organization or individual. Specifications for proprietary protocols may or may not be published, and implementations are not freely distributed. Consequently, any device may not communicate with another device using a proprietary network protocol, without having the license to use the proprietary network protocol, and knowledge of the specifications for proprietary protocol. Ownership by a single organization thus gives the owner the ability to place restrictions on the use of the protocol and to change the protocol unilaterally.

A control program is intended to define any software used for controlling the implant. Such software may comprise an operating system of the implant, of parts of an operating system or an application running on the implant such as software controlling a specific functionality of the implant (e.g. the active unit of the implant, feedback functionality of the implant, a transceiver of the implant, encoding/decoding functionality of the implant, etc.). The control program may thus control the medical function of the implant, for example the pressure applied by the constriction device or the power of the electrical stimulation device. Alternatively, or additionally, the control program may control internal hardware functionality of the implant such as energy usage, transceiver functionality, etc.

The systems and methods disclosed hereinabove may be implemented as software, firmware, hardware, or a combination thereof. In a hardware implementation, the division of tasks between functional units referred to in the above description does not necessarily correspond to the division into physical units; to the contrary, one physical component may have multiple functionalities, and one task may be carried out by several physical components in cooperation. Certain components or all components may be implemented as software executed by a digital signal processor or microprocessor or be implemented as hardware or as an application-specific integrated circuit. Such software may be distributed on computer readable media, which may comprise computer storage media (or non-transitory media) and communication media (or transitory media). As is well known to a person skilled in the art, the term computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by a computer. Further, it is well known to the skilled person that communication media typically embodies computer readable instructions, data structures, program modules or other data in a modulated data signal such as a carrier wave or other transport mechanism and includes any information delivery media.

Figure 23A:
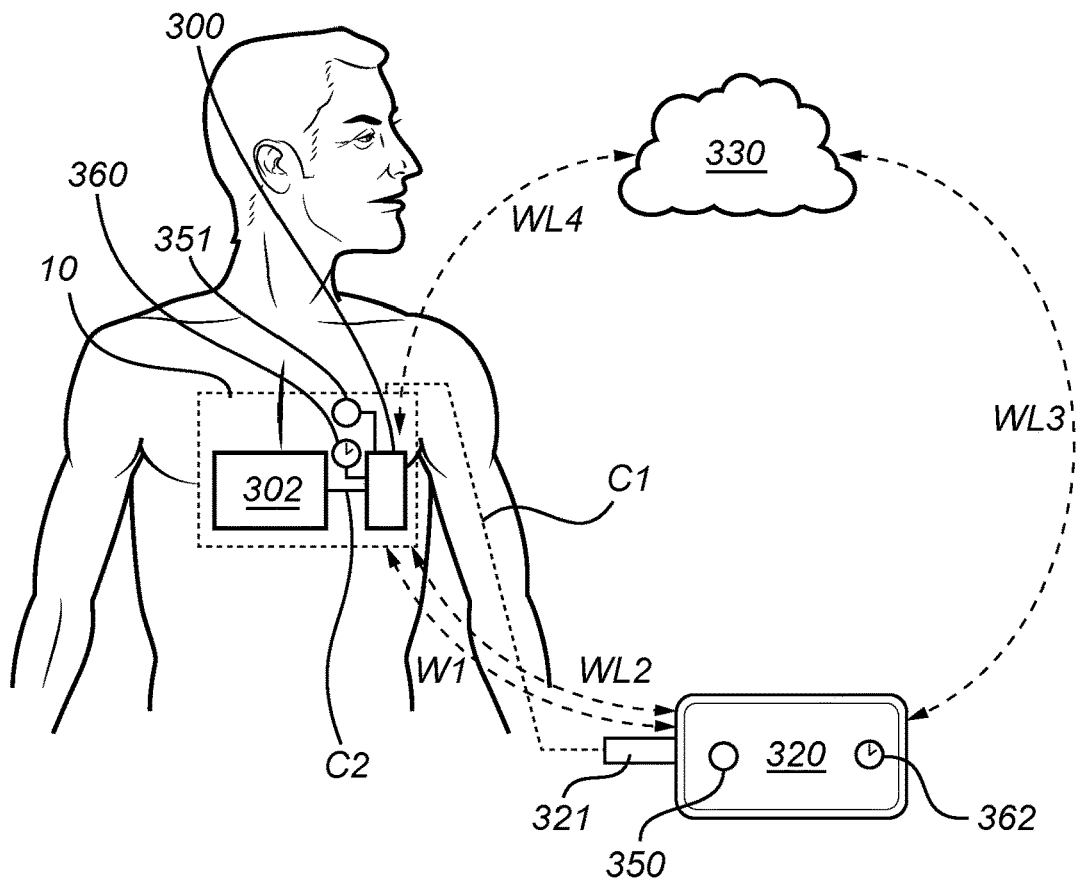
FIG. 23a-23e shows an embodiment and describes various functions of an implantable controller for controlling the implantable constriction device.

A controller for controlling the implantable constriction device according to any of the embodiments herein and for communicating with devices external to the body of the patient and/or implantable sensors will now be described with reference to FIGS. 23a-23c. FIG. 23a shows a patient when an implantable constriction device 10 comprising a controller 300 has been implanted, such as for example the implantable constriction device 10 and controller 300 described in any one of FIGS. 8a-9c. The implantable constriction device 10 comprises an active unit 302, which is the part of the implantable constriction device which comprises the one or more operable hydraulic constriction elements, one or more hydraulic pumps, one or more valves and one or more injection ports etc. The active unit is directly or indirectly connected to the body of the patient for constricting the urethra. The active unit 302 is connected to the controller 300 via an electrical connection C2. The controller 300 (further described with reference to FIG. 23b) is configured to communicate with an external device 320 (further described with reference to FIG. 23c). The controller 300 can communicate wirelessly with the external device 320 through a wireless connection WL1, and/or through an electrical connection C1.

Figure 23B:
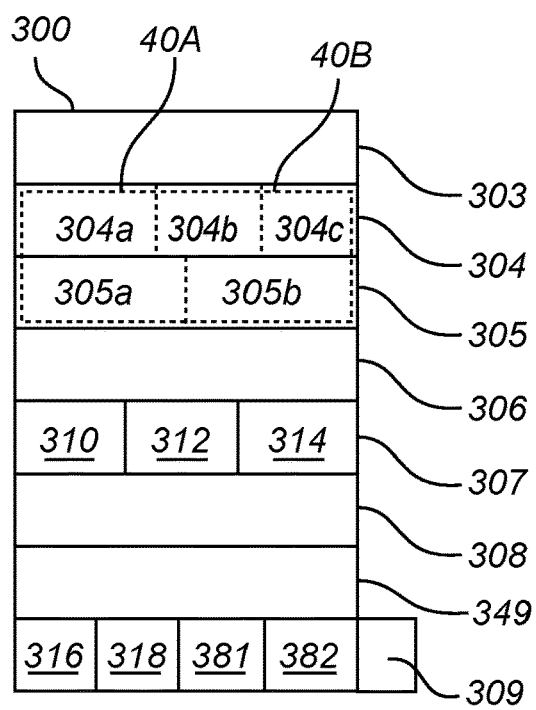

Referring now to FIG. 23b, one embodiment of the controller 300 will be describe in more detail. The controller 300 comprises an internal computing unit 306 configured to control the function performed by the implantable constriction device 10. The computing unit 306 comprises an internal memory 307 configured to store programs thereon. In the embodiment described in FIG. 23b, the internal memory 307 comprises a first control program 310 which can control the function of the implantable constriction device 10. The first control program 310 may be seen as a program with minimum functionality to be run at the implantable constriction device only during updating of the second control program 312. When the implantable constriction device is running with the first control program 310, the implantable constriction device may be seen as running in safe mode, with reduced functionality. For example, the first control program 310 may result in that no sensor data is stored in the implantable constriction device while being run, or that no feedback is transmitted from the implantable constriction device while the first control program 310 is running. By having a low complexity first control program, memory at the implantable constriction device is saved, and the risk of failure of the implantable constriction device during updating of the second control program 312 is reduced.

The second control program 312 is the program controlling the implantable constriction device in normal circumstances, providing the implantable constriction device with full functionality and features.

The memory 307 can further comprise a second, updatable, control program 312. The term updatable is to be interpreted as the program being configured to receive incremental or iterative updates to its code or be replaced by a new version of the code. Updates may provide new and/or improved functionality to the implant as well as fixing previous deficiencies in the code. The computing unit 306 can receive updates to the second control program 312 via the controller 300. The updates can be received wirelessly WL1 or via the electrical connection C1. As shown in FIG. 23b, the internal memory 307 of the controller 300 can possibly store a third program 314. The third program 314 can control the function of the implantable constriction device 10 and the computing unit 306 may be configured to update the second program 312 to the third program 314. The third program 314 can be utilized when rebooting an original state of the second program 312. The third program 314 may thus be seen as providing a factory reset of the controller 300, e.g. restore it back to factory settings. The third program 314 may thus be included in the implant 300 in a secure part of the memory 307 to be used for resetting the software (second control program 312) found in the controller 300 to original manufacturer settings.

The controller 300 may comprise a reset function 316 connected to or part of the internal computing unit 306 or transmitted to said internal computing unit 306. The reset function 316 is configured to make the internal computing unit 306 switch from running the second control program 312 to the first control program 310. The reset function 316 could be configured to make the internal computing unit 306 delete the second control program 312 from the memory 307. The reset function 316 can be operated by palpating or pushing/put pressure on the skin of the patient. This could be performed by having a button on the implant. Alternatively, the reset function 316 can be invoked via a timer or a reset module. Temperature sensors and/or pressure sensors can be utilized for sensing the palpating. The reset function 316 could also be operated by penetrating the skin of the patient. It is further plausible that the reset function 316 can be operated by magnetic means. This could be performed by utilizing a magnetic sensor and applying a magnetic force from outside the body. The reset function 316 could be configured such that it only responds to magnetic forces applied for a duration of time exceeding a limit, such as 2 seconds. The time limit could equally plausible be 5 or 10 seconds, or longer. In these cases, the implant could comprise a timer. The reset function 316 may thus include or be connected to a sensor for sensing such magnetic force.

In addition to or as an alternative to the reset function described above, the implant may comprise an internal computing unit 306 (comprising an internal processor) comprising the second control program 312 for controlling a function of the implantable constriction device, and a reset function 318. The reset function 318 may be configured to restart or reset said second control program 312 in response to: i. a timer of the reset function 318 has not been reset, or ii. a malfunction in the first control program 310.

The reset function 318 may comprise a first reset function, such as, for example, comprise a computer operating properly, COP, function connected to the internal computing unit 306. The first reset function may be configured to restart or reset the first or the second control program 312 using a second reset function. The first reset function comprises a timer, and the first or the second control program is configured to periodically reset the timer.

The reset function 318 may further comprise a third reset function connected to the internal computing unit and to the second reset function. The third reset function may in an example be configured to trigger a corrective function for correcting the first 310 or second control program 312, and the second reset function is configured to restart the first 310 or second control program 312 sometime after the corrective function has been triggered. The corrective function may be a soft reset or a hard reset.

The second or third reset function may, for example, configured to invoke a hardware reset by triggering a hardware reset by activating an internal or external pulse generator which is configured to create a reset pulse. Alternatively, the second or third reset function may be implemented by software.

The controller 300 may further comprise an internal wireless transceiver 308. The transceiver 308 communicates wirelessly with the external device 320 through the wireless connection W1. The transceiver may further communicate with an external device 320, 300 via wireless connection WL2 or WL4. The transceiver may both transmit and receive data via either of the connections C1, WL1, WL2 and WL4. Optionally, the external devices 320 and 300, when present, may communicate with each other, for example via a wireless connection WL3.

The controller 300 can further be electrically connected C1 to the external device 320 and communicate by using the patient's body as a conductor. The controller 300 may thus comprise a wired transceiver 303 or an internal transceiver 303 for the electrical connection C1.

The confirmation/authentication of the electrical connection can be performed as described herein in the section for confirmation and/or authentication. In these cases, the implantable constriction device and/or external device(s) 320 comprises the necessary features and functionality (described in the respective sections of this document) for performing such confirmation/authentication. By authenticating according to these aspects, security of the authentication may be increased as it may require a malicious third party to know or gain access to either the transient physiological parameter of the patient or detect randomized sensations generated at or within the patient.

Figure 23C:
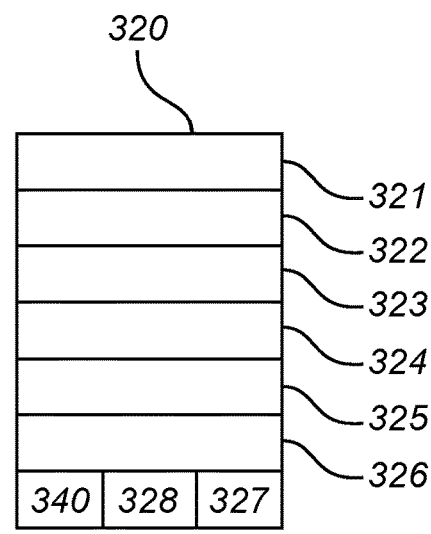

In FIGS. 23a-23c the patient is a human, but other mammals are equally plausible. It is also plausible that the communication is performed by inductive means. It is also plausible that the communication is direct.

The controller 300 of the implantable constriction device 10 according to FIG. 23b further comprises a feedback unit 349. The feedback unit 349 provides feedback related to the switching from the second control program 312 to the first control program 310. The feedback could for example represent the information on when the update of the software, i.e. the second control program 312, has started, and when the update has finished. This feedback can be visually communicated to the patient, via for example a display on the external device 320. This display could be located on a watch, or a phone, or any other external device 320 coupled to the controller 300. Preferably, the feedback unit 349 provides this feedback signal wirelessly WL1 to the external device 320. Potentially, the words "Update started", or "Update finished", could be displayed to the patient, or similar terms with the same meaning. Another option could be to display different colors, where green for example could mean that the update has finished, and red or yellow that the update is ongoing. Obviously, any color is equally plausible, and the user could choose these depending on personal preference. Another possibility would be to flash a light on the external device 320. In this case the external device 320 comprises the light emitting device(s) needed. Such light could for example be a LED. Different colors could, again, represent the status of the program update. One way of representing that the update is ongoing and not yet finished could be to flash the light, i.e. turning the light on and off. Once the light stops flashing, the patient would be aware of that the update is finished. The feedback could also be audible, and provided by the implantable constriction device 300 directly, or by the external device 320. In such cases, the implantable constriction device 10 and external device 320 comprises means for providing audio. The feedback could also be tactile, for example in the form of a vibration that the user can sense. In such case, either the implantable constriction device 10 or external device 320 comprises means for providing a tactile sensation, such as a vibration and/or a vibrator.

As seen in FIG. 23b, the controller 300 can further comprise a first energy storage unit 40A. The first energy storage unit 40A runs the first control program 310. The controller 300 further comprises a second energy storage unit 40B which runs the second control program 312. This may further increase security during update, since the first control program 310 has its own separate energy storage unit 40A. The first power supply 40A can comprise a first energy storage 304a and/or a first energy receiver 305a. The second energy storage unit 40B can comprise a second energy storage 304b and/or a second energy receiver 305b. The energy can be received wirelessly by inductive or conductive means. An external energy storage unit can for example transfer an amount of wireless energy to the energy receiver 305a, 305b inside the patient's body by utilizing an external coil which induces a voltage in an internal coil (not shown in figures). It is plausible that the first energy receiver 305a receives energy via a RFID pulse. The feedback unit 349 can provide feedback pertaining to the amount of energy received via the RFID pulse. The amount of RFID pulse energy that is being received can be adjusted based on the feedback, such that the pulse frequency is successively raised until a satisfying level is reached.

The controller 300 of the implantable constriction device 10 according to FIG. 23b further comprises a feedback unit an electrical switch 309. The electrical switch 309 could be mechanically connected to the implantable element configured to exert a force on a body portion of a patient and being configured to be switched as a result of the force exerted on the body portion of a patient exceeding a threshold value. The switch 309 could for example be bonded to a portion of the constriction element in any of the embodiments herein, or to a portion of a fluid conduit, reservoir or hydraulic operation device, such as a pump, being in fluid connection with the constriction element and be switched by the expansion, movement or bending of such element. The switch 309 could alternatively be electrically connected to the operation device and being configured to be switched as a result of the current supplied to the operation device exceeding a threshold value. The switch 309 could for example be connected to the motor and be configured to be switched if the current to the motor exceeds a threshold value. Such a switch could for example be a switch 309 configured to switch if exposed to a temperature exceeding a threshold value, such as a bimetal switch which is switched by the heat created by the flow of current to e.g. the motor. In the alternative, the switch 309 configured to switch if exposed to a temperature exceeding a threshold value could be placed at a different location on the implantable constriction device 10 to switch in case of exceeding temperatures, thereby hindering the implantable constriction device from overheating which may cause tissue damage.

The switch 309 could either be configured to cut the power to the operation device or to generate a control signal to the processor 306 of the implantable controller 300, such that the controller 300 can take appropriate action, such as reducing power or turning off the operation device.

The external device 320 is represented in FIG. 23c. The external device 320 can be placed anywhere on the patient's body, preferably on a convenient and comfortable place. The external device 320 could be a wristband, and/or have the shape of a watch. It is also plausible that the external device is a mobile phone or other device not attached directly to the patient. The external device as shown in FIG. 23*c* comprises a wired transceiver 323, and an energy storage 324. It also comprises a wireless transceiver 328 and an energy transmitter 325. It further comprises a computing unit 326 and a memory 327. The feedback unit 322 in the external device 320 is configured to provide feedback related to the computing unit 326. The feedback provided by the feedback unit 322 could be visual. The external device 320 could have a display showing such visual feedback to the patient. It is equally plausible that the feedback is audible, and that the external device 320 comprises means for providing audio. The feedback given by the feedback unit 322 could also be tactile, such as vibrating. The feedback could also be provided in the form of a wireless signal WL1, WL2, WL3, WL4.

The second, third or fourth communication methods WL2, WL3, WL4 may be a wireless form of communication. The second, third or fourth communication method WL2, WL3, WL4 may preferably be a form of electromagnetic or radio-based communication. The second, third and fourth communication method WL2, WL3, WL4 may be based on telecommunication methods. The second, third or fourth communication method WL2, WL3, WL4 may comprise or be related to the items of the following list: Wireless Local Area Network (WLAN), Bluetooth, Bluetooth 5, BLE, GSM or 2G (2nd generation cellular technology), 3G, 4G or 5G.

The external device 320 may be adapted to be in electrical connection C1 with the implantable constriction device 10, using the body as a conductor. The electrical connection Cl is in this case used for conductive communication between the external device 320 and the implantable constriction device 10.

In one embodiment, the communication between controller 300 and the external device 320 over either of the communication methods WL2, WL3, WL4, Cl may be encrypted and/or decrypted with public and/or private keys, now described with reference to FIGS. 23*a*-23*c*. For example, the controller 300 may comprise a private key and a corresponding public key, and the external device 320 may comprise a private and a corresponding public key.

The controller 320 and the external device 320 may exchange public keys and the communication may thus be performed using public key encryption. The person skilled in the art may utilize any known method for exchanging the keys.

The controller may encrypt data to be sent to the external device 320 using a public key corresponding to the external device 320. The encrypted data may be transmitted over a wired, wireless, or electrical communication channel C1, WL1, WL2, WL3 to the external device. The external device 320 may receive the encrypted data and decode it using the private key comprised in the external device 320, the private key corresponding to the public key with which the data has been encrypted. The external device 320 may transmit encrypted data to the controller 300. The external device 320 may encrypt the data to be sent using a public key corresponding to the private key of the controller 300. The external device 320 may transmit the encrypted data over a wired, wireless, or electrical connection C1, WL1, WL2, WL3, WL4, directly or indirectly, to the controller of the implant. The controller may receive the data and decode it using the private key comprised in the controller 300.

In an alternative to the public key encryption, described with reference to FIGS. 23*a*-23*c*, the data to be sent between the controller 300 of the implantable constriction device 10 and an external device 320, 330 or between an external device 320, 330 and the controller 300 may be signed. In a method for sending data from the controller 300 to the external device 320, 330, the data to be sent from the controller 300 may be signed using the private key of the controller 300. The data may be transmitted over a communication channel or connection Cl, WL1, WL2, WL3, WL4. The external device 320, 330 may receive the message and verify the authenticity of the data using the public key corresponding to the private key of the controller 300. In this way, the external device 320, 330 may determine that the sender of the data was sent from the controller 300 and not from another device or source.

A method for communication between an external device 320 and the controller 300 of the implantable constriction device 10 using a combined key is now described with reference to FIGS. 23*a*-23*c*. A first step of the method comprises receiving, at the implant, by a wireless transmission WL1, WL2, WL3, WL4 or otherwise, a first key from an external device 320, 330. The method further comprises receiving, at the implant, by a wireless transmission WL1, WL2, WL3, a second key. The second key may be generated by a second external device, separate from the external device 320, 330 or by another external device being a generator of the second key on behalf of the second external device 320, 330. The second key may be received at the implant from anyone of, the external device 320, the second external device 330, and the generator of the second key. The second external device may be controlled by a caretaker, or any other stakeholder. Said another external device may be controlled by a manufacturer of the implant, or medical staff, caretaker, etc.

In case the controller 300 is receiving the second key from the external device 320, this means that the second key is routed through the external device from the second external device 330 or from another external device (generator). The routing may be performed as described herein under the tenth aspect. In these cases, the implant and/or external device(s) comprises the necessary features and functionality (described in the respective sections of this document) for performing such routing. Using the external device 320 as a relay, with or without verification from the patient, may provide an extra layer of security as the external device 320 may not need to store or otherwise handle decrypted information. As such, the external device 320 may be lost without losing decrypted information. The controller 300 a computing unit 306 configured for deriving a combined key by combining the first key and the second key with a third key held by the controller 300, for example in memory 307 of the controller 300. The third key could for example be a license number of the implant or a chip number of the implantable constriction device. The combined key may be used for decrypting, by the computing unit 306, encrypted data transmitted by a wireless transmission WL1 from the external device 320 to the controller 300. Optionally, the decrypted data may be used for altering, by the computing unit 306 an operation of the implantable constriction device. The altering an operation of the implantable constriction device may comprise controlling or switching an active unit 302 of the implant. In some embodiments, the method further comprises at least one of the steps of, based on the decrypted data, updating a control program running in the controller 300, and operating the implantable constriction device 10 using operation instructions in the decrypted data.

Methods for encrypted communication between an external device 320 and the controller 300 are provided. These methods comprise:

receiving, at the external device 320, by a wireless transceiver 328, a first key, the first key being generated by a second external device 330, separate from the external device 320 or by another external device being a generator of the second key on behalf of the second external device 330, the first key being received from anyone of the second external device 330 and the generator of the second key, receiving, at the external device 320 by the wireless transceiver 328, a second key from the controller 300, deriving a combined key, by a computing unit 326 of the external device 320, by combining the first key and the second key with a third key held by the external device 320 (e.g. in memory 307), transmitting encrypted data from the implant to the external device and receiving the encrypted data at the external device by the wireless transceiver 328, and decrypting, by the computing unit 326, the encrypted data, in the external device 320, using the combined key.

As described above, further keys may be necessary to decrypt the data. Consequently, the wireless transceiver 328 is configured for:

receiving a fourth key from a third external device, wherein the computing unit 326 is configured for:

deriving a combined key by combining the first, second and fourth key with the third key held by the external device, and decrypting the encrypted data using the combined key.

These embodiments further increase the security in the communication. The computing unit 326 may be configured to confirm the communication between the implant and the external device, wherein the confirmation comprises:

measuring a parameter of the patient, by the external device 320, receiving a measured parameter of the patient, from the implantable constriction device 10, comparing the parameter measured by the implantable constriction device 10 to the parameter measured by the external device 320, performing confirmation of the connection based on the comparison, and as a result of the confirmation, decrypting the encrypted data, in the external device, using the combined key.

The keys described in this section may in some embodiments be generated based on data sensed by sensors described herein under the twelfth or thirteenth aspect, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) and the implantable constriction device is provided.

A method of communication between an external device 320 and an implantable constriction device 10 is now described with reference to FIGS. 23a-23c, when the implantable constriction device 10 is implanted in a patient and the external device 320 is positioned external to the body of the patient. The external device 320 is adapted to be in electrical connection C1 with the controller 300, using the body as a conductor. The electrical connection C1 is used for conductive communication between the external device 320 and the implantable constriction device 10. The implantable constriction device 10 comprises the controller 300. Both the controller 300 and the external device 320 comprises a wireless transceiver 308, 208 for wireless communication C1 between the controller 300 and the external device 320. The wireless transceiver 308 (included in the controller 300) may in some embodiments comprise sub-transceivers for receiving data from the external device 320 and other external devices, e.g. using different frequency bands, modulation schemes etc.

In a first step of the method, the electrical connection C1 between the controller 300 and the external device 320 is confirmed and thus authenticated. The confirmation and authentication of the electrical connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

The implant may comprise a first transceiver 303 configured to be in electrical connection C1 with the external device, using the body as a conductor. The implant may comprise a first external transmitter 203 configured to be in electrical connection C1 with the implant, using the body as a conductor, and the wireless transmitter 208 configured to transmit wireless communication W1 to the controller 300. The first transmitter 323 of the external device 320 may be wired or wireless. The first transmitter 323 and the wireless transmitter 208 may be the same or separate transmitters. The first transceiver 303 of the controller 300 may be wired or wireless. The first transceiver 303 and the wireless transceiver 102 may be the same or separate transceivers.

The controller 300 may comprise a computing unit 306 configured to confirm the electrical connection between the external device 320 and the internal transceiver 303 and accept wireless communication WL1 (of the data) from the external device 320 on the basis of the confirmation.

Data is transmitted from the external device 320 to the controller 300 wirelessly, e.g. using the respective wireless transceiver 308, 208 of the controller 300 and the external device 320. Data may alternatively be transmitted through the electrical connection C1. As a result of the confirmation, the received data may be used for instructing the implantable constriction device 10. For example, a control program 310 running in the controller 300 may be updated, the controller 300 may be operated using operation instructions in the received data. This may be handled by the computing unit 306.

The method may comprise transmitting data from the external device 320 to the controller 300 wirelessly comprises transmitting encrypted data wirelessly. To decrypt the encrypted data (for example using the computing unit 306), several methods may be used.

In one embodiment, a key is transmitted using the confirmed conductive communication channel C1 (i.e. the electrical connection) from the external device 320 to the controller 300. The key is received at the controller (by the first internal transceiver 303). The key is then used for decrypting the encrypted data.

In some embodiments the key is enough to decrypt the encrypted data. In other embodiments, further keys are necessary to decrypt the data. In one embodiment, a key is transmitted using the confirmed conductive communication channel C1 (i.e. the electrical connection) from the external device 320 to the controller 300. The key is received at the controller 300 (by the first internal transceiver 303). A second key is transmitted (by the wireless transceiver 208) from the external device 320 using the wireless communication WL1 and received at the controller 300 by the wireless transceiver 308. The computing unit 306 is then deriving a combined key from the key and second key and uses this for decrypting the encrypted data.

In yet other embodiments, a key is transmitted using the confirmed conductive communication channel C1 (i.e. the electrical connection) from the external device 320 to the controller 300. The key is received at the controller (by the first internal transceiver 303). A third key is transmitted from a second external device 330, separate from the external device 320, to the implant wirelessly WL2. The third key may be received by a second wireless receiver (part of the wireless transceiver 308) of the controller 300 configured for receiving wireless communication WL2 from second external device 330.

The first and third key may be used to derive a combined key by the computing unit 306, which then decrypts the encrypted data. The decrypted data is then used for instructing the implantable constriction device 10 as described above.

The second external device 330 may be controlled by for example a caregiver, to further increase security and validity of data sent and decrypted by the controller 300.

It should be noted that in some embodiments, the external device is further configured to receive WL2 secondary wireless communication from the second external device 330, and transmit data received from the secondary wireless communication WL2 to the implantable constriction device. This routing of data may be achieved using the wireless transceivers 308, 208 (i.e. the wireless connection WL1, or by using a further wireless connection WL4 between the controller 300 and the external device 320. In these cases, the implant and/or external device(s) comprises the necessary features and functionality for performing such routing. Consequently, in some embodiments, the third key is generated by the second external device 330 and transmitted WL2 to the external device 320 which routes the third key to the controller 300 to be used for decryption of the encrypted data. In other words, the step of transmitting a third key from a second external device, separate from the external device, to the implant wirelessly, comprises routing the third key through the external device 320. Using the external device 320 as a relay, with or without verification from the patient, may provide an extra layer of security as the external device 320 may not need to store or otherwise handle decrypted information. As such, the external device 320 may be lost without losing decrypted information.

In yet other embodiments, a key is transmitted using the confirmed conductive communication channel C1 (i.e. the electrical connection) from the external device 320 to the controller 300. The key is received at the implant (by the first internal transceiver 303). A second key is transmitted from the external device 320 to the controller 300 wirelessly WL1, received at the at the controller 300. A third key is transmitted from the second external device, separate from the external device 320, to the controller 300 wirelessly WL4. Encrypted data transmitted from the external device 320 to the controller 300 is then decrypted using a derived combined key from the key, the second key and the third key. The external device may be a wearable external device.

The external device 320 may be a handset. The second external device 330 may be a handset. The second external device 330 may be a server. The second external device 330 may be cloud based.

In some embodiments, the electrical connection C1 between the external device 320 and the controller 300 is achieved by placing a conductive member 201, configured to be in connection with the external device 200, in electrical connection with a skin of the patient for conductive communication C1 with the implant. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 320, conductive member 201, conductive connection C1, controller 300, meaning the communication will be excessively difficult to be intercepted by a third party not in physical contact with, or at least proximal to, the patient.

The keys described in this section may in some embodiments be generated based on data sensed by sensors described herein, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Increased security for communication between an external device(s) and an implant is provided, now described with reference to FIGS. 23A-23C.

In these embodiments, a method for communication between an external device 320 and the implantable controller 300 is provided. The wireless transceiver 308 (included in the controller 300) may in some embodiments comprise sub-transceivers for receiving data from the external device 320 and other external devices 330, e.g. using different frequency bands, modulation schemes etc.

A first step of the method comprises receiving, at the implant, by a wireless transmission WL1 or otherwise, a first key from an external device 320. The method further comprises receiving, at the implant, by a wireless transmission WL1, WL2, WL3, a second key. The second key may be generated by a second external device 330, separate from the external device 320 or by another external device being a generator of the second key on behalf of the second external device 330. The second key may be received at the implant from anyone of, the external device 320, the second external device 330, and a generator of the second key. The second external device 330 may be controlled by a caretaker, or any other stakeholder. Said another external device may be controlled by a manufacturer of the implant, or medical staff, caretaker, etc.

In case the implant is receiving the second key from the external device 320, this means that the second key is routed through the external device from the second external device 330 or from the another external device (generator). In these cases, the implant and/or external device(s) comprises the necessary features and functionality (described in the respective sections of this document) for performing such routing. Using the external device 320 as a relay, with or without verification from the patient, may provide an extra layer of security as the external device 320 may not need to store or otherwise handle decrypted information. As such, the external device 320 may be lost without losing decrypted information.

The controller 300 comprises a computing unit 306 configured for deriving a combined key by combining the first key and the second key with a third key held by the controller 300, for example in memory 307 of the controller. The combined key may be used for decrypting, by the computing unit 306, encrypted data transmitted by a wireless transmission WL1 from the external device 320 to the controller 300. Optionally, the decrypted data may be used for altering, by the computing unit 306 an operation of the implantable constriction device 10. The altering an operation of the implantable constriction device may comprise controlling or switching an active unit 302 of the implant. In some embodiments, the method further comprises at least one of the steps of, based on the decrypted data, updating a control program running in the implant, and operating the implantable constriction device 10 using operation instructions in the decrypted data.

In some embodiments, further keys are necessary to derive a combined key for decrypting the encrypted data received at the controller 10. In these embodiments, the first and second key are received as described above. Further, the method comprises receiving, at the implant, a fourth key from a third external device, the third external device being separate from the external device, deriving a combined key by combining the first, second and fourth key with the third key held by the controller 300, and decrypting the encrypted data, in the controller 300, using the combined key. Optionally, the decrypted data may be used for altering, by the computing unit 306, an operation of the implant as described above. In some embodiments, the fourth key is routed through the external device from the third external device.

In some embodiments, further security measures are needed before using the decrypted data for altering, by the computing unit 306, an operation of the implantable constriction device. For example, an electrical connection C1 between the implantable constriction device and the external device 320, using the body as a conductor, may be used for further verification of validity of the decrypted data. The electrical connection C1 may be achieved by placing a conductive member 201, configured to be in connection with the external device, in electrical connection with a skin of the patient for conductive communication C1 with the implant. The communication may thus be provided with an extra layer of security in addition to the encryption by being electrically confined to the conducting path e.g. external device 320, conductive member 201, conductive connection C1, controller 300, meaning the communication will be excessively difficult to be intercepted by a third party not in physical contact with, or at least proximal to, the patient.

Accordingly, in some embodiments, the method comprising confirming the electrical connection between the controller 300 and the external device 320, and as a result of the confirmation, altering an operation of the implantable constriction device based on the decrypted data. The confirmation and authentication of the electrical connection may be performed as described herein under the general features section. In these cases, the implantable constriction device and/or external device(s) 320 comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

In some embodiments, the confirmation of the electrical connection comprises: measuring a parameter of the patient, by e.g. a sensor of the implantable constriction device 10, measuring the parameter of the patient, by the external device 320, comparing the parameter measured by the implantable constriction device to the parameter measured by the external device 320, and authenticating the connection based on the comparison. As mentioned above, as a result of the confirmation, an operation of the implantable constriction device may be altered based on the decrypted data.

Further methods for encrypted communication between an external device 320 and an implantable constriction device 10 are provided. These methods comprise:
  receiving, at the external device 320 by a wireless transceiver 328, a first key, the first key being generated by a second external device 330, separate from the external device 320 or by another external device being a generator of the second key on behalf of the second external device 320, the first key being received from anyone of the second external device 330 and the generator of the second key,
  receiving, at the external device 320 by the wireless transceiver 328, a second key from the controller 300,
  deriving a combined key, by a computing unit 326 of the external device 320, by combining the first key and the second key with a third key held by the external device 320 (e.g. in memory 327),
  transmitting encrypted data from the implant to the external device and receiving the encrypted data at the external device by the wireless transceiver 328, and
  decrypting, by the computing unit 326, the encrypted data, in the external device 320, using the combined key.

As described above, further keys may be necessary to decrypt the data. Consequently, the wireless transceiver 328 is configured for:
  receiving a fourth key from a third external device,
  wherein the computing unit 326 is configured for:
  deriving a combined key by combining the first, second and fourth key with the third key held by the external device, and
  decrypting the encrypted data using the combined key.

In some embodiments, the communication between the controller 300 and the external device 320 needs to be confirmed (authenticated) before decrypting the data. In these cases, the implant and/or external device(s) comprises the necessary features and functionality (described in the respective sections of this document) for performing such authentication.

These embodiments further increase the security in the communication. In these embodiments the computing unit 326 is configured to confirm the communication between the implant and the external device, wherein the confirmation comprises:
  measuring a parameter of the patient, by the external device 320,
  receiving a measured parameter of the patient, from the implantable constriction device 10,
  comparing the parameter measured by the implantable constriction device 320 to the parameter measured by the external device 320,
  performing confirmation of the connection based on the comparison, and
  as a result of the confirmation, decrypting the encrypted data, in the external device, using the combined key.

One or more of the first, second and third key may comprise a biometric key.

The keys described in this section may in some embodiments be generated based on data sensed by sensors, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) 320, 330 and an implant is provided, described with reference to FIGS. 23a-23c. The system for communication between an external device 320 and the controller 300 implanted in a patient. The system comprises a conductive member 321 configured to be in connection (electrical/conductive or wireless or otherwise) with the external device, the conductive member 321 being configured to be placed in electrical connection with a skin of the patient for conductive communication C1 with the implantable constriction device 10. By using a conductive member 321 as defined herein, an increased security for communication between the external device and the implant may be achieved. For example, when a sensitive update of a control program of the controller 300 is to be made, or if sensitive data regarding physical parameters of the patient is to be sent to the external device 320 (or otherwise), the conductive member 321 may ensure that the patient is aware of such communication and actively participate in validating that the communication may take place. The conductive member may, by being placed in connection with the skin of the patient, open the conductive communication channel C1 between the external device and the controller to be used for data transmission.

Electrical or conductive communication, such as this or as described under the other embodiments, may be very hard to detect remotely, or at least relatively so, in relation to wireless communications such as radio transmissions. Direct electrical communication may further safeguard the connection between the implantable constriction device 10 and the external device 320 from electromagnetic jamming i.e. high-power transmissions other a broad range of radio frequencies aimed at drowning other communications within the frequency range. Electrical or conductive communication will be excessively difficult to be intercepted by a third party not in physical contact with, or at least proximal to, the patient, providing an extra level of security to the communication.

In some embodiments, the conductive member comprises a conductive interface for connecting the conductive member to the external device.

In some embodiments, the conductive member 201 is a device which is plugged into the external device 200, and easily visible and identifiable for simplified usage by the patient. In other embodiments, the conductive member 321 is to a higher degree integrated with the external device 320, for example in the form of a case of the external device 320 comprising a capacitive area configured to be in electrical connection with a skin of the patient. In one example, the case is a mobile phone case (smartphone case) for a mobile phone, but the case may in other embodiments be a case for a personal computer, or a body worn camera or any other suitable type of external device as described herein. The case may for example be connected to the phone using a wire from the case and connected to the headphone port or charging port of the mobile phone.

The conductive communication C1 may be used both for communication between the controller 300 and the external device 320 in any or both directions. Consequently, according to some embodiments, the external device 320 is configured to transmit a conductive communication (conductive data) to the controller 300 via the conductive member 321.

According to some embodiments, the controller 300 is configured to transmit a conductive communication to the external device 320. These embodiments start by placing the conductive member 321, configured to be in connection with the external device 320, in electrical connection with a skin of the patient for conductive communication C1 with the controller 300. The conductive communication between the external device 320 and the controller 300 may follow an electrically/conductively confined path comprising e.g. the external device 320, conductive member 321, conductive connection C1, controller 300.

For the embodiments when the external device 320 transmits data to the controller, the communication may comprise transmitting a conductive communication to the controller 300 by the external device 320.

The transmitted data may comprise instructions for operating the implantable constriction device 10. Consequently, some embodiments comprise operating the implantable constriction device 10 using operation instructions, by an internal computing unit 306 of the controller 300, wherein the conductive communication C1 comprises instructions for operating the implantable constriction device 10. The operation instruction may for example involve adjusting or setting up (e.g. properties or functionality of) the active unit 302 of the implantable constriction device 10.

The transmitted data may comprise instructions for updating a control program 310 stored in memory 307 of the controller 300. Consequently, some embodiments comprise updating the control program 310 running in the controller 300, by the internal computing unit 306 of the implant, wherein the conductive communication comprises instructions for updating the control program 310.

For the embodiments when the controller 300 transmits data to the external device 320, the communication may comprise transmitting conductive communication C1 to the external device 320 by the controller 300. The conductive communication may comprise feedback parameters. Feedback parameters could include battery status, energy level at the controller, the fluid level of the hydraulic restriction device, number of operations that the restriction device has performed, properties, version number etc. relating to functionality of the implantable constriction device 10. In other embodiments, the conductive communication C1 comprises data pertaining to least one physiological parameter of the patient, such as blood pressure etc. The physiological parameter(s) may be stored in memory 307 of the controller 300 or sensed in prior (in real time or with delay) to transmitting the conductive communication C1. Consequently, in some embodiments, the implantable constriction device 10 comprises a sensor 351 for sensing at least one physiological parameter of the patient, wherein the conductive communication comprises said at least one physiological parameter of the patient.

To further increase security of the communication between the controller 300 and the external device 320, different types of authentication, verification and/or encryption may be employed. In some embodiments, the external device 320 comprises a verification unit 340. The verification unit 340 may be any type of unit suitable for verification of a user, i.e. configured to receive authentication input from a user, for authenticating the conductive communication between the implant and the external device. In some embodiments, the verification unit and the external device comprises means for collecting authentication input from the user (which may or may not be the patient). Such means may comprise a fingerprint reader, a retina scanner, a camera, a GUI for inputting a code, a microphone, device configured to draw blood, etc. The authentication input may thus comprise a code or any be based on a biometric technique selected from the list of: a fingerprint, a palm vein structure, image recognition, face recognition, iris recognition, a retinal scan, a hand geometry, and genome comparison. The means for collecting the authentication input may alternatively be part of the conductive member which comprise any of the above examples of functionality, such as a fingerprint reader or other type of biometric reader.

In some embodiments, the security may thus be increased by receiving an authentication input from a user by the verification unit 340 of the external device 320 and authenticating the conductive communication between the controller 300 and the external device using the authentication input. Upon a positive authentication, the conductive communication channel C1 may be employed for comprising transmitting a conductive communication to the controller 300 by external device 320 and/or transmitting a conductive communication to the external device 320 by the controller 300. In other embodiments, a positive authentication is needed prior to operating the implantable constriction device 10 based on received conductive communication, and/or updating a control program running in the controller 300 as described above.

FIGS. 23a-23c further shows an implantable constriction device 10 implanted in a patient and being connected to a sensation generator 381.

The sensation generator 381 may be configured to generate a sensation. The sensation generator 381 may be contained within the implantable constriction device 10 or be a separate unit. The sensation generator 381 may be implanted. The sensation generator 381 may also be located so that it is not implanted as such but still is in connection with a patient so that only the patient may experience sensations generated. The controller 300 is configured for storing authentication data, related to the sensation generated by the sensation generator 381.

The controller 300 is further configured for receiving input authentication data from the external device 320. Authentication data related to the sensation generated may by stored by a memory 307 of the controller 300. The authentication data may include information about the generated sensation such that it may be analyzed, e.g. compared, to input authentication data to authenticate the connection, communication, or device. Input authentication data relates to information generated by a patient input to the external device 320. The input authentication data may be the actual patient input or an encoded version of the patient input, encoded by the external device 320. Authentication data and input authentication data may comprise a number of sensations or sensation components.

The authentication data may comprise a timestamp. The input authentication data may comprise a timestamp of the input from the patient. The timestamps may be a time of the event such as the generation of a sensation by the sensation generator 381 or the creation of input authentication data by the patient. The timestamps may be encoded. The timestamps may feature arbitrary time units, i.e. not the actual time. Timestamps may be provided by an internal clock 360 of the controller 300 and an external clock 362 of the external device 320. The clocks 360, 362 may be synchronized with each other. The clocks 360, 362 may be synchronized by using a conductive connection C1 or a wireless connection WL1 for communicating synchronization data from the external device 320, and its respective clock 362, to the controller 300, and its respective clock 360, and vice versa. Synchronization of the clocks 360, 362 may be performed continuously and may not be reliant on secure communication.

Authentication of the connection may comprise calculating a time difference between the timestamp of the sensation and the timestamp of the input from the patient, and upon determining that the time difference is less than a threshold, authenticating the connection. An example of a threshold may be 1 s. The analysis may also comprise a low threshold as to filter away input from the patient that is faster than normal human response times. The low threshold may e.g. be 50 ms.

Authentication data may comprise a number of times that the sensation is generated by the sensation generator, and wherein the input authentication data comprises an input from the patient relating to a number of times the patient detected the sensation. Authenticating the connection may then comprise: upon determining that the number of times that the authentication data and the input authentication data are equal, authenticating the connection.

A method of authenticating the connection between an implantable constriction device 10 implanted in a patient, and an external device 320 according includes the following steps.

Generating, by a sensation generator 381, a sensation detectable by a sense of the patient. The sensation may comprise a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm.

Sensations may be configured to be consistently felt by a sense of the patient while not risking harm to or affecting internal biological processes of the patient.

The sensation generator 381, may be contained within the controller 300 or be a separate entity connected to the controller 300. The sensation may be generated by a motor (denoted as M in several embodiments shown herein) of the implantable constriction device 10, wherein the motor being the sensation generator 381. The sensation may be a vibration, or a sound created by running the motor. The sensation generator 381 may be located close to a skin of the patient and thus also the sensory receptors of the skin. Thereby the strength of some signal types may be reduced.

Storing, by the controller 300, authentication data, related to the generated sensation.

Providing, by the patient input to the external device, resulting in input authentication data. Providing the input may e.g. comprise an engaging an electrical switch, using a biometric input sensor or entry into digital interface running on the external device 320 to name just a few examples.

Transmitting the input authentication data from the external device to the controller 300. If the step was performed, the analysis may be performed by the controller 300.

Transmitting the authentication data from the implantable constriction device 10 to the external device 320. If the step was performed, the analysis may be performed by the external device 320. The wireless connection WL1 or the conductive connection C1 may be used to transmit the authentication data or the input authentication data.

Authenticating the connection based on an analysis of the input authentication data and the authentication data e.g. by comparing a number of sensations generated and experienced or comparing timestamps of the authentication data and the input authentication data. If step was performed, the analysis may be performed by the implantable constriction device 10.

Communicating further data between the controller 300 and the external device 320 following positive authentication. The wireless connection WL1 or the conductive connection Cl may be used to communicate the further data. The further data may comprise data for updating a control program 310 running in the controller 300 or operation instructions for operating the implantable constriction device 10. The further data may also comprise data sensed by a sensor 351 connected to the controller 300.

If the analysis was performed by the controller 300, the external device 320 may continuously request or receive, information of an authentication status of the connection between the controller 300 and the external device 320, and upon determining, at the external device 320, that the connection is authenticated, transmitting further data from the external device 320 to the controller 300.

If the analysis was performed by the external device 320, the controller 300 may continuously request or receive, information of an authentication status of the connection between the controller 300 and the external device 320, and upon determining, at the controller 300, that the connection is authenticated, transmitting further data from the controller 300 to the external device 320.

A main advantage of authenticating a connection according to this method is that only the patient may be able to experience the sensation. Thus, only the patient may be able to authenticate the connection by providing authentication input corresponding to the sensation generation.

The sensation generator 381, sensation, sensation components, authentication data, input authentication data, and further data may be further described herein. In these cases, the implantable constriction device 10 and/or external device(s) comprises the necessary features and functionality (described in the respective sections of this document). Further information and definitions can be found in this document in conjunction with the other aspects.

The method may further comprise transmitting further data between the controller 300 and the external device, wherein the further data is used or acted upon, only after authentication of the connection is performed.

The analysis or step of analyzing may be understood as a comparison or a step of comparing.

In one method, increased security for communication between an external device(s) and an implanted controller is provided. FIGS. 23a-23c show an implantable constriction device 10 comprising a controller 300 and an external device 320 which may form a system.

The controller 300 comprises a transceiver 308, 303 configured to establish a connection with an external device 320, i.e. with a corresponding transceiver 328, 323. The connection may be an electrical connection C1 using the transceivers 303, 323, or a wireless connection WL1 using the transceivers 308, 328. The controller 300 further comprises a computing unit 306 configured to verify the authenticity of instructions received at the transceiver 308, 303 from the external device 320. In this aspect, the concept of using previously transmitted instructions for verifying a currently transmitted instructions are employed. Consequently, the transmitting node (in this case the external device) need to be aware of previously instructions transmitted to the implant, which reduces the risk of a malicious device instructing the implant without having the authority to do so.

In an embodiment, the computing unit 306 is configured to verify the authenticity of instructions received at the transceiver 308, 303 by extracting a previously transmitted set of instructions from a first combined set of instructions received by the transceiver. The external device 320 may thus comprise an external device comprising a computing unit 326 configured for: combining a first set of instructions with a previously transmitted set of instructions, forming a combined set of instructions, and transmitting the combined set of instructions to the implant. The previously transmitted set of instructions, or a representation thereof, may be stored in memory 327 of the external device 320.

The combined set of instructions may have a data format which facilitates such extraction, for example including metadata identifying data relating to the previously transmitted set of instructions in the combined set of instructions. In some embodiments, the combined set of instructions comprises the first set of instructions and a cryptographic hash of the previously transmitted set of instructions. Consequently, the method comprises combining, at the external device, a first set of instructions with a previously transmitted set of instructions, forming a first combined set of instructions. A cryptographic hash function is a special class of hash function that has certain properties which make it suitable for use in cryptography. It is a mathematical algorithm that maps data of arbitrary size to a bit string of a fixed size (a hash) and is designed to be a one-way function, that is, a function which is infeasible to invert. Examples include MD5, SHA1, SHA 256, etc. Increased security is thus achieved.

The first combined set of instructions is then transmitted to the implanted controller 300, where it is received by e.g. the transceiver 303, 308. The first combined set of instructions may be transmitted to the implant using a proprietary network protocol. The first combined set of instructions may be transmitted to the controller 300 using a standard network protocol. In these cases, the controller 300 and/or external device(s) comprises the necessary features and functionality (described in the respective sections of this document) for performing transmission of data. By using different communication protocols, at the external device 320, for communication with the controller 300 and with a second external device 330, an extra layer of security is added as the communication between controller 300 and the external device 320 may be made less directly accessible to remote third parties.

At the controller 300, the computing unit 306 verifies the authenticity of the received first combined set of instructions, by: extracting the previously transmitted set of instructions from the first combined set of instructions, and comparing the extracted previously transmitted set of instructions with previously received instructions stored in the implant.

Upon determining that the extracted previously transmitted set of instructions equals the previously received instructions stored in the controller 300, the authenticity of the received first combined set of instructions may be determined as valid, and consequently, the first set of instructions may be safely run at the controller 300, and the first combined set of instructions may be stored in memory 307 of the controller 300, to be used for verifying a subsequent received set of instructions.

In some embodiments, upon determining by the internal computing unit 306 that the extracted previously transmitted set of instructions differs from the previously received instructions stored in the controller 300, feedback related to an unauthorized attempt to instruct the implantable constriction device 10 may be provided. For example, the transceiver 308, 303 may send out a distress signal to e.g. the external device 320 or to any other connected devices. The controller 300 may otherwise inform the patient that something is wrong by e.g. vibration or audio. The implantable constriction device 10 may be run in safe mode, using a preconfigured control program which is stored in memory 307 of the controller 300 and specifically set up for these situations, e.g. by requiring specific encoding to instruct the implantable constriction device 10, or only allow a predetermined device (e.g. provided by the manufacturer) to instruct the implantable constriction device 10. In some embodiments, when receiving such feedback at the external device 320, the external device 320 retransmits the first combined set of instructions again, since the unauthorized attempt may in reality be an error in transmission (where bits of the combined set of instructions are lost in transmission), and where the attempt to instruct the implantable constriction device 10 is indeed authorized.

The step of comparing the extracted previously transmitted set of instructions with previously received instructions stored in the controller 300 may be done in different ways. For example, the step of comparing the extracted previously transmitted set of instructions with previously received instructions stored in the controller 300 comprises calculating a difference between the extracted previously transmitted set of instructions with previously received instructions stored in the controller 300, and comparing the difference with a threshold value, wherein the extracted previously transmitted set of instructions is determined to equal the previously received instructions stored in the controller 300 in the case of the difference value not exceeding the threshold value. This embodiment may be used when received instructions is stored in clear text, or a representation thereof, in the controller 300, and where the combined set of instructions, transmitted from the external device also includes such a representation of the previously transmitted instructions. This embodiment may be robust against error in transmission where bits of information are lost or otherwise scrambled.

In other embodiments, the combined set of instructions comprises the first set of instructions and a cryptographic hash of the previously transmitted set of instructions, wherein the method further comprises, at the controller 300, calculating a cryptographic hash of the previously received instructions stored in the controller 300 and comparing the calculated cryptographic hash to the cryptographic hash included in the first combined set of instructions. This embodiment provides increased security since the cryptographic hash is difficult to decode or forge.

The above way of verifying the authenticity of received instructions at the controller 300 may be iteratively employed for further sets if instructions.

To further increase security, the transmission of a first set of instructions, to be stored at the controller 300 for verifying subsequent sets of combined instructions, where each set of received combined instructions will comprise data which in some form will represent, or be based on, the first set of instruction, may be performed.

In one example, the external device 320 may be adapted to communicate with the controller 300 using two separate communication methods. A communication range of a first communication method WL1 may be less than a communication range of a second communication method WL2. A method may comprise the steps of: sending a first part of a key from the external device 320 to the controller 300, using the first communication method WL1 and sending a second part of the key from the external device 320 to the controller 300, using the second communication method WL2. The method may further comprise deriving, in the controller 300, a combined key from the first part of the key and the second part of the key and decrypting the encrypted data, in the controller 300, using the combined key. The encrypted data may also be sent from the external device 320 to the controller 300 using the second communication method WL2. The method may then further comprise confirming an electrical connection C1 between the controller 300 and the external device 320 and as a result of the confirmation, decrypting the encrypted data in the controller 300 and using the decrypted data for instructing the controller 300.

The method may also comprise placing a conductive member 321, configured to be in connection with the external device 320, in electrical connection with a skin of the patient for conductive communication with the controller 300. By means of the electrical connection an extra layer of security is added as a potential hacker would have to be in contact with the patient to access or affect the operation of the implantable constriction device 10.

Using a plurality of communication methods, may increase the security of the authentication and the communication with the implantable constriction device 10 as more than one channel for communication may need to be hacked or hijacked by an unauthorized entity to gain access to the implantable constriction device 10 or the communication.

The electrical connection C1 the conductive member 321 and conductive communication may be further described herein in the general definitions section. In these cases, the controller 300 and/or external device 320 comprise the necessary features and functionality (described in the respective sections of this document).

It should also be noted that any one of the first and second communication methods WL1, WL2 may be needed to be confirmed in order to decrypt the encrypted data in the controller 300 and using the decrypted data for instructing the implantable constriction device 10.

The method may further comprise the step of wirelessly receiving, at the controller 300, a third part of the key from the second external device 330. In this case, the combined key may be derived from the first part of the key, the second part of the key and the third part of the key.

The first communication method WL1 may be a wireless form of communication. The first communication method WL1 may preferably be a form of electromagnetic or radio-based communication however, other forms of communication are not excluded. The first communication method WL1 may comprise or be related to the items of the following list: Radio-frequency identification (RFID), Bluetooth, Bluetooth 5, Bluetooth Low Energy (BLE), Near Field Communication (NFC), NFC-V, Infrared (IR) based communication, Ultrasound based communication.

RFID communication may enable the use of a passive receiver circuit such as those in a RFID access/key or payment card. IR based communication may comprise fiber optical communication and IR diodes. IR diodes may alternatively be used directly, without a fiber, such as in television remote control devices. Ultrasound based communication may be based on the non-invasive, ultrasound imaging found in use for medical purposes such as monitoring the development of mammal fetuses.

The first communication method WL1 may use a specific frequency band. The frequency band of the first communication method WL1 may have a center frequency of 13.56 MHz or 27.12 MHz. These bands may be referred to as industrial, scientific, and medical (ISM) radio bands. Other ISM bands not mentioned here may also be utilized for the communication methods WL1, WL2. A bandwidth of the 13.56 MHz centered band may be 14 kHz and a bandwidth of the 27.12 MHz centered band may be 326 kHz.

The communication range of the first communication method WL1 may be less than 10 meters, preferably less than 2 meters, more preferably less than 1 meter and most preferably less than 20 centimeters. The communication range of the first communication method WL1 may be limited by adjusting a frequency and/or a phase of the communication. Different frequencies may have different rates of attenuation. By implementing a short communication range of the first communication method, security may be increased since it may be ensured or made probable that the external device is under control of the patient (holding the external device close to the implant)

The communication range of the first communication method WL1 should be evaluated by assuming that a patient's body, tissue, and bones present the propagation medium. Such a propagation medium may present different attenuation rates as compared to a free space of an air-filled atmosphere or a vacuum.

By restricting the communication range, it may be established that the external device communicating with the implanted controller 300 is in fact on, or at least proximal to, the patient. This may add extra security to the communication.

The second communication method WL2 may be a wireless form of communication. The second communication method WL2 may preferably be a form of electromagnetic or radio-based communication. The second communication method WL2 may be based on telecommunication methods. The second communication method WL2 may comprise or be related to the items of the following list: Wireless Local Area Network (WLAN), Bluetooth, Bluetooth 5, BLE, GSM or 2G (2nd generation cellular technology), 3G, 4G, 5G.

The second communication method WL2 may utilize the ISM bands as mentioned in the above for the first communication method WL1.

A communication range of the second communication method WL2 may be longer than the communication range of the first communication method WL1. The communication range of the second communication method WL2 may preferably be longer than 10 meters, more preferably longer than 50 meters, and most preferably longer than 100 meters.

Encrypted data may comprise instructions for updating a control program 310 running in the implantable constriction device 10. Encrypted data may further comprise instructions for operating the implantable constriction device 10.

In one embodiment, the implantable constriction device 10 may transmit data to an external device 320 which may add an additional layer of encryption and transmit the data to a second external device 330, described with reference to FIGS. 23a-23c. By having the external device add an additional layer of encryption, less computing resources may be needed in the implanted controller 300, as the controller 300 may transmit unencrypted data or data encrypted using a less secure or less computing resource requiring encryption. In this way, data can still be relatively securely transmitted to a third device. The transmission of data can be performed using any of the method described herein in addition to the method or in the system described below.

Thus, in an embodiment, a system is provided. The system comprises an implantable constriction device 10 comprising a controller 300 configured to transmit data from the body of the patient to an external device 320, and an encryption unit 382 for encrypting the data to be transmitted. The system further comprises an external device 320 configured to receive the data transmitted by the controller 300, encrypt the received data using a first key and transmit the encrypted received data to a third external device 330. The encryption can be performed using any of the keys described above or below. In some embodiments, the external device 320 is configured to decrypt the data received from the controller 300 before encrypting and transmitting the data. Alternatively, the external device 320 may encrypt and transmit the data received from the controller 300 without decrypting it first.

In one example, the encryption unit 382 is configured to encrypt the data to be transmitted using a second key. The first key or the second key may, for example, information specific to the implantable constriction device 10, a secret key associated with the external device 320, an identifier of the implantable constriction device 10 or an identifier of the controller 300. The second key could be a key transmitted by the external device 320 to the controller 300. In some examples, the second key is a combined key comprising a third key received by the controller 300 from the external device 320.

The first key may be a combined key comprising a fourth key, wherein the fourth key is received by the external device 320 from a fourth device. The fourth device may be a verification unit, either comprised in the external device, or external to the external device and connected to it. The verification unit may have a sensor 350 for verification, such as a fingerprint sensor. More details in regard to this will be described below. Alternatively, the verification unit may be a generator, as described above.

The system may be configured to perform a method for transmitting data using a sensed parameter. The method may comprise transmitting a parameter measured by the external device 320 from the external device 320 to the controller 300. In this case, the comparison of the parameter of the patient measured by the external device 320 and the parameter of the patient measured by the controller 300 may be performed by the controller 300. The implantable constriction device 10 may comprise a first sensor 351 for measuring the parameter of the patient at the implantable constriction device 10. The external device 320 may comprise an external sensor 350 for measuring the parameter of the patient at the external device 320.

Authentication of the connection between the controller 300 and the external device 320 may be performed automatically without input, authentication, or verification from a user or patient. This is because the comparison of parameters measured internally and externally, by the internal and external sensors 351, 350 respectively may be enough to authenticate the connection. This may typically be the case when the parameter of the patient is related to an automatically occurring physiological function of the patient such as e.g. a pulse of the patient. Certain types of authentication may however require actions from the patient, e.g. having the patient perform specific movements.

In the embodiments described herein, the controller 300 may comprise or be connected to a sensation generator 381 as described above. In response to an event in the implant, such as a reset, a restart, receipt of new instructions, receipt of a new configuration or update, installation or activation of new instructions or configuration or update, the controller 300 may be configured to cause the sensation generator 381 to generate a sensation detectable by the patient in which the implantable constriction device 10 is implanted. In some examples, the user may after the sensation verify an action, for example via a user interface of an external device 320.

The implantable constriction device 10 may further implement a method for improving the security of the data transmitted from the controller 300. The method, for encrypted communication between a controller 300, when implanted in a patient's body, and an external device 320, comprises encoding or encrypting, by the controller 300 or a processor 306 comprised in or connected to the controller 300, data relating to the implantable constriction device 10 or the operation thereof; transmitting, by the controller 300, the data; receiving, by a second communication unit comprised the external device 320, the data; encrypting, by the external device 320, the data using an encryption key to obtain encrypted data; and transmitting the encrypted data to a third external device 330. In this way, the external device 320 may add or exchange the encryption, or add an extra layer of encryption, to the data transmitted by the controller 300. When the controller 300 encodes the data to be transmitted it may be configured to not encrypt the data before transmitting, or only using a light weight encryption, thus not needing as much processing power as if the controller were to fully encrypt the data before the transmission.

The encrypting, by the controller 300, may comprise encrypting the data using a second key. The encryption using the second key may be a more light weight encryption than the encryption performed by the external device using the second key, i.e. an encryption that does not require as much computing resources as the encryption performed by the external device 320.

The first or the second key may comprise a private key exchanged as described above with reference to encryption and authentication, or the first or the second key may comprise an information specific to the implantable constriction device 10, a secret key associated with the external device, an identifier of the implantable constriction device 10 or an identifier of the controller 300. They may be combined keys as described in this description, and the content of the keys, any combination of keys, and the exchange of a key or keys is described in the encryption and/or authentication section.

In an embodiment, the implantable constriction device 10 comprises at least one sensor for sensing at least one physiological parameter of the patient or a functional parameter of the implantable constriction device 10, now described with reference to FIGS. 23a-23c. The sensor 351 may, for example, be a pressure sensor, an electrical sensor, a clock, a temperature sensor, a motion sensor, an optical sensor, a sonic sensor (such as a microphone), an ultrasonic sensor. The sensor 351 is configured to periodically sense the parameter and the controller 300 is configured to, in response to the sensed parameter being above a predetermined threshold, wirelessly broadcast information relating to the sensed parameter. The controller 300 may be configured to broadcast the information using a short to mid-range transmitting protocol, such as a Radio Frequency type protocol, a RFID type protocol, a WLAN type protocol, a Bluetooth type protocol, a BLE type protocol, a NFC type protocol, a 3G/4G/5G type protocol, or a GSM type protocol.

The controller of the implant may be connected to the sensor 351 and be configured to anonymize the information before it is transmitted. The transmission of data may also be called broadcasting of data.

In addition to or as an alternative to transmitting the data when the sensed parameter is above a predetermined threshold, the controller 300 may be configured to broadcast the information periodically. The controller 300 may be configured to broadcast the information in response to a second parameter being above a predetermined threshold. The second parameter may, for example, be related to the controller 300 itself, such as a free memory or free storage space parameter, or a battery status parameter. When the implantable constriction device 10 comprises an implantable energy storage unit and an energy storage unit indicator, the energy storage unit indicator is configured to indicate a functional status of the implantable energy storage unit and the indication may be comprised in the transmitted data. The functional status may indicate at least one of charge level and temperature of the implantable energy storage unit.

In some embodiments the external device 320 is configured to receive the broadcasted information, encrypt the received information using an encryption key and transmit the encrypted received information. In this way, the external device 320 may add an additional layer of encryption or exchange the encryption performed by the controller 300.

In an embodiment, the controller 300 is configured to transmit the data using the body of the patient as a conductor C1, and the external device 320 is configured to receive the data via the body. Alternatively, or in combination, the controller 300 of the implant is configured to transmit the data wirelessly to the external device WL2.

Thus, the controller 300 may implement a method for transmitting data from the controller 300 comprising a processor 306, comprising: obtaining sensor measurement data via a sensor 351 connected to or comprised in the controller 300, the sensor measurement relating to at least one physiological parameter of the patient or a functional parameter of the implantable constriction device 10, and transmitting by the controller 300 the sensor measurement data in response to the sensor measurement being above a predetermined threshold, wherein the sensor 351 is configured to periodically sense the parameter. The method may further comprise broadcasting the sensor measurement data, to be received by an external device 320. The transmitting or broadcasting may comprise using at least one of a Radio Frequency type protocol, RFID type protocol, WLAN type protocol, Bluetooth type protocol, BLE type protocol, NFC type protocol, 3G/4G/5G type protocol, or a GSM type protocol.

The method may further comprise, at the processor 306, anonymizing, by the processor, the sensor measurement data before it is transmitted, or encrypting the sensor measurement data, using an encryptor 382 comprised in the processing unit 306, before it is transmitted. The transmitting of the data may further comprise to encode the data before the transmitting. The type of encoding may be dependent on the communication channel or the protocol used for the transmission.

The transmitting may be performed periodically, or in response to a signal received by the processor, for example, by an internal part of the implantable constriction device 10 such as a sensor 351, or by an external device 320.

The parameter may, for example, be at least one of a functional parameter of the implantable constriction device 10 (such as a battery parameter, a free memory parameter, a temperature, a pressure, an error count, a status of any of the control programs, or any other functional parameter mentioned in this description) or a parameter relating to the patient (such as a temperature, a blood pressure, or any other parameter mentioned in this description). In one example, the implantable constriction device 10 comprises an implantable energy storage unit 40 and an energy storage unit indicator 304c, and the energy storage unit indicator 304c is configured to indicate a functional status of the implantable energy storage unit 40, and the sensor measurement comprises data related to the energy storage unit indicator.

In one example, the transmitting comprises transmitting the sensor measurement to an internal processor 306 configured to cause a sensation generator 381 to cause a sensation detectable by the patient in which the implant 100 is implanted.

The method may be implemented in a system comprising the implant 100 and an external device 320, and further comprise receiving the sensor measurement data at the external device 320, and, at the external device 320, encrypting the sensor measurement data using a key to obtain encrypted data, and, transmitting the encrypted data. The transmitting may, for example, be performed wirelessly WL3 or conductively Cl.

In the examples or embodiments transmitting data from or to the implantable constriction device 10, the following method may be implanted in order to verify the integrity of the data, described with reference to FIGS. 23a-23b. By verifying the integrity of the data, an external device 320 or a processor 306 comprised in the controller 300 may verify that the data has not been corrupted or tampered with during the transmission. In some examples, data integrity for data communicated between a controller 300 and an external device 320 or between an external device 320 and the controller 300 may be performed using a cyclic redundancy check.

Thus, in a first example, a method for evaluating a parameter of a controller 300 implanted in a patient is described. The controller 300 comprises a processor 306 and a sensor 351 for measuring the parameter. The method comprises measuring, using the sensor 351, the functional parameter to obtain measurement data; establishing a connection between the internal controller 300 and an external device 320 configured to receive data from the implant; determining, by the processor 306, a cryptographic hash or a metadata relating to the measurement data and adapted to be used by the external device 320 to verify the integrity of the received data; transmitting the cryptographic hash or metadata; and transmitting, from the controller 300, the measurement data.

The parameter may, for example, be a parameter of the controller 300, such as a temperature, a pressure, a battery status indicator, a time period length, s pressure at a restriction device, a pressure at a sphincter, or a physiological parameter of the patient, such as a pulse, a blood pressure, or a temperature. In some examples, multiple parameters may be used.

The method may further comprise evaluating the measurement data relating to the functional parameter. By evaluating it may be meant to determine if the parameter is exceeding or less than a predetermined value, to extract another parameter from the measurement data, compare the another parameter to a predetermined value, or displaying the another parameter to a user. For example, the method may further comprise, at the external device 320, to determining, based on the evaluating, that the implantable constriction device 10 is functioning correctly, or determining based on the evaluating that the implantable constriction device 10 is not functioning correctly.

If it is determined that the implantable constriction device 10 is not functioning correctly, the method may further comprise sending, from the external device 320, a corrective command to the controller 300, receiving the corrective command at the controller 300, and by running the corrective command correcting the functioning of the implantable constriction device 10 according to the corrective command.

The method may further comprise, at the external device 320, receiving the transmitted cryptographic hash or metadata, receiving the measurement data, and verifying the integrity of the measurement data using the cryptographic hash or metadata. The cryptographic hash algorithm be any type of hash algorithm, i.e. an algorithm comprising a one-way function configured to have an input data of any length as input and produce a fixed-length hash value. For example, the cryptographic hash algorithm may be MD5, SHA1, SHA 256, etc.

In some examples, the cryptographic hash is a signature obtained by using a private key of the controller 300, and wherein the verifying, by the external device 320, comprises verifying the signature using a public key corresponding to the private key.

When using a cryptographic hash, the method may further comprise calculating a second cryptographic hash for the received measurement data using a same cryptographic hash algorithm as the processor, and determining that the measurement data has been correctly received based on that the cryptographic hash and the second cryptographic hash are equal (i.e. have the same value).

When using a metadata the verifying the integrity of the data may comprises obtaining a second metadata for the received measurement data relating to the functional parameter, and determining that the data has been correctly received based on that metadata and the second metadata are equal. The metadata may, for example, be a length of the data or a timestamp. In some examples the measurement data is transmitted in a plurality of data packets. In those examples, the cryptographic hash or metadata comprises a plurality of cryptographic hashes or metadata each corresponding to a respective data packet, and the transmitting of each the cryptographic hashes or metadata is performed for each of the corresponding data packets.

A similar method may be utilized for communicating instructions from an external device 320 to a controller 300 implanted in a patient. The method comprises establishing a first connection between the external device 320 and the controller 300, establishing a second connection between a second external device 330 and the controller 300, transmitting, from the external device 320, a first set of instructions to the controller 300 over the first connection, transmitting, from the second external device 330, a first cryptographic hash or metadata corresponding to the first set of instructions to the controller 300, and, at the controller 300, verifying the integrity of the first set of instructions and the first cryptographic hash or metadata, based on the first cryptographic hash or metadata. The external device 320 may be separate from the second external device 330.

The first connections may be established between the controller 300 and a transceiver of the external communication unit 323. In some examples, the communication using the second connection is performed using a different protocol than a protocol used for communication using the first communication channel. In some examples, the first connection is a wireless connection and the second connection is an electrical connection. The second connection may, for example, be an electrical connection using the patient's body as a conductor (using 321). The protocols and ways of communicating may be any communication protocols described in this description with reference to C1, and WL1-WL4. The establishing of the first and second connections are performed according to the communication protocol used for each of the first and the second connections.

When using a cryptographic hash, the verifying the integrity of the first set of instructions may comprise calculating a second cryptographic hash for the received first set of instructions using a same cryptographic hash algorithm as the processor 306, and determining that the first set of instructions has been correctly received based on that the cryptographic hash and the second cryptographic hash are equal. The cryptographic hash may, for example, be a signature obtained by using a private key of the implantable constriction device 10, and wherein the verifying comprises verifying the signature using a public key corresponding to the private key. In some examples, the cryptographic hash is a signature obtained by using a private key of the implantable constriction device 10, and wherein the verifying comprises verifying the signature using a public key corresponding to the private key. The private keys and public keys, as well as the exchange or transmittal of keys have been described in this description. Alternatively, other well-known methods can be used for transmitting or exchanging a key or keys between the external device 320 and the controller 300.

When using a metadata, and wherein the verifying the integrity of the data may comprise obtaining a second metadata for the received first set of instructions, and determining that the first set of instructions has been correctly received based on that metadata and the second metadata are equal. The metadata may, for example, be any type of data relating to the data to be transmitted, in this example the first set of instructions. For example, the metadata may be a length of the data to be transmitted, a timestamp on which the data was transmitted or retrieved or obtained, a size, a number of packets, or a packet identifier.

In some examples, the controller 300 may transmit data to an external device 320 relating to the data information in order to verify that the received data is correct. The method may thus further comprise, transmitting, by the controller 300, information relating to the received first set of instructions, receiving, by the external device 320, the information, and verifying, by the external device 320, that the information corresponds to the first set of instructions sent by the external device 320. The information may, for example, comprise a length of the first set of instructions.

The method may further comprise, at the controller 300, verifying the authenticity of the first set of instructions by i. calculating a second cryptographic hash for the first set of instructions, ii. comparing the second cryptographic hash with the first cryptographic hash, iii. determining that the first set of instructions are authentic based on that the second cryptographic hash is equal to the first cryptographic hash, and upon verification of the authenticity of the first set of instructions, storing them at the controller 300.

In some examples, the first set of instructions comprises a cryptographic hash corresponding to a previous set of instruction, as described in other parts of this description.

In some examples, the first set of instructions may comprise a measurement relating to the patient of the body for authentication, as described in other parts of this description.

A system and a method for communication of instructions or control signals between an external device 320 and an implant 10 will now be described with reference to FIGS. 23*a*-*c*.

The system shown in FIGS. 23*a*-*c* comprises an implantable constriction device 10, a first external device 320, and a second external device 330. The implant comprises a controller 300 and an implantable restriction device 302. The controller 300 is adapted to receive an instruction from an external device 320 over the communication channel WL1, C1 and run the instruction to control a function of the implant 10, such as a function of the implantable constriction device 10. The communication channel WL1, C1 may be any type of communication channel, such as a wireless connection WL1 or a conductive connection C1 described herein. For example, the wireless connection may comprise at least one of the following protocols: Radio Frequency type protocol, RFID type protocol, WLAN type protocol, Bluetooth type protocol, a BLE type protocol, a NFC type protocol, a 3G/4G/5G/6G type protocol, a GSM type protocol, and/or Bluetooth 5.

The first external device 320 is adapted to receive, such as through a user interface, or determine an instruction to be transmitted to the implant 10. The determination of the instruction may, for example, be based on received data from the implantable constriction device 10, such as measurement data or data relating to a state of the implant, such as a battery status or a free memory status. The first external device 320 may be any type of device capable of transmitting information to the implant and capable of determining or receiving an instruction to be transmitted to the implantable constriction device 10. In a preferred embodiment, the first external device 320 is a hand-held device, such as a smartphone, smartwatch, tablet etc. handled by the patient, having a user interface for receiving an instruction from a user, such as the patient or a caregiver.

The first external device 320 is further adapted to transmit the instruction to a second external device 330 via communication channel WL3. The second external device 320 is adapted to receive the instruction, encrypt the instruction using an encryption key, and then transmit the encrypted instruction to the implantable constriction device 10. The implantable constriction device 10 is configured to receive the instruction at the controller 300. The controller 300 thus comprises a wired transceiver or a wireless transceiver for receiving the instruction. The implantable constriction device 10 is configured to decrypt the received instruction. The decryption may be performed using a decryption key corresponding to the encryption key. The encryption key, the decryption key and methods for encryption/decryption and exchange of keys may be performed as described in the "general definition of features" or as described with reference to FIGS. 23*a*-*c*. Further, there are many known methods for encrypting data which the skilled person would understand to be usable in this example.

The second external device 330 may be any computing device capable of receiving, encrypting, and transmitting data as described above. For example, the second external device 320 may be a network device, such as a network server, or it may be an encryption device communicatively coupled to the first external device.

The instruction may be a single instruction for running a specific function or method in the implantable constriction device 10, a value for a parameter of the implantable constriction device 10, or a set of sub-steps to be performed by the controller 300 comprised in the implant.

In this way, the instruction for controlling a function of the implantable constriction device 10 may be received at the first external device 320 and transmitted to the implant 10 via the second external device 330. By having a second external device 330 encrypting the instruction before transmitting it to the implantable constriction device 10, the instruction may be verified by the second external device 330 and the first external device 320 may function so as to relay the instruction. In some alternatives, the second external device 330 may transmit the instruction directly to the implantable constriction device 10. This may provide an increased security as the instruction sent to the implantable constriction device 10 may be verified by the second external device 330, which, for example, may be a proprietary device managed by the medical professional responsible for the implantable constriction device 10. Further, by having the second medical device 330 verifying and encrypting the instruction, the responsibility authenticity and/or correctness of the instruction may lie with the second external device 330, which may be beneficial for regulatory purposes, as the first external device 320 may not be considered as the instructor of the implantable constriction device 10.

Further, the second external device 330 may verify that the instruction is correct before encrypting or signing and transmitting it to the implantable constriction device 10. The second external device 330 may, for example, verify that the instruction is correct by comparing the instruction with a predetermined set of instructions, and if the instruction is comprised in the predetermined set of instructions determine that the instruction is correct. If the instruction comprises a plurality of sub-steps, the second external device 330 may determine that the instruction is correct if all the sub-steps are comprised in the predetermined set of instructions. If the instruction comprises a value for a parameter of the implantable constriction device 10, the second external device 330 may verify that the value is within a predetermined range for the parameter. The second external device 320 may thus comprise a predetermined set of instructions, or a predetermined interval or threshold value for a value of a parameter, stored at an internal or external memory.

The second external device 330 may be configured to reject the instruction, i.e. to not encrypt and transmit the instruction to the implantable constriction device 10, if the verification of the instruction would fail. For example, the second external device 330 determines that the instruction or any sub-step of the instruction is not comprised in the predetermined set of instructions, or if a value for a parameter is not within a predetermined interval, the second external device 330 may determine that the verification has failed.

In some embodiments, the implantable constriction device 10 may be configured to verify the instruction. The verification of the instruction may be performed in the same way as described with reference to FIGS. 23a-c. If the verification is performed by comparing the instruction or any sub-steps of the instruction with a predetermined set of instructions, the controller 300 may comprise a predetermined set of instructions. The predetermined set of instructions may, for example, be stored in an internal memory of the controller 300. Similarly, the controller 300 may store predetermined reference intervals for any parameter that can be set, and the controller 300 may be configured to compare a received value for a parameter to such a predetermined reference interval. If the verification of the instruction would fail, the controller 300 may be configured to reject the instruction, i.e. not run the instruction.

In an alternative to encrypting and decrypting the instruction, the instruction may be signed by the second external device 330 using a cryptographic hash, and the controller 300 may be configured to verify that the signature is correct before running the instruction.

A corresponding method for transmitting an instruction will now be described with reference to FIGS. 23a-c. The instruction may relate to a function of the implantable constriction device, such as an instruction to run a function or method of the implantable constriction device, or to set a value of a parameter of the implantable constriction device. The method comprises: transmitting an instruction for the implantable constriction device from the first external device 300 to a second external device 320, the instruction relating to a function of the implantable constriction device 10, encrypting, at the second external device 330 using a first encryption key, the instruction into an encrypted instruction, and transmitting the encrypted instruction from the second external device 330 to the implantable constriction device 10, decrypting, at the implantable constriction device, the instructions using a second encryption key corresponding to the first encryption key. The steps performed by or at the implantable constriction device may be executed by the controller 300.

The instruction may be any type of instruction for controlling a function of the implantable constriction device. For example, the instruction may be an instruction to run a function or method of the implantable constriction device 10 or controller 300, an instruction comprising a plurality of sub-steps to be run at the controller 300, or a value for a parameter at the controller 300. The first external device 320 may, for example, receive the instruction from a user via a user interface displayed at or connected to the first external device 320. In another example, the first external device 320 may determine the instruction in response to data received from the implantable constriction device 10, such as measurement data, or from another external device. Thus, in some examples, the method may further comprise receiving, at the first external device 320, an instruction to be transmitted to the implantable constriction device 10. The method may further comprise displaying a user interface for receiving the instruction. In another example, the method comprises determining, at the first external device 320, an instruction to be transmitted to the implantable constriction device 10.

In some embodiments, the transmitting of the encrypted instruction from the second external device 330 to the implantable constriction device 10 comprises transmitting the encrypted instruction from the second external device 330 to the first external device 320, and transmitting the encrypted instruction from the first external device 320 to the controller 300 of the implantable constriction device 10. In other words, the first external device 320 may relay the encrypted instruction from the second external device 330 to the controller 300, preferably without decrypting the instruction before transmitting it.

The method may further comprise to, at the controller 300, running the instruction or performing the instruction. The running of the instruction may be performed by an internal computing unit or a processor 306 comprised in the controller 300, and may, for example, cause the internal computing unit or processor 306 to instruct the implantable restriction device 302 to perform an action.

The method may further comprise verifying, at the second external device 330, that the instructions are correct. The verifying may be performed as described above with reference to the corresponding system.

The method may further comprise verifying, at the controller 300, that the instructions are correct. The verifying may be performed as described above with reference to the corresponding system.

The method may further comprise authenticating the connection between the first external device 320 and the controller 300 over which the encrypted instruction is to be transmitted. The authentication may be performed as described herein.

As described above, a control program of the controller 300 may be updatable, configurable, or replaceable. A system and a method for updating or configuring a control program of the controller 300 is now described with reference to FIGS. 23a-23c. The controller may comprise an internal computing unit 306 configured to control a function of the implantable constriction device 10, the internal computing unit 306 comprises an internal memory 307 configured to store: i. a first control program 310 for controlling the internal computing unit, and ii. a second, configurable or updatable, with predefined program steps, control program 312 for controlling said function of the implantable constriction device 10, and iii. a set of predefined program steps for updating the second control program 312. The controller 300 is configured to communicate with an external device 320. The internal computing unit 306 is configured to receive an update to the second control program 312 via the controller 300, and a verification function of, connected to, or transmitted to the controller 300. The verification function is configured to verify that the received update to the second control program 312 comprises program steps comprised in the set of predefined program steps. In this way, the updating or programming of the second control program may be performed using predefined program steps, which may decrease the risk that the new or updated control program is incorrect or comprises malicious software, such as a virus, spyware or a malware.

The predefined program steps may comprise setting a variable related to a pressure, a time, a minimum or maximum temperature, a current, a voltage, an intensity, a frequency, an amplitude of electrical stimulation, a feedback mode (sensorics or other), a post-operative mode or a normal mode, a catheter mode, a fibrotic tissue mode (for example semi-open), an time open after urination, a time open after urination before bed-time.

The verification function may be configured to reject the update in response to the update comprising program steps not comprised in the set of predefined program steps and/or be configured to allow the update in response to the update only comprising program steps comprised in the set of predefined program steps.

The internal computing unit 306 may be configured to install the update in response to a positive verification, for example by a user using an external device, by a button or similarly pressed by a user, or by another external signal.

The authentication or verification of communications between the implant and an external device has been described above.

When updating a control program of the controller 300, it may be beneficial to transmit a confirmation to a user or to an external device or system. Such a method is now described with reference to FIGS. 23a-23b.

The method for updating a control program of a controller 300 comprised in the implantable constriction device 10 according to any of the embodiments herein. The controller 300 is adapted for communication with a first external device 320 and a second external device 330, which may comprise receiving, by the internal computing unit, an update or configuration to the control program from the first external device, wherein the update is received using a first communication channel; installing, by the internal computing unit 306, the update; and transmitting, by the internal computing unit, logging data relating to the receipt of the update or configuration and/or logging data relating to an installation of the update to the second external device 330 using the second communication channel; wherein the first and the second communication channels are different communication channels. By using a first and a second communication channels, in comparison to only using one, the security of the updating may be improved as any attempts to update the control program will be logged via the second communication channel, and thus, increasing the chances of finding incorrect or malicious update attempts.

The update or configuration comprises a set of instructions for the control program, and may, for examples comprise a set of predefined program steps as described above. The configuration or update may comprise a value for a predetermined parameter.

In some examples, the method further comprises confirming, by a user or by an external control unit, that the update or configuration is correct based on the received logging data.

The logging data may be related to the receipt of the update or configuration, and the controller 300 is configured to install the update or configuration in response to receipt of a confirmation that the logging data relates to a correct set of instructions. In this way, the controller 300 may receive data, transmit a logging entry relating to the receipt, and then install the data in response to a positive verification that the data should be installed.

In another example, or in combination with the one described above, the logging data is related to the installation or the update or configuration. In this example the logging data may be for information purposes only and not affect the installation, or the method may further comprise activating the installation in response to the confirmation that the update or configuration is correct.

If the update or configuration is transmitted to the controller 300 in one or more steps, the verification as described above may be performed for each of the steps.

The method may further comprise, after transmitting the logging data to the second external device, verifying the update via a confirmation from the second external device 330 via the second communication channel.

In one embodiment the controller may be provided with at least one sensor 351 for sensing audio signals, e.g. a microphone. The microphone may be configured to be used as input for controlling the implantable constriction device or may be used for the purpose of authenticating the implantable constriction device, the controller, an external device or a communication stream.

With reference to FIG. 23a-23c there is provided an implantable controller 300. The controller 300 is connected to a sensor 351 wherein the sensor 351 is at least one microphone sensor 351 configured to record acoustic signals. For instance, the controller 300 may be configured to register a sound related to at least one of a bodily function of the patient and a function of the implantable constriction device 10. The controller 300 comprises a computing unit 306 configured to derive at least one of a pulse of the patient from the registered sound related to a bodily function, such as information related to the patient urinating, from the registered sound related to a bodily function. In the alternative, the controller 300 could be configured to derive information related to a functional status of the implantable constriction device 10 from the registered sound, such as RPM of the motor. To this end the computing unit 306 may be configured to perform signal processing on the registered sound (e.g. on a digital or analog signal representing the registered sound) so as to derive any of the above mentioned information related to a bodily function of the patient or a function of the implantable constriction device 10. The signal processing may comprise filtering the registered sound signals of the microphone sensor 351.

The implantable controller is placed in an implantable housing for sealing against fluid, and the microphone sensor 351 is placed inside of the housing. Accordingly, the controller and the microphone sensor 351 does not come into contact with bodily fluids when implanted which ensures proper operation of the controller and the microphone sensor 351.

In some implementations, the computing unit 306 is configured to derive information related to the functional status of an active unit 302 of the implantable constriction device 10, from the registered sound related to a function of the implantable constriction device 10. Accordingly, the computing unit 306 may be configured to derive information related to the functional status of at least one of: a motor, a pump and a transmission of the active unit 302 of the implantable constriction device 10, from the registered sound related to a function of the implantable constriction device 10.

The controller may comprise a transceiver 303,308 configured to transmit a parameter derived from the sound registered by the at least one microphone sensor 351 using the transceiver 303,308. For example, the transceiver 303, 308 is a transceiver configured to transmit the parameter conductively (303) to an external device 320 or wirelessly (308) to an external device 320.

A method of authenticating the implantable constriction device 10, the external device 320 or a communication signal or data stream between the external device 320 and the implantable constriction device 10 is also described with reference to FIGS. 23a-23c. The method comprises the steps of registering a sound related to at least one of a bodily function and a function of the implantable constriction device 10, using the at least one microphone sensor 351, connected to the controller 300. The method could in a first authentication embodiment comprise transmitting a signal derived from the registered sound, using the transceiver 303,308, receiving the signal in the external device 320, using the receiver 323,328 and comparing, in the external device 320, a parameter derived from the received signal with a reference parameter, using the computing unit 306. The method could in a second authentication embodiment comprise receiving a signal in the controller 300, from the external device 320, using the transceiver 323,328 and deriving a reference parameter from the received signal, using the computing unit 306 of the controller 300, and comparing, in the controller 300, a parameter derived from the received signal with the derived reference parameter, using the computing unit 306 of the controller 300. The methods further comprise the steps of the implantable controller 300 authenticating the external device 320, or the external device 320 authenticating the implantable controller 300, on the basis of the comparison. The registered sound could for example be related to the pulse of the patient or to the patient urinating.

Figure 23D:
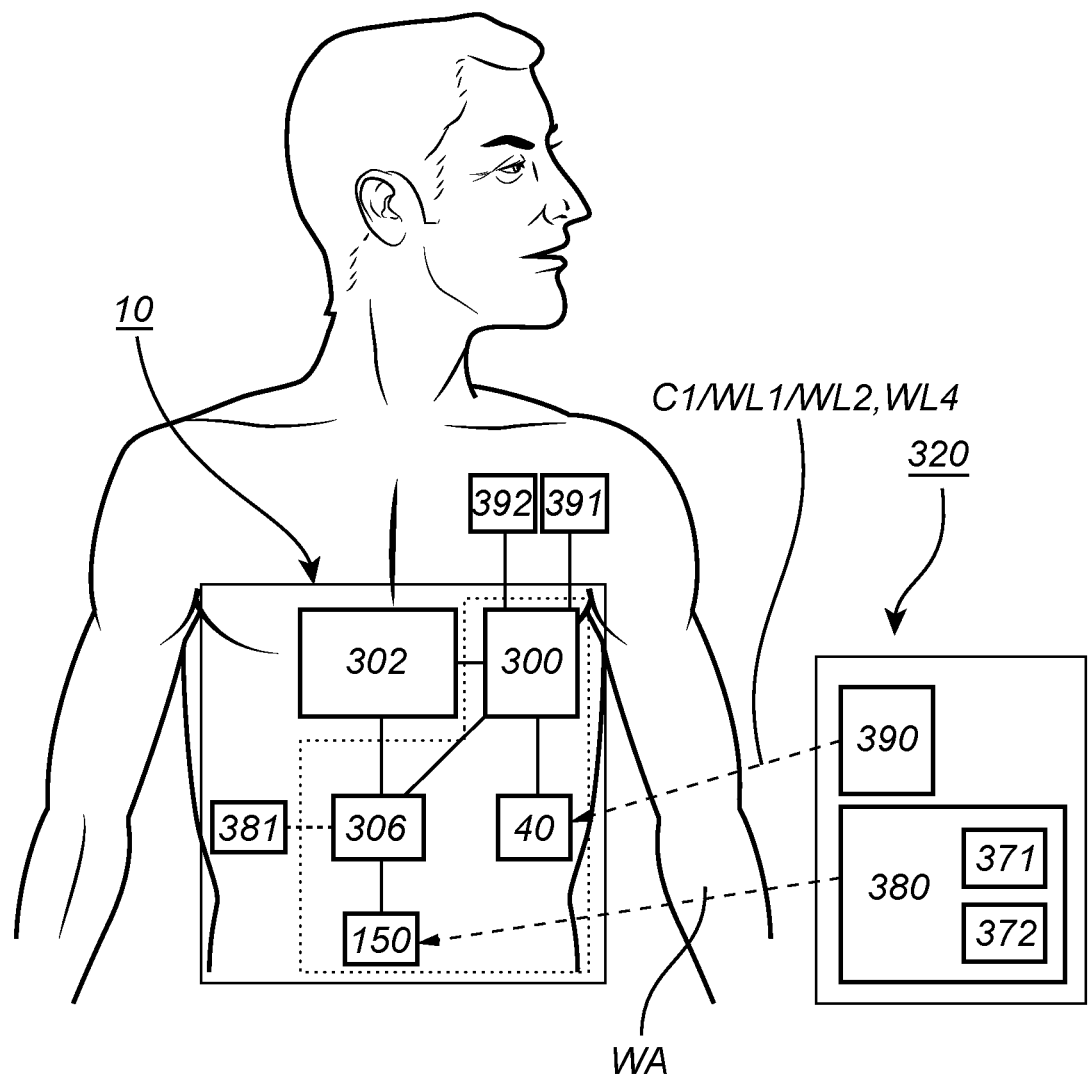
Figure 23E:
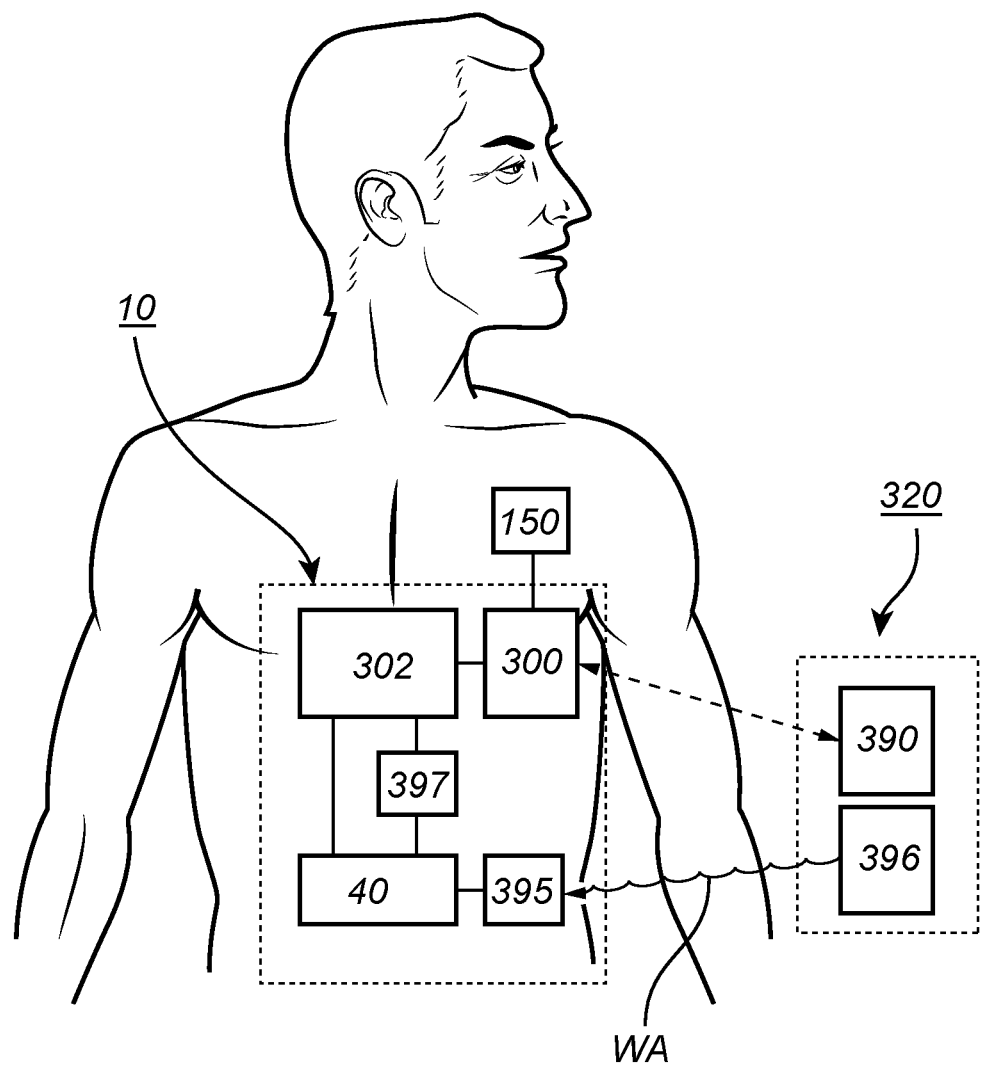

Embodiments relating to an implantable constriction device 10 having a controller 300 having a processor 306 with a sleep mode and an active mode will now be described with reference to FIG. 23d. The implant, the internal communication unit and the external device(s) may have the features described above with reference to FIGS. 23a-23c.

In an embodiment in which the controller 300 comprises a processor 306 having a sleep mode and an active mode, the controller 300 comprises or is connected to a sensor 351 and a processing unit 306 having a sleep mode and an active mode. The sensor 351 is configured to periodically measure a physical parameter of the patient, and the controller 300 is further configured to, in response to a sensor measurement preceding a predetermined value, setting the processing unit 306 in an active mode. That is, the controller 300 may "wake up" or be set in an active mode in response to a measurement from, for example, the body. A physical parameter of the patient could for example be a local or systemic temperature, saturation/oxygenation, blood pressure or a parameter related to an ischemia marker such as lactate.

By sleeping mode it is meant a mode with less battery consumption and/or processing power used in the processing unit 306, and by "active mode" it may be meant that the processing unit 306 is not restricted in its processing.

The sensor 351 may, for example, be a pressure sensor. The pressure sensor may be adapted to measure a pressure in an organ of a patient, a reservoir of the implant or a restriction device of the active unit 302. The sensor 351 may be an analog sensor or a digital sensor, i.e. a sensor 351 implemented in part in software. In some examples, the sensor is adapted to measure one or more of a battery or energy storage status of the implantable constriction device 10 and a temperature of the implantable constriction device 10. In this way, the sensor 351 may periodically sense a pressure of the implantable constriction device 10 or of the patient and set the processing unit 306 in an active mode if the measured pressure is above a predetermined value. Thus, less power, i.e. less of for example a battery or energy storage comprised in the implant, may be used, thereby prolonging the lifetime of the implantable constriction device 10 or increasing the time between charging occasions of the implantable constriction device 10.

In some examples, the processor 306, when in set in the active mode, may cause a sensation generator 381 connected to the implant, comprised in the implantable constriction device 10 or comprised in an external device 320, 330, to generate a sensation detectable by a sense of the patient. For example, the processor may cause the sensation generator to generate a sensation in response to a measure battery status, for example that the battery is above or below a predetermined level, that a measured pressure is above or below a predetermined level, or that another measured parameter has an abnormal value, i.e. less than or exceeding a predetermined interval or level. The sensation generator has been described in further detail earlier in this description.

The processing unit 306 may be configured to perform a corrective action in response to a measurement being below or above a predetermined level. Such a corrective action may, for example, be increasing or decreasing a pressure, increasing, or decreasing electrical stimulation, increasing, or decreasing power.

The controller 300 may comprise a signal transmitter 320 connected to the processing unit, and wherein the processing unit is configured to transmit data relating to the measurement via the transceiver 308 of the controller 300 or an additional internal signal transmitter 392. The transmitted data may be received by an external device 320.

The external device may have an external communication unit 390. The external device 320 may comprise a signal provider 380 for providing a wake signal to the controller 300. In some examples, the signal provider comprises a coil or magnet 371 for providing a magnetic wake signal.

The controller 300 may implement a corresponding method for controlling an implantable constriction device 10 when implanted in a patient. The method comprises measuring, with a sensor of the controller 300 connected to or comprised in the controller 300, a physiological parameter of the patient or a parameter of the implantable constriction device 10, and, in response to a sensor measurement having an abnormal value, setting, by the controller 300, a processor 306 of the controller 300 from a sleep mode to an active mode. The measuring may be carried out periodically. By "abnormal value" it may be meant a measured value exceeding or being less than a predetermined value, or a measured value being outside a predetermined interval. The method may further comprise generating, with a sensation generator 381 as described above, a sensation detectable by the patient. In some examples, the generating comprises requesting, by the processor, the sensation generator 381 to generate the sensation.

The method may further comprise to perform a medical intervention in response to a sensor measurement having an abnormal value, preferably after the processing unit has been set in the active mode.

A system comprising an implantable constriction device 10 having a controller 300 having a sleep mode and an active mode will now be described with reference to FIG. 23d. In one embodiment, the controller 300 comprises a sensor 351 adapted to detect a magnetic field and a processing unit 306 having a sleep mode and an active mode, now described with reference to FIGS. 23a-23c. The external control unit 320 comprises a signal provider 380 adapted to provide a magnetic field detectable by the internal sensor 351. The controller 300 is further configured to, in response to a detected magnetic field exceeding a predetermined value, setting the processing unit 306 in an active mode. In this way, the external device 320 may cause a sleeping controller 300 or processor 306 to "wake up".

The sensor 351 may, for example, be a hall effect sensor, a fluxgate sensor, an ultra-sensitive magnetic field sensor, a magneto-resistive sensor, an AMR or GMR sensor, or the sensor may comprise a third coil having an iron core.

The magnetic field provider 380 may have an off state, wherein it does not provide any magnetic field, and an on state, wherein it provides a magnetic field. For example, the magnetic field provider 380 may comprise a magnet 371, a coil 371, a coil having a core 371, or a permanent magnet 371. In some embodiments, the magnetic field provider 380 may comprise a shielding means for preventing a magnet 371 or permanent magnet 371 from providing a magnetic field in the off state. In order to provide a substantially even magnetic field, the magnetic field provider may comprise a first and a second coil arranged perpendicular to each other.

After the processing unit 306 has been set in an active mode, i.e. when the processing unit 306 has been woken, the implant may determine a frequency for further communication between the controller 300 and the external device 320. The controller 300 may thus comprise a frequency detector 391 for detecting a frequency for communication between the controller 300 and the second communication unit 390. The frequency detector 391 is, for example, an antenna. The external device 320 may comprise a frequency indicator 372, for transmitting a signal indicative of a frequency. The frequency indicator 372, may, for example, be a magnetic field provider capable of transmitting a magnetic field with a specific frequency. In some examples the frequency indicator is comprised in or the same as the magnetic field provider 371. In this way, the frequency signal is detected using means separate from the sensor, and can, for example, be detected using a pin on a chip.

Alternatively, the controller 300 and the external device 320 may communicate using a predetermined frequency or a frequency detected by means defined by a predetermined method according to a predetermined protocol to be used for the communication between the controller 300 and the external device 320.

In some embodiments, the sensor 351 may be used for the communication. The communication may in these embodiments be performed with such that a frequency of the magnetic field generated by the coil is 9-315 kHz, or the magnetic field generated by the coil is less than or equal to 125 kHz, preferably less than 58 kHz. The frequency may be less than 50 Hz, preferably less than 20 Hz, more preferably less than 10 Hz, in order to be transmittable through a titan box.

In some embodiments, the controller 300 comprises a receiver unit 392, and the internal control unit and the external control unit are configured to transmit and/or receive data via the receiver unit 392 via magnetic induction. The receiver unit 392 may comprise a high-sensitivity magnetic field detector, or the receiver unit may comprise a fourth coil for receiving the magnetic induction.

The system may implement a method for controlling a medical implant implanted in a patient. The method comprises monitoring for signals by a sensor 351 comprised in the controller 300 communicatively coupled to the active unit 302, providing, from a signal provider 380 comprised in an external device 320, a wake signal, the external device 320 being adapted to be arranged outside of the patient's body, and setting, by the controller 300 and in response to a detected wake signal WS, a mode of a processing unit 306 comprised in the internal control unit from a sleep mode to an active mode.

The method may also comprise detecting, using a frequency detector 391, a frequency for data communication between the controller 300 and a second communication unit 390 being associated with the external device 320. The frequency detector 391 is communicatively coupled to the controller 300 or the external device 320. The detection may be performed using a detection sequence for detecting the frequency. This detection sequence may, for example, be a detection sequence defined in the protocol to be used for communication between the controller 300 and the second communication unit 390. Potential protocols that may be used for communication between the controller 300 an and the external device 320 has been described earlier in this description. Thus, the method may comprise determining, using the frequency detector 391, the frequency for data communication, and initiating data communication between the controller 300 and the second communication unit 390. The data communication can, for example, comprise one or more control instructions for controlling the implantable constriction device 10 transmitted from the external device 320, or, for example, comprise data related to the operation of the implantable constriction device 10 and be transmitted from the controller 300.

In some examples, the medical implant may comprise or be connected to a power supply for powering the implantable constriction device 10. This will now be described with reference to FIG. 23e. The medical implant, the internal control unit, and the external device(s) may comprise all elements described above with reference to FIGS. 23a-23c and FIG. 23d. The power supply may comprise an implantable energy storage unit 40 for providing energy to the medical implant, an energy provider 397 connected to the implantable energy storage unit 40 and connected to an energy consuming part of the implantable constriction device 10, the energy provider 397 being configured to store energy to provide a burst of energy to the energy consuming part, wherein the energy provider 397 is configured to be charged by the implantable energy storage unit 40 and to provide the energy consuming part with electrical power during startup of the energy consuming part.

Alternatively, the implantable constriction device 10 may comprise a first implantable energy storage unit 40 for providing energy to an energy consuming part of the implantable constriction device 10, a second implantable energy storage unit 397 connected to the implantable energy storage unit 40 and connected to the energy consuming part, wherein the second implantable energy storage unit 397 is configured to be charged by the implantable energy storage unit 40 and to provide the energy consuming part with electrical power during startup of the energy consuming part. The second implantable energy storage unit 397 has a higher energy density than the first implantable energy storage unit 40. By having a "higher energy density" it may be meant that the second implantable energy storage unit 397 has a higher maximum energy output per time unit than the first implantable energy storage unit 40. The second energy storage 397 may be an energy provider as discussed below.

The energy consuming part may be any part of the implantable constriction device 10, such as a motor for powering the hydraulic pump, a valve, a processing or computing unit, a communication unit, a device for providing electrical stimulation to a tissue portion of the body of the patient, a CPU for encrypting information, a transmitting and/or receiving unit for communication with an external unit (not shown as part of the energy consuming part in the drawings, that is, the communication unit may be connected to the energy storage unit 40 and to the energy provider 397), a measurement unit or a sensor, a data collection unit, a solenoid, a piezo-electrical element, a memory metal unit, a vibrator, a part configured to operate a valve comprised in the medical implant, or a feedback unit.

In this way, an energy consuming part requiring a quick start or an energy consuming part which requires a high level or burst of energy for a start may be provided with sufficient energy. This may be beneficial as instead of having an idle component using energy, the component may be completely turned off and quickly turned on when needed. Further, this may allow the use of energy consuming parts needing a burst of energy for a startup while having a lower energy consumption when already in use. In this way, a battery or an energy storage unit having a slower discharging (or where a slower discharging is beneficial for the lifetime or health of the battery) may be used for the implant, as the extra energy needed for the startup is provided by the energy provider.

Energy losses may occur in a battery or energy storage unit of an implant if the battery or energy storage unit is discharged too fast. These energy losses may for example be in the form of heat, which may damage the battery or energy storage unit. By the apparatus described in these examples, energy may be provided from the battery or energy storage unit in a way that does not damage the battery or energy storage unit, which may improve the lifetime of the battery or energy storage unit and thereby the lifetime of the medical implant.

In some examples, the discharging from the implantable energy storage unit 40 during startup of the energy consuming part is slower than the energy needed for startup of the energy consuming part, i.e. the implantable energy storage unit 40 is configured to have a slower discharging than the energy needed for startup of the energy consuming part. That is, there is a difference between the energy needed by the energy consuming part and the energy the implantable energy storage unit 40 is capable of providing without damaging the implantable energy storage unit 40. In other words, a maximum energy consumption of the energy consuming part may be higher than the maximum energy capable of being delivered by the implantable energy storage unit 40 without causing damage to the implantable energy storage unit, and the energy provider 397 may be adapted to deliver an energy burst corresponding to difference between the required energy consumption and the maximum energy capable of being delivered by the implantable energy storage unit 40. The implantable energy storage unit 40 may be configured to store a substantially larger amount of energy than the energy burst provider 397 but may be slower to charge.

The implantable energy storage unit 40 may be any type of energy storage unit suitable for an implant, such as a re-chargeable battery or a solid-state battery, such as a thionyl chloride battery. The implantable energy storage unit 40 may be connected to the energy consuming part and configured to power the energy consuming part after it has been started using the energy provider 397.

The energy provider 397 may be any type of part configured to provide a burst of energy for the energy consuming part. In some examples, the energy provider 397 is a capacitor, such as a start capacitor, a run capacitor, a dual run capacitor or a supercapacitor. The energy provider 397 may be connected to the implantable energy storage unit 40 and be adapted to be charged using the implantable energy storage unit 40. In some examples, the energy provider may be a second energy provider 397 configured to be charged by the implantable energy storage unit 40 and to provide the energy consuming part with electrical energy. The implantable constriction device 10 may further comprising a temperature sensor for sensing a temperature of the capacitor and the temperature sensor may be integrated or connected to the controller 300 such that the sensed temperature can be used as input for controlling the implantable constriction device 10 or as feedback to be sent to an external device 320.

A corresponding method for powering a medical implant may also be contemplated. The method comprises the steps of initiating an energy consuming part 302 of the implant, the energy consuming part being connected to an implantable energy storage unit 40, providing an initial burst of energy to the energy consuming part using an energy provider 397 connected to the implantable energy storage unit 40 and to the energy consuming part 302, the energy provider 397 being adapted to provide a burst of energy to the energy consuming part, and subsequently powering the energy consuming part 302 using the implantable energy storage unit 40.

In some examples, a maximum energy consumption of the energy consuming part is higher than the maximum energy capable of being delivered by the implantable energy storage unit 40 without causing damage to the implantable energy storage unit 40, and the energy provider 397 is adapted to deliver an energy burst corresponding to difference between the required energy consumption and the maximum energy capable of being delivered by the implantable energy storage unit 40.

The method may further comprise the step of charging the energy provider 397 using the implantable energy storage unit 40.

Initiating an energy consuming part 302 may comprise transitioning a control unit of the medical implant from a sleep mode to an operational or active mode.

The implantable energy storage unit 40 may be adapted to be wirelessly charged and the implantable energy storage unit may be connected to an internal charger 395 for receiving wireless energy from an external device 320 via an external charger 396, and the method may comprise wirelessly charging the implantable energy storage unit 40. In some examples, the method comprises controlling a receipt of electrical power from an external energy storage unit at the internal charger 395. The internal energy storage unit 40 may be charged via the receipt of a transmission of electrical power from an external energy storage unit 396 by the internal charger 395.

The embodiments described herein may advantageously be combined. For example, all the embodiments relating to the communication and controlling of the implant may be combined with the embodiments relating to the programming of the implant, the methods and systems for improving energy consumption or the power supply. The embodiments relating to the programming of the implant may be combined with any of the embodiments relating to improving the energy consumption or the power supply. The embodiments relating to the power supply maybe combined with the methods and systems for improving the energy consumption.

A computer program product of, or adapted to be run on, an internal computing unit or an external device is also provided, which comprises a computer-readable storage medium with instructions adapted to make the internal computing unit and/or the external device perform the actions as described in any embodiment or example above.

Figure 24A:
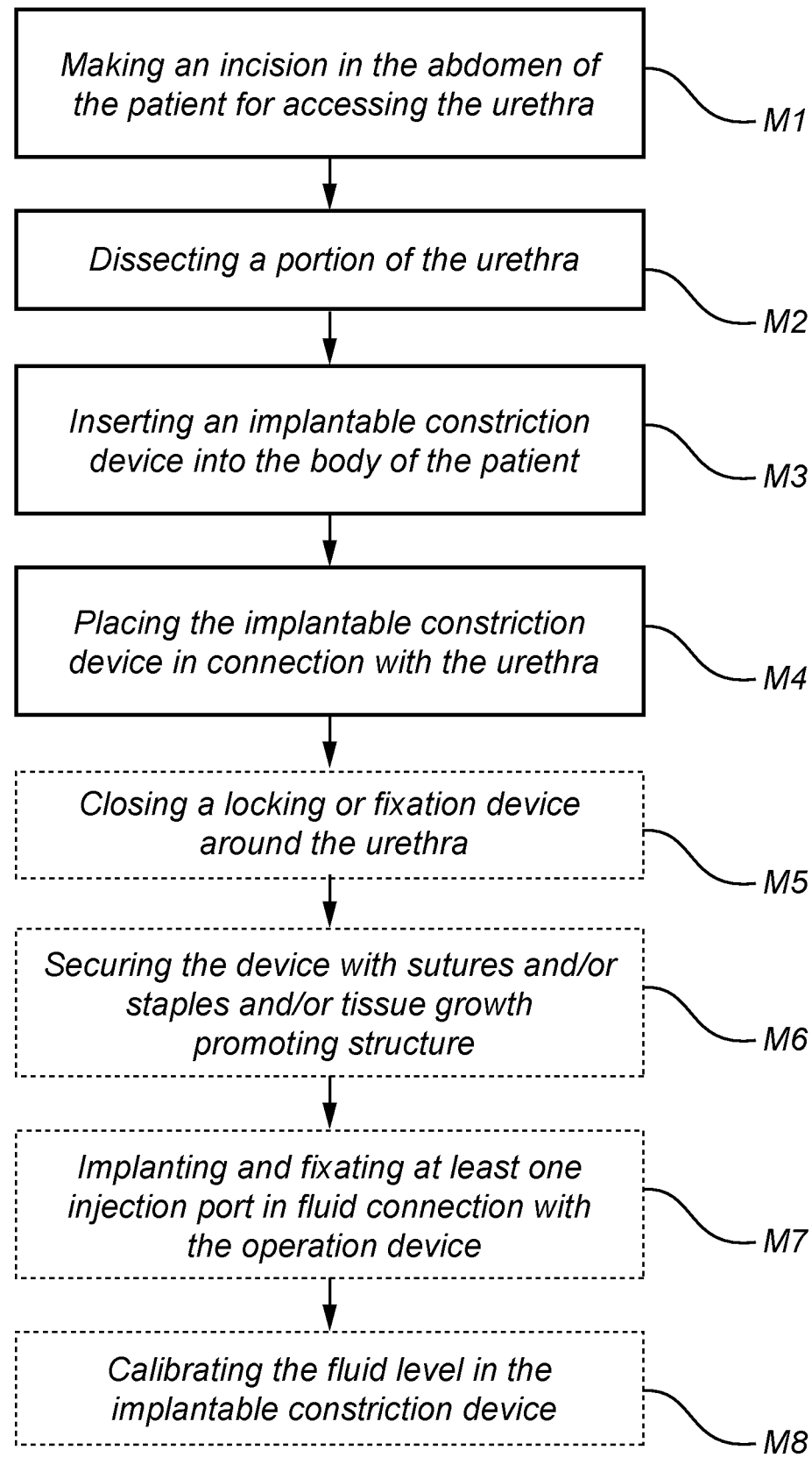
FIGS. 24a-24c are flow charts describing various aspect of the surgical procedure required for implanting and testing the implantable constriction device.
Figure 24B:
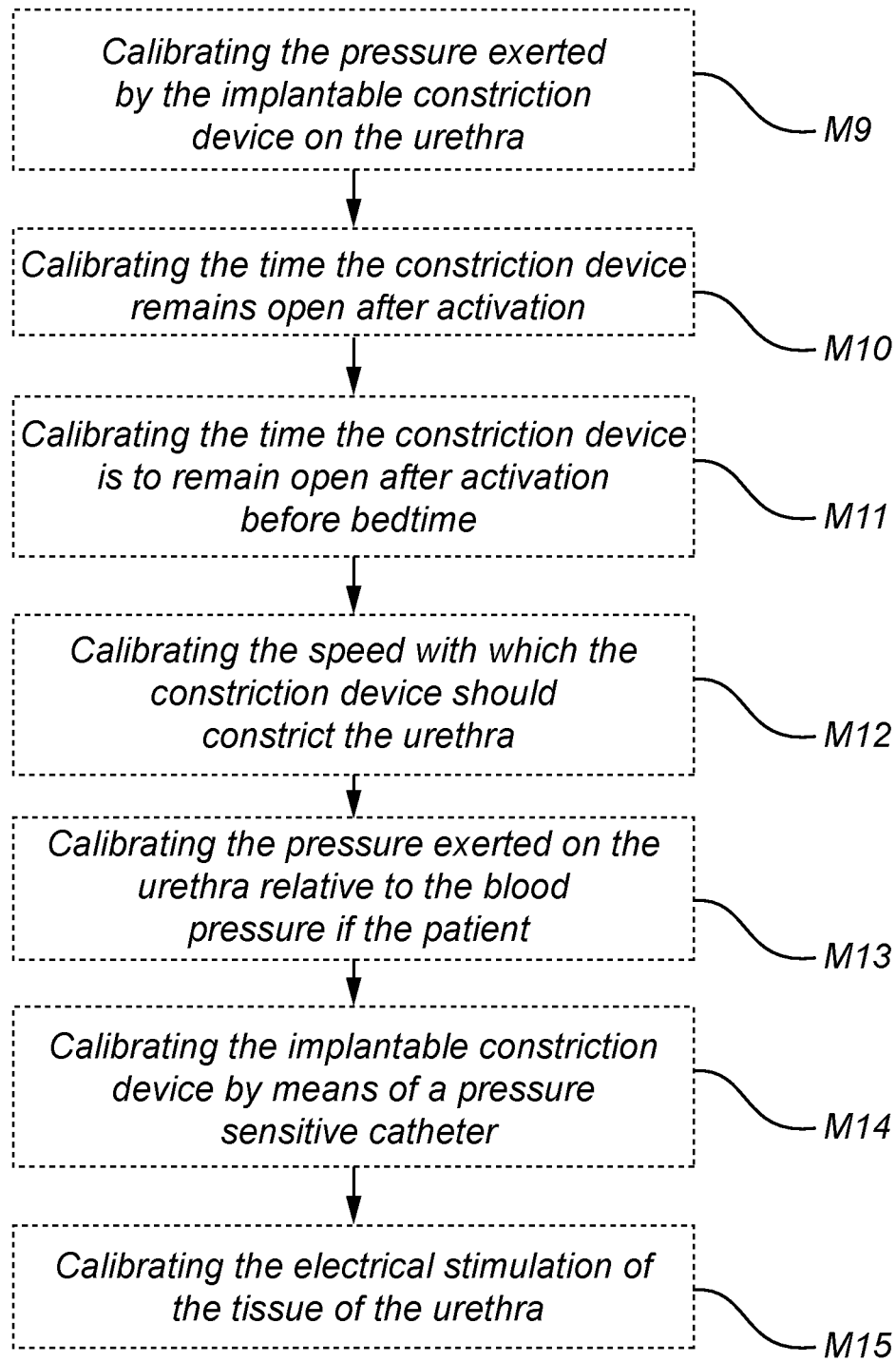
Figure 24C:
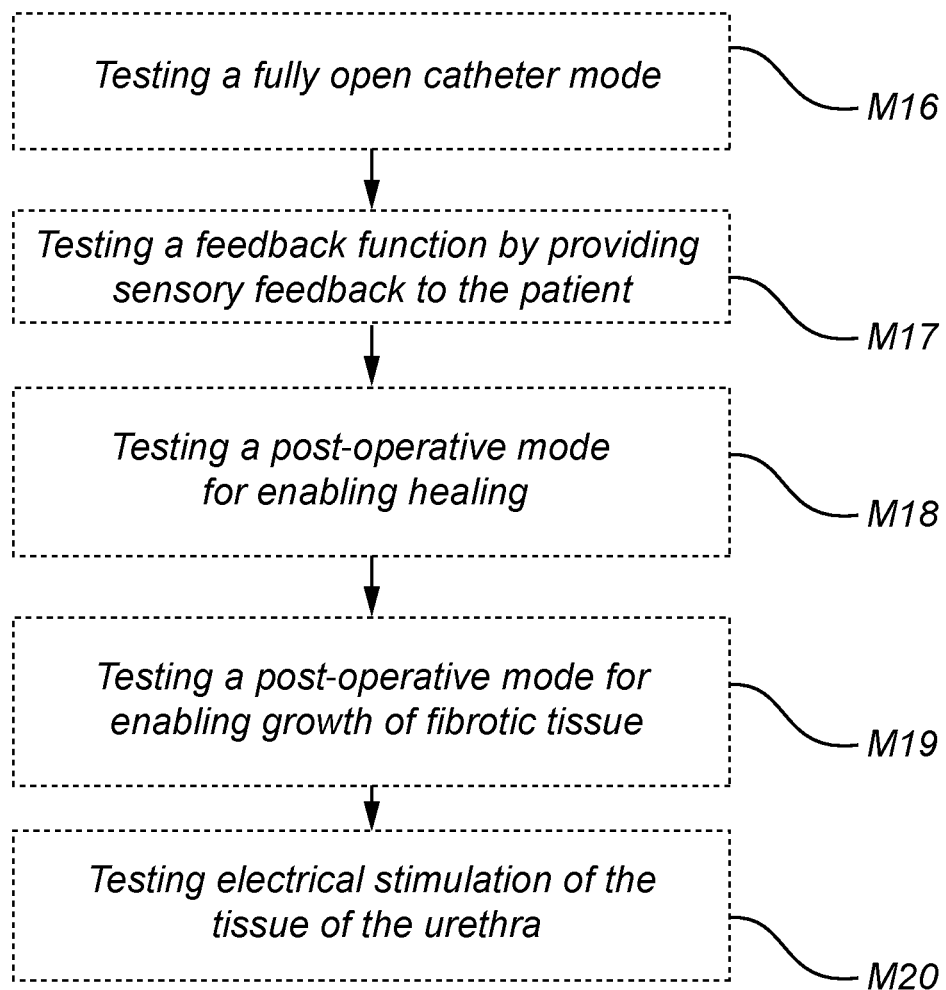

FIG. 24a-24c is a flowchart describing a method of implanting, calibrating, and testing an implantable constriction device, according to any one of the embodiments herein. Method steps outlined with dotted lines are to be considered as optional and as such not required to fulfill a surgical method of implanting an implantable constriction device. The method comprises the step M1 of making an incision in the abdomen of the patient, for accessing the urethra. The incision may be a single incision for implanting the implantable constriction device using open surgical techniques or may be a plurality of incisions for implanting the implantable constriction device using minimally invasive, endoscopic techniques, or a combination of open and endoscopic techniques. In alternative embodiments the incision could be a single incision for the insertion of a laparoscopic port with multiple entry port enabling a laparoscopic procedure with a single incision (SILS). For enabling optical inspection in a minimally invasive procedure a cavity within the body needs to be created, which is typically done by means of pressurized CO2 gas being introduced through a trocar placed in an incision.

The method further comprises the step M2 of dissecting a portion of the urethra for preparing the portion of the urethra for the placement and fixation of an implantable constriction devise.

The method further comprises the step M3 of inserting an implantable constriction device into the body of the patient. The method may be commenced as a minimally invasive procedure (such as Laparoscopic, SILS, NOTES etc.) and continued as open surgery when the implantable constriction device should be inserted. The procedure could also be performed as a hand assisted minimally invasive procedure in which the surgeon can insert a hand through a small incision in the abdomen. Hand assisted surgery has the benefit of providing sensory perception and the possibility to guide the surgical instruments whilst maintaining the possibility of visually observing the entire procedure on a TV screen overhead.

The step M3 of inserting an implantable constriction device into the body of the patient could comprise inserting the implantable constriction device 10 described with reference to FIGS. 1a-1e.

The step M3 of inserting an implantable constriction device into the body of the patient could comprise inserting the implantable constriction device 10 described with reference to FIGS. 2a-2b.

The step M3 of inserting an implantable constriction device into the body of the patient could comprise inserting the implantable constriction device 10 described with reference to FIGS. 3a-3f.

The step M3 of inserting an implantable constriction device into the body of the patient could comprise inserting the implantable constriction device 10 described with reference to FIG. 4.

The step M3 of inserting an implantable constriction device into the body of the patient could comprise inserting the implantable constriction device 10 described with reference to FIG. 5.

The step M3 of inserting an implantable constriction device into the body of the patient could comprise inserting the implantable constriction device 10 described with reference to FIGS. 6a-6b.

The step M3 of inserting an implantable constriction device into the body of the patient could comprise inserting the implantable constriction device 10 described with reference to FIG. 7.

The step M3 of inserting an implantable constriction device into the body of the patient could comprise inserting the implantable constriction device 10 described with reference to FIG. 8a.

The step M3 of inserting an implantable constriction device into the body of the patient could comprise inserting the implantable constriction device 10 described with reference to FIG. 8b.

The step M3 of inserting an implantable constriction device into the body of the patient could comprise inserting the implantable constriction device 10 described with reference to FIG. 8c.

The step M3 of inserting an implantable constriction device into the body of the patient could comprise inserting the implantable constriction device 10 described with reference to FIGS. 9a-9c.

The step M3 of inserting an implantable constriction device into the body of the patient could comprise inserting the implantable constriction device 10 described with reference to FIGS. 10a-10b.

The step M3 of inserting an implantable constriction device into the body of the patient could comprise inserting the implantable constriction device 10 described with reference to FIGS. 10c-10d.

The step M3 of inserting an implantable constriction device into the body of the patient could comprise inserting the implantable constriction device 10 described with reference to FIGS. 11a-11b.

The step M3 of inserting an implantable constriction device into the body of the patient could comprise inserting the implantable constriction device 10 described with reference to FIG. 11c.

The step M3 of inserting an implantable constriction device into the body of the patient could comprise inserting the implantable constriction device 10 described with reference to FIG. 11d.

The step M3 of inserting an implantable constriction device into the body of the patient could comprise inserting the implantable constriction device 10 described with reference to FIG. 11e.

The step M3 of inserting an implantable constriction device into the body of the patient could comprise inserting the implantable constriction device 10 described with reference to FIG. 11f.

The step M3 of inserting an implantable constriction device into the body of the patient could comprise inserting the implantable constriction device 10 described with reference to FIG. 18a.

The step M3 of inserting an implantable constriction device into the body of the patient could comprise inserting the implantable constriction device 10 described with reference to FIG. 18b.

The step M3 of inserting an implantable constriction device into the body of the patient could comprise inserting the implantable constriction device 10 described with reference to FIG. 18c.

The step M3 of inserting an implantable constriction device into the body of the patient could comprise inserting the implantable constriction device 10 described with reference to FIG. 18d.

The method of implanting the implantable constriction device described in the flow chart of FIG. 24a further comprises the step M4 of placing the implantable constriction device in connection with the urethra, such that the implantable constriction device can constrict the urethra to restrict the flow of urine therethrough. The step M4 of placing the implantable constriction device in connection with the urethra could optionally comprise the step M5 of closing a locking or fixation device of the implantable constriction device around the urethra to fixate the implantable constriction device to the urethra of the patient. The locking or fixation device of the implantable constriction device could for example be a lock comprising the locking members as described in connection with FIGS. 1a-1d.

The step M4 of placing the implantable constriction device in connection with the urethra could optionally comprise the step M6 of securing the implantable constriction device by means of at least one of sutures, staples and tissue growth promoting structure. A tissue growth promoting structure could for example comprise a mesh configured to be integrated with fibrotic tissue or a structure made from a microporous material.

The step M3 of inserting an implantable constriction device into the body of the patient may comprise the step of inserting an implantable controller into the body of the patient, for controlling the implantable constriction device. The step of inserting an implantable controller may comprise fixating the implantable controller to tissue or bone in the body of the patient. The implantable controller could be the controller described with reference to FIGS. 8a-9c and 23.

The step M3 of inserting an implantable constriction device into the body of the patient could comprise inserting an operation device comprising at least one of: an implantable hydraulic pump and an implantable valve and fixating the implantable operation device to tissue or bone in the body of the patient. The hydraulic pump could be the hydraulic pump of FIG. 12a, 12b, or could be the hydraulic pump of FIG. 14, or could be the hydraulic pump of FIG. 15a, or could be the hydraulic pump of FIG. 15b, or could be the hydraulic pump of FIG. 16.

The method could further comprise the step M7 of implanting at least one injection port, which is in fluid connection with the operation device. The step M7 of implanting at least one injection port could comprise fixating the at least one injection port, which may be done subcutaneously, for example by means of at least one of sutures, staples and tissue growth promoting structure. The injection port comprises a self-sealing membrane which may be penetrated by an injection needle for injecting a fluid into the implantable injection port.

The method may further comprise the step M8 of calibrating the fluid level in the implantable constriction device through injection or retraction of fluid via the implantable injection port. Calibration of fluid levels can be done at routine check-up or in response to the implantable constriction device not functioning optimally or in response to the implantable constriction device transmitting a signal indicating that the fluid level needs to be calibrated. The need for calibration can be based on leakage or diffusion of fluid from the implantable constriction device.

The method may further comprise the step M9 of calibrating the pressure exerted by the implantable constriction device on the urethra, which may comprise calibrating the pressure in the implantable constriction device through the measurement of the pressure in the implantable constriction device, e.g. by means of a pressure sensor in direct or indirect contact with the fluid in the implantable constriction device. The calibration of the pressure exerted by the implantable constriction device on the urethra my alternatively be performed by means of a pressure sensitive catheter M14 inserted into the urethra and measuring the force exerted thereon by the implantable constriction device.

The method may further comprise the step M10 of calibrating the time during which the implantable constriction device is to remain open after activation, such that suitable time for completion of the urination is provided after the device has been activated.

The method may further comprise the step M11 of calibrating the time during which the implantable constriction device is to remain open before bedtime after activation, such that suitable time for complete bladder emptying is provided after the device has been activated.

The method may further comprise the step M12 of calibrating the speed with which the implantable constriction device should constrict the urethra. This could allow the patient to provide feedback to the device with regards to the closing such that the implantable constriction device functions in an optimal way.

The method may further comprise the step M13 of calibrating the pressure exerted on the urethra relative to the blood pressure if the patient. This could be used to make sure that the tissue of the urethra is not constricted such that the blood flow in the tissue is adversely affected or hampered. The pressure exerted on the urethra could be calibrated relative to the systolic blood pressure of the patient, such that the pressure does not exceed the systolic blood pressure, to allow blood to be pressed into the tissue during the systolic cardiac phase. In the alternative, the pressure exerted on the urethra could be calibrated relative to the diastolic blood pressure of the patient, such that the pressure does not exceed the diastolic blood pressure, to allow normal circulation through the tissue of the urethra.

The method may further comprise the step M15 of calibrating the electrical stimulation of the tissue of the urethra on the basis of a physiological marker, such as an ischemia marker, or on the basis of input from the patient e.g. related to a sensory response induced by the electrical stimulation, such as pain related to the electrical stimulation.

The method may further comprise the steps M16-M20 of performing tests related to the function of the implantable constriction device. These tests may be performed during the surgical procedure or in closely after the surgical procedure.

The method may comprise the step M16 of testing a fully open catheter mode, in which a hydraulic constriction element is emptied as much as possible to allow the urethra to expand maximally such that a catheter can be inserted through the implantable constriction device.

The method may comprise the step M17 of testing a feedback function by providing sensory feedback to the patient, which could be sensory feedback in the form of vibrations created by the motor of the implantable constriction device, or created by a separate vibrator. Sensory feedback could in the alternative be created in the form of electrical stimulation.

The method may comprise the step M18 of testing a post-operative mode for enabling healing of the urethra and the surrounding tissue after implantation. It may be the case that the tissue surrounding the device needs to heal before the device may be used to restrict the flow of urine in the urethra. It may also be the case that the device needs to be fixated by the ingrowth of fibrotic tissue into a fixating structure for the fixation of the implantable constriction device, which may be tested in a test of a post-operative mode for enabling growth of fibrotic tissue M19.

The method may comprise the step M20 of testing an electrical stimulation of the tissue of the urethra to establish that the electrical stimulation and the control and calibration of the electrical stimulation functions as intended.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way. All examples herein should be seen as part of the general description and therefore possible to combine in any way in general terms.

In the following, numbered aspect groups 280SE-302SE of the present invention are provided. The different aspects are numbered individually within the groups and the references to other aspects relate to aspects within the same group. The protective scope is however defined by the appended claims.

ASPECT_280SE_Constriction_Urine_Ring_Integrated-Channel

1. A support element (24*a*) for an implantable constriction device for constricting a urethra of a patient, the support element (24*a*) being configured to form at least a portion of a surrounding structure (20) configured to surround and support at least one operable hydraulic constriction element (101) configured to constrict the urethra (U) for restricting the flow of urine therethrough, wherein the support element (24*a*) comprises at least one fluid conduit (109*a*) at least partially integrated in the support element (24*a*).

2. The support element (24*a*) according to aspect 1, wherein the at least one fluid conduit (109*a*) is completely integrated in the support element (24*a*).

3. The support element (24*a*) according to any one of the preceding aspects, wherein the support element (24*a*) comprises at least one curvature (C) adapted for the curvature of the urethra (U).

4. The support element (24*a*) according to aspect 3, wherein the curvature (C) has a radius (R) in the range 3 mm-50 mm.

5. The support element (24*a*) according to aspect 3, wherein the curvature (C) has a radius (R) in the range 5 mm-30 mm.

6. The support element (24*a*) according to any one of the preceding aspects, wherein the support element (24*a*) comprises:
   a first curvature (C) having a first radius (R1), and
   a second curvature (C) having a second radius (R2), and wherein
   the first radius (R1) is smaller than the second radius (R2).

7. The support element (24*a*) according to any one of the preceding aspects, wherein the support element (24*a*) is substantially rigid.

8. The support element (24*a*) according to aspect 7, wherein a major portion of the support element (24*a*) is made from a material having a modulus of elasticity (E) in the range 0.2 GPa-1000 GPa or in the range 1 GPa-400 GPa.

9. The support element (24*a*) according to aspect 7, wherein the support element (24*a*) has a modulus of elasticity (E) in the range 0.2 GPa-1000 GPa or in the range 1 GPa-400 GPa.

10. The support element (24*a*) according to any one of the preceding aspects, wherein the support element (24*a*) comprises a connection portion (24*a*') for connecting the support element (24*a*) to another support element (24*b*) for at least partially forming the surrounding structure (20).

11. The support element (24*a*) according to aspect 10, wherein the support element (24*a*) comprises a portion of a hinge (26) for hingedly connecting the support element (24*a*) to another support element (24*b*) for at least partially forming the surrounding structure (20).

12. The support element (24*a*) according to aspect 11, wherein the support element (24*a*) comprises the portion of a hinge (26) at a first end of the support element (24*a*) and wherein the support element comprises another connection portion (24*a*') at a second end for connecting to:
   a. another portion of the support element (24*a*), or
   b. another support element (24*b*), for at least partially forming the surrounding structure (20).

13. The support element (24*a*) according to any one of the preceding aspects, wherein the support element (24*a*) comprises an inner surface (28*a*) configured to be directed towards the urethra (U), when implanted, wherein the inner surface (28*a*) comprises a fixation surface for fixating the at least one operable hydraulic constriction element (101), and wherein the fixation surface comprises at least one outlet (23*a*) from the at least partially integrated fluid conduit (109*a*), such that a fluid can flow through the at least partially integrated fluid conduit (109*a*) into the operable hydraulic constriction element (101) for constricting the urethra (U).

14. The support element (24*a*) according to aspect 13, wherein the inner surface (28*a*) comprises a fixation surface for fixating at least two operable hydraulic constriction elements (101a,101b).

15. The support element (24a) according to aspect 14, wherein the support element (24a) comprises a second fluid conduit (109b) at least partially integrated in the support element (24a), and wherein the first at least partially integrated fluid conduit (109a) is configured to conduct fluid to the first operable hydraulic constriction element (101a) and the second at least partially integrated fluid conduit (109b) is configured to conduct fluid to the second operable hydraulic constriction element (101b).

16. The support element (24a) according to any one of aspects 1-15, wherein the support element (24a) comprises at least one operable hydraulic constriction element (101a) configured to constrict the urethra (U) for restricting the flow of urine therethrough, and wherein the at least one operable hydraulic constriction element (101a) is in fluid connection with the at least one fluid conduit (109a) at least partially integrated in the support element (24a).

17. The support element (24a) according to aspect 16, wherein the support element (24a) comprises a second operable hydraulic constriction element (101b), and wherein the at least one second operable hydraulic constriction element (101b) is in fluid connection with the second fluid conduit (109b) at least partially integrated in the support element (24a).

18. The support element (24a) according to aspect 17, wherein the first operable hydraulic constriction element (101a) has a larger volume than the second operable hydraulic constriction element (101b).

19. The support element (24a) according to aspect 18, wherein the first operable hydraulic constriction element (101a) has a volume which is at least 1.5 times larger than the volume of the second operable hydraulic constriction element (101b).

20. The support element (24a) according to any one of the preceding aspects, wherein the support element (24a) comprises an outer surface (21) configured to be directed away from the urethra, when implanted, wherein the outer surface (21) comprises at least one inlet to the at least one fluid conduit (109a), and wherein the at least one inlet is configured to be in fluid connection with a hydraulic pump (104) for pumping fluid to the operable hydraulic constriction element (101a) for constricting the urethra (U).

21. The support element (24a) according to any one of aspects 14-20, wherein the support element (24) has a length (l1) in the axial direction (AD) of the urethra (U), when implanted, and wherein at least one operable hydraulic constriction element (101) has a length (l2) in the axial direction (AD) of the urethra (U), when implanted, and wherein the length (l2) of the at least one operable hydraulic constriction element (101) is longer than the length (l1) of the support element (24).

22. The support element (24a) according to any one of the preceding aspects, wherein the support element (24a) further comprises an electrode arrangement configured to be arranged between the support element (24a) and the urethra (U) and to engage and electrically stimulate muscle tissue of the urethra (U) to exercise the muscle tissue to improve the conditions for long term implantation of the implantable constriction device (10).

23. A surrounding structure (20) for an implantable constriction device (10) for constricting a urethra (U) of a patient, the surrounding structure (20) being configured to surround the urethra (U) when implanted, the surrounding structure (20) comprises at least one support element (24a,24b24c,24d) according to any one of aspects 1-21.

24. The surrounding structure (20) according to aspect 23, wherein the surrounding structure (20) comprises a second support element (24b), and wherein the first and second support elements (24a,24b) are configured to be connected and together form at least a portion of the surrounding structure (20).

25. The surrounding structure (20) according to aspect 24, wherein the first and second support elements (24a, 24b) are configured for forming the surrounding structure (20) and thereby surround the urethra (U).

26. The surrounding structure (20) according to aspect 25, wherein the first and second support elements (24a, 24b) are hingedly connected to each other for forming the surrounding structure (20), such that a periphery (P) of the surrounding structure (20) is possible to open, such that the surrounding structure (20) can be placed around the urethra (U).

27. The surrounding structure (20) according to any one of aspects 24-26, wherein the second support element (24b) comprises at least one operable hydraulic constriction element (101a) configured to constrict the urethra (U) for restricting the flow of urine therethrough, and wherein the at least one operable hydraulic constriction element (101) is in fluid connection with at least one fluid conduit (109) at least partially integrated in the second support element (24b).

28. The surrounding structure (20) according to aspect 27, wherein the second support element (24b) comprises at least a second operable hydraulic constriction element (101b), and wherein the at least one second operable hydraulic constriction element (101b) is in fluid connection with a second fluid conduit (109b) at least partially integrated in the second support element.

29. The surrounding structure (20) according to any one of aspects 24-26, wherein the second support element (24b) comprises at least one cushioning element (30) configured to contact the urethra (U), wherein the cushioning element (30) is more resilient than the support element (24b).

30. The surrounding structure (20) according to any one of aspects 23-29, wherein the surrounding structure (20) further comprises an electrode arrangement configured to be arranged between the surrounding structure (20) and the urethra (U) and configured to engage and electrically stimulate muscle tissue of the urethra (U) to exercise the muscle tissue to improve the conditions for long term implantation of the implantable constriction device (10).

ASPECT_281SE_Constriction_Urine_Ring_Two-Parts

1. A surrounding structure (20) for an implantable constriction device (10) for constricting a urethra (U) of a patient, the surrounding structure (20) having a periphery (P) surrounding the urethra (U) when implanted, the surrounding structure (20) comprises at least two support elements (24a, 24b) connected to each other for forming at least a portion of the periphery (P) of the surrounding structure (20), wherein at least one of the support elements (24a, 24b) are configured to support at least one first operable hydraulic constriction element (101) configured to constrict the urethra (U) for restricting the flow of urine therethrough.

2. The surrounding structure (20) according to aspect 1, wherein at least one of the support elements (20)

comprises at least one curvature (C) adapted for the curvature of the urethra (U).
3. The surrounding structure (20) according to aspect 2, wherein the curvature has a radius in the range 3 mm-50 mm.
4. The surrounding structure (20) according to aspect 2, wherein the curvature (C) has a radius (R) in the range 5 mm-30 mm.
5. The surrounding structure (20) according to any one of the preceding aspects, wherein the surrounding structure (20) comprises:
   a first curvature (C) having a first radius (R1), and
   a second curvature (C) having a second radius (R2), and wherein
   the first radius (R1) is smaller than the second radius (R2).
6. The surrounding structure (20) according to any one of the preceding aspects, wherein the surrounding structure (20) is substantially rigid.
7. The surrounding structure according to aspect 6, wherein a major portion of the surrounding structure (20) is made from a material having a modulus of elasticity (E) in the range 0.2 GPa-1000 GPa or in the range 1 GPa-400 GPa.
8. The surrounding structure (20) according to aspect 6, wherein the surrounding structure (20) has a modulus of elasticity (E), radially, in the range 0.2 GPa-1000 GPa or in the range 1 GPa-400 GPa.
9. The surrounding structure (20) according to any one of the preceding aspects, wherein the first and second support elements (24a, 24b) are configured for forming the surrounding structure (20) and thereby surround the urethra (U).
10. The surrounding structure (20) according to any one of the preceding aspects, wherein the support elements (24a, 24b) are hingedly connected to each other for at least partially forming the surrounding structure (20), such that a periphery (P) of the surrounding structure (20) is possible to open, such that the surrounding structure (20) can be placed around the urethra (U).
11. The surrounding structure (20) according to any one of aspects 1-10, wherein the first support element (24a) comprises the first operable hydraulic constriction element (101a) configured to constrict the urethra (U) for restricting the flow of urine therethrough.
12. The surrounding structure (20) according to aspects 11, wherein the first support element (24a) comprises at least one second operable hydraulic constriction element (101b) configured to constrict the urethra (U) for restricting the flow of urine therethrough.
13. The surrounding structure (20) according to aspect 12, wherein the first operable hydraulic constriction element (101a) has a larger volume than the second operable hydraulic constriction element (101b).
14. The surrounding structure (20) according to any one of aspects 1-10, wherein the second support element (24b) comprises a third operable hydraulic constriction element (101c) configured to constrict the urethra (U) for restricting the flow of urine therethrough.
15. The surrounding structure (20) according to aspect 13, wherein the second support element (24b) comprises a fourth operable hydraulic constriction element (101d) configured to constrict the urethra (U) for restricting the flow of urine therethrough.
16. The surrounding structure (20) according to aspect 15, wherein the third operable hydraulic constriction element (101c) has a larger volume than the fourth operable hydraulic constriction element (101d).
17. The surrounding structure (20) according to any one of aspects 1-10, wherein the second support element (24b) comprises at least one cushioning element (30) configured to contact the urethra (U), wherein the cushioning element (30) is more resilient than at least one of the support elements (24a, 24b).
18. The surrounding structure (20) according to any one of the preceding aspects, wherein the surrounding structure (20) has a length (l1) in the direction of the axial direction (AD) of the urethra (U), when implanted, and wherein the at least one first operable hydraulic constriction element (101a) has a length (l2) in the direction of the axial direction (AD) of the urethra (U), when implanted, and wherein the length (l2) of the at least one first operable hydraulic constriction element (101a) is longer than the length of the surrounding structure (20).
19. The surrounding structure (20) according to any one of the preceding aspects, wherein the surrounding structure (20) further comprises an electrode arrangement configured to be arranged between the surrounding structure (20) and the urethra (U) and to engage and electrically stimulate muscle tissue of the urethra (U) to exercise the muscle tissue to improve the conditions for long term implantation of the implantable constriction device (10).
20. An implantable constriction device (10) comprising the surrounding structure (20) according to any one of the preceding aspects, wherein the implantable constriction device (10) further comprises at least one hydraulic pump (104) and a control unit (300), wherein the control unit (300) is configured to control the flow of fluid from the hydraulic pump (104), such that:
   the first operable hydraulic constriction element (101a) is inflated, and
   the second operable hydraulic constriction element (101b) is deflated, for constricting the urethra (U) and restricting the flow of urine therethrough.
21. The implantable constriction device (10) according to aspect 20, wherein the control unit (300) is further configured to control the flow of fluid from the hydraulic pump (104), such that:
   the third operable hydraulic constriction element (101c) is inflated, and
   the fourth operable hydraulic constriction element (101d) is deflated, for constricting the urethra (U) and restricting the flow of urine therethrough.
22. The implantable constriction device (10) according to aspect 20, wherein the control unit (300) is further configured to control the flow of fluid from the hydraulic pump (104), such that:
   the first operable hydraulic constriction element (101a) is deflated, and
   the second operable hydraulic constriction element (101b) is inflated, for releasing the constriction of the urethra (U) for restoring the flow of urine therethrough.
23. The implantable constriction device (10) according to aspect 21, wherein the control unit (300) is further configured to control the flow of fluid from the hydraulic pump (104), such that:
   the third operable hydraulic constriction element (101c) is deflated, and the fourth operable hydraulic constriction element (101*d*) is inflated, for releasing the constriction of the urethra (U) for restoring the flow of urine therethrough.
24. The implantable constriction device (10) according to any one of aspects 19-23, wherein the implantable constriction device (10) further comprises an electrode arrangement (353) configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_282SE_Constriction_Urine_Ring_Three-Points

1. An implantable constriction device (10) for constricting a urethra (U) of a patient, the implantable constriction device (10) comprises a first, second and third urethra contacting elements, wherein:
   the first urethra contacting element comprises a first operable hydraulic constriction element (101*a*) configured to be inflated to constrict the urethra (U) for restricting the flow of urine therethrough,
   the second urethra contacting element comprises a second operable hydraulic constriction element (101*b*) configured to be inflated to assist in releasing the constriction of the urethra (U) for restoring the flow of urine therethrough, and
   the third urethra contacting element comprises at least one cushioning element (30) configured to contact the urethra (U).
2. The implantable constriction device (10) according to aspect 1, wherein the implantable constriction device comprises a surrounding structure (20) having a periphery (P) surrounding the urethra (U) when implanted.
3. The implantable constriction device (10) according to aspect 2, wherein at least one of the first, second and third urethra contacting elements are connected to the surrounding structure (20).
4. The implantable constriction device (10) according to any one of aspects 2 and 3, wherein the surrounding structure (20) is comprised of at least a first and a second support element (24*a*,24*b*).
5. The implantable constriction device (10) according to aspect 4, wherein the first urethra contacting element is connected to the first supporting element (24*a*) and the second urethra contacting element is connected to the second support element (24*b*).
6. The implantable constriction device (10) according to aspect 5, wherein the third urethra contacting element is connected to the second support element (24*b*).
7. The implantable constriction device (10) according to aspect 4, wherein the first urethra contacting element is connected to the first support element (24*a*), the second urethra contacting element is connected to the second support element (24*b*) and the third urethra contacting element is connected to a third support element (24*c*).
8. The implantable constriction device (10) according to any one of the preceding aspects, wherein at least one of the first, second and third support elements (24*a*,24*b*,24*c*) have a curvature (C) adapted for the curvature of the urethra (U).
9. The implantable constriction device (10) according to aspect 8, wherein the curvature (C) has a radius (R1, R2,R3) in the range 3 mm-50 mm.
10. The implantable constriction device (10) according to aspect 8, wherein the curvature has a radius in the range 5 mm-30 mm.
11. The implantable constriction device according to any one of aspects 2-10, wherein the surrounding structure (20) is substantially rigid.
12. The implantable constriction device according to aspect 11, wherein a major portion of the surrounding structure (20) is made from a material having a modulus of elasticity (E) in the range 0.2 GPa-1000 GPa or in the range 1 GPa-400 GPa.
13. The implantable constriction device (10) according to aspect 11, wherein the surrounding structure (20) has a modulus of elasticity (E), radially, in the range 0.2 GPa-1000 GPa or in the range 1 GPa-400 GPa.
14. The implantable constriction device (10) according to any one of aspects 2-10, wherein at least two of the support elements (24*a*,24*b*) are hingedly connected to each other for at least partially forming the surrounding structure (20).
15. The implantable constriction device (10) according to any one of the preceding aspects, further comprising at least one hydraulic pump (104) and a controller (300), wherein the controller (300) is configured to control the flow of fluid from the hydraulic pump (104), such that:
    the first operable hydraulic constriction element is inflated (101*a*), and
    the second operable hydraulic constriction element (101*b*) is deflated, for constricting the urethra (U) and restricting the flow (F) of urine therethrough.
16. The implantable constriction device (10) according to aspect 15, wherein the controller (300) is further configured to control the flow (F) of fluid from the hydraulic pump (104), such that:
    the first operable hydraulic constriction element (101*a*) is deflated, and
    the second operable hydraulic constriction element (101*b*) is inflated, for releasing the constriction of the urethra (U) for restoring the flow (F) of urine therethrough.
17. The implantable constriction device (10) according to any one of aspects 15 and 16, wherein the first and second operable hydraulic constriction element (101*a*, 101*b*) are connected to a shared hydraulic system, such that the hydraulic fluid is:
    pumped from the first operable hydraulic constriction element (101*a*) to the second operable hydraulic constriction element (101*b*) for releasing the constriction of the urethra (U) for restoring the flow (F) of urine therethrough, and
    pumped from the second operable hydraulic constriction element (101*b*) to the first operable hydraulic constriction element (101*a*) for constricting the urethra (U) and restricting the flow (F) of urine therethrough.
18. The implantable constriction device (10) according to any one of the preceding aspects, wherein the surrounding structure has a length (l1) in the axial direction (AD) of the urethra (U), when implanted, and wherein at least one of the first, second and third urethra contacting elements has a length (l2) in the axial direction (AD) of the urethra (U), when implanted, and wherein the length (l2) of at least one of the first, second and third urethra contacting element is longer than the length (l1) of the surrounding structure.
19. The implantable constriction device (10) according to any one of the preceding aspects, wherein the implantable constriction device (10) further comprises an electrode arrangement configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_283SE—Constriction_Urine_Ring_Kit

1. A kit for a surrounding structure (20) for an implantable constriction device (10) for constricting a urethra (U) of a patient, the surrounding structure (20) being configured to have a periphery (P) surrounding the urethra (U) when implanted, the kit comprising at least a first, second and third support element (24a,24b,24c), and wherein:
   the second support element (24b) is configured to be connected to the first support element (24a) for forming at least a portion of the surrounding structure (20), the third support element (24c) is configured to be connected to the first support element (24a) for forming at least a portion of the surrounding structure (20), and at least one of the second and third support element (24b,24c) is connected to the first support element (24a) for forming at least a portion of the surrounding structure (20) when the surrounding structure (20) is implanted.
2. The kit according to aspect 1, wherein the first support element (24a) is configured to support at least one first operable hydraulic constriction element (101a) configured to constrict the urethra (U) for restricting the flow (F) of urine therethrough.
3. The kit according to any one of the preceding aspects, wherein at least one of the support elements (24a,24b,24c,24d) comprises at least one curvature (C) adapted for the curvature (C) of the urethra (U).
4. The kit according to aspect 3, wherein the curvature (C) has a radius (R) in the range 3 mm-50 mm.
5. The kit according to aspect 3, wherein the curvature (C) has a radius (R) in the range 5 mm-30 mm.
6. The kit according to any one of aspect 3-5, wherein:
   the second support element (24b) comprises a second curvature adapted for the curvature of a first urethra (U),
   the third support element (24c) comprises a third curvature adapted for the curvature of a second urethra (U), and
   the second curvature is different than the third curvature.
7. The kit according to aspect 6, wherein:
   the second curvature has a second radius (R2),
   the third curvature has a third radius (R3), and
   the second radius (R2) is larger than the third radius (R3).
8. The kit according to aspect 7, wherein the second radius (R2) is more than 1.2 times as large as the third radius (R3).
9. The kit according to any one of the preceding aspects, wherein:
   the second support element (24b) has a second length (l2) configured to extend along a portion of the periphery (P) of the surrounding structure (20),
   the third support element (24c) has a third length (l3) extending along a portion of the periphery (P) of the surrounding structure (20), and
   the third length (l3) is longer than the second length (l2).
10. The kit according to any one of the preceding aspects, wherein a major portion of at least one of the first, second and third support structures (24a,24b,24c) is made from a material having a modulus of elasticity (E) in the range 0.2 GPa-1000 GPa or in the range 1 GPa-400 GPa.
11. The kit according to any one of the preceding aspects, wherein the surrounding structure (20) has a modulus of elasticity (E), radially, in the range 0.2 GPa-1000 GPa or in the range 1 GPa-400 GPa.
12. The kit structure according to any one of the preceding aspects, wherein:
   the first and second support elements (24a,24b) are configured to form the surrounding structure (20) and thereby surround the urethra (U), or
   the first and third support elements (24a,24c) are configured to form the surrounding structure (20) and thereby surround the urethra (U).
13. The kit according to any one of the preceding aspects, wherein the second and third support elements (24b, 24c) are configured to be hingedly connected to the first support element (24a) for at least partially forming the surrounding structure (20), such that a periphery (P) of the surrounding structure (20) is possible to open, such that the surrounding structure (20) can be placed around the urethra (U).
14. The kit according to any one of the preceding aspects, wherein the first support element (24a) comprises the first operable hydraulic constriction element (101a) configured to constrict the urethra (U) for restricting the flow (F) of urine therethrough.
15. The kit according to aspects 14, wherein the first support element (24a) comprises at least one second operable hydraulic constriction element (101b) configured to constrict the urethra (U) for restricting the flow (F) of urine therethrough.
16. The kit according to aspect 15, wherein the first operable hydraulic constriction element (101a) has a larger volume than the second operable hydraulic constriction element (101b).
17. The kit according to any one of the preceding aspects, wherein at least one of the second and third support element (24b,24c) comprises a third operable hydraulic constriction element (24c) configured to constrict the urethra (U) for restricting the flow (F) of urine therethrough.
18. The kit according to any one of the preceding aspects, wherein at least one if the second and third support element (24b,24c) comprises at least one cushioning element configured to contact the urethra, wherein the cushioning element is more resilient than at least one of the support elements.
19. The kit according to any one of the preceding aspects, wherein the surrounding structure (20) has a length (l1) in the axial direction (AD) of the urethra (U), when implanted, and wherein the at least one first operable hydraulic constriction element (101a) has a length (l2) in the axial direction (AD) of the urethra (U), when implanted, and wherein the length (l2) of the at least one first operable hydraulic constriction element (101a) is longer than the length (l1) of the surrounding structure (20).
20. The kit according to any one of the preceding aspects, wherein at least one of the first, second and third support elements (24a,24b,24c) comprises an electrode arrangement configured to be arranged between at least one of the first, second and third support elements (24a,24b,24c) and the urethra (U) and configured to engage and electrically stimulate muscle tissue of the urethra (U) to exercise the muscle tissue to improve the conditions for long term implantation of the implantable constriction device (10).

ASPECT_284SE—Constriction_Urine_Additional_Close

1. An implantable constriction device (10) for constricting a urethra (U) of a patient, the implantable constriction device (10) comprises:
    a first operable hydraulic constriction element (101') configured to be inflated to constrict the urethra (U) for restricting the flow (F) of urine therethrough,
    a second operable hydraulic constriction element (101") configured to be inflated to constrict the urethra (U) for restricting the flow (F) of urine therethrough, and
    an interconnecting fluid conduit (116) fluidly connecting the first operable hydraulic constriction element (101') to the second operable hydraulic constriction element (101"), wherein
        the first operable hydraulic constriction element (101') is configured to be placed at a first portion (p1) of the urethra (U) for constricting the first portion (p1) of the urethra (U) for restricting the flow (F) of urine therethrough,
        the second operable hydraulic constriction element (101") is configured to be placed at a second portion (p2) of the urethra (U), downstream the first portion (p1), for constricting the second portion (p2) of the urethra (U) for restricting the flow (F) of urine therethrough, and
        the interconnecting fluid conduit (116) is configured to conduct fluid from the first operable hydraulic constriction element (101') to the second operable hydraulic constriction element (101") when the pressure increases in the first operable hydraulic constriction element (101'), such that second operable hydraulic constriction element (101") constricts the second portion (p2) of the urethra (U) further.
2. The implantable constriction device (10) according to aspect 1, wherein a lumen 103' of the first operable hydraulic constriction element (101') has a larger volume than a lumen (103") of the second operable hydraulic constriction element (101").
3. The implantable constriction device (10) according to aspect 2, wherein the lumen (103') of the first operable hydraulic constriction element (101') has a volume which is more than 1.5 times larger than the volume of the lumen (103") of the second operable hydraulic constriction element (101").
4. The implantable constriction device (10) according to any one of the preceding aspects, wherein the first interconnecting fluid conduit (116) comprises a first electrically operable valve (119), such that a flow of fluid between the first operable hydraulic constriction element (101') and the second operable hydraulic constriction element (101") can be controlled.
5. The implantable constriction device (10) according to aspect 4, wherein the electrically operable valve (119) is a solenoid valve.
6. The implantable constriction device (10) according to any one of the preceding aspects, wherein the first interconnecting fluid conduit (116) comprises a check valve (114), such that fluid can flow in a direction from the first operable hydraulic constriction element (101') to the second operable hydraulic constriction element (101") but not in a direction from the second operable hydraulic constriction element (101") to the first operable hydraulic constriction element (101').
7. The implantable constriction device (10) according to any one of the preceding aspects, further comprising a second interconnecting fluid conduit (117) fluidly connecting the first operable hydraulic constriction element (101') to the second operable hydraulic constriction element (101"), wherein a cross section of a tubular lumen of the second interconnecting fluid conduit (117) has an area which is less than 0.5 times a cross section area of a tubular lumen of the first interconnecting fluid conduit (116).
8. The implantable constriction device (10) according to any one of the preceding aspects, further comprising:
    a hydraulic pump (104),
    a reservoir (107) for holding hydraulic fluid, and
    a first reservoir conduit (109), fluidly connecting the reservoir (107) to the first
    operable hydraulic constriction element (101'), wherein the hydraulic pump (104) is configured to pump fluid from the reservoir (107) to the first operable hydraulic constriction element (101') through the first reservoir conduit (109), for constricting the first portion (p1) of the urethra (U) for restricting the flow (F) of urine therethrough.
9. The implantable constriction device (10) according to aspect 8, wherein the first reservoir conduit (109) comprises a second electrically operable valve (105), such that a flow of fluid between the reservoir (107) and the first operable hydraulic constriction element (101') can be controlled.
10. The implantable constriction device (10) according to any one of aspects 8 and 9, further comprising a second reservoir conduit (109") fluidly connecting the reservoir (107) to the second operable hydraulic constriction element (101").
11. The implantable constriction device (10) according to aspect 10, wherein the second reservoir conduit (109') comprises a check valve (113) such that fluid can flow in a direction from the reservoir (107) to the second operable hydraulic constriction element (101") but not in a direction from the second operable hydraulic constriction element (101") to the reservoir (107).
12. The implantable constriction device (10) according to any one of aspects 8-11, further comprising an injection port (108) in fluid connection with the reservoir (107), for injecting fluid into the reservoir (107) when the reservoir (107) is implanted.
13. The implantable constriction device (10) according to aspect 12, wherein the injection port (108) is configured to be placed subcutaneously, and wherein the implantable constriction device (10) further comprises an injection port conduit (110) fluidly connecting the injection port (108) to the reservoir (107).
14. The implantable constriction device (10) according to any one of the preceding aspects, further comprising at least one of:
    a first pressure sensor (106') configured to sense the pressure in the first operable hydraulic constriction element (101'), and
    a second pressure sensor (106") configured to sense the pressure in the second operable hydraulic constriction element (101").
15. The implantable constriction device (10) according to aspect 14, further comprising a controller (300) configured to receive a pressure sensor signal from at least one of the first and second pressure sensor (106',106"), and control at least one of: the first electrically operable valve (119), the second operable valve and the hydraulic pump, on the basis of the received pressure sensor signal.
16. The implantable constriction device (10) according to aspect 15, wherein the controller (300) comprises a pressure threshold value, and wherein the controller (300) is configured to open the first electrically operable valve (119) if the received pressure sensor signal from the second pressure sensor (106") exceeds the pressure threshold value.
17. The implantable constriction device (10) according to any one of the preceding aspects, further comprising a supporting operable hydraulic constriction element (201), wherein the supporting operable hydraulic constriction element (201) is configured to be placed along at least a portion of the first portion (p1) of the urethra (U) and along at least a portion of the second portion (p2) of the urethra (U), and configured to assist in the constriction of the first and second portions (p1,p2) of the urethra (U).
18. The implantable constriction device (10) according to aspect 17, wherein the supporting operable hydraulic constriction element (201) is connected to the first and second operable hydraulic constriction elements (101', 101").
19. The implantable constriction device (10) according to any one of aspects 17 and 18, wherein the supporting operable hydraulic constriction element (201) is less resilient than at least one of the first and second operable hydraulic constriction element (101',101").
20. The implantable constriction device (10) according to aspect 19, wherein each of the first, second and supporting operable hydraulic constriction element (101', 101",201) comprises a lumen (103',103",203) surrounded by a resilient wall (102,202), and wherein the resilient wall (202) of the supporting operable hydraulic constriction element (201) is thicker than the wall (102) of at least one of the first and second operable hydraulic constriction element (101',101").
21. The implantable constriction device (10) according to any one of aspects 17-20, further comprising:
   a second hydraulic pump (204),
   a second reservoir (207) for holding hydraulic fluid, and
   a supporting reservoir conduit (209), fluidly connecting the second reservoir (207) to the supporting operable hydraulic constriction element (201), wherein the second hydraulic pump (204) is configured to pump fluid from the second reservoir (207) to the supporting operable hydraulic constriction element (201) through the supporting reservoir conduit (209), for assisting in the constriction of the urethra.
22. The implantable constriction device (10) according to any one of aspect 17-21, further comprising a third pressure sensor (206) configured to sense the pressure in the supporting operable hydraulic constriction element (201).
23. The implantable constriction device (10) according to any one of aspects 17-22, further comprising a second injection port (208) in fluid connection with the second reservoir (207), for injecting fluid into the second reservoir (207) when the second reservoir (207) is implanted.
24. The implantable constriction device (10) according to aspect 23, wherein the second injection port (208) is configured to be placed subcutaneously, and wherein the implantable constriction device (10) further comprises a second injection port conduit (210) fluidly connecting the second injection port (208) to the second reservoir (207).
25. The implantable constriction device (10) according to any one of aspects 17-24, wherein the supporting operable hydraulic constriction element (201) has a length (l3) in the axial direction (AD) of the urethra (U), when implanted, and wherein the first and second operable hydraulic constriction element (101',101") has a combined length (l2) in the axial direction AD of the urethra (U), and wherein the combined length (l2) is longer than the length (l3) of the supporting operable hydraulic constriction element (201).
26. The implantable constriction device (10) according to any one of the preceding aspects, wherein the implantable constriction device (10) comprises a surrounding structure (20) having a periphery surrounding the urethra (U) when implanted.
27. The implantable constriction device (10) according to aspect 26, wherein the surrounding structure (20) is substantially rigid.
28. The implantable constriction device (10) according to aspect 27, wherein a major portion of the surrounding structure (20) is made from a material having a modulus of elasticity (E) in the range 0.2 GPa-1000 GPa or in the range 1 GPa-400 GPa.
29. The implantable constriction device (10) according to aspect 27, wherein the surrounding structure (20) has a modulus of elasticity (E), radially, in the range 0.2 GPa-1000 GPa or in the range 1 GPa-400 GPa.
30. The implantable constriction device (10) according to any one of aspects 26-29, wherein the surrounding structure (20) comprises an inner surface (22) configured to face the urethra (U), when implanted, and wherein the supporting operable hydraulic constriction device (201) is fixated to the inner surface (22) of the surrounding structure (20), such that the supporting operable hydraulic constriction device (201) can use the surrounding structure (20) as support for constricting the urethra (U).
31. The implantable constriction device (10) according to any one of aspects 26-30, further comprising at least one cushioning element (30) configured to contact the urethra (U), wherein the cushioning element (30) is fixated to the inner surface (22) of the surrounding structure (20) and is more resilient than the surrounding structure (20).
32. The implantable constriction device (10) according to any one of aspects 26-31, wherein the surrounding structure (20) is comprised of at least a first and a second supporting element configured to be connected to each other for forming at least a portion of the periphery of the surrounding structure (20).
33. The implantable constriction device (10) according to aspect 32, wherein the supporting operable hydraulic constriction device (201) is fixated to the first supporting element, and the at least one cushioning element (30) is fixated to the second supporting element.
34. The implantable constriction device (10) according to any one of aspects 32 and 33, wherein at least one of the first and second supporting elements have a curvature adapted for the curvature of the urethra (U).
35. The implantable constriction device (10) according to aspect 34, wherein the curvature has a radius in the range 3 mm-50 mm.

36. The implantable constriction device (10) according to aspect 34, wherein the curvature has a radius in the range 5 mm-30 mm.
37. The implantable constriction device (10) according to any one of the preceding aspects, wherein the implantable constriction device (10) further comprises an electrode arrangement configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_285SE—Constriction_Urine_Dual_Member

1. An implantable constriction device (10) for constricting a urethra (U) of a patient, the urethra (U) being a tubular, luminary organ having a substantially circular cross section and being elongated in an axial direction (AD), the implantable constriction device (10) comprises:
   a first operable hydraulic constriction element (101) configured to be inflated and thereby expand in a first direction (d1) towards the urethra (U) to constrict a first portion (p1) of the urethra (U) for restricting the flow of urine therethrough, and
   a supporting operable hydraulic constriction element (201) configured to be inflated and thereby expand in the first direction (d1) towards the urethra (U) to support the first operable hydraulic constriction element (101) in constricting the first portion (p1) of the urethra (U) for restricting the flow of urine therethrough.
2. The implantable constriction device (10) according to aspect 1, wherein the supporting operable hydraulic constriction element (201) is connected to the first operable hydraulic constriction element (101).
3. The implantable constriction device (10) according to any one of preceding aspects, wherein the supporting operable hydraulic constriction element (201) is less resilient than the first operable hydraulic constriction element (101).
4. The implantable constriction device (10) according to aspect 3, wherein the first operable hydraulic constriction element (101) comprises a lumen (103) surrounded by a resilient wall (102) and the supporting operable hydraulic constriction element (201) comprises a lumen (203) surrounded by a resilient wall (202), and wherein a portion of the resilient wall (202) of the supporting operable hydraulic constriction element (201) is thicker than a portion of the resilient wall (102) of the first operable hydraulic constriction element (101).
5. The implantable constriction device (10) according to aspect 4, wherein a portion of the resilient wall (202) of the supporting operable hydraulic constriction element (201) is more than 1.5 times thicker than a portion of the resilient wall (102) of the first operable hydraulic constriction element (101).
6. The implantable constriction device (10) according to aspect 4, wherein a portion of the resilient wall (202) of the supporting operable hydraulic constriction element (201) is more than 2 times thicker than a portion of the resilient wall (102) of the first operable hydraulic constriction element (101).
7. The implantable constriction device (10) according to any one of aspects 3-6, wherein the first operable hydraulic constriction element (101) comprises a lumen (103) surrounded by a resilient wall (102) and the supporting operable hydraulic constriction element (201) comprises a lumen (203) surrounded by a resilient wall (202), and wherein
   a portion of the resilient wall (102) of the first operable hydraulic constriction element (101) comprises a first material, and
   a portion of the resilient wall (202) of the supporting operable hydraulic constriction element (201) comprises a second material, and
   the second material has a modulus of elasticity which is higher than a modulus of elasticity of the first material.
8. The implantable constriction device (10) according to aspect 7, wherein the modulus of elasticity of the second material is more than 1.5 times higher than the modulus of elasticity of the first material.
9. The implantable constriction device (10) according to aspect 7, wherein the modulus of elasticity of the second material is more than 2 times higher than the modulus of elasticity of the first material.
10. The implantable constriction device (10) according to any one of aspects 1-4, further comprising:
    a first hydraulic pump (104),
    a second hydraulic pump (204),
    a first reservoir (107) for holding hydraulic fluid,
    a second reservoir (207) for holding hydraulic fluid,
    a first reservoir conduit (109), fluidly connecting the first reservoir (107) to the
    first operable hydraulic constriction element (101), and
    a supporting reservoir conduit (209), fluidly connecting the second reservoir (207) to the supporting operable hydraulic constriction element (201), wherein
    the first hydraulic pump (104) is configured to pump fluid from the first reservoir (107) to the first operable hydraulic constriction element (101) through the first reservoir conduit (109), for constricting the urethra (U), and
    the second hydraulic pump (204) is configured to pump fluid from the second reservoir (207) to the supporting operable hydraulic constriction element (201) through the supporting reservoir conduit (209), for assisting in the constriction of the urethra (U).
11. The implantable constriction device (10) according to any one of aspect 1-10, further comprising a first pressure sensor (106) configured to sense the pressure in the first operable hydraulic constriction element (101).
12. The implantable constriction device (10) according to any one of aspect 1-11, further comprising a second pressure sensor (206) configured to sense the pressure in the supporting operable hydraulic constriction element (201).
13. The implantable constriction device (10) according to any one of aspect 11-12, further comprising an implantable controller (300), wherein the implantable controller (300) is configured to control at least one of the:
    first hydraulic pump (104) on the basis of input from the first pressure sensor (106), and
    the second hydraulic pump (204) on the basis of input from the second pressure sensor (206).
14. The implantable constriction device (10) according to aspect 13, wherein at least one of:
    the first reservoir conduit (109) comprises an electrically operable valve (105), and
    the second reservoir conduit (209) comprises an electrically operable valve (205), and wherein the controller (300) is configured to control at least one of:
- the electrically operable valve (105) on the first reservoir conduit (109), on the basis of input from the first pressure sensor (106), and
- the electrically operable valve (205) on the second reservoir conduit (209), on the basis of input from the second pressure sensor (206).

15. The implantable constriction device (10) according to any one of aspects 10-12, wherein at least one of:
- the first reservoir conduit (109) comprises a check valve, and
- the second reservoir conduit (209) comprises a check valve.

16. The implantable constriction device (10) according to any one of aspect 1-15, further comprising a first injection port (108) in fluid connection with the first reservoir (107), for injecting fluid into the first reservoir (107) when the first reservoir is implanted.

17. The implantable constriction device (10) according to any one of aspect 1-16, further comprising a second injection port (208) in fluid connection with the second reservoir (207), for injecting fluid into the second reservoir (207) when the second reservoir (207) is implanted.

18. The implantable constriction device (10) according to any one of aspects 16 and 17, wherein at least one of:
- the first injection port (108) is configured to be placed subcutaneously, and wherein the implantable constriction device further comprises a first injection port conduit (110) fluidly connecting the first injection port (108) to the first reservoir (107), and
- the second injection port (208) is configured to be placed subcutaneously, and wherein the implantable constriction device (10) further comprises a second injection port (208) conduit fluidly connecting the second injection port (208) to the second reservoir (207).

19. The implantable constriction device (10) according to any one of the preceding aspects, wherein the supporting operable hydraulic constriction element (201) has a length (l3) in the axial direction (AD) of the urethra (U), when implanted, and wherein the first operable hydraulic constriction element (101) has a length (l2) in the axial direction (AD) of the urethra (U), and wherein the length of the first operable hydraulic constriction element (12) is longer than the length (l3) of the supporting operable hydraulic constriction element (201).

20. The implantable constriction device (10) according to any one of the preceding aspects, wherein the implantable constriction device (10) comprises a surrounding structure (20) having a periphery surrounding the urethra (U) when implanted.

21. The implantable constriction device (10) according to aspect 20, wherein the surrounding structure (20) is substantially rigid.

22. The implantable constriction device (10) according to aspect 21, wherein a major portion of the surrounding structure (20) is made from a material having a modulus of elasticity (E) in the range 0.2 GPa-1000 GPa or in the range 1 GPa-400 GPa.

23. The implantable constriction device (10) according to aspect 21, wherein the surrounding structure (20) has a modulus of elasticity (E), radially, in the range 0.2 GPa-1000 GPa or in the range 1 GPa-400 GPa.

24. The implantable constriction device (10) according to any one of aspects 20-23, wherein the surrounding structure (20) comprises an inner surface (22) configured to face the urethra (U), when implanted, and wherein the supporting operable hydraulic constriction device (201) is fixated to the inner surface (22) of the surrounding structure (20), such that the supporting operable hydraulic constriction device (201) can use the surrounding structure (20) as support for constricting the urethra (U).

25. The implantable constriction device (10) according to any one of aspects 20-24, further comprising at least one cushioning element (30) configured to contact the urethra (U), wherein the cushioning element (30) is fixated to the inner surface (22) of the surrounding structure (20) and is more resilient than the surrounding structure (20).

26. The implantable constriction device (10) according to any one of aspects 20-25, wherein the surrounding structure (20) is comprised of at least a first and a second supporting element configured to be connected to each other for forming at least a portion of the periphery of the surrounding structure (20).

27. The implantable constriction device (10) according to aspect 26, wherein the supporting operable hydraulic constriction device (201) is fixated to the first supporting element, and the at least one cushioning element (30) is fixated to the second supporting element.

28. The implantable constriction device (10) according to any one of aspects 26 and 27, wherein at least one of the first and second supporting element have a curvature adapted for the curvature of the urethra (U).

29. The implantable constriction device (10) according to aspect 28, wherein the curvature has a radius in the range 3 mm-50 mm.

30. The implantable constriction device (10) according to aspect 28, wherein the curvature has a radius in the range 5 mm-30 mm.

31. The implantable constriction device (10) according to any one of the preceding aspects, wherein the implantable constriction device (10) further comprises an electrode arrangement configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_286SE_Constriction_Urine_Separate_Systems

1. An implantable constriction device (10) for constricting a urethra (U) of a patient, the implantable constriction device (10) comprises:
- a first operable hydraulic constriction element (101a) configured to be inflated to exert a pressure on the urethra (U) in a first direction (d1) to constrict a first portion of the urethra (U) for restricting the flow (F) of urine therethrough,
- a second operable hydraulic constriction element (101b) configured to be inflated to exert a pressure on the urethra (U) in a second direction to constrict the first portion of the urethra (U) for restricting the flow (F) of urine therethrough, and
- a first hydraulic system in fluid connection with the first operable hydraulic constriction element (101a), and
- a second hydraulic system in fluid connection with the second operable hydraulic constriction element (101b), wherein the first and second operable hydraulic constriction elements (101a,101b) are adjustable independently from each other.
2. The implantable constriction device (10) according to aspect 1, wherein the second direction (d2) is substantially opposite to the first direction (d1).
3. The implantable constriction device (10) according to any one of the preceding aspects, wherein the first hydraulic systems comprises a first hydraulic pump (104') and the second hydraulic systems comprises a second hydraulic pump (104").
4. The implantable constriction device (10) according to any one of the preceding aspects, wherein each of the first and second hydraulic systems comprises a reservoir (107) for holding hydraulic fluid.
5. The implantable constriction device (10) according to any one of the aspects 1-3, wherein the first and second hydraulic systems are connected to a reservoir (107) for holding hydraulic fluid.
6. The implantable constriction device (10) according to any one of the preceding aspects, wherein each of the first and second hydraulic systems comprises an injection port (108) for injecting hydraulic fluid into the respective first and second hydraulic systems.
7. The implantable constriction device (10) according to aspect 6, wherein the injection ports (108) is configured to be placed subcutaneously, and wherein the implantable constriction device (10) further comprises an injection port conduit (110) fluidly connecting the injection ports (108) to the first and second hydraulic systems.
8. The implantable constriction device (10) according to any one of the preceding aspects, wherein the first operable hydraulic constriction element (101a) lacks a fluid connection to the second operable hydraulic constriction element (101a).
9. The implantable constriction device (10) according to any one of the preceding aspects, further comprising at least one of:
   a first pressure sensor (106') configured to sense the pressure in the first operable hydraulic constriction element (101'), and
   a second pressure sensor (106") configured to sense the pressure in the second operable hydraulic constriction element (101").
10. The implantable constriction device (10) according to aspect 9, further comprising a controller (300) configured to receive a pressure sensor signal from at least one of the first and second pressure sensor (106',106"), and control at least one of: the first hydraulic pump (104') and the second hydraulic pump (104"), on the basis of the received pressure sensor signal.
11. The implantable constriction device (10) according to any one of the preceding aspects, wherein the implantable constriction device (10) comprises a surrounding structure (20) having a periphery surrounding the urethra (U) when implanted.
12. The implantable constriction device (10) according to aspect 11, wherein the surrounding structure (20) is substantially rigid.
13. The implantable constriction device (10) according to aspect 12, wherein a major portion of the surrounding structure (20) is made from a material having a modulus of elasticity (E) in the range 0.2 GPa-1000 GPa or in the range 1 GPa-400 GPa.
14. The implantable constriction device (10) according to aspect 12, wherein the surrounding structure (20) has a modulus of elasticity (E), radially, in the range 0.2 GPa-1000 GPa or in the range 1 GPa-400 GPa.
15. The implantable constriction device (10) according to any one of aspects 11-14, wherein the surrounding structure (20) comprises an inner surface (22) configured to face the urethra (U), when implanted, and wherein the first and second operable hydraulic constriction element (101a,101b) are fixated to the inner surface (22) of the surrounding structure (20).
16. The implantable constriction device (10) according to any one of aspects 11-15, wherein the surrounding structure (20) is comprised of at least a first and a second support element (24a,24b) configured to be connected to each other for forming at least a portion of the periphery (P) of the surrounding structure (20).
17. The implantable constriction device (10) according to aspect 16, wherein the first operable hydraulic constriction device (101a) is fixated to the first support element (24a), and the second operable hydraulic constriction device (101b) is fixated to the second support element (24b).
18. The implantable constriction device (10) according to any one of aspects 16 and 17, wherein at least one of the first and second support elements (24a,24b) have a curvature (C) adapted for the curvature of the urethra (U).
19. The implantable constriction device (10) according to aspect 18, wherein the curvature (C) has a radius (R) in the range 3 mm-50 mm.
20. The implantable constriction device (10) according to any one of the preceding aspects, wherein the implantable constriction device (10) further comprises an electrode arrangement configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_287SE_Constriction_Urine_Pump_Injection-port
1. An implantable constriction device (10) for constricting a urethra (U) of a patient, the implantable constriction device (10) comprises:
   an operable hydraulic constriction element (101) configured to be inflated to exert a pressure on the urethra (U),
   a hydraulic reservoir (107) for holding a hydraulic fluid,
   a hydraulic pump (104) for pumping fluid from the hydraulic reservoir (107) to the operable hydraulic constriction element (101),
   a first fluid conduit (109') creating a fluid connection between the hydraulic reservoir (107) and the hydraulic pump (104),
   a second fluid conduit (109") creating a fluid connection between the hydraulic pump (104) and the operable hydraulic constriction element (101),
   an injection port (108) for injecting and removing hydraulic fluid from the implantable constriction device (10), when implanted, and a third fluid conduit (109''') creating a fluid connection between the injection port (108) and at least one of the second fluid conduit (109") and the operable hydraulic constriction element (101), such that hydraulic fluid can be removed from the operable hydraulic constriction element (101) through the injection port (108).
2. The implantable constriction device (10) according to aspect 1, further comprising a supporting operable hydraulic constriction element (201) configured to be inflated to support the first operable hydraulic constriction element (101) in constricting the urethra (U) for restricting the flow of urine therethrough.

3. The implantable constriction device (10) according to aspect 2, further comprising:
   a second hydraulic reservoir (207) for holding a hydraulic fluid,
   a second hydraulic pump (204) for pumping fluid from the hydraulic reservoir (207) to the supporting operable hydraulic constriction element (201),
   a fourth fluid conduit (209') creating a fluid connection between the second hydraulic reservoir (207) and the second hydraulic pump (204), and
   a fifth fluid conduit (209") creating a fluid connection between the second hydraulic pump (204) and the supporting operable hydraulic constriction element (201), and
   a second injection port (208) for injecting and removing hydraulic fluid from the implantable constriction device (10), when implanted, and
   a sixth fluid conduit (209''') creating a fluid connection between the second injection port (208) and at least one of the second fluid conduit (209") and the supporting operable hydraulic constriction element (201), such that hydraulic fluid can be removed from the supporting operable hydraulic constriction element (201) through the second injection port (208).

4. The implantable constriction device (10) according to aspect 2 or 3, wherein the supporting operable hydraulic constriction element (201) is connected to the first operable hydraulic constriction element (101).

5. The implantable constriction device (10) according to any one of aspects 2-4, wherein the supporting operable hydraulic constriction element (201) is less resilient than the first operable hydraulic constriction element (101).

6. The implantable constriction device (10) according to aspect 5, wherein the first operable hydraulic constriction element (101) comprises a lumen (103) surrounded by a resilient wall (102) and the supporting operable hydraulic constriction element (201) comprises a lumen (203) surrounded by a resilient wall (202), and wherein a portion of the resilient wall (202) of the supporting operable hydraulic constriction element (201) is thicker than a portion of the resilient wall (102) of the first operable hydraulic constriction element (101).

7. The implantable constriction device (10) according to aspect 6, wherein a portion of the resilient wall (202) of the supporting operable hydraulic constriction element (201) is more than 1.5 times thicker than a portion of the resilient wall (102) of the first operable hydraulic constriction element (101).

8. The implantable constriction device (10) according to any one of aspects 5-7, wherein the first operable hydraulic constriction element (101) comprises a lumen (103) surrounded by a resilient wall (102) and the supporting operable hydraulic constriction element (201) comprises a lumen (203) surrounded by a resilient wall (202), and wherein
   a portion of the resilient wall (102) of the first operable hydraulic constriction element (101) comprises a first material, and
   a portion of the resilient wall (202) of the supporting operable hydraulic constriction element (201) comprises a second material, and
   the second material has a modulus of elasticity which is higher than a modulus of elasticity of the first material.

9. The implantable constriction device (10) according to aspect 8, wherein the modulus of elasticity of the second material is more than 1.5 times higher than the modulus of elasticity of the first material.

10. The implantable constriction device (10) according to any one of aspect 1-9, further comprising a first pressure sensor (106) configured to sense the pressure in the first operable hydraulic constriction element (101).

11. The implantable constriction device (10) according to any one of aspect 2-10, further comprising a second pressure sensor (206) configured to sense the pressure in the supporting operable hydraulic constriction element (201).

12. The implantable constriction device (10) according to any one of aspect 11-12, further comprising an implantable controller (300), wherein the implantable controller (300) is configured to control at least one of the:
    first hydraulic pump (104) on the basis of input from the first pressure sensor (106), and
    the second hydraulic pump (204) on the basis of input from the second pressure sensor (206).

13. The implantable constriction device (10) according to aspect 12, wherein at least one of:
    the first reservoir conduit (109) comprises an electrically operable valve (105), and
    the second reservoir conduit (209) comprises an electrically operable valve (205), and wherein
    the controller (300) is configured to control at least one of:
    the electrically operable valve (105) on the first reservoir conduit (109), on the basis of input from the first pressure sensor (106), and
    the electrically operable valve (205) on the second reservoir conduit (209), on the basis of input from the second pressure sensor (206).

14. The implantable constriction device (10) according to any one of aspects 10-11, further comprising an implantable controller (300), wherein the implantable controller (300) is configured to provide a feedback signal to the patient if the pressure in at least one of the operable hydraulic constriction element (101) and the supporting operable hydraulic constriction element (201) exceeds a threshold value.

15. The implantable constriction device (10) according to any one of the preceding aspects, wherein at least one of:
    the first injection port (108) is configured to be placed subcutaneously, and
    the second injection port (208) is configured to be placed subcutaneously.

16. The implantable constriction device (10) according to any one of the preceding aspects, wherein the supporting operable hydraulic constriction element (201) has a length (l3) in the axial direction (AD) of the urethra (U), when implanted, and wherein the first operable hydraulic constriction element (101) has a length (l2) in the axial direction (AD) of the urethra (U), and wherein the length of the first operable hydraulic constriction element (l2) is longer than the length (l3) of the supporting operable hydraulic constriction element (201).

17. The implantable constriction device (10) according to any one of the preceding aspects, wherein the implantable constriction device (10) comprises a surrounding structure (20) having a periphery surrounding the urethra (U) when implanted.
18. The implantable constriction device (10) according to aspect 17, wherein the surrounding structure (20) is substantially rigid.
19. The implantable constriction device (10) according to aspect 18, wherein a major portion of the surrounding structure (20) is made from a material having a modulus of elasticity (E) in the range 0.2 GPa-1000 GPa or in the range 1 GPa-400 GPa.
20. The implantable constriction device (10) according to aspect 18, wherein the surrounding structure (20) has a modulus of elasticity (E), radially, in the range 0.2 GPa-1000 GPa or in the range 1 GPa-400 GPa.
21. The implantable constriction device (10) according to any one of aspects 17-20, wherein the surrounding structure has a curvature adapted for the curvature (C) of the urethra (U).
22. The implantable constriction device (10) according to aspect 21, wherein the curvature (C) has a radius in the range 3 mm-50 mm.
23. The implantable constriction device (10) according to aspect 21, wherein the curvature (C) has a radius in the range 5 mm-30 mm.
24. The implantable constriction device (10) according to any one of the preceding aspects, wherein the implantable constriction device (10) further comprises an electrode arrangement configured to be arranged between the implantable constriction device (10) and the urethra (U) and configured to engage and electrically stimulate muscle tissue of the urethra (U) to exercise the muscle tissue to improve the conditions for long term implantation of the implantable constriction device (10).

ASPECT_288SE_Constriction_Urine_Electrical_Stimulation

1. An implantable constriction device (10) for constricting a urethra (U) of a patient, the implantable constriction device (10) comprises:
   an operable hydraulic constriction element (101) configured to be inflated to exert a pressure on the urethra (U),
   a hydraulic reservoir (107) for holding a hydraulic fluid,
   a hydraulic pump (104) for pumping fluid from the hydraulic reservoir (107) to the operable hydraulic constriction element (101),
   a first fluid conduit (109') creating a fluid connection between the hydraulic reservoir (107) and the hydraulic pump (104),
   an electrode arrangement configured to be arranged between the implantable constriction device (10) and the urethra (U) and to engage and electrically stimulate muscle tissue of the urethra (U) to exercise the muscle tissue to improve the conditions for long term implantation of the implantable constriction device (10).
2. The implantable constriction device (10) according to aspect 1, wherein the electrode arrangement is arranged on an outer surface of the operable hydraulic constriction element (101).
3. The implantable constriction device (10) according to aspect 1 or 2, wherein the electrode arrangement comprises a plurality of electrode elements (E1,E2,E3,E4), each of which being configured to engage and electrically stimulate tissue of the urethra (U).
4. The implantable constriction device (10) according to any of the preceding aspects, wherein the electrode arrangement comprises a coiled wire for increasing a contact surface between the electrode arrangement and the tissue of the urethra (U) and for allowing the electrode arrangement to follow contraction and relaxation of the tissue of the urethra (U).
5. The implantable constriction device (10) according to any of the preceding aspects, wherein the electrode arrangement comprises a bare electrode portion configured to form a metal-tissue interface with the tissue of the urethra (U), thereby allowing faradaic charge transfer to the be predominant charge transfer mechanism over said interface.
6. The implantable constriction device (10) according to any of the preceding aspects, wherein the electrode arrangement comprises an electrode portion at least partly covered by a dielectric material configured to form a dielectric-tissue interface with the tissue of the urethra (U), thereby allowing for a faradaic portion of the charge transfer mechanism over said interface to be reduced.
7. The implantable constriction device (10) according to any one of the preceding aspects, wherein the electrode arrangement comprises at least two electrode elements (E1,E2,E3,E4) configured to be arranged on opposing sides of the urethra (U).
8. The implantable constriction device (10) according to any of the preceding aspects, further comprising a stimulation controller (350) configured to be operably connected to the electrode arrangement for controlling the electrical stimulation of the tissue of the urethra (U).
9. The implantable constriction device (10) according to aspect 9, wherein the stimulation controller (350) is configured to control the electrical stimulation such that the tissue of the urethra (U) is stimulated by a series of electrical pulses.
10. The implantable constriction device (10) according to aspect 10, wherein the stimulation controller (350) is configured to control the electrical stimulation such that a pulse of a first polarity is followed by a pulse of a second, reversed polarity.
11. The implantable constriction device (10) according to any of aspects 8-10, wherein the stimulation controller (350) is configured to generate a pulsed electrical stimulation signal comprising a pulse frequency of 0.01-150 Hz.
12. The implantable constriction device (10) according to aspect 11, wherein the electrical stimulation signal comprises a pulse duration of 0.01-100 ms.
13. The implantable constriction device (10) according to aspect 11 or 12, wherein the electrical stimulation signal comprises a pulse amplitude of 1-15 mA.
14. The implantable constriction device (10) according to any of aspects 11-13, wherein the electrical stimulation signal comprises a pulse frequency of 0.15-0.25 Hz, a pulse duration of 20-30 ms and a pulse amplitude of 3-10 mA.
15. The implantable constriction device (10) according to any of aspects 11-14, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

16. The implantable constriction device (10) according to any of aspects 8-15, wherein the stimulation controller (350) is configured to receive input from a wireless remote control.
17. The implantable constriction device (10) according to any of aspects 8-16, further comprising an implantable sensor configured to sense actions potentials generated by pacemaker cells of the tissue of the urethra (U), and wherein the stimulation controller (350) is configured to control the electrical simulation based at least partly on the sensed action potentials.
18. The implantable constriction device (10) according to aspect 17, wherein the stimulation controller (350) is configured to generate electrical pulses amplifying the sensed action potentials.
19. The implantable constriction device (10) according to any one of the preceding aspects, wherein the implantable constriction device (10) comprises a surrounding structure (20) having a periphery surrounding the urethra (U) when implanted.
20. The implantable constriction device (10) according to aspect 19, wherein the electrode arrangement is connected to the surrounding structure (20).
21. The implantable constriction device (10) according to aspect 20, wherein the surrounding structure (20) comprises at least one cushioning element (30), and wherein at least one electrode element (E1,E2,E3,E4) of the electrode arrangement is placed on the surface of the cushioning element (30).

ASPECT_289SE_Constriction_Urine_Two-Pumps
1. An implantable constriction device (10) for constricting a urethra (U) of a patient for restricting the flow of urine therethrough, the implantable constriction device (10) comprises:
    a first operable hydraulic constriction element (101) configured to be inflated to exert a pressure on the urethra (U),
    a second operable hydraulic constriction element (201) configured to be inflated to exert a pressure on the urethra (U),
    a first hydraulic pump (104) for pumping fluid to the operable hydraulic constriction element (101),
    a second hydraulic pump (204) for pumping fluid to the operable hydraulic constriction element (101), and
    a motor (M),
    wherein the motor is mechanically connected to the first and second hydraulic pump (104, 204) for propelling the first and second hydraulic pump (104, 204).
2. The implantable constriction device (10) according to aspect 1, wherein the motor (M) is an electrical motor.
3. The implantable constriction device (10) according to aspect 2, wherein the motor (M) is a brushless implantable DC motor.
4. The implantable constriction device (10) according to any one of aspects 1-3, further comprising a gear system (G) placed between the motor (M) and the first and second hydraulic pump (104, 204), and wherein the gear system (G) is configured to reduce the velocity and increase the force of the movement generated by the motor (M) for propelling the first and second hydraulic pump (104, 204) with a mechanical force with a lower velocity and a greater force.
5. The implantable constriction device (10) according to any one of the preceding aspects, wherein the motor (M) is configured to generate a rotating force and propel the first and second hydraulic pump (104, 204) with a rotating mechanical force.
6. The implantable constriction device (10) according to aspect 7, wherein
    a rotating force output of the motor (M) is connected to a force input of the gear system (G), and
    a rotating force output of the gear system (G) is connected to the first and second hydraulic pump (104, 204).
7. The implantable constriction device (10) according to any one of the preceding aspects, wherein at least one of the first and second hydraulic pump (104, 204) comprises a gear pump.
8. The implantable constriction device (10) according to any one of the preceding aspects, wherein at least one of the first and second hydraulic pump (104, 204) comprises a peristaltic pump.
9. The implantable constriction device (10) according to any one of the preceding aspects, wherein at least one of the first and second hydraulic pump (104, 204) comprises a pump comprising at least one compressible hydraulic reservoir (107*a*, 107*b*).
10. The implantable constriction device (10) according to any one of the preceding aspects, wherein at least one of the first and second hydraulic pump (104, 204) comprises a gerotor pump (460).
11. The implantable constriction device (10) according to aspect 10, wherein:
    the first hydraulic pump (104) comprises a first gerotor pump (460'),
    the second hydraulic pump (104) comprises a second gerotor pump (460"),
    the implantable constriction device (10) further comprises a common rotating shaft (463) mechanically connected to the motor (M),
    an inner rotor (461') of the first gerotor pump (460') is mechanically connected to the common rotating shaft (463), and wherein
    an inner rotor (461") of the second gerotor pump (460") is mechanically connected to the common rotating shaft (463), such that the motor (M) propels the first and second gerotor pump (460', 460").
12. The implantable constriction device (10) according to any one of the preceding aspects, further comprising an implantable reservoir (107), and wherein at least one of the first and second hydraulic pump (104, 204) is connected to the implantable reservoir.
13. The implantable constriction device (10) according to any one of aspects 1-11, further comprising a first implantable reservoir (107) and a second implantable reservoir (207), and wherein
    the first hydraulic pump (104) is connected to the first implantable reservoir, and
    the second hydraulic pump (204) is connected to the second implantable reservoir.
14. The implantable constriction device (10) according to any one of aspects 1-11, further comprising an implantable reservoir (107), and wherein the first and second hydraulic pump (104,204) is connected to the implantable reservoir, for pumping hydraulic fluid from the first reservoir to the first operable hydraulic constriction element (101) and from the second reservoir to the second operable hydraulic constriction element (201).
15. The implantable constriction device (10) according to any one of the preceding aspects, wherein the first operable hydraulic constriction element (101) is configured to be inflated and thereby expand in a first direction (d1) towards the urethra (U) to constrict a first portion (p1) of the urethra (U) for restricting the flow of urine therethrough, and the second operable hydraulic constriction element (201) is a supporting operable hydraulic constriction element (201) configured to be inflated and thereby expand in the first direction (d1) towards the urethra (U) to support the first operable hydraulic constriction element (101) in constricting the first portion (p1) of the urethra (U) for restricting the flow of urine therethrough.

16. The implantable constriction device (10) according to aspect 15, wherein the supporting operable hydraulic constriction element (201) is connected to the first operable hydraulic constriction element (101).

17. The implantable constriction device (10) according to any one of aspects 15-16, wherein the supporting operable hydraulic constriction element (201) is less resilient than the first operable hydraulic constriction element (101).

18. The implantable constriction device (10) according to aspect 17, wherein the first operable hydraulic constriction element (101) comprises a lumen (103) surrounded by a resilient wall (102) and the supporting operable hydraulic constriction element (201) comprises a lumen (203) surrounded by a resilient wall (202), and wherein a portion of the resilient wall (202) of the supporting operable hydraulic constriction element (201) is thicker than a portion of the resilient wall (102) of the first operable hydraulic constriction element (101).

19. The implantable constriction device (10) according to any one of the preceding aspects, further comprising a first pressure sensor (106) configured to sense the pressure in the first operable hydraulic constriction element (101).

20. The implantable constriction device (10) according to any one of the preceding aspects, further comprising a second pressure sensor (206) configured to sense the pressure in the second operable hydraulic constriction element (201).

21. The implantable constriction device (10) according to any one of aspect 19-20, further comprising an implantable controller (300), wherein the implantable controller (300) is configured to control at least one of the:
first hydraulic pump (104) on the basis of input from the first pressure sensor (106), and
the second hydraulic pump (204) on the basis of input from the second pressure sensor (206).

22. The implantable constriction device (10) according to any one of the preceding aspects, further comprising a first implantable injection port (108) in fluid connection with the first operable hydraulic constriction element (101).

23. The implantable constriction device (10) according to any one of the preceding aspects, further comprising a second implantable injection port (208) in fluid connection with the second operable hydraulic constriction element (201).

24. The implantable constriction device (10) according to any one of the preceding aspects, wherein the second operable hydraulic constriction element (201) has a length (l3) in the axial direction (AD) of the urethra (U), when implanted, and wherein the first operable hydraulic constriction element (101) has a length (l2) in the axial direction (AD) of the urethra (U), and wherein the length of the first operable hydraulic constriction element (l2) is longer than the length (l3) of the second operable hydraulic constriction element (201).

ASPECT_290SE_Constriction_Urine_Sensor

1. An implantable constriction device (10) for constricting a urethra (U) of a patient for restricting the flow of urine therethrough, the implantable constriction device (10) comprises:
an operable hydraulic constriction element (101) configured to be inflated to exert a pressure on the urethra (U),
a pressure sensor (106) configured to sense the pressure in the operable hydraulic constriction element (101)
a hydraulic pump (104) for pumping a hydraulic fluid to the operable hydraulic constriction element (101), and
a controller (300) configured to receive pressure sensor input from the pressure sensor (106) and control the hydraulic pump (104) on the basis of the received pressure sensor input, wherein
the pressure sensor (106) comprises a diaphragm (471), and wherein the diaphragm (471) is:
in fluid connection with the hydraulic fluid in the operable hydraulic constriction element (101), and
connected to a pressure sensing element (472) of the pressure sensor (106), such that the pressure sensing element (472) is separated from the hydraulic fluid in the operable hydraulic constriction element (101) by the diaphragm (471).

2. The implantable constriction device (10) according to aspect 1, wherein the pressure sensor (106) comprises a strain gauge-based pressure sensor.

3. The implantable constriction device (10) according to aspect 2, wherein the pressure sensor (106) comprises a piezoresistive or piezoelectric strain gauge-based pressure sensor.

4. The implantable constriction device (10) according to aspect 2, wherein the pressure sensor (106) comprises an optical strain gauge-based pressure sensor.

5. The implantable constriction device (10) according to aspect 1, wherein the pressure sensor (106) comprises a capacitive pressure sensor.

6. The implantable constriction device (10) according to aspect 1, wherein the pressure sensor (106) comprises an electromagnetic pressure sensor.

7. The implantable constriction device (10) according to any one of aspects 1-6, wherein the diaphragm (471) is in connection with an enclosed lumen configured to hold a gaseous fluid, and wherein the pressure sensing element is configured to sense the pressure of the gaseous fluid.

8. The implantable constriction device (10) according to any one of aspects 1-7, further comprising an electrically controllable valve (105) connected to the controller (300), and wherein the controller (300) is configured to control the electrically controllable valve (105) on the basis of the received pressure sensor input.

9. The implantable constriction device (10) according to aspect 8, further comprising a reservoir (107) for holding a hydraulic fluid, wherein the reservoir (107) is in fluid connection with the operable hydraulic constriction element (101), and wherein the electrically controllable valve (105) is configured to open and close the fluid connection between the reservoir (107) and the operable hydraulic constriction element (101).

10. The implantable constriction device (10) according to any one of aspects 1-9, further comprising a second operable hydraulic constriction element (101") and a second pressure sensor (106") configured to sense the pressure in the second operable hydraulic constriction element (101").

11. The implantable constriction device (10) according to aspect 10, further comprising a second hydraulic pump (104") for pumping hydraulic fluid to the second operable hydraulic constriction element (101"), and wherein the controller (300) is configured to receive pressure sensor input from the second pressure sensor (106") and control the second hydraulic pump (104") on the basis of the received pressure sensor input.

12. The implantable constriction device (10) according to any one of aspects 8-11, further comprising a second electrically controllable valve (105', 205) connected to the controller (300), and wherein the controller (300) is configured to control the second electrically controllable valve (105', 205) on the basis of the received pressure sensor input.

13. The implantable constriction device (10) according to aspect 12, further comprising a second reservoir (107", 207) for holding a hydraulic fluid, wherein the second reservoir (107", 207) is in fluid connection with the second operable hydraulic constriction element (101", 201), and wherein the second electrically controllable valve (105', 205) is configured to open and close the fluid connection between the second reservoir (107", 207) and second the operable hydraulic constriction element (101", 201).

14. The implantable constriction device (10) according to any one of the preceding aspects, wherein the diaphragm (471) comprises a medical grade silicone material.

15. The implantable constriction device (10) according to any one of the preceding aspects, wherein the diaphragm (471) makes up a portion of a wall of at least one of the operable hydraulic constriction element (101), and the reservoir (107).

ASPECT_291SE_Constriction_Urine_Axial-Bearing

1. An implantable constriction device (10) for constricting a urethra (U) of a patient for restricting the flow of urine therethrough, the implantable constriction device (10) comprises:
   an operable hydraulic constriction element (101) configured to be inflated to exert a pressure on the urethra (U),
   a hydraulic pump (104) for pumping a hydraulic fluid to the operable hydraulic constriction element (101), wherein the hydraulic pump (104) comprises a compressible reservoir (107) configured to hold a hydraulic fluid to be moved to the operable hydraulic constriction element (101),
   a motor (M) comprising a shaft (481), wherein the motor (M) is configured to generate force in a radial direction by rotation of the shaft (481),
   a transmission (T) configured to transfer the force in the radial direction to a force substantially in an axial direction of the shaft (481) for compressing the compressible reservoir (107), and
   at least one bearing (482) for the shaft (481), wherein the bearing (482) is configured to withhold at least half of the force in the axial direction, for reducing the axial load on at least one of the motor (M) and a gear system (G), caused by the compression of the reservoir (107).

2. The implantable constriction device (10) according to aspect 1, wherein the at least one bearing (482) comprises at least one of a ball bearing and a roller bearing.

3. The implantable constriction device (10) according to any one of aspects 1 and 2, wherein the bearing (482) is placed between the gear system (G) and the compressible reservoir (107) for reducing the axial load on the gear system (G) caused by the compression of the reservoir (107).

4. The implantable constriction device (10) according to any one of the preceding aspects, wherein the compressible reservoir (107) comprises a first resilient wall portion (102a), and wherein the shaft (481) is directly or indirectly connected to the first resilient wall portion (102a).

5. The implantable constriction device (10) according to any one of the preceding aspects, wherein the compressible reservoir (107) comprises a first resilient wall portion (102a) and a second resilient wall portion (102b), wherein the first resilient wall portion (102a) is more resilient than the second resilient wall portion (102b).

6. The implantable constriction device (10) according to any one of the preceding aspects, further comprising the gear system (G) connected to the motor (M) and adapted to receive mechanical work via the shaft (481) having a force and a velocity, and output mechanical work having a stronger force and a lower velocity.

7. The implantable constriction device (10) according to aspect 6, wherein the gear system (G) is placed between the motor (M) and the transmission (T).

8. The implantable constriction device (10) according to any one of the preceding aspects, wherein the shaft (481) comprises a threaded portion (481t), and wherein the implantable constriction device further comprises a compression member (483) directly or indirectly connected to the first resilient wall portion (102a), wherein the compression member (483) comprising a corresponding threaded portion (483t) such that the threaded portions of the shaft and the compression member together creates the transmission (T).

9. The implantable constriction device (10) according to aspect 8, wherein the compression member (483) is integrated in the first resilient wall portion (102a).

10. The implantable constriction device (10) according to any one of the preceding aspects, further comprising a pressure sensor (106) configured to sense the pressure in the compressible reservoir (107).

11. The implantable constriction device (10) according to aspect 10, wherein the pressure sensor (106) is integrated in a wall portion (102b) of the compressible reservoir (107).

12. The implantable constriction device (10) according to any one of aspects 10 or 11, wherein the pressure sensor (106) comprises a strain gauge-based pressure sensor 13. The implantable constriction device (10) according to any one of aspects 4-12, wherein the first resilient wall portion (102a) comprises a convex portion configured to be compressed and thus inverted, for creating a concave portion.

14. The implantable constriction device (10) according to aspect 13, wherein the second resilient wall portion (102b) comprises a concave portion towards the lumen of the compressible reservoir (107), and wherein the first resilient wall portion (102a) is configured to be compressed and thus inverted into the concave portion of the second resilient wall portion (102b).

15. The implantable constriction device (10) according to aspect 14, wherein the compression member (483) comprises a convex portion configured to engage the first resilient wall portion (102a) for facilitating the inversion of the convex portion of the first resilient wall portion (102a).

16. The implantable constriction device (10) according to any one of the preceding aspects, further comprising a shaft sealing (486) configured to engage the shaft and provide a seal between the transmission (T) at least one of the motor (M) and a gear system (G).
17. The implantable constriction device (10) according to aspect 16, further comprising an elastic element configured to exert an elastic force on the shaft sealing (486), such that the shaft sealing (486) exerts a sealing force on the shaft (481).
18. The implantable constriction device (10) according to any one of aspects 16 and 17, wherein the shaft sealing (486) comprises a self-lubricating polymer material.
19. The implantable constriction device (10) according to aspect 18, wherein the shaft sealing (486) comprises PTFE.

ASPECT_292SE_Constriction_Urine_Wall-Varying-Thickness

1. An implantable operable hydraulic constriction element (101) configured to be inflated to exert a pressure on a urethra (U) of a patient for constricting the urethra (U) and thereby restrict the flow of urine therethrough, the implantable operable hydraulic constriction element (101) comprising:
   a contacting wall portion (102a) configured to engage the urethra (U) for exerting force thereon,
   a withholding wall portion (102b) configured to be connected to a withholding structure (20) for withholding the force exerted on the urethra (U), such that the urethra (U) is constricted,
   a connecting wall portion (W), connecting the contacting wall portion (102a) to the withholding wall portion (102b), wherein
      and a first portion (W1) of the connecting wall portion (W) is connected to the contacting wall portion (102a),
      a second portion (W2) of the connecting wall portion (W) is connected to the withholding wall portion (102b),
      the first portion (W1) of the connecting wall portion (W) is more resilient than the second portion (W2) of the connecting wall portion (W).
2. The implantable operable hydraulic constriction element (101) according to aspect 1, wherein the first portion (W1) of the connecting wall portion (W) has a lower average wall thickness (T1) than the average wall thickness (T2) of the second portion (W2) of the connecting wall portion (W).
3. The implantable operable hydraulic constriction element (101) according to aspect 2, wherein the first portion (W1) of the connecting wall portion (W) has an average wall thickness (T1) which is less than 0.8 times the average wall thickness (T2) of the second portion (W2) of the connecting wall portion (W).
4. The implantable operable hydraulic constriction element (101) according to any one of the preceding aspects, wherein:
   the first portion (W1) of the connecting wall portion (W) comprises a first and a second sub portion (W1',W1") and wherein the first sub portion (W1') of the first portion (W1) is connected to the contacting wall portion (102a),
   the second portion (W2) of the connecting wall portion (W) comprises a first and a second sub portion (W2',W2") and wherein the second sub portion (W2") of the second portion (W2) is connected to the withholding wall portion (102b),
   the first sub portion (W1') of the first portion (W1) is more resilient than the second sub portion (W1") of the first portion (W1).
5. The implantable operable hydraulic constriction element (101) according to aspect 4, wherein the first sub portion (W1') of the first portion (W1) has a lower average wall thickness (Ti) than the average wall thickness (T1") of the second sub portion (W1") of the first portion (W1).
6. The implantable operable hydraulic constriction element (101) according to aspect 5, wherein the first sub portion (W1') of the first portion (W1) has an average wall thickness (T1) which is less than 0.9 times the average wall thickness (T1") of the second sub portion (W1") of the first portion (W1).
7. The implantable operable hydraulic constriction element (101) according to aspect 4, wherein the first sub portion (W2') of the first portion (W2) is more resilient than the second sub portion (W2") of the first portion (W2).
8. The implantable operable hydraulic constriction element (101) according to aspect 7, wherein the first sub portion (W2') of the second portion (W2) has a lower average wall thickness (T2) than the average wall thickness (T2") of the second sub portion (W2") of the second portion (W2).
9. The implantable operable hydraulic constriction element (101) according to aspect 8, wherein the first sub portion (W2') of the second portion (W2) has an average wall thickness (T2) which is less than 0.9 times the average wall thickness (T2") of the second sub portion (W2") of the second portion (W2).
10. The implantable operable hydraulic constriction element (101) according to any one of the preceding aspects, wherein the first portion (W1) of the connecting wall portion (W) comprises a first material and the second portion (W2) of the connecting wall portion (W) comprises a second material, and wherein the first material has a lower modulus of elasticity than the first material.
11. The implantable operable hydraulic constriction element (101) according to aspect 10, wherein the modulus of elasticity of the first material is less than 0.8 times the modulus of elasticity of the second material.
12. The implantable operable hydraulic constriction element (101) according to any one of aspects 10 or 11, wherein the first material is a medical grade silicone material and the second material is a less elastic medical grade silicone material.
13. An implantable constriction device (10) for constricting a urethra (U) of a patient for restricting the flow of urine therethrough, the implantable constriction device (10) comprises:
   the implantable operable hydraulic constriction element (101) according to any one of aspect 1-12, and
   a withholding structure (20) for withholding the force exerted on the urethra (U), such that the urethra (U) is constricted.
14. The implantable operable hydraulic constriction element (101) according to aspect 13, wherein the withholding structure (20) comprises a surrounding structure (20) configured to surround the urethra (U).
15. The implantable operable hydraulic constriction element (101) according to any one of aspects 13 and 14, wherein the surrounding structure (20) is comprised of a first and second support element (24a,24b) configured to be connected to each other for forming the surrounding structure (20).
16. The implantable operable hydraulic constriction element (101) according to aspect 15, wherein the first and second support element (24a,24b) are hingedly connected to each other.
17. The implantable operable hydraulic constriction element (101) according to any one of aspects 13-16, wherein the surrounding structure (20) comprises at least one cushioning element (30) configured to contact the urethra (U), wherein the cushioning element (30) is more resilient than the surrounding structure (20).

ASPECT_293SE_Constriction_Urine_Power_Supply
1. An implantable constriction device (10) for constricting a urethra (U) of a patient for restricting the flow of urine therethrough, the implantable constriction device (10) comprises:
   an operable hydraulic constriction element (101) configured to be inflated to exert a pressure on the urethra (U),
   a hydraulic pump (104) for pumping a hydraulic fluid to the operable hydraulic constriction element (101),
   an implantable energy storage unit (40),
   a capacitor (397) connected to the implantable energy storage unit (40) and connected to the hydraulic pump (104),
   wherein the capacitor (397) is configured to be charged by the implantable energy storage unit (40) and to provide the hydraulic pump (104) with electrical power.
2. The implantable constriction device (10) according to aspect 1, wherein the implantable energy storage unit (40) is a re-chargeable battery (40).
3. The implantable constriction device (10) according to aspect 1, wherein the implantable energy storage unit (40) is a solid-state battery.
4. The implantable constriction device (10) according to aspect 3, wherein the battery (40) is a thionyl chloride battery.
5. The implantable constriction device (10) according to any one of the preceding aspects, wherein the implantable energy storage unit (40) is connected to the hydraulic pump (104) and configured to power the hydraulic pump (104) after it has been started using the capacitor
6. The implantable constriction device (10) according to any one of the preceding aspects, wherein the capacitor (397) is configured to store energy to provide a burst of energy to the hydraulic pump (104).
7. The implantable constriction device (10) according to any one of the preceding aspects, wherein the capacitor (397) is a start capacitor.
8. The implantable constriction device (10) according to any one of the preceding aspects, wherein the capacitor (397) is a run capacitor.
9. The implantable constriction device (10) according to any one of the preceding aspects, wherein the capacitor (397) is a dual run capacitor.
10. The implantable constriction device (10) according to any one of the preceding aspects, further comprising a second capacitor configured to be charged by the implantable energy storage unit (40) and to provide the hydraulic pump (104) with electrical power.
11. The implantable constriction device (10) according to any one of the preceding aspects, wherein the capacitor (397) is a supercapacitor.
12. The implantable constriction device (10) according to any one of the preceding aspects, wherein the hydraulic pump (104) comprises an electrical motor (M) for operating a hydraulic pump (104).
13. The implantable constriction device (10) according to any one of the preceding aspects, wherein the capacitor (397) is further configured to provide electrical power to at least one of:
   a device for providing electrical stimulation to a tissue portion of the body of the patient,
   a CPU for encrypting information
   a transmitting and/or receiving unit for communication with an external unit
   a measurement unit or a sensor
   a data collection unit
   a solenoid
   a piezo-electrical element
   a memory metal unit.
14. The implantable constriction device (10) according to any one of the preceding aspects, wherein the capacitor (397) is further configured to provide electrical power to a valve (105).
15. The implantable constriction device (10) according to any one of the preceding aspects, wherein the capacitor (397) is further configured to provide electrical power to a controller (300) for controlling at least a part of the implantable constriction device (10).
16. The implantable constriction device (10) according to any one of the preceding aspects, further comprising:
   an external energy storage unit (40) configured be arranged outside of the patient's body and configured to provide energy to the implantable energy storage unit (40),
   an implantable energy receiver (395) configured to be electrically connected to the implantable energy storage unit (40) and enable charging of the implantable energy storage unit (40) by the external energy storage unit (396).
17. The implantable constriction device (10) according to any one of the preceding aspects, further comprising a temperature sensor (351) for sensing a temperature of the implantable energy storage unit (40).
18. The implantable constriction device (10) according to any one of the preceding aspects, further comprising a temperature sensor (351) for sensing a temperature of the capacitor (397).

ASPECT_294SE_Constriction_Urine_Remote-Control
1. An implantable constriction device (10) for constricting a urethra (U) of a patient for restricting the flow of urine therethrough, the implantable constriction device (10) comprises:
   an operable hydraulic constriction element (101) configured to be inflated to exert a pressure on the urethra (U),
   a hydraulic pump (104) for pumping a hydraulic fluid to the operable hydraulic constriction element (101),
   a controller (300) configured to control the hydraulic pump (104), the controller comprising a sensor (351) adapted to detect a magnetic field and a processing unit (306) having a sleep mode and an active mode,
   an external control unit (320) adapted to be arranged outside of the patient's body, the external control unit (320) comprising a first coil adapted to create a magnetic field detectable by the internal sensor (351), wherein the controller (300) is further configured to, in response to a detected magnetic field exceeding a predetermined value, setting the processing unit in an active mode.
2. The implantable constriction device (10) according to aspect 1, wherein the sensor (351) is at least one of: a hall effect sensor, a fluxgate sensor, an ultra-sensitive magnetic field sensor or a magneto-resistive sensor.
3. The implantable constriction device (10) according to any one of the preceding aspects, wherein the frequency of the magnetic field generated by the coil is 9-315 kHz.
4. The implantable constriction device (10) according to any one of the preceding aspects, wherein the frequency of the magnetic field generated by the coil is less than or equal to 125 kHz, preferably less than 58 kHz.
5. The implantable constriction device (10) according to any one of the preceding aspects, wherein the controller (300) comprises a receiver unit (303), and wherein the controller (300) and the external control unit are configured to transmit and/or receive data via the receiver unit (303) and the first coil via magnetic induction.
6. The implantable constriction device (10) according to aspect 5, wherein the receiver unit (303) comprises a high-sensitivity magnetic field detector (351).
7. The implantable constriction device (10) according to aspect 5, wherein the receiver unit (303) comprises a second coil.
8. The implantable constriction device (10) according to aspect 7, further comprising an implantable energy storage unit (40) electrically connected to the receiver unit (303), wherein the implantable energy storage (40) unit is adapted to be charged by the external control unit (320) via the receiver unit (395).
9. The implantable constriction device (10) according to aspect 7, wherein the implantable energy storage unit (40) is configured to be charged via magnetic induction between the first and the second coils.
10. The implantable constriction device (10) according to any one of aspects 8-9, wherein the receiver unit (395) is configured to control the charging of the implantable energy storage unit (40) by controlling a receipt of electrical power from the external control unit (320) at the receiver unit (395).
11. The implantable constriction device (10) according to any one of aspects 8-10, wherein the internal receiver unit (395) is configured to control the charging of the implantable energy storage unit (40) by controlling a transmission of electrical power from the external control unit (320) to the receiver unit (395).
12. The implantable constriction device (10) according to any one of the preceding aspects, further comprising a sensation generator (381) adapted to generate a sensation detectable by a sense of the patient, the sensation generator (381) being connected to the controller (300) or the external control unit (320), and being configured to, upon request, generate the sensation when implanted in a patient.
13. The implantable constriction device (10) according to aspect 12, wherein the sensation generator (381) is configured to receive the request from the controller (300) or the medical implant (10).
14. The implantable constriction device (10) according to any one of aspects 12-13, wherein the sensation generator (381) is configured to receive the request from an external device
15. The implantable constriction device (10) according to any one of aspects 12-14, wherein the sensation generator (381) is configured to create the sensation comprising a plurality of sensation components.
16. The implantable constriction device (10) according to any one of aspects 12-15, wherein the sensation generator (381) is configured to create the sensation or sensation components by at least one of:
a vibration of the sensation generator
producing a sound
providing a photonic signal
providing a light signal
providing an electric signal
a heat signal.
17. The implantable constriction device (10) according to any one of aspects 12-16, wherein the sensation generator (381) is adapted to be implanted in the patient.
18. The implantable constriction device (10) according to any one of aspects 12-16, wherein the sensation generator (381) is configured to be worn in contact with the skin of the patient.
19. The implantable constriction device (10) according to any one of aspects 12-16, wherein the sensation generator (381) is configured generate the sensation without being in physical contact with the patient.
20. The apparatus according to any one of the preceding aspects, wherein the external control unit (320) comprises a wireless remote control.
21. The implantable constriction device (10) according to aspect 20, wherein the wireless remote control comprises an external signal transmitter (390), and wherein the internal receiver is further configured to receive a signal transmitted by the external signal transmitter (323, 390) and to control an operation of the apparatus based on said signal, when the processing unit (306) is in the active state.
22. The implantable constriction device (10) according to aspect 21 wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

ASPECT_295SE_Constriction_Urine_Method
1. A method of implanting an implantable constriction device, the method comprises the steps of:
making an incision in the abdomen of the patient, for accessing the urethra,
dissecting a portion of the urethra,
inserting an implantable constriction device into the body of the patient,
placing the implantable constriction device in connection with the urethra, such that the implantable constriction device can constrict the urethra to restrict the flow of urine therethrough.
2. The method according to aspect 1, wherein the step of inserting an implantable constriction device into the body of the patient comprises inserting an implantable constriction device comprising a first, second and third urethra contacting element, wherein:
the first urethra contacting element comprises a first operable hydraulic constriction element (101*a*) configured to be inflated to constrict the urethra (U) for restricting the flow of urine therethrough,
the second urethra contacting element comprises a second operable hydraulic constriction element (101*b*) configured to be inflated to assist in releasing the constriction of the urethra (U) for restoring the flow of urine therethrough, and the third urethra contacting element comprises at least one cushioning element (30) configured to contact the urethra (U).

3. The method according to aspect 1, wherein the step of inserting an implantable constriction device into the body of the patient comprises inserting an implantable constriction device comprising:

a first operable hydraulic constriction element (101') configured to be inflated to constrict the urethra (U) for restricting the flow (F) of urine therethrough, a second operable hydraulic constriction element (101") configured to be inflated to constrict the urethra (U) for restricting the flow (F) of urine therethrough, and an interconnecting fluid conduit (116) fluidly connecting the first operable hydraulic constriction element (101') to the second operable hydraulic constriction element (101"), wherein the first operable hydraulic constriction element (101') is configured to be placed at a first portion (p1) of the urethra (U) for constricting the first portion (p1) of the urethra (U) for restricting the flow (F) of urine therethrough, the second operable hydraulic constriction element (101") is configured to be placed at a second portion (p2) of the urethra (U), downstream the first portion (p1), for constricting the second portion (p2) of the urethra (U) for restricting the flow (F) of urine therethrough, and the interconnecting fluid conduit (116) is configured to conduct fluid from the first operable hydraulic constriction element (101') to the second operable hydraulic constriction element (101") when the pressure increases in the first operable hydraulic constriction element (101'), such that second operable hydraulic constriction element (101") constricts the second portion (p2) of the urethra (U) further.

4. The method according to aspect 1, wherein the step of inserting an implantable constriction device into the body of the patient comprises inserting an implantable constriction device comprising:

a first operable hydraulic constriction element (101) configured to be inflated and thereby expand in a first direction (d1) towards the urethra (U) to constrict a first portion (p1) of the urethra (U) for restricting the flow of urine therethrough, and a supporting operable hydraulic constriction element (201) configured to be inflated and thereby expand in the first direction (d1) towards the urethra (U) to support the first operable hydraulic constriction element (101) in constricting the first portion (p1) of the urethra (U) for restricting the flow of urine therethrough.

5. The method according to aspect 1, wherein the step of inserting an implantable constriction device into the body of the patient comprises inserting an implantable constriction device comprising:

a first operable hydraulic constriction element (101a) configured to be inflated to exert a pressure on the urethra (U) in a first direction (d1) to constrict a first portion of the urethra (U) for restricting the flow (F) of urine therethrough, a second operable hydraulic constriction element (101b) configured to be inflated to exert a pressure on the urethra (U) in a second direction to constrict the first portion of the urethra (U) for restricting the flow (F) of urine therethrough, and a first hydraulic system in fluid connection with the first operable hydraulic constriction element (101a), and a second hydraulic system in fluid connection with the second operable hydraulic constriction element (101b), wherein the first and second operable hydraulic constriction elements (101a,101b) are adjustable independently from each other.

6. The method according to aspect 1, wherein the step of inserting an implantable constriction device into the body of the patient comprises inserting an implantable constriction device comprising:

an operable hydraulic constriction element (101) configured to be inflated to exert a pressure on the urethra (U), a hydraulic reservoir (107) for holding a hydraulic fluid, a hydraulic pump (104) for pumping fluid from the hydraulic reservoir (107) to the operable hydraulic constriction element (101), a first fluid conduit (109') creating a fluid connection between the hydraulic reservoir (107) and the hydraulic pump (104), a second fluid conduit (109") creating a fluid connection between the hydraulic pump (104) and the operable hydraulic constriction element (101), an injection port (108) for injecting and removing hydraulic fluid from the implantable constriction device (10), when implanted, and a third fluid conduit (109''') creating a fluid connection between the injection port (108) and at least one of the second fluid conduit (109") and the operable hydraulic constriction element (101), such that hydraulic fluid can be removed from the operable hydraulic constriction element (101) through the injection port (108).

7. The method according to aspect 1, wherein the step of inserting an implantable constriction device into the body of the patient comprises inserting an implantable constriction device comprising:

an operable hydraulic constriction element (101) configured to be inflated to exert a pressure on the urethra (U), a hydraulic reservoir (107) for holding a hydraulic fluid, a hydraulic pump (104) for pumping fluid from the hydraulic reservoir (107) to the operable hydraulic constriction element (101), a first fluid conduit (109') creating a fluid connection between the hydraulic reservoir (107) and the hydraulic pump (104), an electrode arrangement configured to be arranged between the implantable constriction device (10) and the urethra (U) and to engage and electrically stimulate muscle tissue of the urethra (U) to exercise the muscle tissue to improve the conditions for long term implantation of the implantable constriction device (10).

8. The method according to aspect 1, wherein the step of inserting an implantable constriction device into the body of the patient comprises inserting an implantable constriction device comprising:

a first operable hydraulic constriction element (101) configured to be inflated to exert a pressure on the urethra (U),
a second operable hydraulic constriction element (201) configured to be inflated to exert a pressure on the urethra (U),
a first hydraulic pump (104) for pumping fluid to the operable hydraulic constriction element (101),
a second hydraulic pump (204) for pumping fluid to the operable hydraulic constriction element (101), and
a motor (M),
wherein the motor is mechanically connected to the first and second hydraulic pump (104,204) for propelling the first and second hydraulic pump (104,204).

9. The method according to aspect 1, wherein the step of inserting an implantable constriction device into the body of the patient comprises inserting an implantable constriction device comprising:
an operable hydraulic constriction element (101) configured to be inflated to exert a pressure on the urethra (U),
a pressure sensor (106) configured to sense the pressure in the operable hydraulic constriction element (101),
a hydraulic pump (104) for pumping a hydraulic fluid to the operable hydraulic constriction element (101), and
a controller (300) configured to receive pressure sensor input from the pressure sensor (106) and control the hydraulic pump (104) on the basis of the received pressure sensor input, wherein
the pressure sensor comprises a diaphragm, and wherein the diaphragm is:
in fluid connection with the hydraulic fluid in the operable hydraulic constriction element (101), and
connected to a pressure sensing element of the pressure sensor, such that the pressure sensing element is separated from the hydraulic fluid in the operable hydraulic constriction element (101) by the diaphragm.

10. The method according to aspect 1, wherein the step of inserting an implantable constriction device into the body of the patient comprises inserting an implantable constriction device comprising:
an operable hydraulic constriction element (101) configured to be inflated to exert a pressure on the urethra (U),
a hydraulic pump (104) for pumping a hydraulic fluid to the operable hydraulic constriction element (101), wherein the hydraulic pump (104) comprises a compressible reservoir (107) configured to hold a hydraulic fluid to be moved to the operable hydraulic constriction element (101),
a motor (M) comprising a shaft (481), wherein the motor (M) is configured to generate force in a radial direction by rotation of the shaft (481),
a transmission (T) configured to transfer the force in the radial direction to a force substantially in an axial direction of the shaft (481) for compressing the compressible reservoir (481), and
at least one bearing (482) for the shaft (481), wherein the bearing (482) is configured to withhold at least half of the force in the axial direction, for reducing the axial load on at least one of the motor (M) and a gear system (G), caused by the compression of the reservoir (107).

11. The method according to aspect 1, wherein the step of inserting an implantable constriction device into the body of the patient comprises inserting an implantable constriction device comprising at least one implantable operable hydraulic constriction element (101) comprising:
a contacting wall portion (102a) configured to engage the urethra (U) for exerting force thereon,
a withholding wall portion (102b) configured to be connected to a withholding structure (20) for withholding the force exerted on the urethra (U), such that the urethra (U) is constricted,
a connecting wall portion (W), connecting the contacting wall portion (102a) to the withholding wall portion (102b), wherein
and a first portion (W1) of the connecting wall portion (W) is connected to the contacting wall portion (102a),
a second portion (W2) of the connecting wall portion (W) is connected to the withholding wall portion (102b),
the first portion (W1) of the connecting wall portion (W) is more resilient than the second portion (W2) of the connecting wall portion (W).

12. The method according to aspect 1, wherein the step of inserting an implantable constriction device into the body of the patient comprises inserting an implantable constriction device comprising:
an operable hydraulic constriction element (101) configured to be inflated to exert a pressure on the urethra (U),
a hydraulic pump (104) for pumping a hydraulic fluid to the operable hydraulic constriction element (101),
an implantable energy storage unit (40), and
a capacitor connected to the implantable energy storage unit (40) and connected to the hydraulic pump (104), wherein the capacitor is configured to be charged by the implantable energy storage unit (40) and to provide the hydraulic pump (104) with electrical power.

13. The method according to aspect 1, wherein the step of inserting an implantable constriction device into the body of the patient comprises inserting an implantable constriction device comprising:
an operable hydraulic constriction element (101) configured to be inflated to exert a pressure on the urethra (U),
a hydraulic pump (104) for pumping a hydraulic fluid to the operable hydraulic constriction element (101),
a controller (300) configured to control the hydraulic pump (104), the controller comprising a sensor (351) adapted to detect a magnetic field and a processing unit (306) having a sleep mode and an active mode,
an external control unit (320) adapted to be arranged outside of the patient's body, the external control unit (320) comprising a first coil adapted to create a magnetic field detectable by the internal sensor (351),
wherein the controller (300) is further configured to, in response to a detected magnetic field exceeding a predetermined value, setting the processing unit (306) in an active mode.

14. The method according to any one of the preceding aspects, wherein the step of placing the implantable constriction device (10) in connection with the urethra (U) comprises placing the implantable constriction device (10) around the urethra (U) of the patient.

15. The method according to any one of the preceding aspects, wherein the step of placing the implantable constriction device in connection with the urethra (U)

comprises closing a locking or fixation device of the implantable constriction device (10) around the urethra (U) to fixate the implantable constriction device (10) to the urethra (U) of the patient.
16. The method according to any one of the preceding aspects, wherein the step of placing the implantable constriction device (10) in connection with the urethra (U) comprises securing the implantable constriction device (10) by means of at least one of sutures, staples and tissue growth promoting structure.
17. The method according to any one of the preceding aspects, wherein the step of inserting an implantable constriction device (10) into the body of the patient comprises inserting an implantable controller (300) into the body of the patient and fixating the implantable controller (300) to tissue or bone in the body of the patient.
18. The method according to any one of the preceding aspects, wherein the step of inserting an implantable constriction device (10) into the body of the patient comprises inserting an operation device comprising at least one of: an implantable hydraulic pump (104) and an implantable valve (105) and fixating the implantable operation device to tissue or bone in the body of the patient.
19. The method according to aspect 18, further comprising the step of implanting and fixating at least one injection port (108) in fluid connection with the operation device.
20. The method according to aspect 19, wherein the step of fixating the at least one injection port (108) comprises the step of fixating the injection port subcutaneously.
21. The method according to aspect 19, further comprising the step of calibrating the fluid level in the implantable constriction device (10).
22. The method according to any one of the preceding aspects, further comprising calibrating at least one of:
    the pressure exerted by the implantable constriction device on the urethra,
    the time during which implantable constriction device is to remain open after activation,
    the time during which implantable constriction device is to remain open after activation before bedtime,
    the speed with which the implantable constriction device should constrict the urethra,
    the pressure exerted on the urethra relative to the blood pressure if the patient,
    the pressure exerted on the urethra by the implantable constriction device by means of a pressure sensitive catheter, and
    the electrical stimulation of the tissue of the urethra.
23. The method according to any one of the preceding aspects, further comprising testing at least one of:
    a fully open catheter mode,
    a feedback function by providing sensory feedback to the patient,
    a post-operative mode for enabling healing
    a post-operative mode for enabling growth of fibrotic tissue, and
    electrical stimulation of the tissue of the urethra.

ASPECT_296SE_Constriction_Urine_Two-Liquids
1. An implantable operation device for operating a hydraulic constriction element configured to exert a force on a urethra of a patient, the implantable operation device comprising:
    a housing (484) comprising a first and a second chamber (C1, 107) separated from each other, wherein the first chamber (C1) comprises a first liquid and the second chamber (107) comprises a second liquid, and wherein the second liquid is a hydraulic liquid configured to transfer force to the hydraulic constriction element.
2. The implantable operation device according to aspect 1, further comprising a motor (M) housed in the first chamber (C1), wherein the motor is configured for transforming electrical energy to mechanical work.
3. The implantable operation device according to any one of aspects 1 and 2, further comprising a hydraulic pump (104), and wherein the hydraulic pump (104) is configured to pump the hydraulic liquid from the operation device to the hydraulic constriction element configured to exert the force on the urethra of the patient.
4. The implantable operation device according to aspects 3, wherein the hydraulic pump (104) comprises a gear pump.
5. The implantable operation device according to aspects 3, wherein the hydraulic pump (104) comprises a peristaltic pump.
6. The implantable operation device according to aspects 3, wherein the hydraulic pump (104) comprises a pump comprising at least one compressible hydraulic reservoir (107).
7. The implantable operation device according to aspects 3, wherein the hydraulic pump (104) comprises a gerotor pump.
8. The implantable operation device according to any one of aspects 3-7, further comprising a transmission (T) coupled between the motor (M) and the hydraulic pump (104).
9. The implantable operation device according to aspect 8, wherein the transmission (T) is configured to transfer a week force with a high velocity into a stronger force with lower velocity.
10. The implantable operation device according to aspect 8, wherein the transmission (T) is configured to transfer a rotating force into a linear force.
11. The implantable operation device according to aspect 8, wherein the transmission comprises a gear system (G).
12. The implantable operation device according to any one of the preceding aspects, wherein a fluid chamber (107) of the hydraulic pump (104) forms a portion of the second chamber.
13. The implantable operation device according to any one of the preceding aspects, further comprising an implantable energy storage unit (40) housed in the first chamber (C1).
14. The implantable operation device according to any one of the preceding aspects, further comprising a controller (300) housed in the first chamber (C1).
15. The implantable operation device according to any one of the preceding aspects, wherein a wall portion (495) of the first chamber (Cl) is resilient to allow an expansion of the first chamber (C1).
16. The implantable operation device according to aspect 15, wherein a wall portion (495) of the first chamber (C1) comprises a resilient membrane.
17. The implantable operation device according to any one of the preceding aspects, wherein the first liquid is a non-conductive liquid.

18. The implantable operation device according to any one of the preceding aspects, wherein the first liquid is a lubricating liquid.
19. The implantable operation device according to any one of the preceding aspects, wherein the first liquid is an oil-based liquid.
20. The implantable operation device according to aspect 19, wherein the first liquid is a mineral oil.
21. The implantable operation device according to aspect 19, wherein the first liquid is a silicone oil.
22. The implantable operation device according to any one of the preceding aspects, wherein the second liquid is an isotone liquid.
23. The implantable operation device according to any one of the preceding aspects, wherein the housing (484) comprises a metallic material.
24. The implantable operation device according to aspect 23, wherein the housing (484) comprises titanium.
25. The implantable operation device according to any one of the preceding aspects, further comprising a conductor (493) for electrical transfer between the first and a second chamber (C1, C2).
26. The implantable operation device according to aspect 25, wherein a wall (484') separating the first chamber (C1) from the second chamber (C2) comprises a portion (494) comprising an electrically insulating material, and wherein the conductor (493) passes from the first chamber (C1) to the second chamber (C2) through the portion (494) comprising the electrically insulating material.
27. The implantable operation device according to aspect 26, wherein the electrically insulating material comprises a ceramic material.
28. An implantable device for exerting a force on a body portion of the patient comprising:
    the implantable operation device according to any one of aspects 1-27,
    a hydraulic constriction element configured to exert a force on a body portion of the patient.

ASPECT_297SE_Constriction_Urine_Magnetic-Coupling

1. An implantable operation device for operating a hydraulic constriction element configured to exert a force on a urethra of a patient, the implantable operation device comprising:
    a housing (484) comprising a first and a second chamber (C1, C2) separated from each other,
    a motor (M) housed in the first chamber (C1), wherein the motor (M) is configured for transforming electrical energy to mechanical work,
    an actuator housed in the second chamber, wherein the actuator is connected to the hydraulic constriction element configured to exert a force on a body portion of a patient,
    a magnetic coupling (490a', 490b') for transferring mechanical work from the motor (M) to the actuator through a barrier (484') separating the first chamber (C1) from the second chamber (C2).
2. The implantable operation device according to aspect 1, wherein the housing (484) comprises a metallic material.
3. The implantable operation device according to aspect 2, wherein the housing (484) comprises titanium.
4. The implantable operation device according to any one of aspects 1-3, wherein the actuator is a hydraulic pump (104) configured to transfer mechanical force to hydraulic force.
5. The implantable operation device according to aspects 4, wherein the hydraulic pump (104) comprises a gear pump.
6. The implantable operation device according to aspects 4, wherein the hydraulic pump (104) comprises a peristaltic pump.
7. The implantable operation device according to aspects 4, wherein the hydraulic pump (104) comprises a pump comprising at least one compressible hydraulic reservoir (107).
8. The implantable operation device according to aspects 4, wherein the hydraulic pump (104) comprises a gerotor pump.
9. The implantable operation device according to any one of aspects 1-3, wherein the actuator is a mechanical actuator configured to transfer mechanical force from the magnetic coupling to the implantable element configured to exert a force on a body portion of a patient.
10. The implantable operation device according to aspect 9, wherein the mechanical actuator is configured to transfer a rotating force into a linear force.
11. The implantable operation device according to any one of the preceding aspects, wherein the magnetic coupling (490a', 490b') comprises
    a first coupling part (490a') comprising magnets (491a') or magnetic material and being:
        comprised in the first chamber (C1),
        connected to the motor (M), and
        configured to perform a rotating movement
    a second coupling part (490b') comprising magnets (491b') or magnetic material and being:
        comprised in the second chamber (C2),
        connected to the actuator, and
        configured to be propelled by the rotating movement of the first coupling part (490a').
12. The implantable operation device according to aspect 11, wherein:
    the first coupling part (490a') comprises magnets (491a') or magnetic material being placed radially along an outer periphery of the first coupling part (490a'), and
    the second coupling part (490b') comprises magnets (491b') or magnetic material being placed radially, such that the radially placed magnets (491a') or magnetic material of the first coupling part (490a') magnetically connects to the radially placed magnets (491b') or magnetic material of the second coupling part (490b').
13. The implantable operation device according to aspect 11, wherein:
    the first coupling part (490a') comprises magnets (491a') or magnetic material being placed axially on a surface of the first coupling part (490a'), and
    the second coupling part (490b') comprises magnets (491b') or magnetic material being placed axially on a surface of the first coupling part (490a'), such that the axially placed magnets (491a') or magnetic material of the first coupling part (490a') magnetically connects to the axially placed magnets (491b') or magnetic material of the second coupling part (490b').
14. The implantable operation device according to any one of the preceding aspects, further comprising a transmission (T) coupled between the motor (M) and the magnetic coupling, the transmission (T) being configured to transfer a week force with a high velocity into a stronger force with lower velocity.

15. The implantable operation device according to aspect 14, wherein the transmission (T) comprises a gear system (G).
16. The implantable operation device according to any one of aspects 11-15, wherein:
    the first coupling part (490a') comprises a first number of magnets (491a'),
    the second coupling part (490b') comprises a second number of magnets (491b'), and
    the first number is different from the second number, such that the magnetic coupling comprises an integrated transmission.
17. The implantable operation device according to aspect 16, wherein the first coupling part (490a') comprises a lower number of magnets (491a') than the second coupling part (490b'), such that the integrated transmission transfers a week force with a high velocity coming from the motor (M), into a stronger force with lower velocity to be provided to the actuator.
18. The implantable operation device according to any one of aspects 16 and 17, further comprising a plurality of intermediate ferromagnetic elements (499) placed between the first and second coupling parts (490a', 490b').
19. The implantable operation device according to aspect 18, wherein two magnets forms a magnetic pole pair, and wherein the implantable operation device comprises a number of intermediate ferromagnetic elements (499) being equal to the sum of magnetic pole pairs on the first and second coupling parts (490a', 490b').
20. The implantable operation device according to any one of aspects 18-19, wherein the barrier (484') comprises the intermediate ferromagnetic elements (499).
21. An implantable constriction device for constricting the urethra to restrict the flow of urine therethrough exerting a force on a body portion of the patient comprising:
    the implantable operation device according to any one of aspects 1-20,
    a hydraulic constriction element configured to exert a force on a urethra of the patient.

ASPECT_298SE_Constriction_Urine_Force-Transfer

1. An implantable hydraulic force transfer device (496) comprising:
    a. a first chamber (V1) configured to house a first fluid, the first chamber (V1) comprising:
        i. a first fluid connection (109a) for fluidly connecting the first chamber (V1) to an implantable operation device (107), and
        ii. at least one movable wall portion (497, 497') for varying the size of the first chamber (V1),
    b. a second chamber (V2) configured to house a second fluid, the second chamber (V2) comprising:
        i. a second fluid connection (109b) for fluidly connecting the second chamber (V2) to a hydraulic constriction element configured to exert a force on a urethra of the patient, and
        ii. at least one movable wall portion (497') for varying the size of the second chamber (V2), wherein:
    the implantable hydraulic force transfer device (496) is configured to transfer hydraulic force from the implantable operation device to the hydraulic constriction element configured to exert a force on a urethra of the patient without mixing the first and second fluids.
2. The implantable hydraulic force transfer device according to aspect 1, comprising a common movable wall portion (497, 497'), wherein:
    at least a portion of the movable wall of the first chamber (V1) comprises the common movable wall portion (497, 497'), and
    at least a portion of the movable wall of the second chamber (V2) comprises the common movable wall portion (497, 497').
3. The implantable hydraulic force transfer device according to any one of aspects 1 and 2, wherein at least one of the movable wall portions comprises a piston (497).
4. The implantable hydraulic force transfer device according to aspect 3, wherein a first side of the piston is facing the first chamber (V1) and a second side of the piston is facing the second chamber (V2).
5. The implantable hydraulic force transfer device according to any one of aspects 1-4, wherein at least one of the movable wall portions comprises a flexible wall portion (497').
6. The implantable hydraulic force transfer device according to aspect 5, wherein the flexible wall portion (497') comprises an elastic wall portion.
7. The implantable hydraulic force transfer device according to any one of aspects 1-6, wherein at least one of the movable wall portions comprises a pleated wall portion (497').
8. The implantable hydraulic force transfer device according to any one of aspects 1-7, wherein at least one of the first and second chambers comprises a bellows (497').
9. The implantable hydraulic force transfer device according to any one of aspects 1-8, wherein the first chamber (V1) is configured to house an oil-based fluid.
10. The implantable hydraulic force transfer device according to any one of aspects 1-9, wherein the second chamber (V2) is configured to house an isotone fluid.
11. An implantable constriction device for constricting the urethra to restrict the flow of urine therethrough:
    an implantable operation device,
    a hydraulic constriction element configured to exert a force on a urethra of the patient,
    the implantable hydraulic force transfer device according to any one of aspects 1-10,
    a first fluid conduit (109a) configured to fluidly connect the implantable operation device to the first chamber (V1) of the implantable hydraulic force transfer device, and
    a second fluid conduit (109b) configured to fluidly connect the hydraulic constriction element to the second chamber (V2) of the implantable hydraulic force transfer device (496).
12. The implantable constriction device according to aspect 11, wherein the operation device comprises a hydraulic pump (107) for pumping hydraulic fluid from the operation device to the first chamber (V1) of the implantable hydraulic force transfer device (496).
13. The implantable device according to any one of aspects 11-12, further comprising a first fluid configured to be transferred between the operation device and the first chamber of the implantable hydraulic force transfer device.
14. The implantable device according to aspect 13, further comprising a second different fluid configured to be transferred between the second chamber and the hydraulic constriction element configured to exert a force on a urethra of the patient.

ASPECT_299SE_Constriction_Urine_Self-Calibration

1. An implantable controller for an implantable constriction device for constricting the urethra to restrict the flow of urine therethrough, the controller being configured to control an operation device configured to operate at least one hydraulic constriction element to exert a force on a urethra of a patient, the implantable controller being further configured to:
receive a first input signal being at least one of:
a sensor input signal related to a physiological parameter of the patient from an implantable sensor (106), and
a control signal from an implanted or external source,
control the operation device to adjust the force exerted on the urethra of a patient, in response to the first input signal, and
receive a second input signal from the implantable sensor (106) related to the physiological parameter of the patient, and
control the operation device to further adjust the force exerted on the urethra in response to the second input signal.
2. The implantable controller according to aspect 1, wherein the physiological parameter is a flow of urine in the urethra.
3. The implantable controller according to aspect 1, wherein the physiological parameter comprises a parameter related to an oxygenation of a tissue portion of the patient.
4. The implantable controller according to aspect 1, wherein the physiological parameter comprises a parameter related to a pulse of the patient.
5. The implantable controller according to aspect 1, wherein the physiological parameter comprises a parameter related to a blood pressure of the patient.
6. The implantable controller according to any one of the preceding aspects, wherein the control signal comprises a patient generated control signal.
7. The implantable controller according to any one of aspects 1-5, wherein the control signal comprises a signal related to a lapsed time or a time of day.
8. The implantable controller according to any one of aspects 1-5, wherein the control signal comprises a signal related to sensor external to the body of the patient.
9. The implantable controller according to aspect 8, wherein the signal related to sensor external to the body of the patient comprises a signal from a motion sensor external to the body of the patient.
10. A method of calibrating an implantable constriction device for constricting the urethra to restrict the flow of urine therethrough, the implantable constriction device comprising at least one hydraulic constriction element configured to exert a force on a urethra of a patient, an operation device for operating the hydraulic constriction element and a controller for controlling the operation device, the method comprising:
receiving, at the controller, a first input signal comprising at least one of:
a sensor input signal related to a physiological parameter of the patient from an implantable sensor (106), and
a control signal from an implanted or external source,
controlling, by the controller, the operation device to adjust the force exerted on the urethra, in response to the first input signal, and
receiving, at the controller, a second input signal from the implantable sensor (106) related to the physiological parameter of the patient, and
controlling, by the controller, the operation device to further adjust the force exerted on the urethra, in response to the second input signal.
a urethra11. The method according to aspect 10, wherein the physiological parameter comprises a parameter related to an oxygenation of a tissue portion of the patient, and wherein the step of controlling the operation device to adjust the force exerted on the urethra comprises controlling the operation device to adjust the force exerted on the urethra in response to the input signal being related to the oxygenation of a tissue portion of the patient.
12. The method according to any one of aspects 10-11, wherein the step of receiving a control signal from an implanted or external source comprises receiving a patient generated control signal.
13. The method according to any one of aspects 10-11, wherein the step of receiving a control signal from an implanted or external source comprises receiving a control signal related to a lapsed time or a time of day.
14. The method according to any one of aspects 10-12, wherein the step of receiving a control signal from an implanted or external source comprises receiving a signal related to a sensor external to the body of the patient.
15. The method according to aspect 15, wherein the step of receiving a control signal from an implanted or external source comprises receiving a signal from a motion sensor external to the body of the patient.

ASPECT_300SE_Constriction_Urine_Hard-Switch
1. An implantable controller (300) for controlling an operation device for operating an implantable constriction device for constricting the urethra to restrict the flow of urine therethrough, the implantable constriction device comprises a hydraulic constriction element configured to exert a force on the urethra of a patient, the implantable controller (300) comprising an electrical switch, wherein the electrical switch comprises at least one of:
a switch being mechanically connected to the hydraulic constriction element and being configured to be switched as a result of the force exerted on the urethra exceeding a threshold value,
a switch being electrically connected to the operation device and being configured to be switched as a result of the current supplied to the operation device exceeding a threshold value, and
a switch being electrically connected to the operation device and being configured to be switched as a result of a temperature exceeding a threshold value.
2. The implantable controller (300) according to aspect 1, wherein the electrical switch is configured to be switched as a result of the pressure in the hydraulic constriction element exceeding a threshold value.
3. The implantable controller (300) according to aspect 1, wherein the operation device comprises a motor (M), and wherein the switch is electrically connected to the motor and configured to be switched as a result of the current supplied to the motor exceeding a threshold value.
4. The implantable controller (300) according to any one of the preceding aspects, wherein the switch is configured to cut the power to the operation device.

5. The implantable controller (300) according to any one of the preceding aspects, wherein the switch is configured to generate a control signal to a processor of the implantable controller (300).
6. An implantable constriction device for constricting the urethra to restrict the flow of urine therethrough by exerting a force on the urethra of the patient, the implantable device comprising:
   an implantable operation device,
   a hydraulic constriction element configured to exert a force on the urethra of the patient, and the implantable controller (300) according to any one of aspects 1-5.
7. The implantable device according to aspect 6, wherein the operation device comprises a motor (M), and wherein the switch is electrically connected to the motor (M) and configured to be switched as a result of the current supplied to the motor (M) exceeding a threshold value.
8. The implantable device according to aspect 7, further comprising a transmission (T, G) coupled between the motor (M) and the hydraulic constriction element configured to exert a force on the urethra of the patient, the transmission (T, G) being configured to transfer a week force with a high velocity into a stronger force with lower velocity.
9. The implantable operation device according to aspect 8, wherein the transmission (T) comprises a gear system (G).
10. The implantable device according to any one of aspects 6-9, wherein the operation device comprises a hydraulic pump (107) for pumping hydraulic fluid from the operation device to the hydraulic constriction element configured to exert a force on the urethra of the patient.
11. The implantable operation device according to aspect 10, wherein the hydraulic pump (107) comprises a gear pump.
12. The implantable operation device according to aspect 10, wherein the hydraulic pump (107) comprises a peristaltic pump.
13. The implantable operation device according to aspect 10, wherein the hydraulic pump (107) comprises a pump comprising at least one compressible hydraulic reservoir.
14. The implantable operation device according to aspect 10, wherein the hydraulic pump (107) comprises a gerotor pump.

ASPECT_301SE_Constriction_Urine_Atmospheric-Pressure

1. An implantable controller for an implantable constriction device for constricting the urethra to restrict the flow of urine therethrough, the controller being configured to control an operation device configured to operate at least one hydraulic constriction element configured to constrict the urethra, the implantable controller being further configured to:
   receive a first input signal being related to a pressure in the hydraulic constriction element,
   receive a second input signal being related to an atmospheric pressure, and
   control the operation device on the basis of the received first and second input signals.
2. The implantable controller according to aspect 1, wherein the implantable controller is configured to receive the second input signal related to the atmospheric pressure from a signal transmitter configured to be located outside the body of the patient.
3. The implantable controller according to aspect 1, wherein the implantable controller is configured to receive the second input signal related to the atmospheric pressure from an implantable pressure sensor.
4. The implantable controller according to any one of aspects 1-3, wherein the implantable controller is configured to control the force exerted on the urethra of the patient on the basis of the received first and second input signals.
5. The implantable controller according to any one of aspects 1-4, wherein the implantable controller is configured to create an absolute pressure by subtracting the atmospheric pressure from the pressure in the hydraulic constriction element, and wherein the implantable controller is configured to control the operation device on the basis of the absolute pressure.
6. An energized implant comprising:
   the implantable controller according to any one of aspects 1-5,
   at least one hydraulic constriction element configured to constrict the urethra of a patient, and
   an operation device configured to operate the at least one hydraulic constriction element.
7. The energized implant according to aspect 6, further comprising a pressure sensor configured to sense the pressure in the hydraulic constriction element and the atmospheric pressure.
8. The energized implant according to aspect 7, further comprising a membrane, and wherein the pressure sensor is configured to sense the pressure in the hydraulic constriction element on a first side of the membrane and the atmospheric pressure on a second side of the membrane.
9. The energized implant according to aspect 8, wherein a portion of a wall in fluid connection with the at least one hydraulic constriction element configured to exert a force on the urethra of a patient comprises the membrane.
10. The energized implant according to any one of aspects 7-9, wherein the sensor is configured to derive an absolute pressure in the hydraulic constriction element by comparing a pressure in the hydraulic constriction element with the atmospheric pressure.
11. The energized implant according to any one of aspects 7-10, wherein the sensor is configured to derive the pressure in the hydraulic constriction element by comparing a pressure in the hydraulic constriction element with vacuum.
12. The energized implant (10) according to any one of aspects 7-11, wherein the pressure sensor (106) comprises at least one of:
   a strain gauge-based pressure sensor,
   a piezoresistive or piezoelectric pressure sensor,
   an optical pressure sensor,
   a capacitive pressure sensor, and
   an electromagnetic pressure sensor.
13. The energized implant according to aspect 6, further comprising:
   a first pressure sensor configured to sense the pressure in the hydraulic constriction element, and
   a second pressure sensor configured to sense the atmospheric pressure.
14. The energized implant according to aspect 13, wherein the first pressure sensor is connected to the at least one hydraulic constriction element configured to exert a force on a body portion of a patient.

15. The energized implant according to any one of aspects 13 and 14, wherein the second pressure sensor is an implantable sensor placed in or connected to the energized implant.

16. The energized implant according to any one of the preceding aspects, wherein the operation device comprises a hydraulic pump.

17. A method in an implantable controller, for controlling an operation device of an implantable constriction device for constricting the urethra to restrict the flow of urine therethrough, the method comprising:
receiving a first input signal, at the implantable controller, the first input signal being related to a pressure in the hydraulic constriction element configured to exert a force on the urethra of the patient,
receiving a second input signal, at the implantable controller, the second input signal being related to an atmospheric pressure, and
controlling, by the controller, the operation device on the basis of the received first and second input signals.

18. The method according to aspect 17, wherein the step of receiving a second input signal comprises receiving the second input signal from a signal transmitter located outside the body of the patient.

19. The method according to aspect 17, wherein the step of receiving a second input signal from a signal transmitter located outside the body of the patient comprises receiving the second input signal in connection with the patient using, activating or controlling the implantable constriction device.

20. The method according to any one of aspects 18 and 19, wherein the step of receiving a second input signal from a signal transmitter located outside the body of the patient comprises receiving the second input signal wirelessly.

21. The method according to aspect 17, wherein the step of receiving a second input signal comprises receiving the second input signal from an implantable pressure sensor.

22. The method according to any one of aspects 17-21, wherein the step of controlling the operation device comprises controlling the force exerted on the urethra of the patient by the hydraulic constriction element on the basis of the received first and second input signals.

23. The method according to any one of aspects 17-22, further comprising the step of creating, in the controller, an absolute pressure by subtracting the atmospheric pressure from the pressure in the hydraulic constriction element, and wherein the step of controlling the operation device comprises controlling the operation device on the basis of the absolute pressure.

ASPECT_302SE_Constriction_Urine_Atmospheric-Pressure2

1. A method in an implantable controller, for controlling an implantable constriction device for constricting the urethra, the method comprising:
releasing the pressure in an implantable hydraulic constriction element such that substantially no pressure is exerted on the urethra,
measuring the pressure in the implantable hydraulic constriction element, when substantially no pressure is exerted on the urethra, and
increasing the pressure in the implantable hydraulic constriction element to a defined level.

2. The method according to aspect 1, wherein the step of measuring the pressure in the implantable hydraulic constriction element, when substantially no pressure is exerted on the urethra, further comprises comparing the measured pressure with the atmospheric pressure.

3. The method according to aspect 2, wherein the step of comparing the measured pressure with the atmospheric pressure comprises measuring the atmospheric pressure using a pressure sensor connected to a signal transmitter located outside the body of the patient.

4. The method according to any one of aspects 1-3, wherein the step of increasing the pressure in the implantable hydraulic constriction element to a defined level, comprises inflating the implantable hydraulic constriction element to a defined cross-sectional distance.

5. The method according to any one of aspects 1-4, further comprising measuring the pressure in the implantable hydraulic constriction element when the pressure in the implantable hydraulic constriction element has been increased.

6. The method according to aspect 5, wherein the step of steps of:
measuring the pressure in the implantable hydraulic constriction element, when substantially no pressure is exerted on the urethra, and
measuring the pressure in the implantable hydraulic constriction element when the pressure in the implantable hydraulic constriction element has been increased, are performed using the same pressure sensor.

7. The method according to any one of aspects 1-6, further comprising the step of creating, in the controller, an absolute pressure by subtracting the pressure in the implantable hydraulic constriction element, when substantially no pressure is exerted on the urethra, from the pressure in the hydraulic constriction element, when the pressure in the implantable hydraulic constriction element has been increased, and wherein the step of controlling the operation device comprises controlling the operation device on the basis of the absolute pressure.

8. A controller for controlling the pressure in an implantable constriction device for constricting the urethra, the controller comprising:
a pressure sensor for measuring the pressure in the implantable hydraulic constriction element, and
a computing unit, wherein the computing unit is configured to create an absolute pressure by subtracting the pressure in the implantable hydraulic constriction element, when substantially no pressure is exerted on the urethra, from the pressure in the hydraulic constriction element, when the pressure in the implantable hydraulic constriction element has been increased.

9. The controller according to aspect 8, wherein the computing unit is further configured to compare the measured pressure with the atmospheric pressure.

10. The controller according to aspect 9, wherein the controller is further configured to receive a pressure signal from a pressure sensor located outside of the body of the patient and compare the measured pressure with a pressure received in the pressure signal.

11. The controller according to any one of aspects 8-10, wherein the controller is configured to increase the pressure in the implantable hydraulic constriction element on the basis of the measured pressure.

12. The controller according to aspect 11, wherein the controller is configured to increase the pressure in the implantable hydraulic constriction element to a defined cross-sectional distance.

The invention claimed is:

1. A method of implanting an implantable constriction device, the method comprises the steps of:
  making an incision in an abdomen of a patient, for accessing a urethra,
  dissecting a portion of the urethra,
  inserting an implantable constriction device into a body of the patient,
  placing the implantable constriction device in connection with the urethra, such that the implantable constriction device can constrict the urethra to restrict a flow of urine therethrough, wherein the step of inserting the implantable constriction device into the body of the patient comprises inserting an implantable constriction device comprising:
  an operable hydraulic constriction element configured to be inflated to exert a pressure on the urethra,
  a hydraulic reservoir for holding a hydraulic fluid,
  a hydraulic pump for pumping fluid from the hydraulic reservoir the operable hydraulic constriction element,
  a first fluid conduit creating a fluid connection between n the hydraulic reservoir and the hydraulic pump,
  a second fluid conduit creating a fluid connection between the hydraulic pump and the operable hydraulic constriction element,
  an injection port for injecting and removing hydraulic fluid from the implantable constriction device, when implanted, and
  a third fluid conduit creating a direct fluid connection between the injection port and at least one of the second fluid conduit and the operable hydraulic constriction element, such that hydraulic fluid can be directly removed from the operable hydraulic constriction element through the injection port, in an event of a failure related to the hydraulic pump.

2. The method according to claim 1, wherein the step of inserting an implantable constriction device into the body of the patient comprises inserting an implantable constriction device comprising:
  an operable hydraulic constriction element configured to be inflated to exert a pressure on the urethra,
  a hydraulic reservoir for holding a hydraulic fluid,
  a hydraulic pump for pumping fluid from the hydraulic reservoir to the operable hydraulic constriction element,
  a first fluid conduit creating a fluid connection between the hydraulic reservoir and the hydraulic pump,
  an electrode arrangement configured to be arranged between the implantable constriction device and the urethra and to engage and electrically stimulate muscle tissue of the urethra to exercise the muscle tissue to improve the conditions for long term implantation of the implantable constriction device.

3. The method according to claim 1, wherein the step of inserting an implantable constriction device into the body of the patient comprises inserting an implantable constriction device comprising:
  a first operable hydraulic constriction element configured to be inflated to exert a pressure on the urethra,
  a second operable hydraulic constriction element configured to be inflated to exert a pressure on the urethra,
  a first hydraulic pump for pumping fluid to the first operable hydraulic constriction element,
  a second hydraulic pump for pumping fluid to the second operable hydraulic constriction element, and
  a motor,
  wherein the motor is mechanically connected to the first and second hydraulic pump for propelling the first and second hydraulic pump.

4. The method according to claim 1, wherein the step of inserting an implantable constriction device into the body of the patient comprises inserting an implantable constriction device comprising:
  an operable hydraulic constriction element configured to be inflated to exert a pressure on the urethra,
  a pressure sensor configured to sense a pressure in the operable hydraulic constriction element,
  a hydraulic pump for pumping a hydraulic fluid to the operable hydraulic constriction element, and
  a controller configured to receive pressure sensor input from the pressure sensor and control the hydraulic pump on a basis of the received pressure sensor input, wherein
the pressure sensor comprises a diaphragm, and wherein the diaphragm is:
  in fluid connection with the hydraulic fluid in the operable hydraulic constriction element, and
  connected to a pressure sensing element of the pressure sensor, such that the pressure sensing element is separated from the hydraulic fluid in the operable hydraulic constriction element by the diaphragm.

5. The method according to claim 1, wherein the step of inserting an implantable constriction device into the body of the patient comprises inserting an implantable constriction device comprising:
  an operable hydraulic constriction element configured to be inflated to exert a pressure on the urethra,
  a hydraulic pump for pumping a hydraulic fluid to the operable hydraulic constriction element, wherein the hydraulic pump comprises a compressible reservoir configured to hold a hydraulic fluid to be moved to the operable hydraulic constriction element,
  a motor comprising a shaft, wherein the motor is configured to generate force in a radial direction by rotation of the shaft,
  a transmission configured to transfer the force in the radial direction to a force substantially in an axial direction of the shaft for compressing the compressible reservoir, and
  at least one bearing for the shaft, wherein the bearing is configured to withhold at least half of the force in the axial direction, for reducing the axial load on at least one of the motor and a gear system, caused by the compression of the reservoir.

6. The method according to claim 1, wherein the step of inserting an implantable constriction device into the body of the patient comprises inserting an implantable constriction device comprising at least one implantable operable hydraulic constriction element comprising:
  a contacting wall portion configured to engage the urethra for exerting force thereon,
  a withholding wall portion configured to be connected to a withholding structure for withholding the force exerted on the urethra, such that the urethra is constricted,
  a connecting wall portion, connecting the contacting wall portion to the withholding wall portion, wherein
  and a first portion of the connecting wall portion is connected to the contacting wall portion, a second portion of the connecting wall portion is connected to the withholding wall portion, the first portion of the connecting wall portion is more resilient than the second portion of the connecting wall portion.

7. The method according to claim 1, wherein the step of inserting an implantable constriction device into the body of the patient comprises inserting an implantable constriction device comprising:

an operable hydraulic constriction element configured to be inflated to exert a pressure on the urethra, a hydraulic pump for pumping a hydraulic fluid to the operable hydraulic constriction element, an implantable energy storage unit, and a capacitor connected to the implantable energy storage unit and connected to the hydraulic pump, wherein the capacitor is configured to be charged by the implantable energy storage unit and to provide the hydraulic pump with electrical power.

8. The method according to claim 1, wherein the step of inserting an implantable constriction device into the body of the patient comprises inserting an implantable constriction device comprising:

an operable hydraulic constriction element configured to be inflated to exert a pressure on the urethra, a hydraulic pump for pumping a hydraulic fluid to the operable hydraulic constriction element, a controller configured to control the hydraulic pump, the controller comprising a sensor adapted to detect a magnetic field and a processing unit having a sleep mode and an active mode, an external control unit adapted to be arranged outside of the body of the patient, the external control unit comprising a first coil adapted to create a magnetic field detectable by an internal sensor, wherein the controller is further configured to, in response to a detected magnetic field exceeding a predetermined value, setting the processing unit in an active mode.

9. The method according to claim 1, wherein the step of placing the implantable constriction device in connection with the urethra comprises placing the implantable constriction device around the urethra of the patient.

10. The method according to claim 1, wherein the step of placing the implantable constriction device in connection with the urethra comprises closing a locking or fixation device of the implantable constriction device around the urethra to fixate the implantable constriction device to the urethra of the patient.

11. The method according to claim 1, wherein the step of placing the implantable constriction device in connection with the urethra comprises securing the implantable constriction device by means of at least one of sutures, staples and tissue growth promoting structure.

12. The method according to claim 1, wherein the step of inserting an implantable constriction device into the body of the patient comprises inserting an implantable controller into the body of the patient and fixating the implantable controller to tissue or bone in the body of the patient.

13. The method according to claim 1, wherein the step of inserting an implantable constriction device into the body of the patient comprises inserting an implantable operation device comprising at least one of: an implantable hydraulic pump and an implantable valve and fixating the implantable operation device to tissue or bone in the body of the patient.

14. The method according to claim 13, further comprising a step of implanting and fixating at least one injection port in fluid connection with the operation device.

15. The method according to claim 14, wherein the step of fixating the at least one injection port comprises the step of fixating the injection port subcutaneously.

16. The method according to claim 14, further comprising the step of calibrating a fluid level in the implantable constriction device.

17. The method according to claim 1, further comprising calibrating at least one of:

a pressure exerted by the implantable constriction device on the urethra, a time during which implantable constriction device is to remain open after activation, a time during which implantable constriction device is to remain open after activation before bedtime, a speed with which the implantable constriction device should constrict the urethra, a pressure exerted on the urethra relative to the blood pressure of the patient, a pressure exerted on the urethra by the implantable constriction device by means of a pressure sensitive catheter, and an electrical stimulation of the tissue of the urethra.

18. The method according to claim 1, further comprising testing at least one of:

a fully open catheter mode, a feedback function by providing sensory feedback to the patient, a post-operative mode for enabling healing a post-operative mode for enabling growth of fibrotic tissue, and electrical stimulation of the tissue of the urethra.

* * * * *